United States Patent
Kang et al.

(10) Patent No.: US 10,032,997 B2
(45) Date of Patent: Jul. 24, 2018

(54) HETEROCYCLIC COMPOUND AND ORGANIC LIGHT-EMITTING ELEMENT USING SAME

(71) Applicant: LG CHEM, LTD., Seoul (KR)

(72) Inventors: Minyoung Kang, Daejeon (KR); Dong Hoon Lee, Daejeon (KR); Boonjae Jang, Daejeon (KR); Jungi Jang, Daejeon (KR); Seong So Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 29 days.

(21) Appl. No.: 15/024,999

(22) PCT Filed: Sep. 29, 2014

(86) PCT No.: PCT/KR2014/009102
§ 371 (c)(1),
(2) Date: Mar. 25, 2016

(87) PCT Pub. No.: WO2015/046987
PCT Pub. Date: Apr. 2, 2015

(65) Prior Publication Data
US 2016/0240793 A1    Aug. 18, 2016

(30) Foreign Application Priority Data
Sep. 30, 2013   (KR) .................. 10-2013-0116594

(51) Int. Cl.
*H01L 51/00* (2006.01)
*C07D 471/06* (2006.01)
(Continued)

(52) U.S. Cl.
CPC ........ *H01L 51/0072* (2013.01); *C07D 471/06* (2013.01); *C07D 487/06* (2013.01);
(Continued)

(58) Field of Classification Search
None
See application file for complete search history.

(56) References Cited

U.S. PATENT DOCUMENTS 4,549,192 A * 10/1985 Hung .................. B41M 5/20
                                                                205/55
2005/0014018 A1   1/2005 Klubek et al.
(Continued)

FOREIGN PATENT DOCUMENTS

| CN | 102939295 A | 2/2013 |
| CN | 104109532 A | 10/2014 |

(Continued)

OTHER PUBLICATIONS

Gritsenko, et al.: "Synthesis in the Phenothiazine Series—XXXII*- 1,2-Dihydroimidazo[4,5,1-n,m]Phenothiazine-1-Thione and Some of its Transformations", Institute of Pharmacology, Academy of Medical Sciences of the USSR, Khimiya Geterotsiklicheskikh Soedinenii, vol. 7, No. 6, Jun. 1971, pp. 770-772.

(Continued)

*Primary Examiner* — Vu A Nguyen
(74) *Attorney, Agent, or Firm* — Dentons US LLP

(57) ABSTRACT

The present specification provides a heterocyclic compound and an organic light emitting device using the same.

11 Claims, 3 Drawing Sheets

(51) Int. Cl.
*C07D 487/06* (2006.01)
*H05B 33/20* (2006.01)
*C07F 9/6561* (2006.01)
*C09K 11/02* (2006.01)
*C09K 11/06* (2006.01)
*C07D 498/06* (2006.01)
*C07D 513/06* (2006.01)
*C07F 9/6584* (2006.01)
*H01L 51/50* (2006.01)
*H01L 51/52* (2006.01)

(52) U.S. Cl.
CPC ......... *C07D 498/06* (2013.01); *C07D 513/06* (2013.01); *C07F 9/6561* (2013.01); *C07F 9/65846* (2013.01); *C09K 11/025* (2013.01); *C09K 11/06* (2013.01); *H01L 51/0052* (2013.01); *H01L 51/0054* (2013.01); *H01L 51/0055* (2013.01); *H01L 51/0056* (2013.01); *H01L 51/0058* (2013.01); *H01L 51/0067* (2013.01); *H01L 51/0068* (2013.01); *H01L 51/0071* (2013.01); *H01L 51/0077* (2013.01); *H01L 51/0085* (2013.01); *H05B 33/20* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1092* (2013.01); *C09K 2211/185* (2013.01); *C09K 2211/188* (2013.01); *H01L 51/0051* (2013.01); *H01L 51/5012* (2013.01); *H01L 51/5016* (2013.01); *H01L 51/5056* (2013.01); *H01L 51/5072* (2013.01); *H01L 51/5076* (2013.01); *H01L 51/5088* (2013.01); *H01L 51/5092* (2013.01); *H01L 51/5096* (2013.01); *H01L 51/5203* (2013.01)

(56) References Cited

U.S. PATENT DOCUMENTS

| | | |
|---|---|---|
| 2008/0018221 A1 | 1/2008 | Egen et al. |
| 2008/0145705 A1 | 6/2008 | Narihiro et al. |
| 2010/0187980 A1 | 7/2010 | Langer et al. |
| 2010/0207513 A1 | 8/2010 | Begley et al. |
| 2010/0219406 A1 | 9/2010 | Kahle et al. |
| 2010/0308714 A1 | 12/2010 | Gessner et al. |
| 2011/0253988 A1 | 10/2011 | Molt et al. |
| 2014/0042412 A1 | 2/2014 | Ryu et al. |
| 2014/0291586 A1 | 10/2014 | Buesing et al. |
| 2015/0115244 A1 | 4/2015 | Joo et al. |
| 2016/0056394 A1* | 2/2016 | Hong .................. H01L 51/0072 257/40 |
| 2016/0218301 A1 | 7/2016 | Kang et al. |
| 2016/0233431 A1 | 8/2016 | Kang et al. |
| 2016/0233432 A1 | 8/2016 | Kang et al. |
| 2016/0240793 A1 | 8/2016 | Kang et al. |

FOREIGN PATENT DOCUMENTS

| | | |
|---|---|---|
| CN | 105377844 A | 3/2016 |
| EP | 0170968 A1 | 2/1986 |
| JP | 61-42569 A | 3/1986 |
| JP | 2008-521946 A | 6/2008 |
| JP | 2008-521947 A | 6/2008 |
| JP | 2011-501878 A | 1/2011 |
| JP | 2016-535077 A | 11/2016 |
| JP | 2016-535078 A | 11/2016 |
| JP | 2016-535461 A | 11/2016 |
| JP | 2016-540032 A | 12/2016 |
| KR | 10-2015-0007570 A | 1/2015 |
| WO | 2006/033563 A1 | 3/2006 |
| WO | 2006/056465 A1 | 6/2006 |
| WO | 2009/047147 A1 | 4/2009 |
| WO | 2012/020327 A1 | 2/2012 |
| WO | 2012/14139 A1 | 10/2012 |
| WO | 2013/089460 A1 | 6/2013 |
| WO | 2015-005536 A1 | 1/2015 |

OTHER PUBLICATIONS

Lopez-Alvarado, P., et al., "Fused Imidazophenothiazines: Studies on the Bernthsen Thionation of 1-Methyl-6-(p-Tolylamino)Benzimidazole and 2-Methyl-1-Phenylbenzimidazole," Heterocyles, vol. 32, No. 5, 1991, pp. 1003-1012.

Rapid Communications in Mass Spectrometry, Aug. 2012, vol. 26, Issue 15, pp. 1687-1704.

* cited by examiner

[FIG. 1]
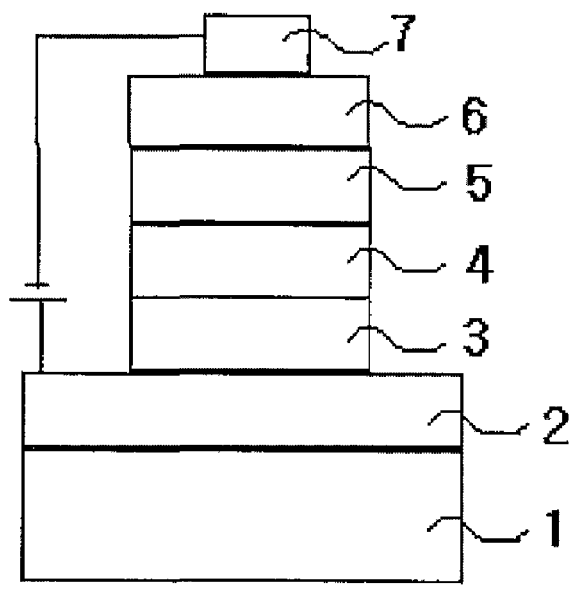
[FIG. 2]
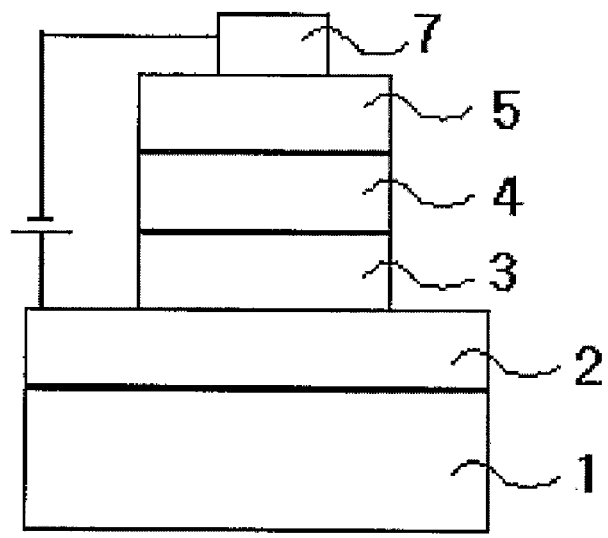

[FIG. 3]
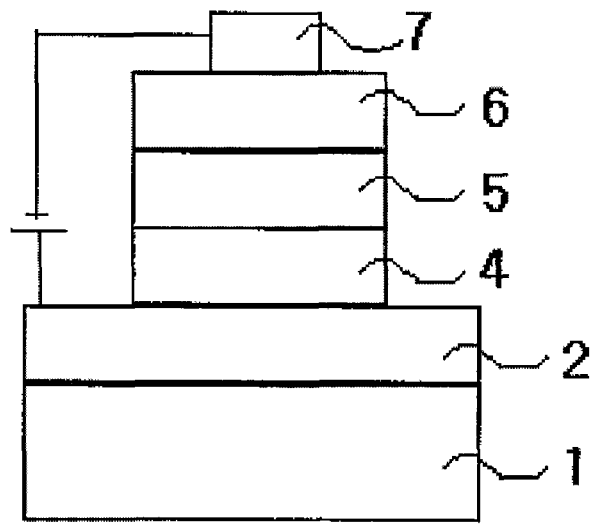
[FIG. 4]
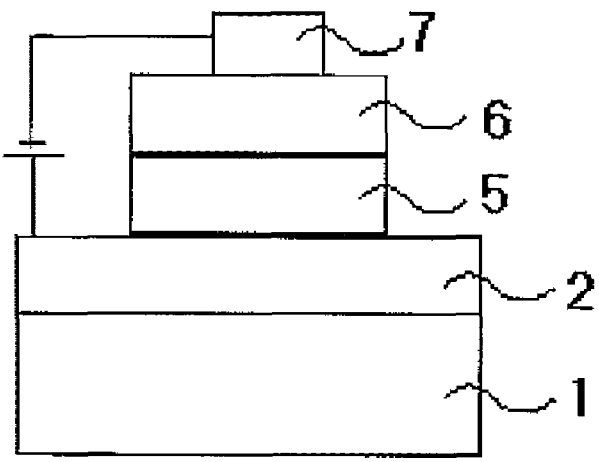

[FIG. 5]
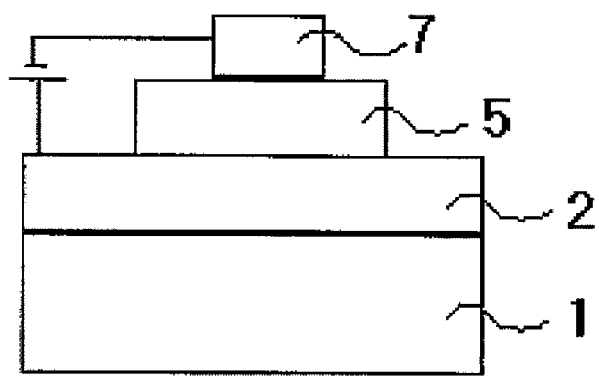

HETEROCYCLIC COMPOUND AND ORGANIC LIGHT-EMITTING ELEMENT USING SAME

TECHNICAL FIELD

This application is a National Stage Entry of International Application No. PCT/KR2014/009102, filed on Sep. 29, 2014, and claims the benefit of and priority to Korean Application No. 10-2013-0116594, filed on Sep. 30, 2013, all of which are incorporated herein by reference in their entirety for all purposes as if fully set forth herein.

The present disclosure relates to a heterocyclic compound and an organic light emitting device using the same.

BACKGROUND ART

An organic light emission phenomenon is one of the examples converting current to visible light by an internal process of a specific organic molecule. The principle of an organic light emission phenomenon is as follows.

When an organic material layer is placed between an anode and a cathode and voltage is applied between the two electrodes, electrons and holes flow into the organic material layer from the cathode and the anode, respectively. The electrons and the holes injected to the organic material layer are recombined to form excitons, and light emits when these excitons fall back to the ground state. An organic light emitting device using such a principle is typically formed with a cathode, an anode, and an organic material layer placed therebetween, which includes, for example, a hole injection layer, a hole transfer layer, a light emitting layer and an electron transfer layer.

Materials used in organic light emitting devices are mostly pure organic materials or complex compounds in which organic materials and metals form complexes, and may be divided into hole injection materials, hole transfer materials, light emitting materials, electron transfer materials, electron injection materials and the like. Herein, as the hole injection material or the hole transfer material, organic materials having p-type properties, that is, readily oxidized and in an electrochemically stable state when oxidized, are generally used. Meanwhile, as the electron injection material or the electron transfer material, organic materials having n-type properties, that is, readily reduced and in an electrochemically stable state when reduced, are generally used. As the light emitting layer material, materials having both p-type properties and n-type properties, that is, in a stable state in both an oxidation and a reduction state, are preferable, and materials having high light emission efficiency that, when excitons are formed, convert the excitons to light are preferable.

Accordingly, the development of new organic materials has been required in the art.

PRIOR ART DOCUMENTS

Patent Documents

Korean Patent Application Laid-Open Publication No. 2007-0092667

DISCLOSURE

Technical Problem

An object of the present specification is to provide a heterocyclic compound and an organic light emitting device using the same.

Technical Solution

The present specification provides a heterocyclic compound represented by the following Chemical Formula 1.

[Chemical Formula 1]

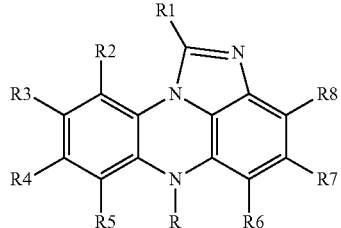

In Chemical Formula 1,

R and R1 to R8 are the same as or different from each other, and each independently hydrogen; deuterium; a halogen group; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted arylphosphine group; a substituted or unsubstituted phosphine oxide group; a substituted or unsubstituted aryl group; or a substituted or unsubstituted heteroring group including one or more of N, O and S atoms, or adjacent groups among R and R2 to R8 bond to each other to form an aliphatic ring, an aromatic ring, an aliphatic heteroring or an aromatic heteroring.

The present specification provides an organic light emitting device including a first electrode; a second electrode provided opposite to the first electrode; and one or more organic material layers including a light emitting layer provided between the first electrode and the second electrode, wherein one or more layers of the organic material layers include the heterocyclic compound described above.

Advantageous Effects

A heterocyclic compound according to one embodiment of the present specification has a proper energy level, and an excellent electrochemical stability and thermal stability. Accordingly, an organic light emitting device including the compound provides high efficiency and/or high driving stability.

DESCRIPTION OF DRAWINGS

FIGS. 1 to 5 are cross-sectional diagrams illustrating structures of an organic light emitting device according to one embodiment of the present invention.

REFERENCE NUMERAL

1: Substrate
2: Anode
3: Hole Injection Layer
4: Hole Transfer Layer
5: Light Emitting Layer
6: Electron Transfer Layer
7: Cathode

MODE FOR DISCLOSURE

Hereinafter, the present specification will be described in more detail.

One embodiment of the present specification provides an organic light emitting device including a heterocyclic compound represented by Chemical Formula 1.

Examples of the substituents are described below, however, the substituents are not limited thereto.

In the present invention, the term "substituted or unsubstituted" means being substituted with one or more substituents selected from the group consisting of deuterium; a halogen group; a nitrile group; a nitro group; an imide group; an amide group; a hydroxyl group; a thiol group; an alkyl group; an alkenyl group; an alkoxy group; a cycloalkyl group; a silyl group; an arylalkenyl group; an aryl group; an aryloxy group; an alkylthioxy group; an arylthioxy group; an alkylsulfoxy group; an arylsulfoxy group; a silyl group; a boron group; an alkylamine group; an aralkylamine group; an arylamine group; a heteroaryl group; a carbazole group; an aryl group; a fluorenyl group; an arylalkyl group; an arylalkenyl group; and a heteroring group including one or more of N, O and S atoms, or having no substituents, or being substituted with a substituent linking two or more substituents of the substituents illustrated above, or having no substituents. For example, "a substituent linking two or more substituents" may include a biphenyl group. In other words, a biphenyl group may be interpreted as an aryl group, or as a substituent linking 2 phenyl groups.

The term "substitution" means a hydrogen atom bonding to a carbon atom of a compound is changed to another substituent, and the position of substitution is not limited as long as it is a position at which a hydrogen atom is substituted, that is, a position at which a substituent may substitute, and when two or more substituents substitute, the two or more substituents may be the same as or different from each other.

In the present specification, examples of the halogen group include fluorine, chlorine, bromine or iodine.

In the present specification, in the ester group, the oxygen of the ester group may be substituted with a linear, branched or cyclic alkyl group having 1 to 25 carbon atoms or an aryl group having 6 to 25 carbon atoms. Specifically, compounds having the following structural formulae may be included, but the compound is not limited thereto.

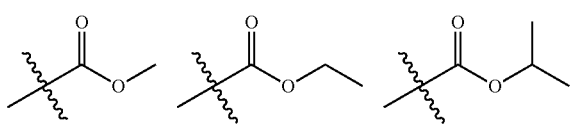

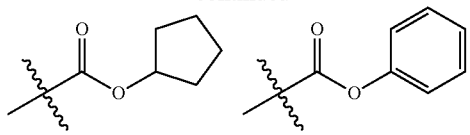

In the present specification, the number of carbon atoms of the imide group is not particularly limited, but is preferably 1 to 25. Specifically, compounds having the following structures may be included, but the compound is not limited thereto.

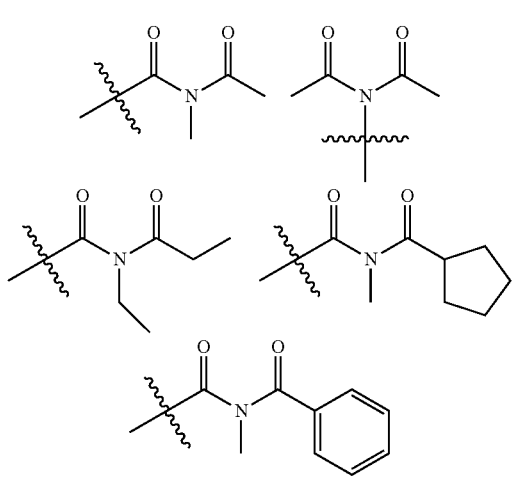

In the present specification, in the amide group, the nitrogen of the amide group may be once or twice substituted with hydrogen, a linear, branched or cyclic alkyl group having 1 to 25 carbon atoms, or an aryl group having 6 to 25 carbon atoms. Specifically, compounds having the following structural formulae may be included, but the compound is not limited thereto.

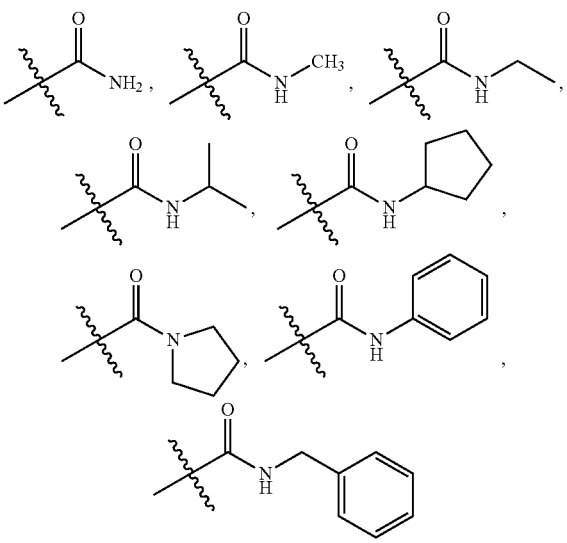

In the present specification, the alkyl group may be linear or branched, and the number of carbon atoms is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 60 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited, the number of carbon atoms is preferably 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the aryl group may be a monocyclic aryl group or a multicyclic aryl group, and includes a case in which an alkyl group having 1 to 25 carbon atoms or an alkoxy group having 1 to 25 carbon atoms is substituted. In addition, the aryl group in the present specification may mean an aromatic ring.

When the aryl group is a monocyclic aryl group, the number of carbon atoms is not particularly limited, but is preferably 6 to 25. Specific examples of the monocyclic aryl group may include a phenyl group, a biphenyl group, a terphenyl group and the like, but are not limited thereto.

When the aryl group is a multicyclic aryl group, the number of carbon atoms is not particularly limited, but is preferably 10 to 24. Specific example of the multicyclic aryl group may include a naphthyl group, an anthryl group, a phenanthryl group, a pyrenyl group, a perylenyl group, a crycenyl group, a fluorenyl group and the like, but are not limited thereto.

In the present specification, the fluorenyl group may be substituted, and adjacent substituents may bond to each other to form a ring.

When the fluorenyl group is substituted,

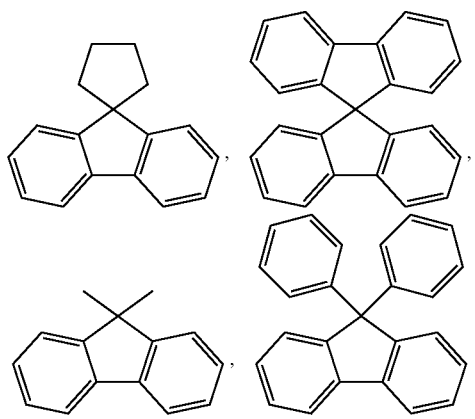

and the like may be included. However, the structure is not limited thereto.

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, the number of carbon atoms of the amine group is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or monocyclic aryl groups and multicyclic aryl groups at the same time.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group and the like, but are not limited thereto.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a multicyclic aryl group. The arylphosphine group including two or more aryl groups may include monocyclic aryl groups, multicyclic aryl groups, or monocyclic aryl groups and multicyclic aryl groups at the same time.

In the present specification, the heteroring group is a heteroring group including one or more of O, N and S as a heteroatom, and although not particularly limited, the number of carbon atoms is preferably 2 to 60. Examples of the heteroring group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

In the present specification, the heteroaryl group in the heteroarylamine group may be the same as the examples of the heteroring group described above.

In the present specification, the aryl group in the aryloxy group, the arylthioxy group, the arylsulfoxy group and the aralkylamine group is the same as the examples of the aryl group described above. Specific examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy and the like, examples of the arylthioxy group include a phenylthioxy group, a 2-methylphenylthioxy group, a 4-tert-butylphenylthioxy group and the like, and examples of the arylsulfoxy group include a benzenesulfoxy group, a p-toluenesulfoxy group and the like, but the examples are not limited thereto.

In the present specification, the alkyl group in the alkylthioxy group and the alkylsulfoxy group is the same as the examples of the alkyl group described above. Specific examples of the alkylthioxy group include a methylthioxy group, an ethylthioxy group, a tert-butylthioxy group, a hexylthioxy group, an octylthioxy group and the like, and examples of the alkylsulfoxy group include a mesyl group, an ethylsulfoxy group, a propylsulfoxy group, a butylsulfoxy group and the like, but the examples are not limited thereto.

In the present specification, an "adjacent" group means a substituent substituting an atom directly linking to an atom substituted by the corresponding substituent, a substituent most closely positioned sterically to the corresponding substituent, or another substituent substituting an atom substituted by the corresponding substituent. For example, two substituents substituting ortho positions in a benzene ring, and two substituents substituting the same carbon in an aliphatic ring may be interpreted as "adjacent" groups.

In one embodiment of the present specification, R1 is a substituted or unsubstituted alkyl group; a substituted or unsubstituted alkenyl group; a substituted or unsubstituted aryl group; a substituted or unsubstituted phosphine oxide group; or a substituted or unsubstituted heteroring group including one or more of N, O and S atoms.

In one embodiment of the present specification, R1 is a substituted or unsubstituted methyl group; a substituted or unsubstituted ethyl group; a substituted or unsubstituted t-butyl group; a substituted or unsubstituted phenyl group; a substituted or unsubstituted naphthyl group; a substituted or unsubstituted phenanthryl group; a substituted or unsubstituted anthracene group; a substituted or unsubstituted pyrenyl group; a substituted or unsubstituted perylenyl group; a substituted or unsubstituted pyridine group; a substituted or unsubstituted benzoquinoline group; a substituted or unsubstituted fluorenyl group; a substituted or unsubstituted triazine group; a substituted or unsubstituted quinoxaline group; a substituted or unsubstituted carbazole group; a substituted or unsubstituted benzocarbazole group; a substituted or unsubstituted benzimidazoquinazoline group; a substituted or unsubstituted styrene group; or a substituted or unsubstituted phosphine oxide group.

In another embodiment, R is a substituted or unsubstituted alkyl group; a substituted or unsubstituted alkenyl group; a substituted or unsubstituted aryl group; a substituted or unsubstituted phosphine oxide group; or a substituted or unsubstituted heteroring group including one or more of N, O and S atoms.

In one embodiment of the present specification, R is a substituted or unsubstituted methyl group; a substituted or unsubstituted ethyl group; a substituted or unsubstituted t-butyl group; a substituted or unsubstituted phenyl group; a substituted or unsubstituted naphthyl group; a substituted or unsubstituted phenanthryl group; a substituted or unsubstituted anthracene group; a substituted or unsubstituted pyrenyl group; a substituted or unsubstituted perylenyl group; a substituted or unsubstituted pyridine group; a substituted or unsubstituted benzoquinoline group; a substituted or unsubstituted fluorenyl group; a substituted or unsubstituted triazine group; a substituted or unsubstituted quinoxaline group; a substituted or unsubstituted carbazole group; a substituted or unsubstituted benzocarbazole group; a substituted or unsubstituted benzimidazoquinazoline group; a substituted or unsubstituted styrene group; or a substituted or unsubstituted phosphine oxide group.

In one embodiment of the present specification, R2 to R8 are the same as or different from each other, and each dependently hydrogen; a substituted or unsubstituted alkyl group; a substituted or unsubstituted alkenyl group; a substituted or unsubstituted aryl group; a substituted or unsubstituted phosphine oxide group; or a substituted or unsubstituted heteroring group including one or more of N, O and S atoms.

In one embodiment of the present specification, R2 to R8 are the same as or different from each other, and each dependently hydrogen; a substituted or unsubstituted methyl group; a substituted or unsubstituted ethyl group; a substituted or unsubstituted t-butyl group; a substituted or unsubstituted phenyl group; a substituted or unsubstituted naphthyl group; a substituted or unsubstituted phenanthryl group; a substituted or unsubstituted anthracene group; a substituted or unsubstituted pyrenyl group; a substituted or unsubstituted perylenyl group; a substituted or unsubstituted pyridine group; a substituted or unsubstituted benzoquinoline group; a substituted or unsubstituted fluorenyl group; a substituted or unsubstituted triazine group; a substituted or unsubstituted quinoxaline group; a substituted or unsubstituted carbazole group; a substituted or unsubstituted benzocarbazole group; a substituted or unsubstituted benzimidazoquinazoline group; a substituted or unsubstituted styrene group; or a substituted or unsubstituted phosphine oxide group.

In one embodiment of the present specification, R and R1 to R8 are the same as or different from each other, and each dependently hydrogen; an alkyl group; an alkenyl group; an aryl group; a phosphine oxide group; or a heterering group including one or more of N, O and S atoms, and the alkyl group; the alkenyl group; the aryl group; the phosphine oxide group; and the heterering group including one or more of N, O and S atoms are unsubstituted or substituted with one, two or more substituents selected from the group consisting of deuterium, a nitrile group, a substituted or unsubstituted alkyl group, a substituted or unsubstituted alkenyl group, a substituted or unsubstituted aryl group, a substituted or unsubstituted silane group, a substituted or unsubstituted phosphine oxide group, and a substituted or unsubstituted heterering group including one or more of N, O and S atoms, or two or more substituents bond to each other to form an aliphatic ring, an aromatic ring, an aliphatic heterering or an aromatic heterering, or form a spiro bond.

In one embodiment of the present specification, R and R1 to R8 are the same as or different from each other, and each dependently hydrogen; a methyl group; an ethyl group; a t-butyl group; a phenyl group; a naphthyl group; a phenanthryl group; an anthracene group; a pyrenyl group; a perylenyl group; a pyridine group; a benzoquinoline group; a fluorenyl group; a spirobifluorenyl group; a triazine group; a quinoxaline group; a carbazole group; a benzocarbazole group; a benzimidazoquinazoline group; a styrene group; or a phosphine oxide group, and the phenyl group; the naphthyl group; the phenanthryl group; the anthracene group; the pyrenyl group; the perylenyl group; the pyridine group; the benzoquinoline group; the fluorenyl group; the triazine group; the quinoxaline group; the carbazole group; the benzocarbazole group; the benzimidazoquinazoline group; the styrene group; and the phosphine oxide group are unsubstituted or substituted with one, two or more substituents selected from the group consisting of deuterium, a phenyl group, a naphthyl group, a biphenyl group, a fluorenyl group substituted with an alkyl group, a phenanthryl group, a pyridine group, a quinoline group, a phenyl group substituted with a nitrile group, a dibenzofuran group, a dibenzothiophene group, a fluorenyl group substituted with an alkyl group and a nitrile group, an anthracenyl group substituted with a phenyl group, an anthracenyl group substituted with a naphthyl group, a phenanthryl group, a thiophene group substituted with a phenyl group, a carbazole group, a benzimidazole group substituted with a phenyl group, a benzothiazole group, a phenanthroline group, and a silane group substituted with a phenyl group, or substituents in the same carbon bond to each other to form a spiro bond.

In the present specification, the substituents in the same carbon bonding to each other to form a spiro bond means two or more rings being linked sharing one carbon atom, and the substituents in the same carbon may bind to each other to form a fluorene structure or a spiroanthracenefluorene structure.

In one embodiment of the present specification, at least one of R and R1 to R8 is any one of the following structures.

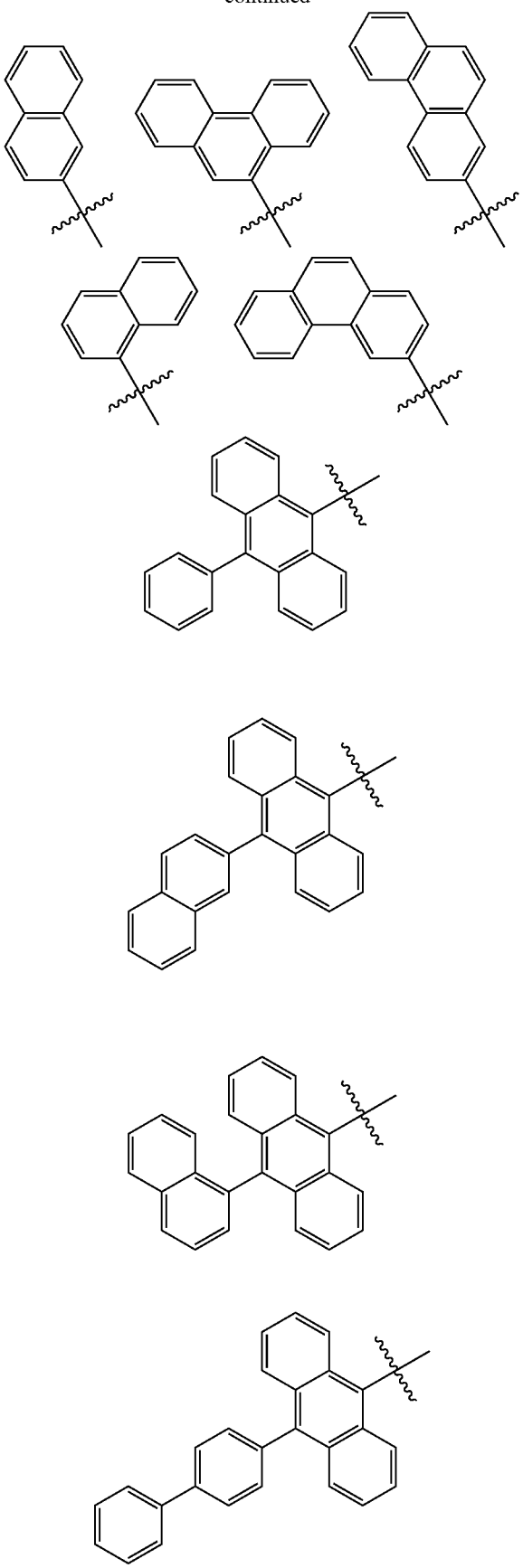

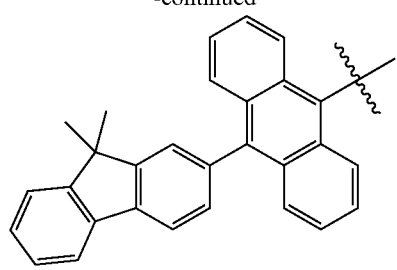
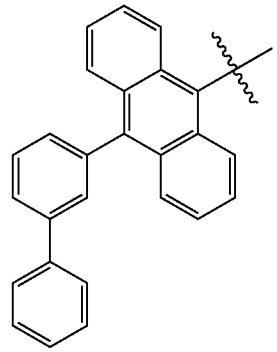
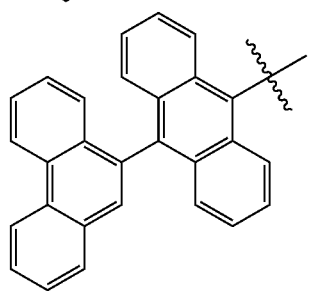
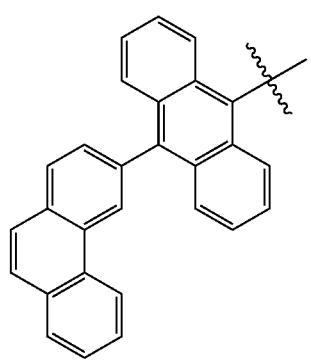
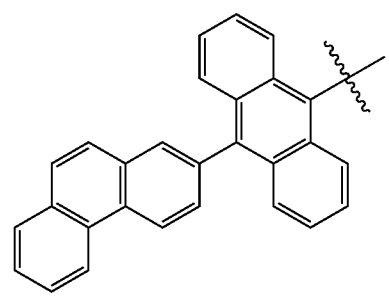
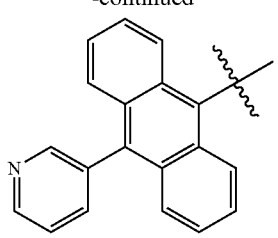
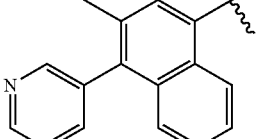
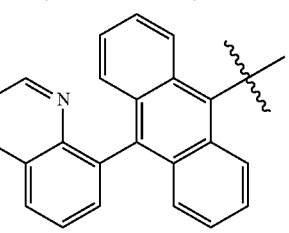
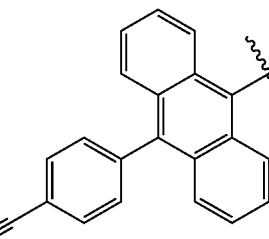
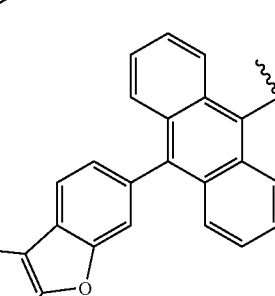
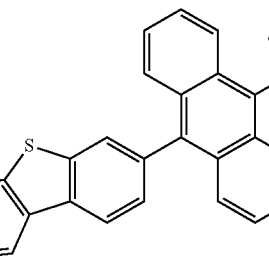
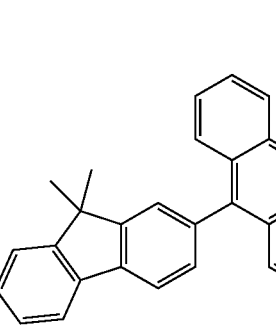

-continued
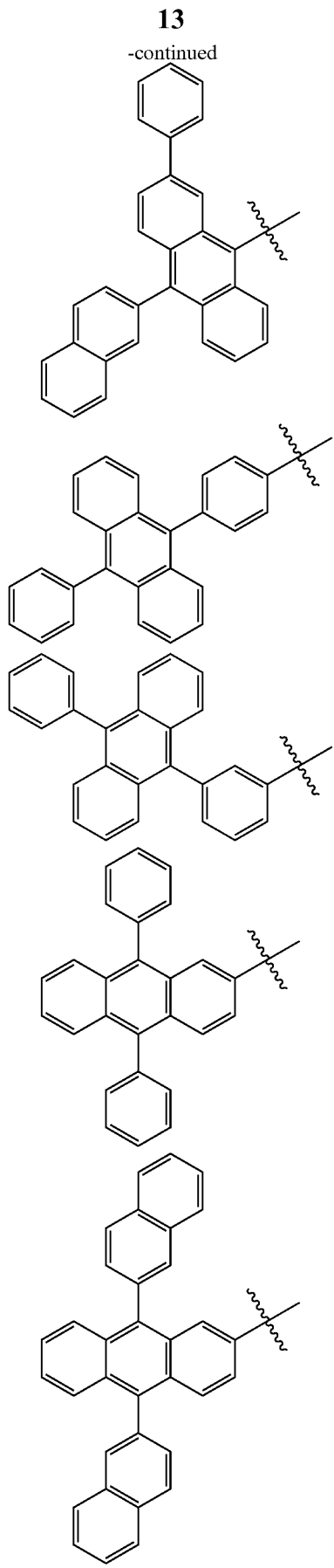
-continued
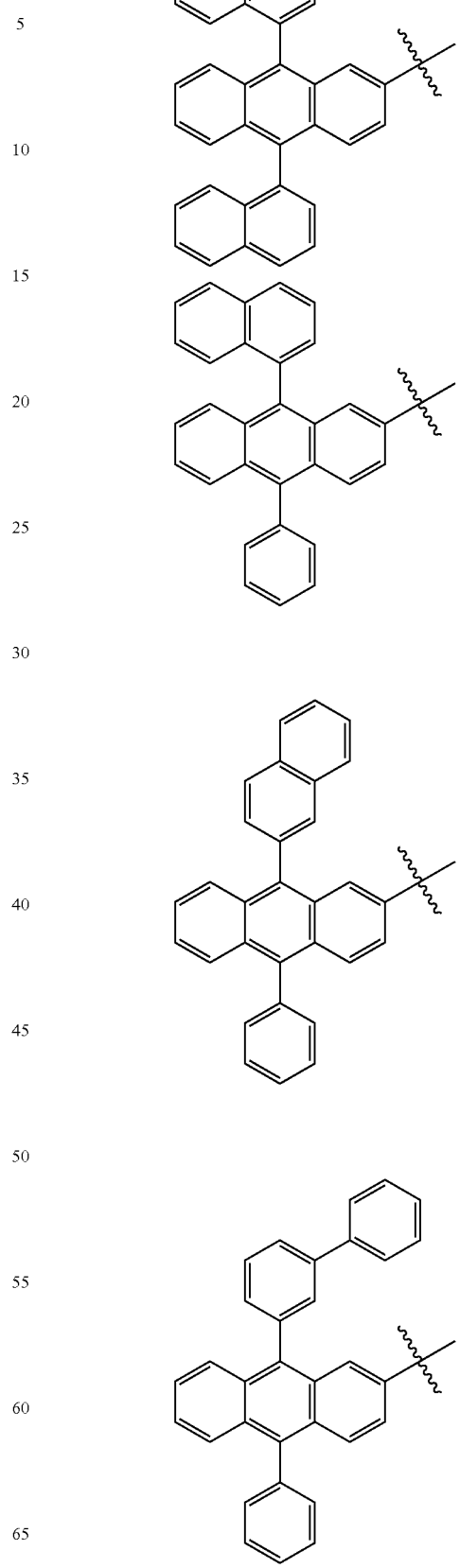

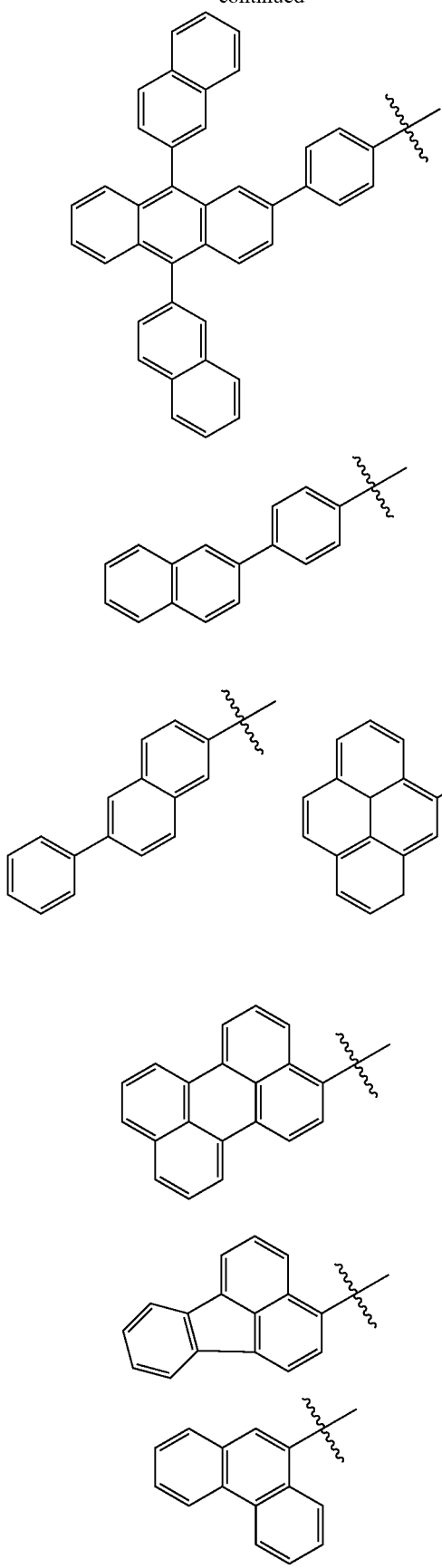
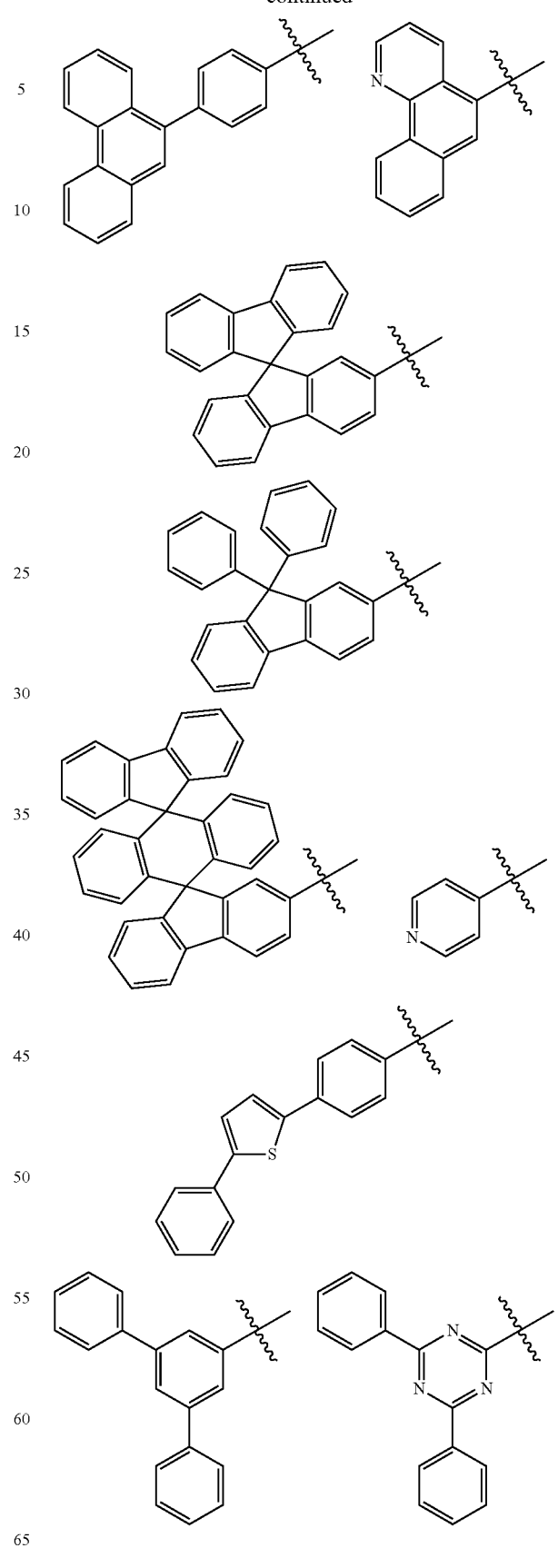

-continued
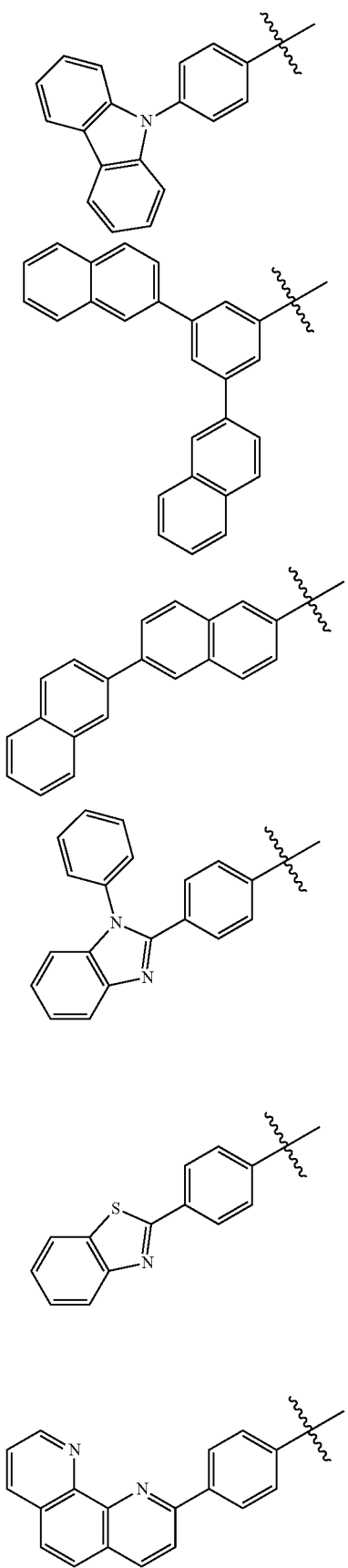
-continued
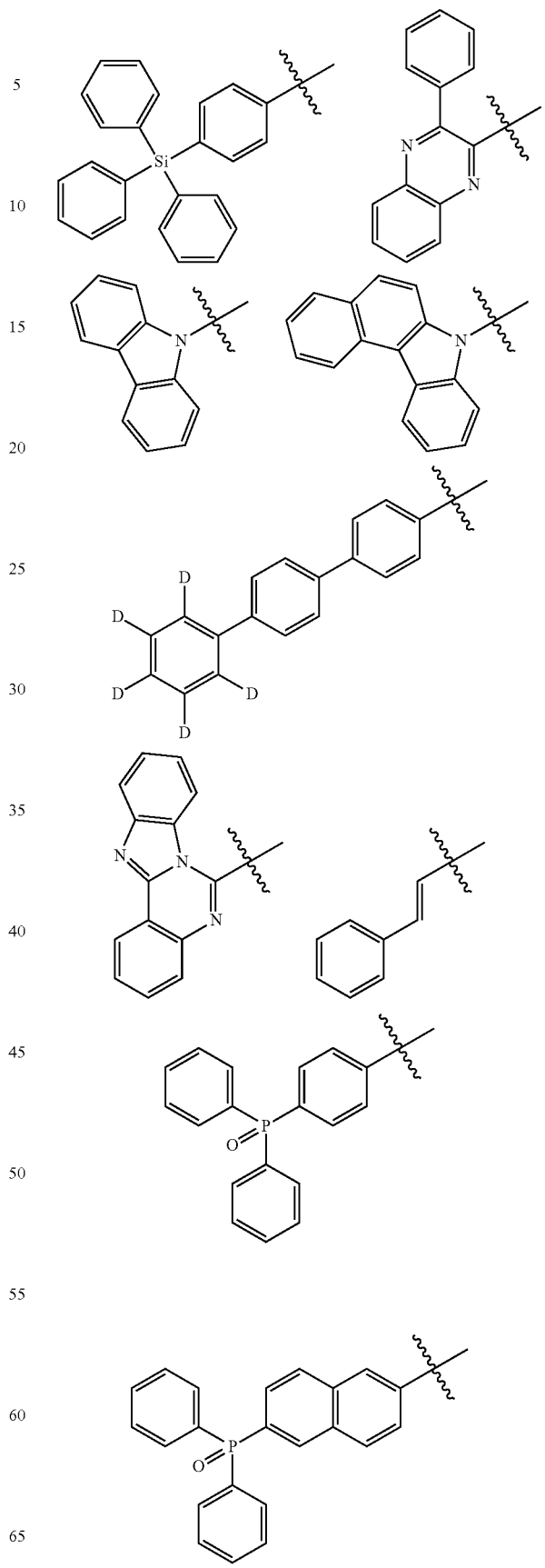

-continued

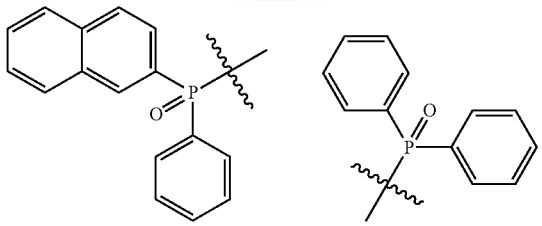 [SMILES: *P(=O)(c1ccccc1)c1ccc2ccccc2c1 ; *P(=O)(c1ccccc1)c1ccccc1]

In one embodiment of the present specification, R is any one of the structures shown above.

In another embodiment, R1 is any one of the structures shown above.

In one embodiment of the present specification, R2 is any one of the structures shown above.

In another embodiment, R2 is hydrogen.

In one embodiment, R3 is any one of the structures shown above.

In another embodiment, R3 is hydrogen.

In one embodiment of the present specification, R4 is any one of the structures shown above.

In another embodiment, R4 is hydrogen.

In another embodiment, R5 is any one of the structures shown above.

In another embodiment, R5 is hydrogen.

In one embodiment of the present specification, R6 is any one of the structures shown above.

In another embodiment, R6 is hydrogen.

In another embodiment of the present specification, R7 is any one of the structures shown above.

In another embodiment, R7 is hydrogen.

In one embodiment of the present specification, R8 is any one of the structures shown above.

In another embodiment, R8 is hydrogen.

In one embodiment of the present specification, the heterocyclic compound represented by Chemical Formula 1 may be represented by any one of the following structures.

[Chemical Formula 1-1]

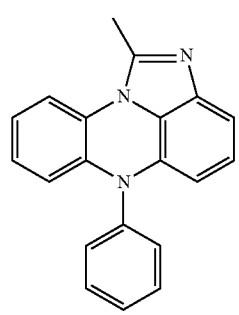

[Chemical Formula 1-2]

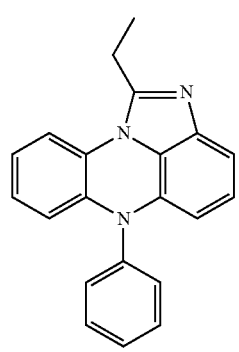

[Chemical Formula 1-3]

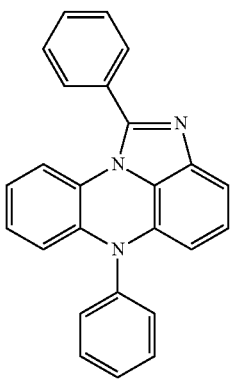

[Chemical Formula 1-4]

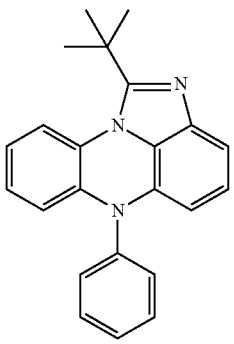

[Chemical Formula 1-5]

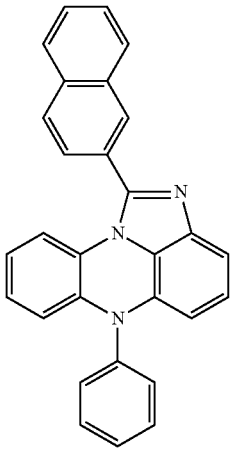

[Chemical Formula 1-6]

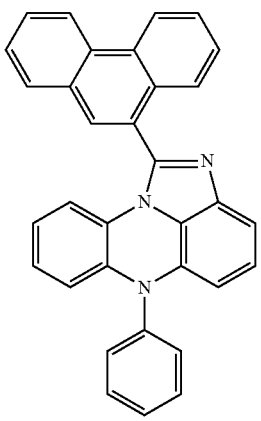

[Chemical Formula 1-7]
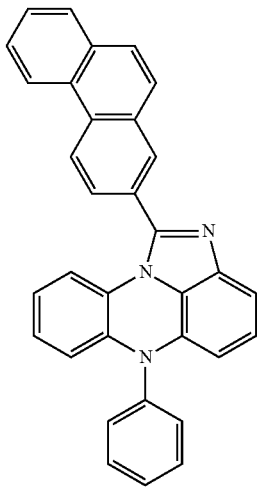
[Chemical Formula 1-8]
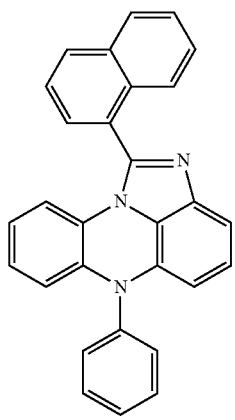
[Chemical Formula 1-9]
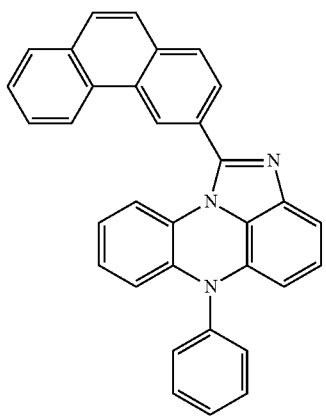
[Chemical Formula 2-1]
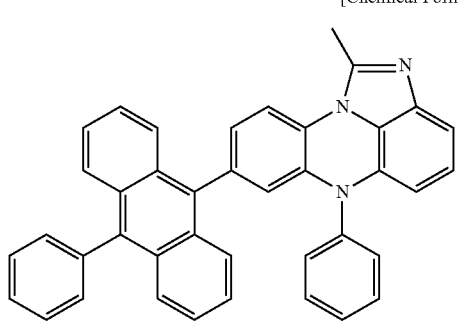
[Chemical Formula 2-2]
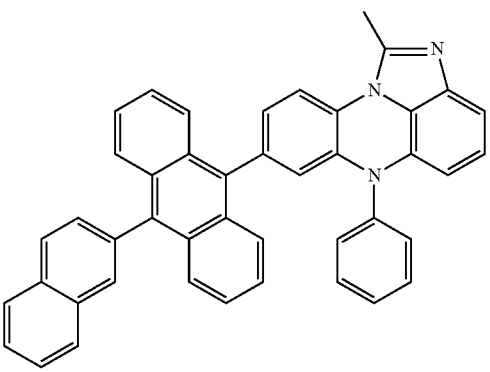
[Chemical Formula 2-3]
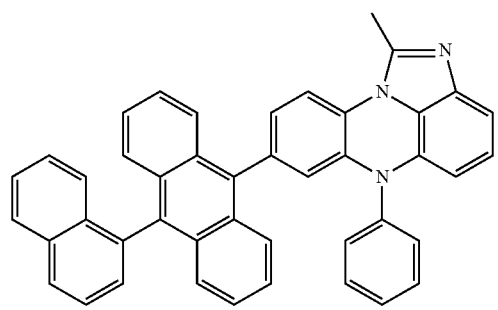
[Chemical Formula 2-4]
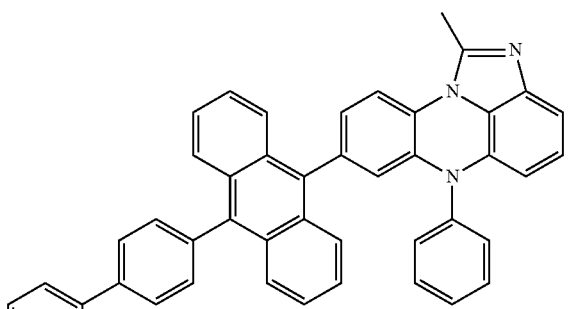
[Chemical Formula 2-5]
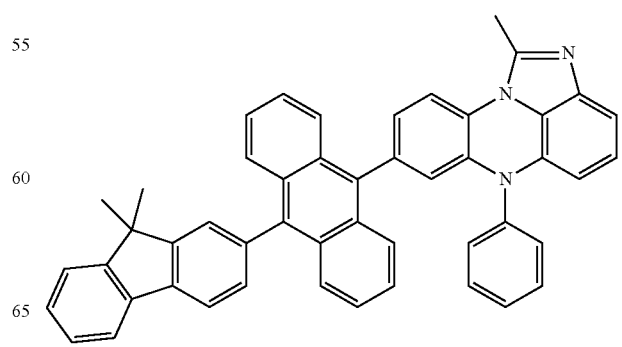

[Chemical Formula 2-6]
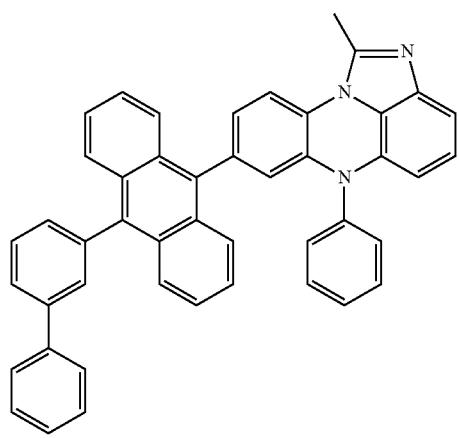
[Chemical Formula 2-7]
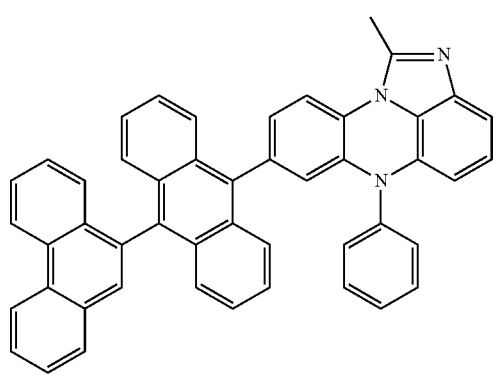
[Chemical Formula 2-8]
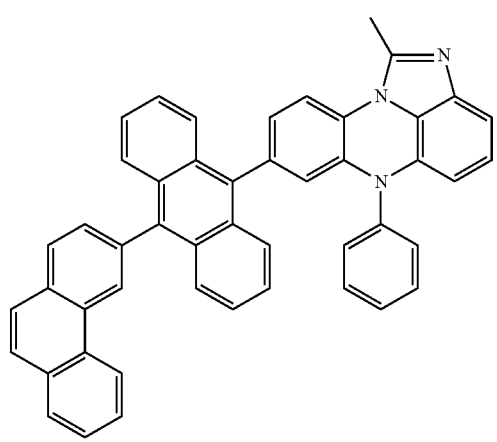
[Chemical Formula 2-9]
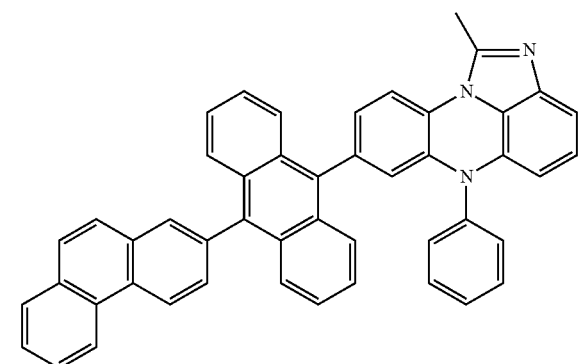
[Chemical Formula 2-10]
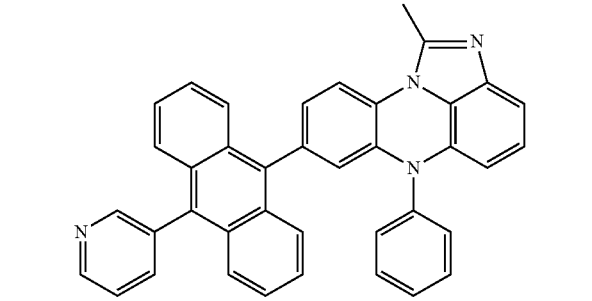
[Chemical Formula 2-11]
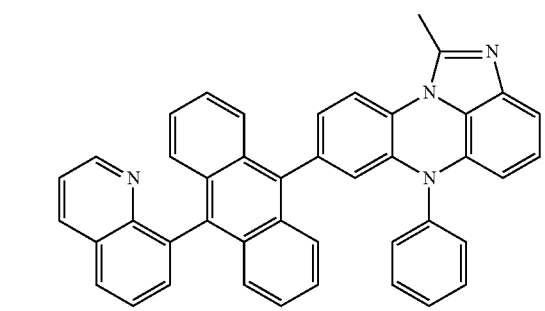
[Chemical Formula 2-12]
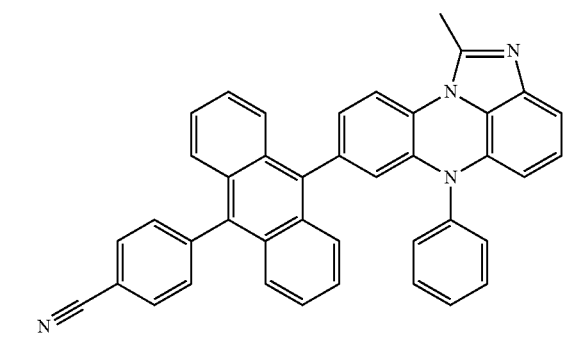

-continued
[Chemical Formula 2-13]
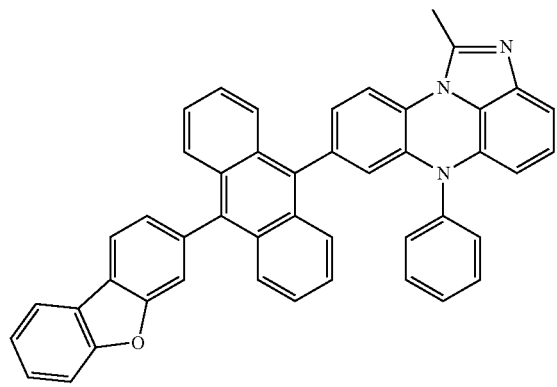
[Chemical Formula 2-14]
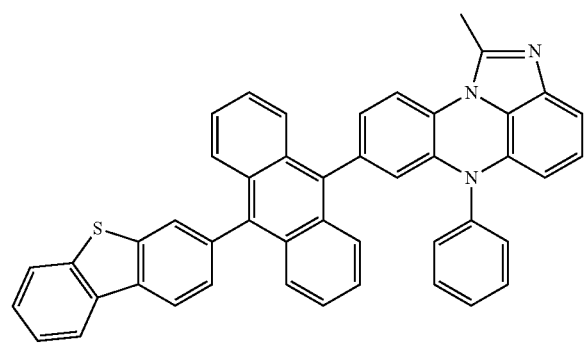
[Chemical Formula 2-15]
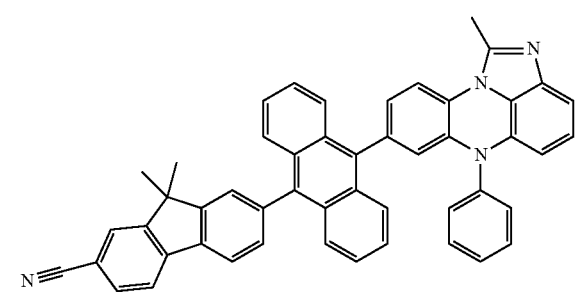
[Chemical Formula 2-16]
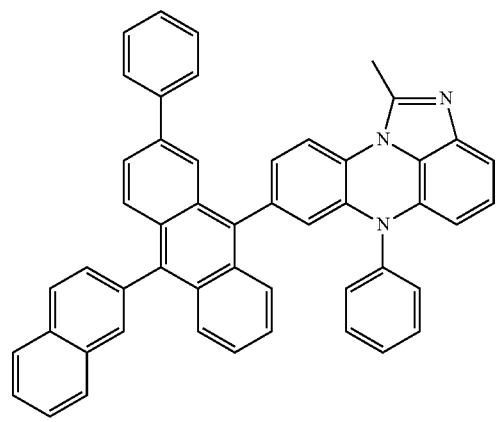
-continued
[Chemical Formula 2-17]
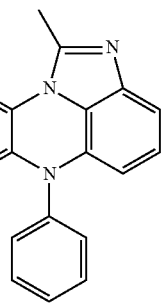
[Chemical Formula 2-18]
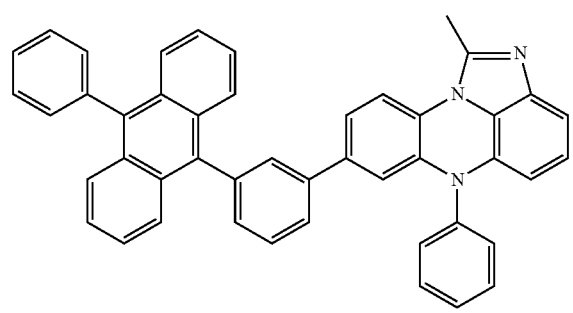
[Chemical Formula 2-19]
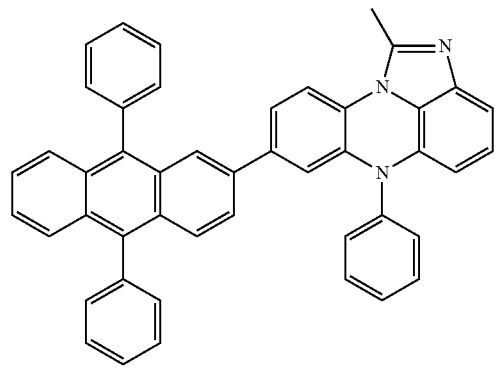
[Chemical Formula 2-20]
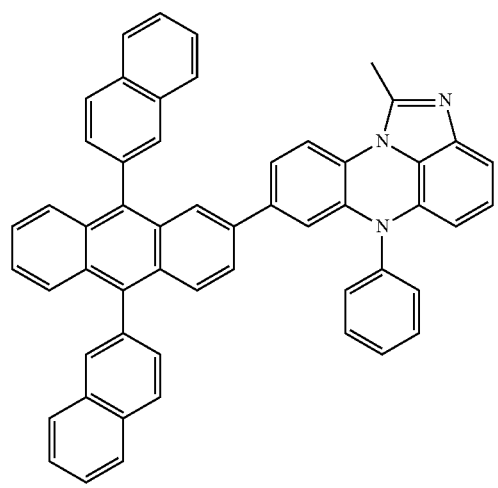

[Chemical Formula 2-21]
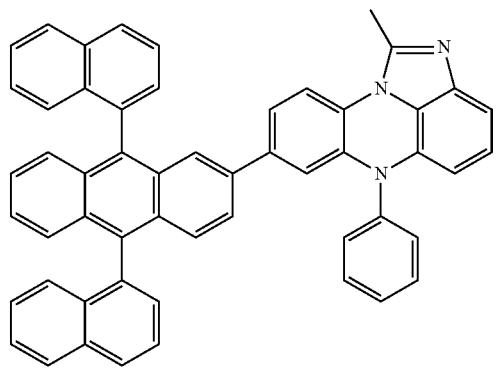
[Chemical Formula 2-22]
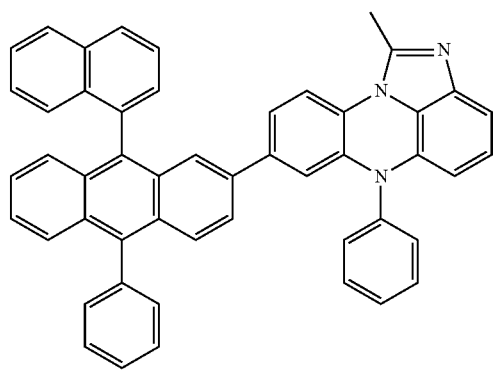
[Chemical Formula 2-23]
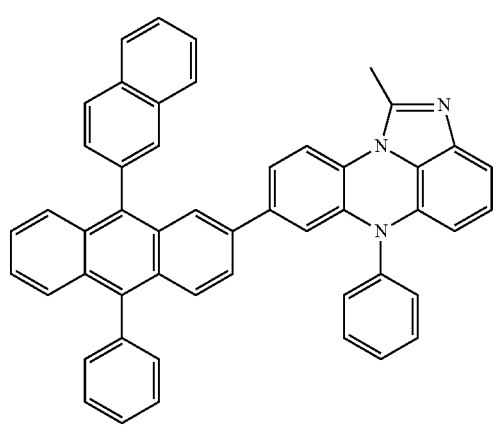
[Chemical Formula 2-24]
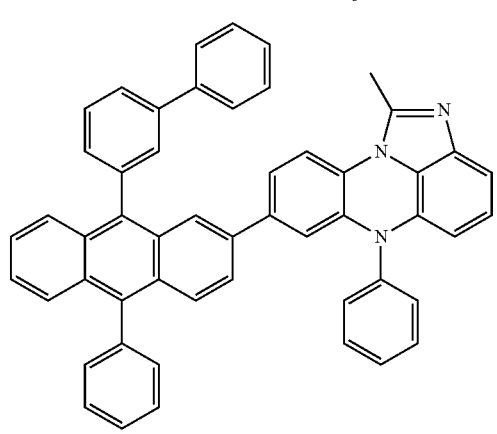
[Chemical Formula 2-25]
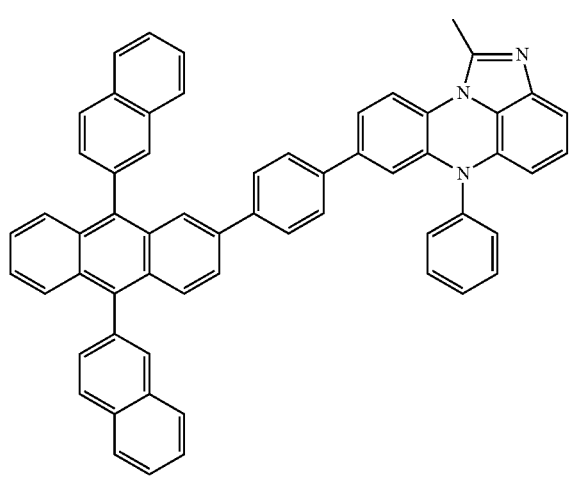
[Chemical Formula 2-26]
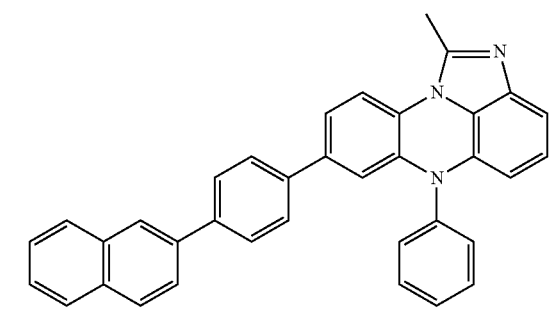
[Chemical Formula 2-27]
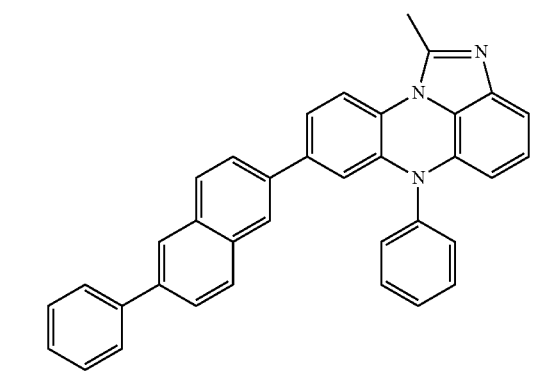
[Chemical Formula 2-28]
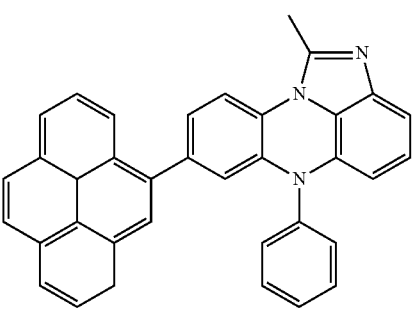

[Chemical Formula 2-29]
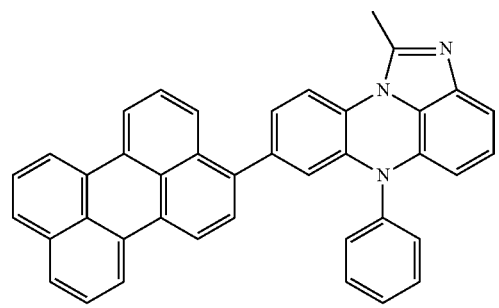
[Chemical Formula 2-33]
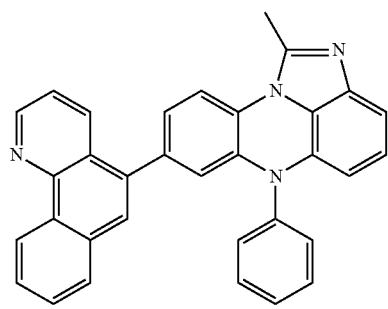
[Chemical Formula 2-30]
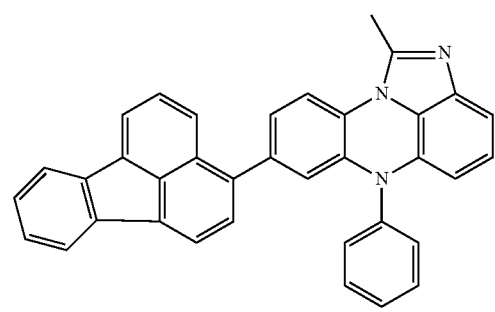
[Chemical Formula 2-34]
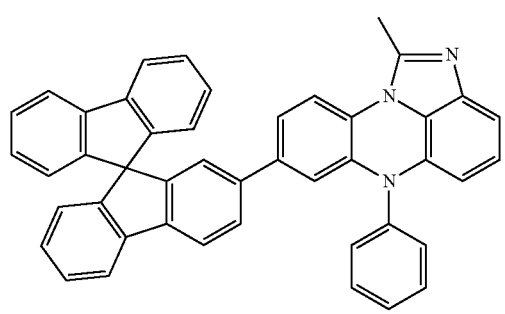
[Chemical Formula 2-31]
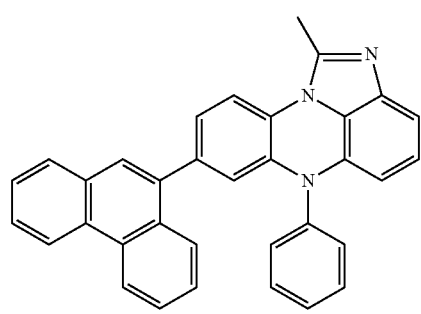
[Chemical Formula 2-35]
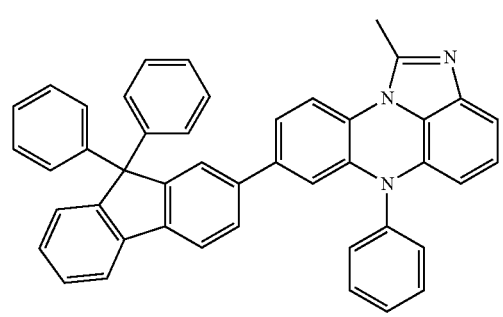
[Chemical Formula 2-32]
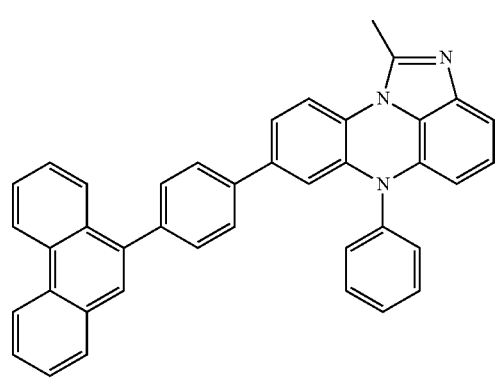
[Chemical Formula 2-36]
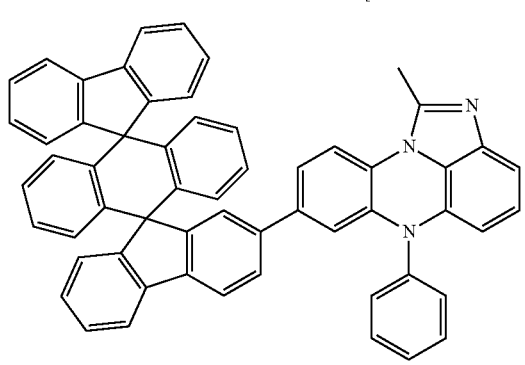

[Chemical Formula 2-37]
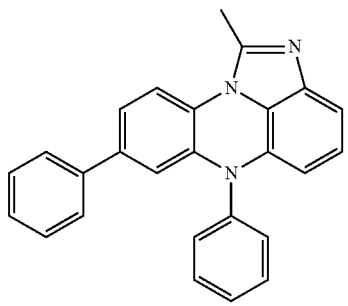
[Chemical Formula 2-38]
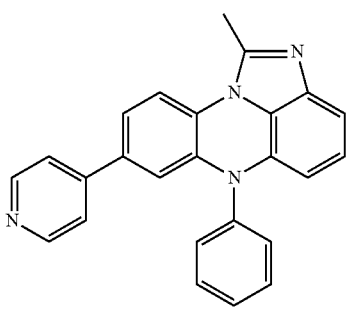
[Chemical Formula 2-39]
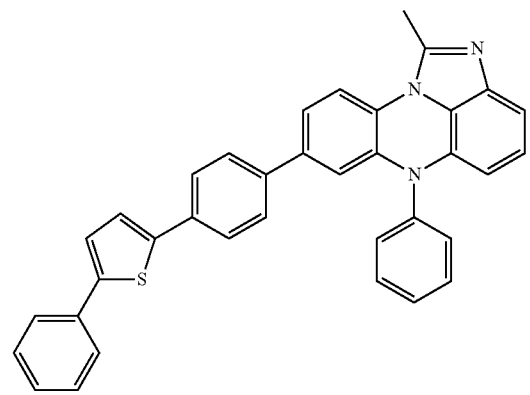
[Chemical Formula 2-40]
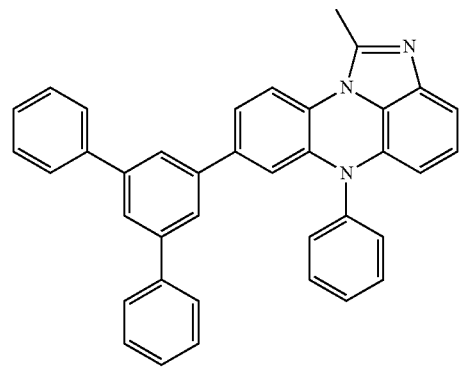
[Chemical Formula 2-41]
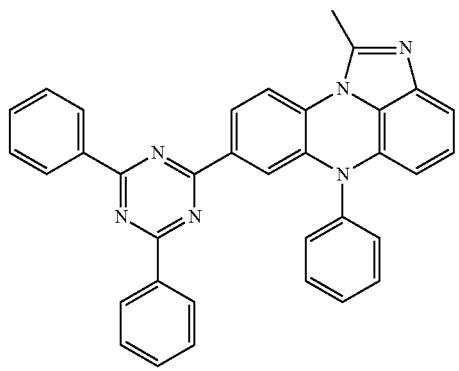
[Chemical Formula 2-42]
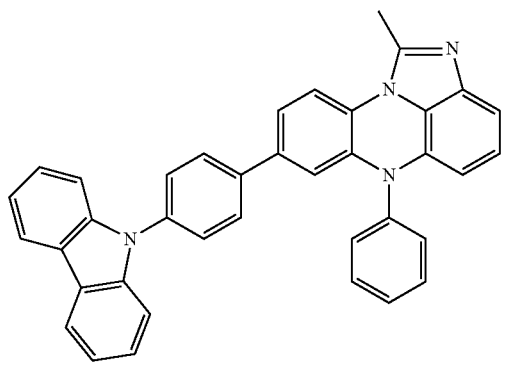
[Chemical Formula 2-43]
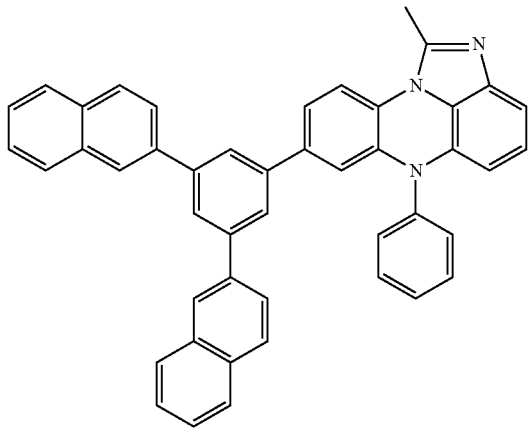
[Chemical Formula 2-44]
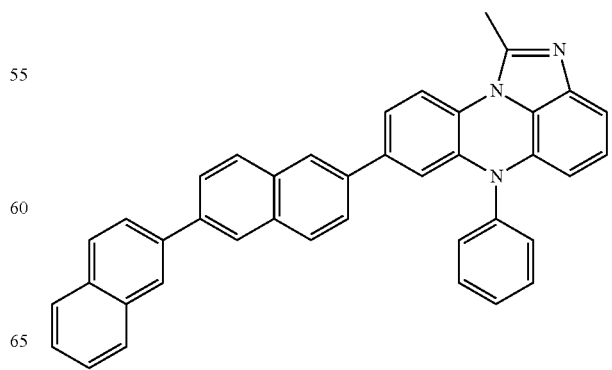

-continued
[Chemical Formula 2-45]
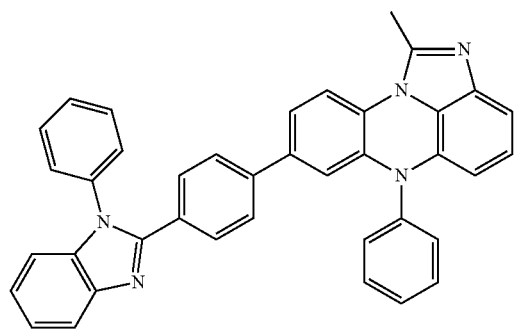
[Chemical Formula 2-46]
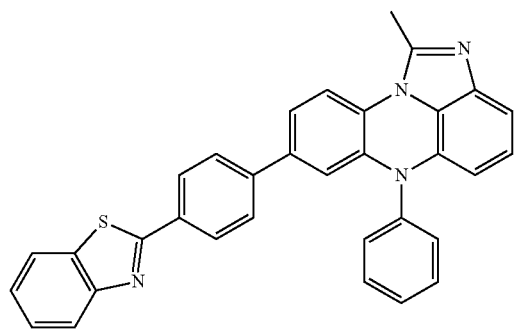
[Chemical Formula 2-47]
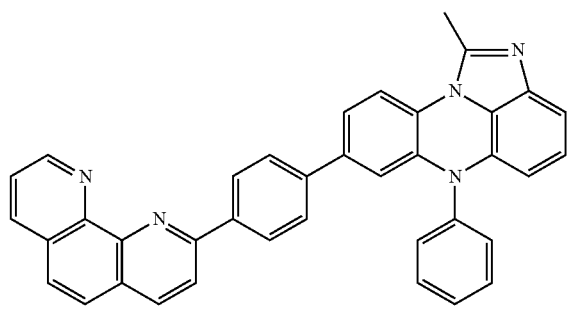
[Chemical Formula 2-48]
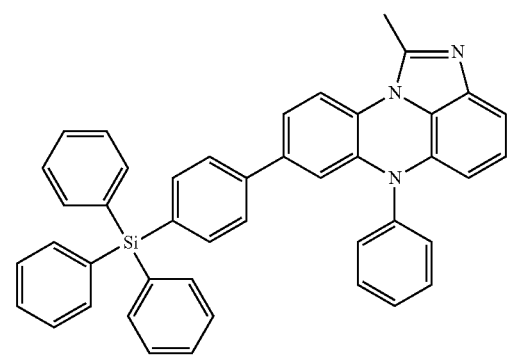
-continued
[Chemical Formula 2-49]
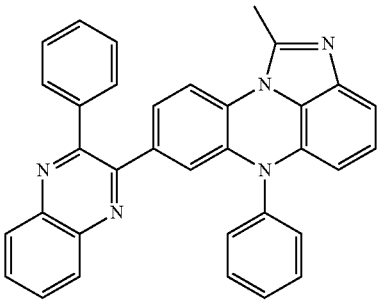
[Chemical Formula 2-50]
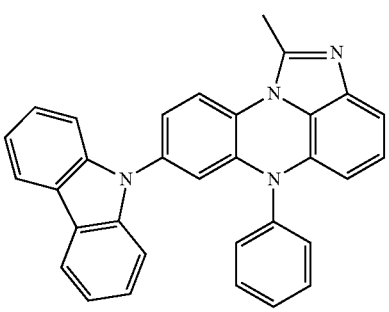
[Chemical Formula 2-51]
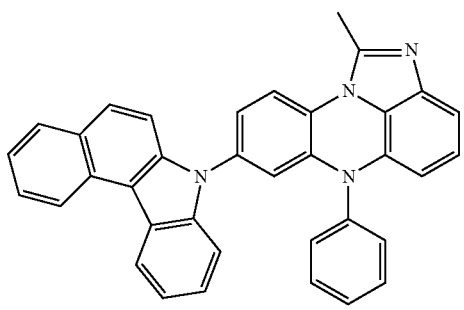
[Chemical Formula 2-52]
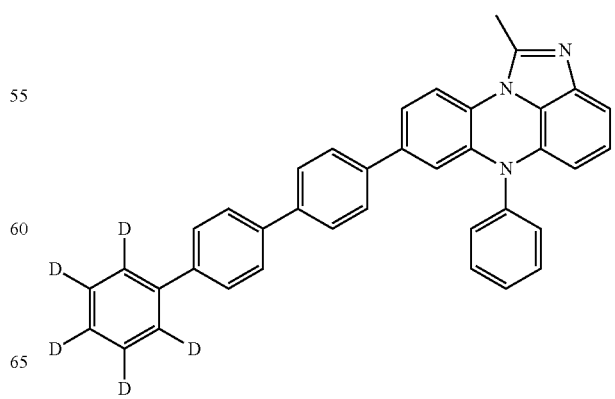

[Chemical Formula 2-53]
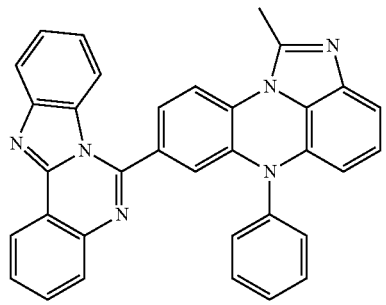
[Chemical Formula 2-54]
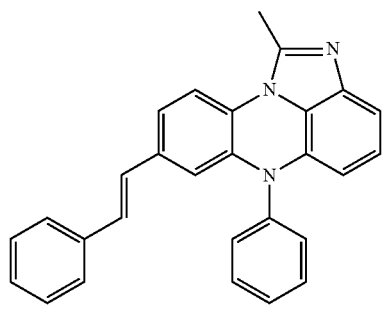
[Chemical Formula 3-1]
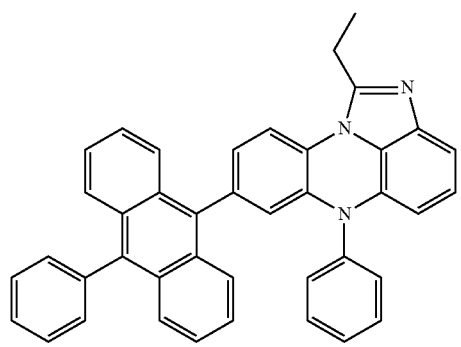
[Chemical Formula 3-2]
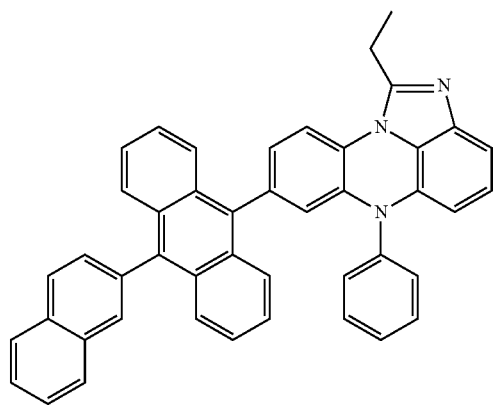
[Chemical Formula 3-3]
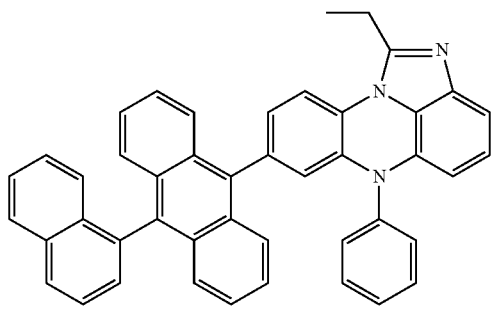
[Chemical Formula 3-4]
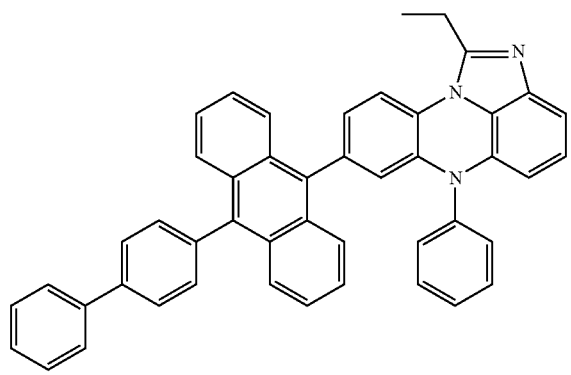
[Chemical Formula 3-5]
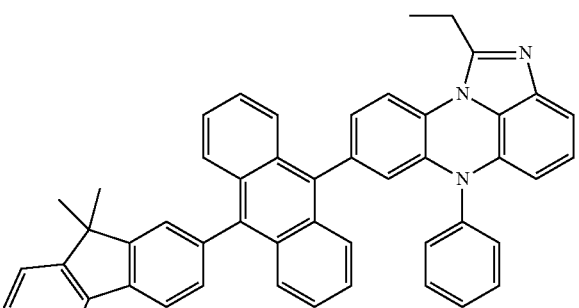
[Chemical Formula 3-6]
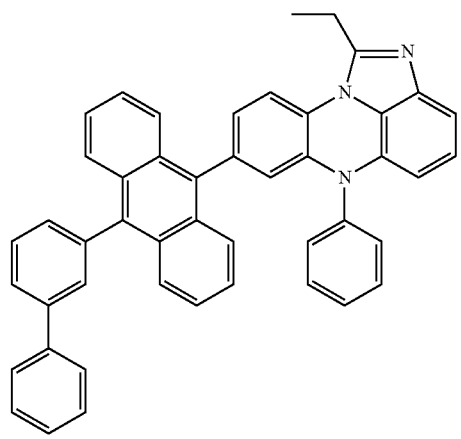

[Chemical Formula 3-7]
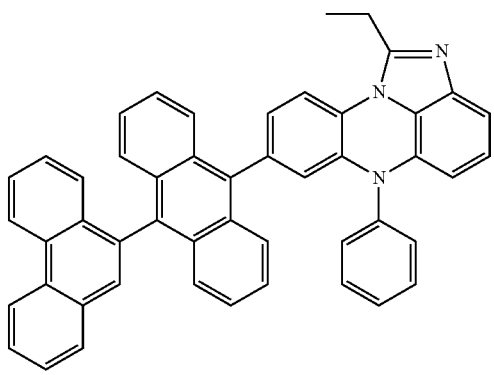
[Chemical Formula 3-8]
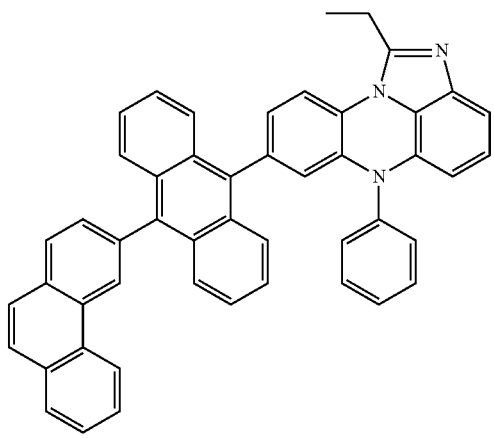
[Chemical Formula 3-9]
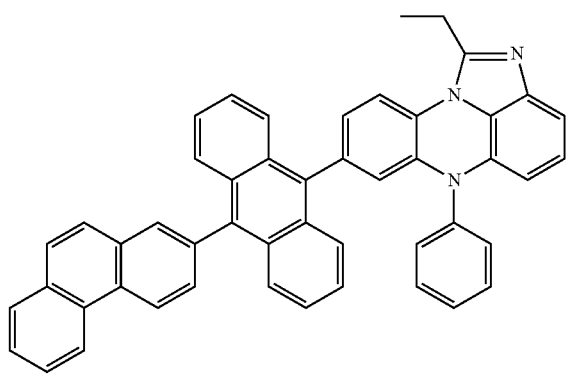
[Chemical Formula 3-10]
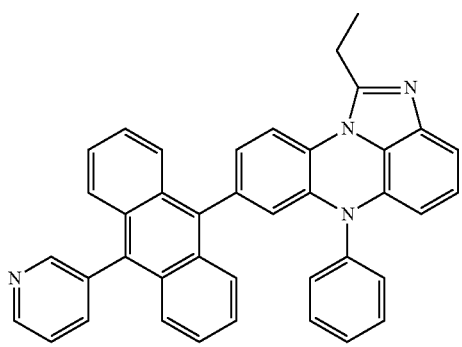
[Chemical Formula 3-11]
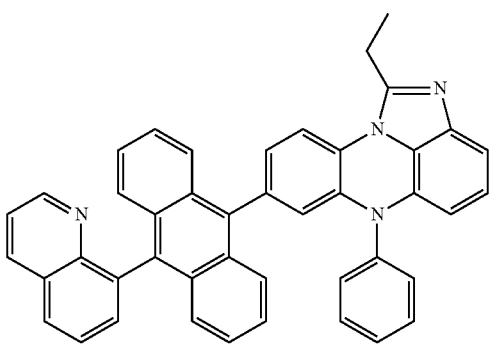
[Chemical Formula 3-12]
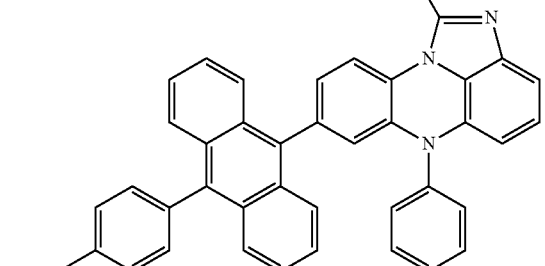
[Chemical Formula 3-13]
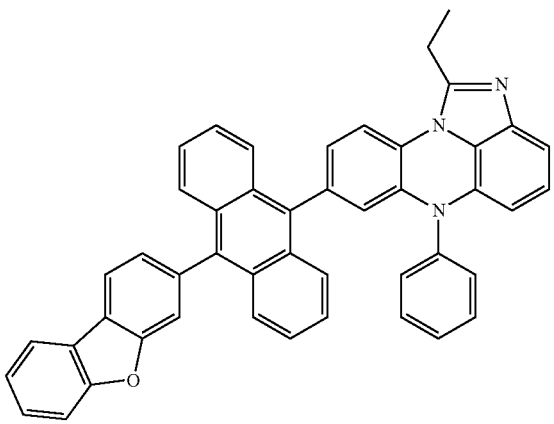
[Chemical Formula 3-14]
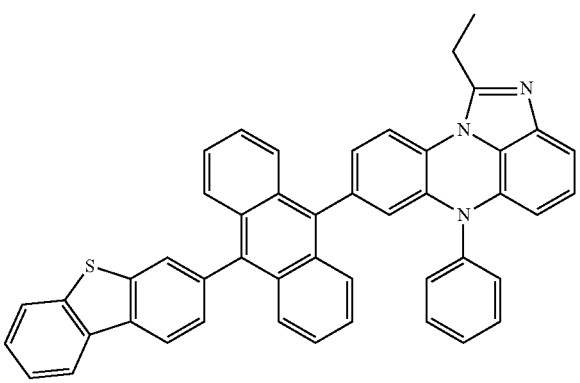

[Chemical Formula 3-15]
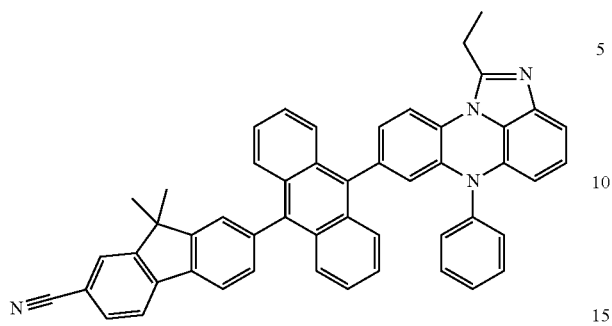
[Chemical Formula 3-16]
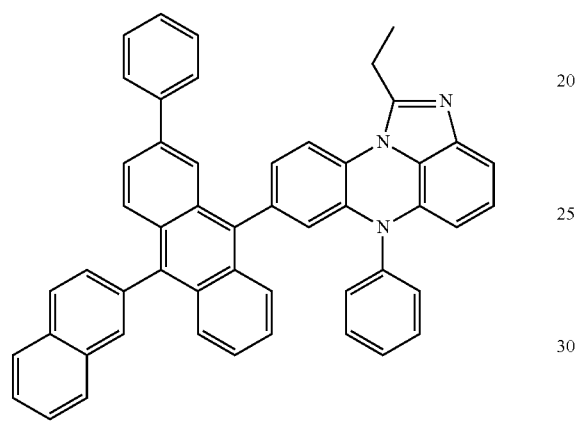
[Chemical Formula 3-17]
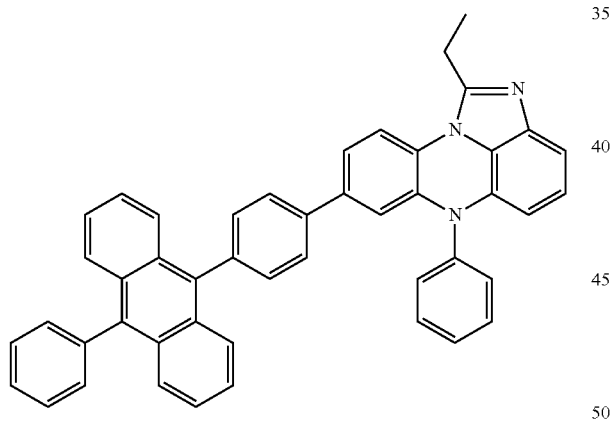
[Chemical Formula 3-18]
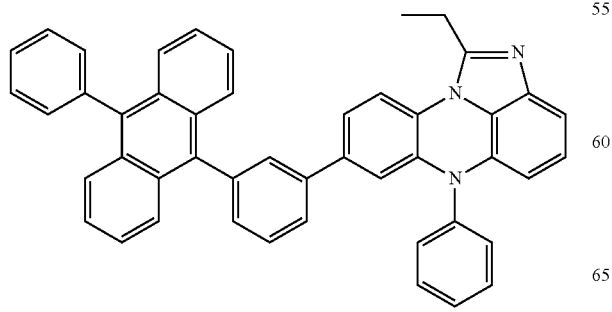
[Chemical Formula 3-19]
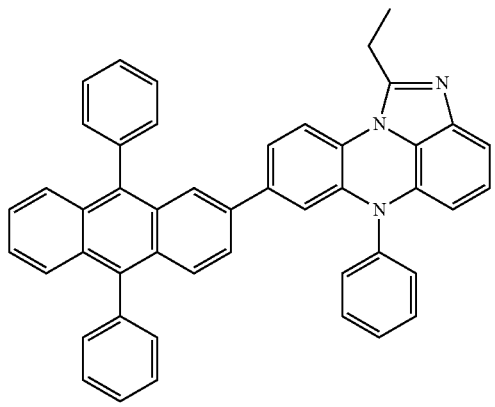
[Chemical Formula 3-20]
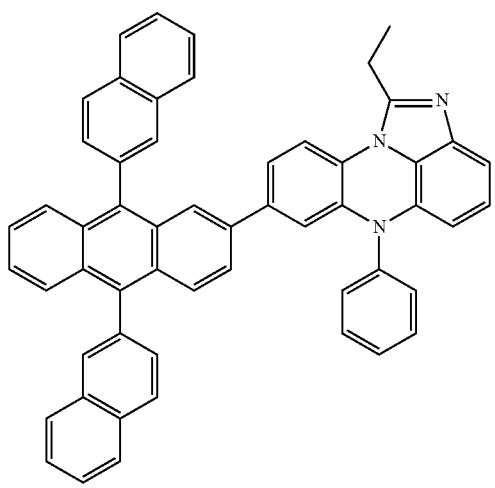
[Chemical Formula 3-21]
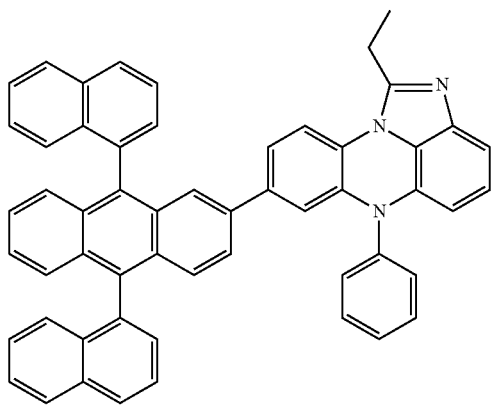

[Chemical Formula 3-22]
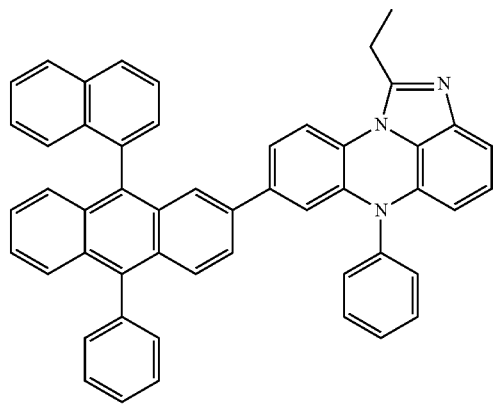
[Chemical Formula 3-23]
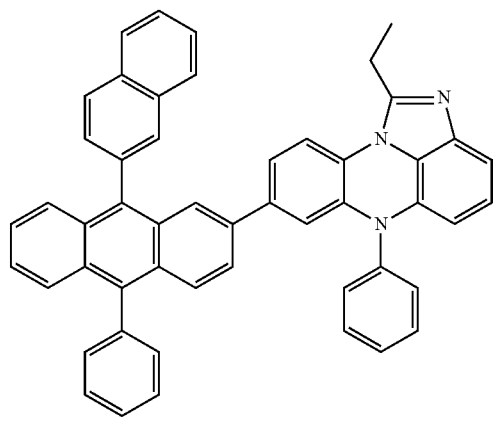
[Chemical Formula 3-24]
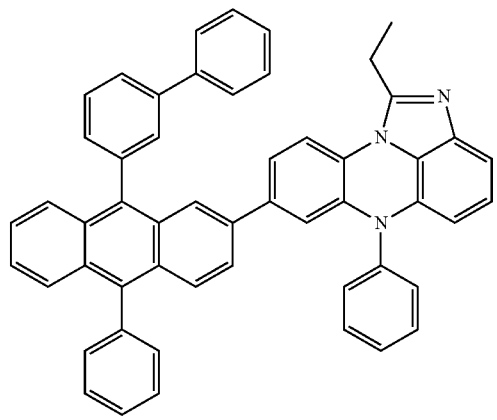
[Chemical Formula 3-25]
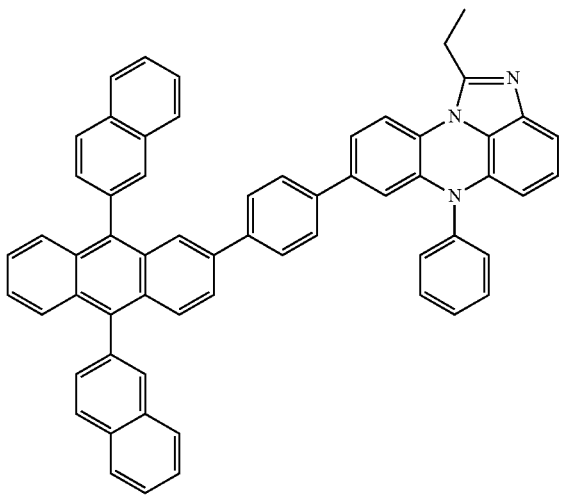
[Chemical Formula 3-26]
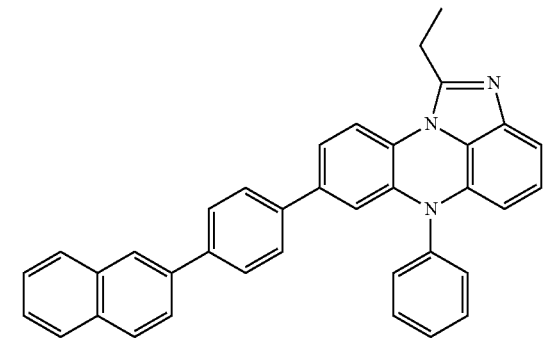
[Chemical Formula 3-27]
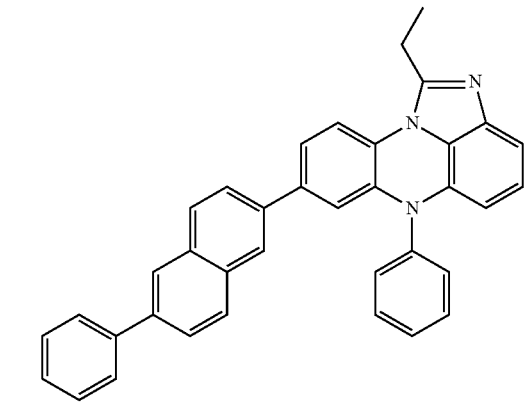
[Chemical Formula 3-28]
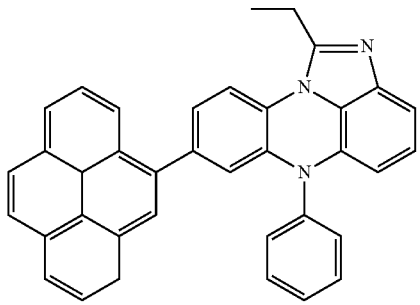

-continued
[Chemical Formula 3-29]
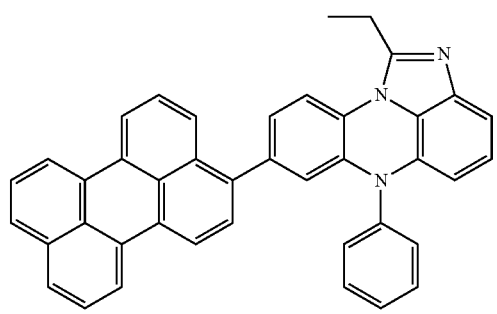
[Chemical Formula 3-30]
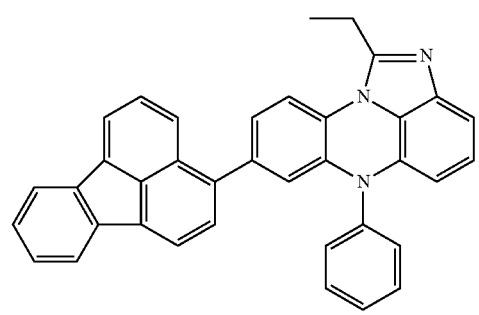
[Chemical Formula 3-31]
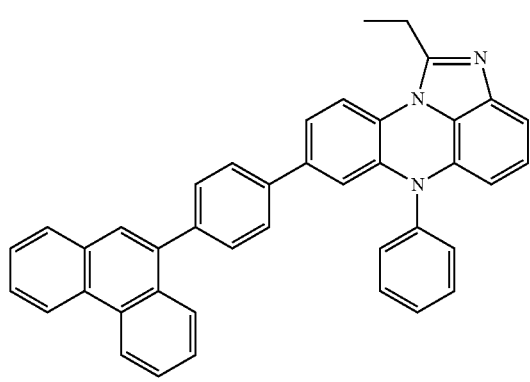
[Chemical Formula 3-32]
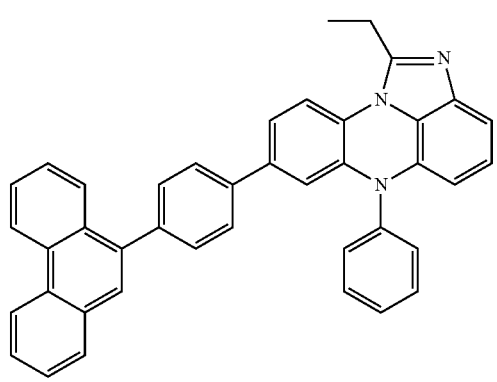
-continued
[Chemical Formula 3-33]
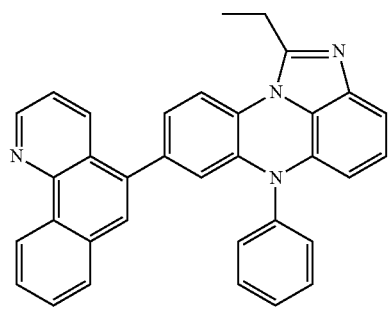
[Chemical Formula 3-34]
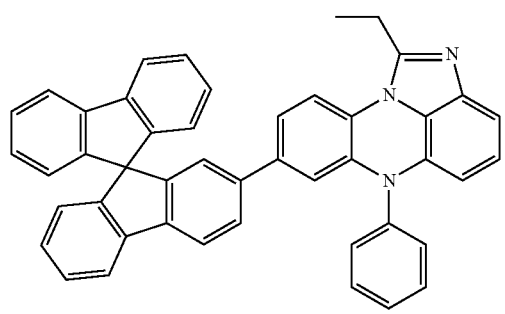
[Chemical Formula 3-35]
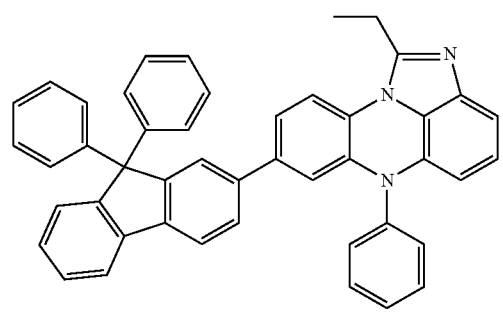
[Chemical Formula 3-36]
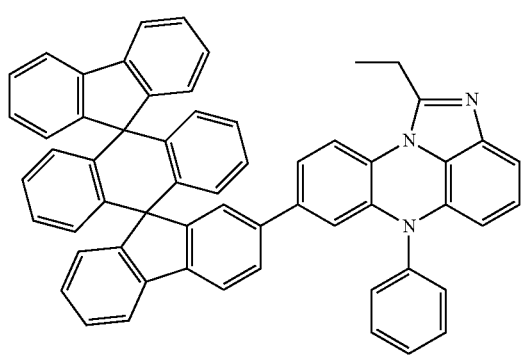

[Chemical Formula 3-37]
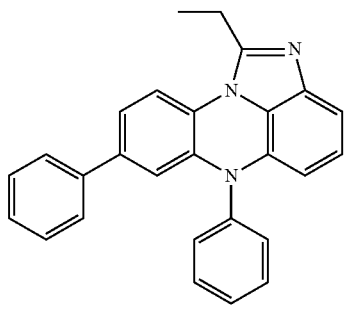
[Chemical Formula 3-38]
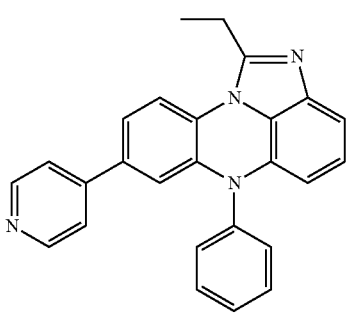
[Chemical Formula 3-39]
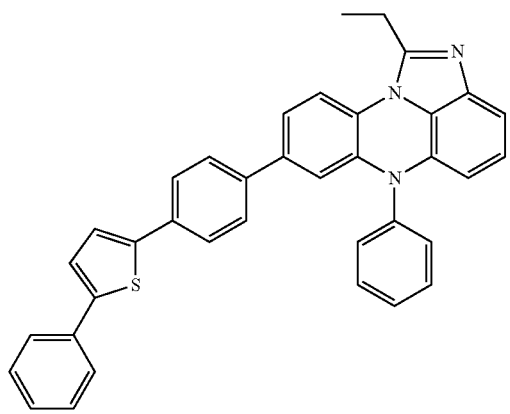
[Chemical Formula 3-40]
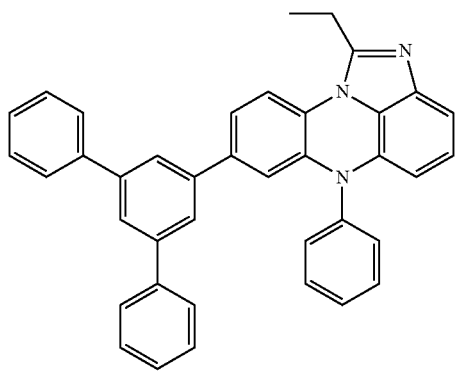
[Chemical Formula 3-41]
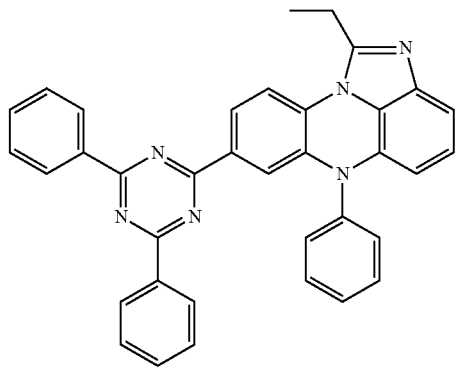
[Chemical Formula 3-42]
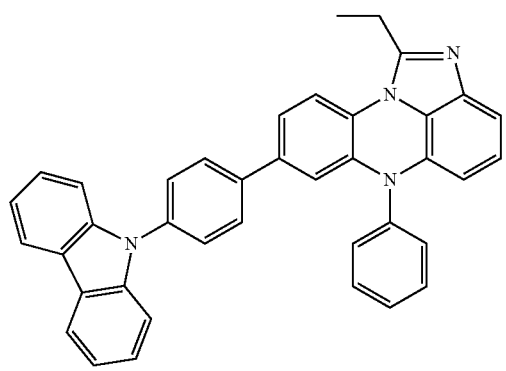
[Chemical Formula 3-43]
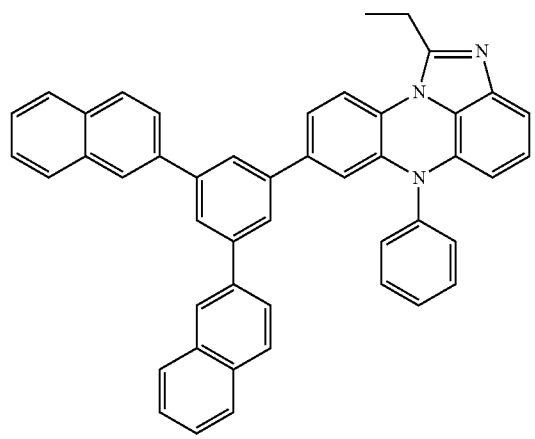
[Chemical Formula 3-44]
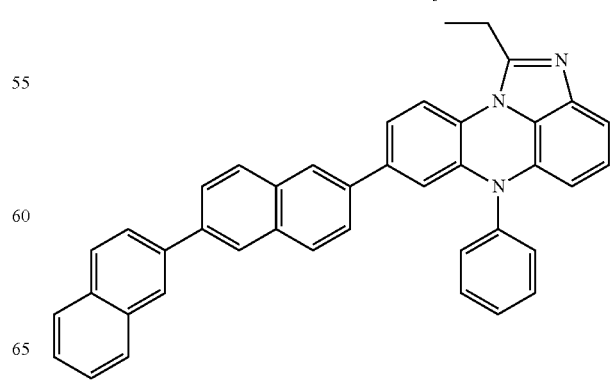

[Chemical Formula 3-45]
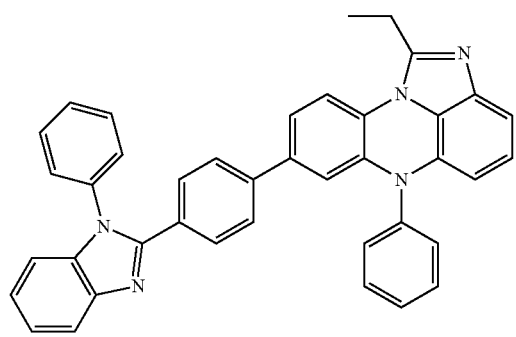
[Chemical Formula 3-46]
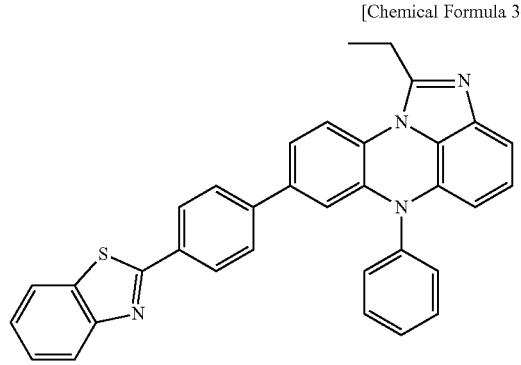
[Chemical Formula 3-47]
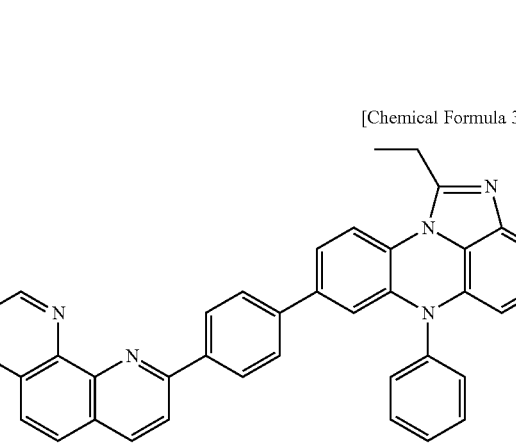
[Chemical Formula 3-48]
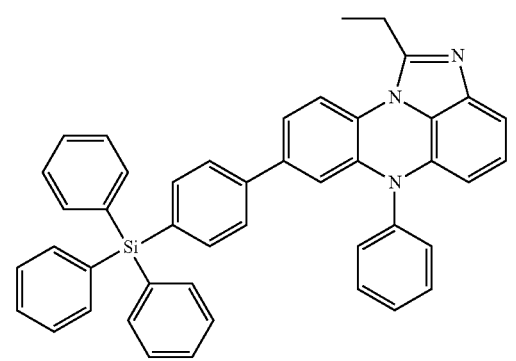
[Chemical Formula 3-49]
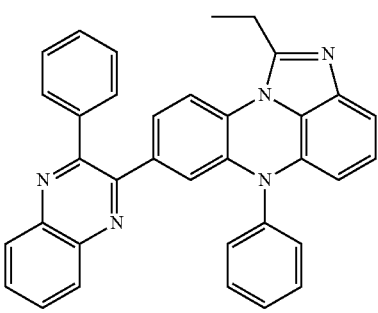
[Chemical Formula 3-50]
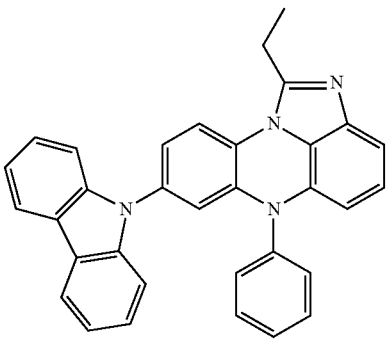
[Chemical Formula 3-51]
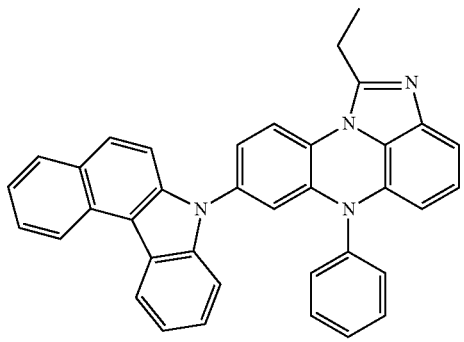
[Chemical Formula 3-52]
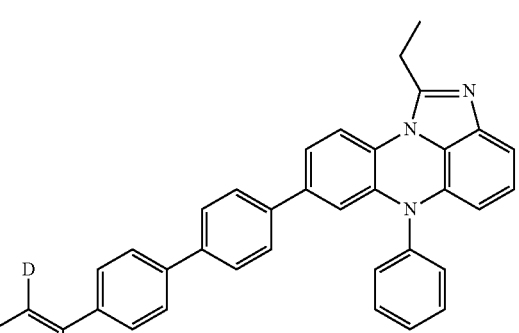

-continued
[Chemical Formula 3-53]
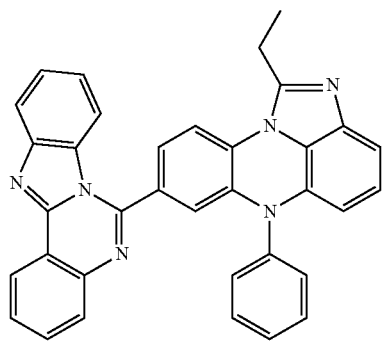
[Chemical Formula 3-54]
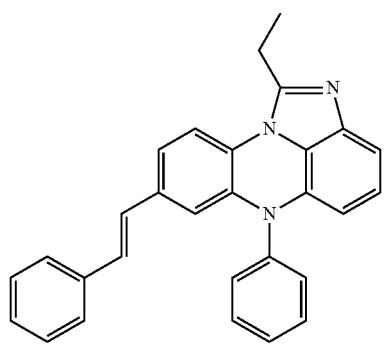
[Chemical Formula 4-1]
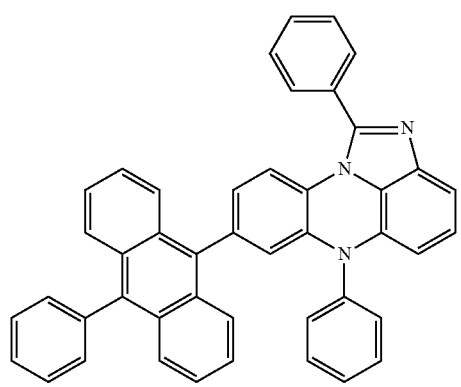
[Chemical Formula 4-2]
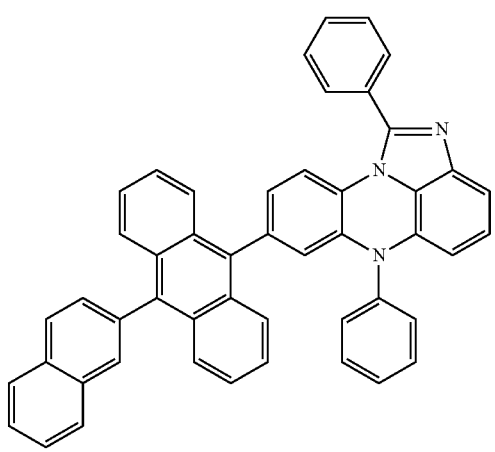
[Chemical Formula 4-3]
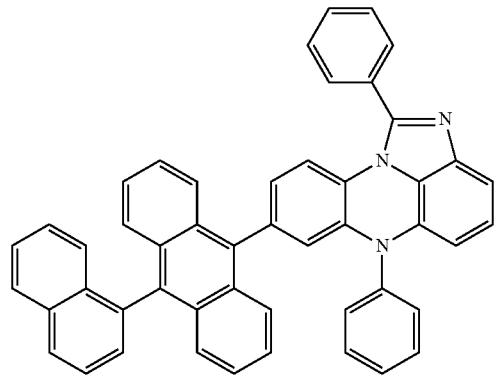
[Chemical Formula 4-4]
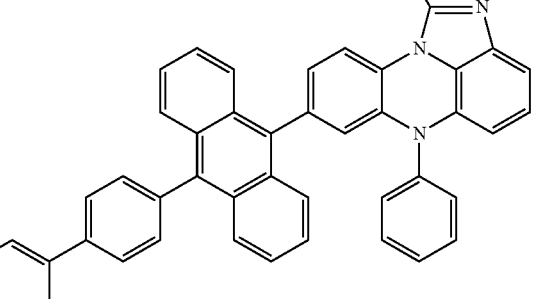
[Chemical Formula 4-5]
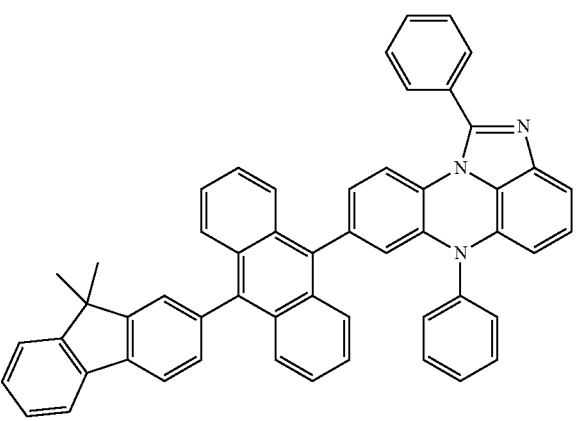

[Chemical Formula 4-6]
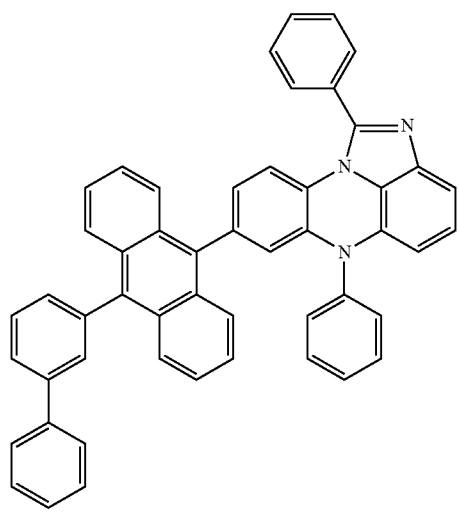
[Chemical Formula 4-7]
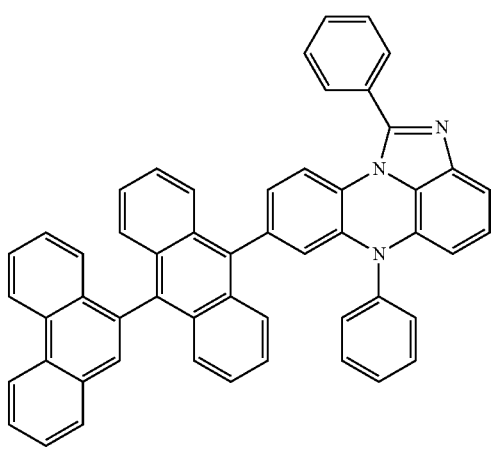
[Chemical Formula 4-8]
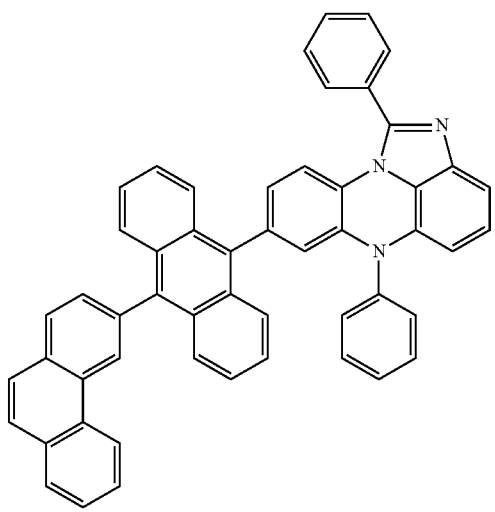
[Chemical Formula 4-9]
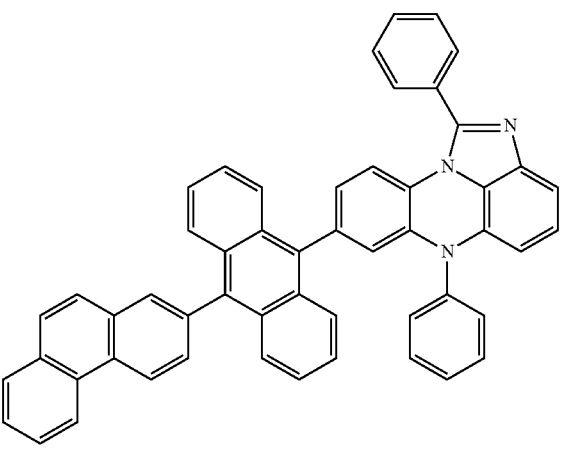
[Chemical Formula 4-10]
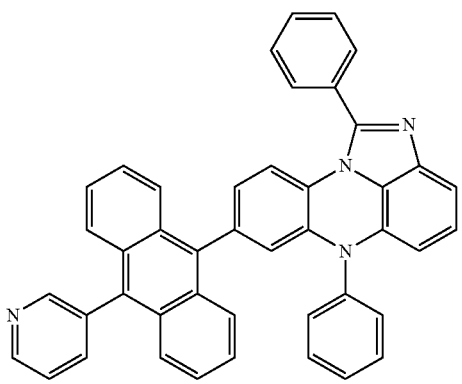
[Chemical Formula 4-11]
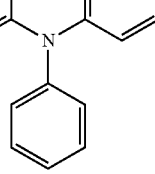

[Chemical Formula 4-12]
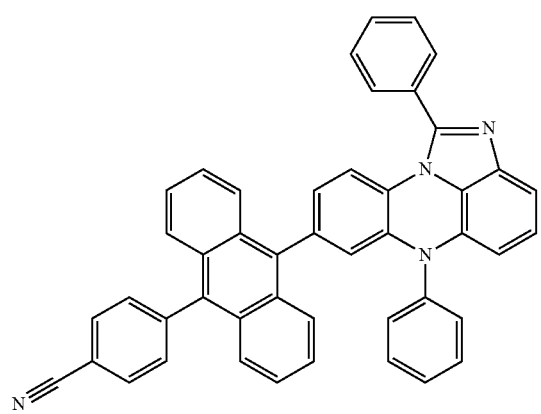
[Chemical Formula 4-15]
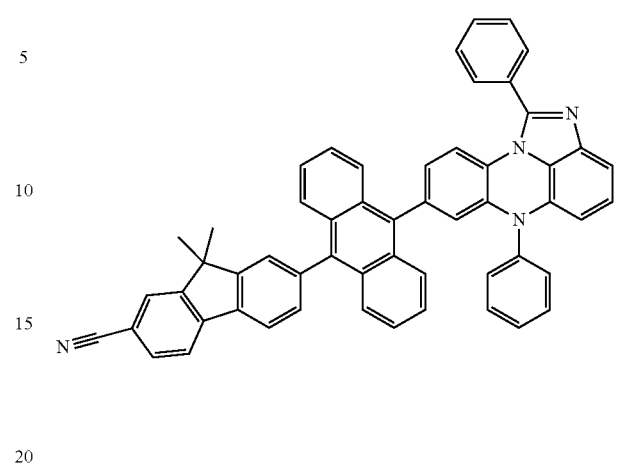
[Chemical Formula 4-13]
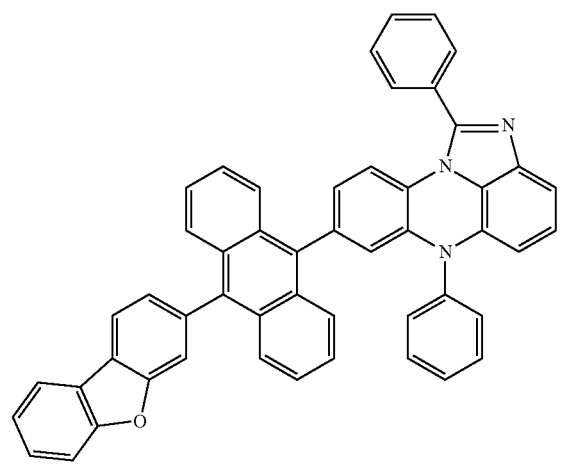
[Chemical Formula 4-16]
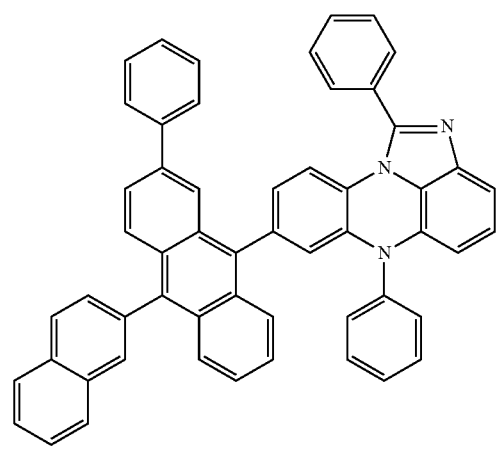
[Chemical Formula 4-14]
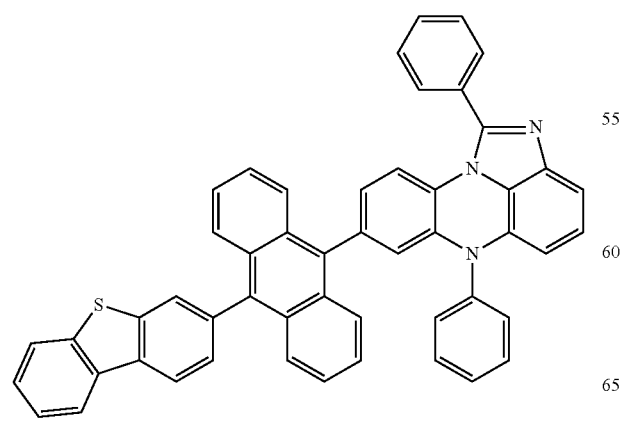
[Chemical Formula 4-17]
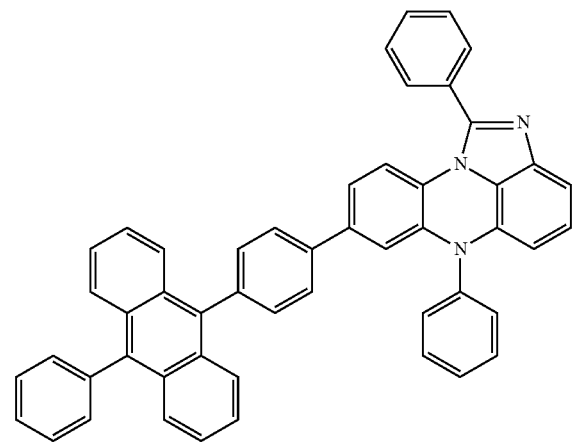

[Chemical Formula 4-18]
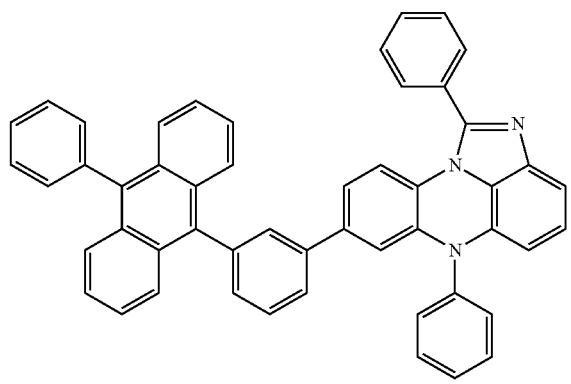
[Chemical Formula 4-19]
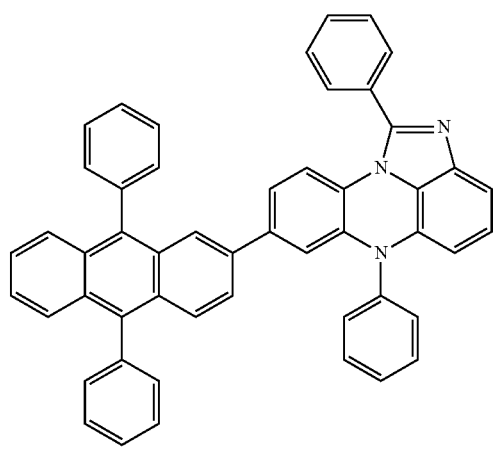
[Chemical Formula 4-20]
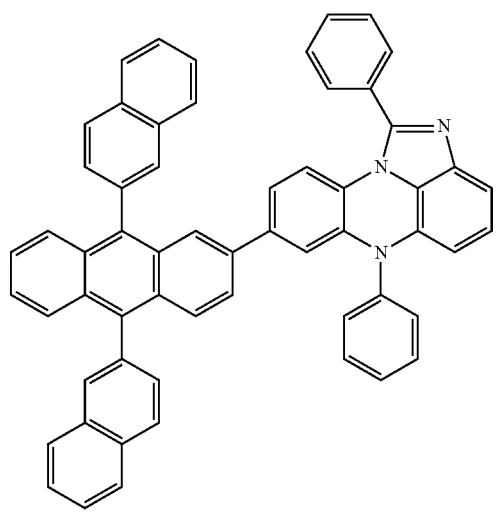
[Chemical Formula 4-21]
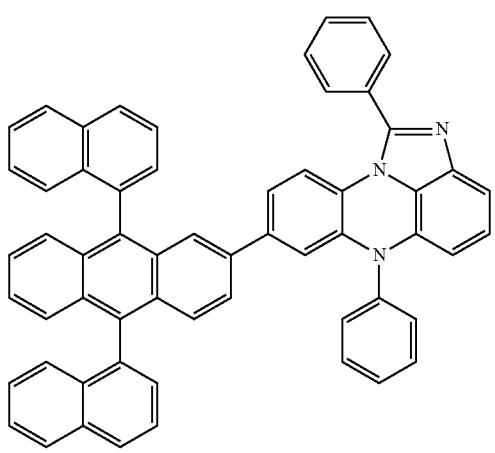
[Chemical Formula 4-22]
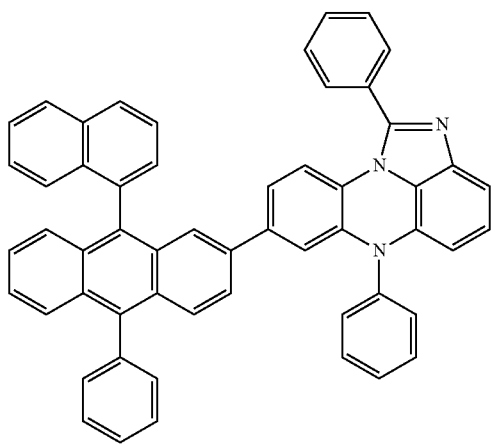
[Chemical Formula 4-23]
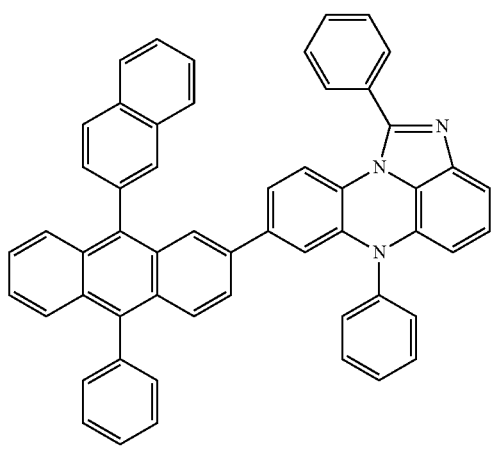

[Chemical Formula 4-24]
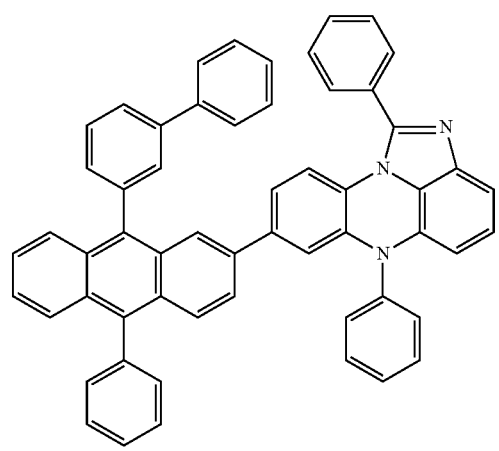
[Chemical Formula 4-27]
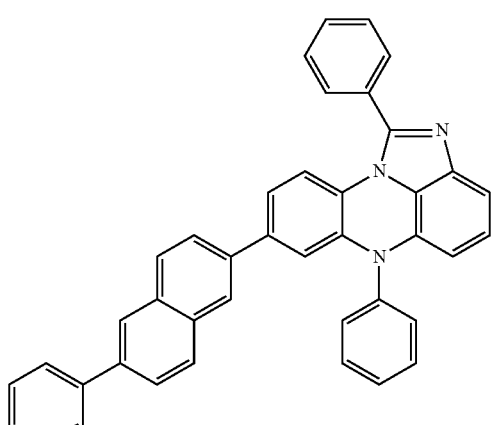
[Chemical Formula 4-25]
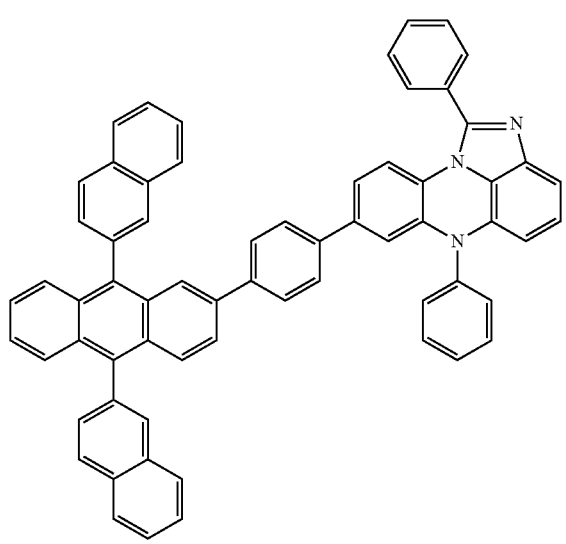
[Chemical Formula 4-28]
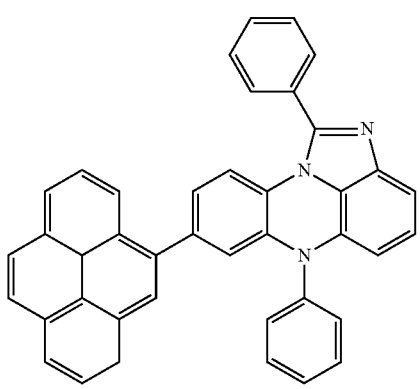
[Chemical Formula 4-26]
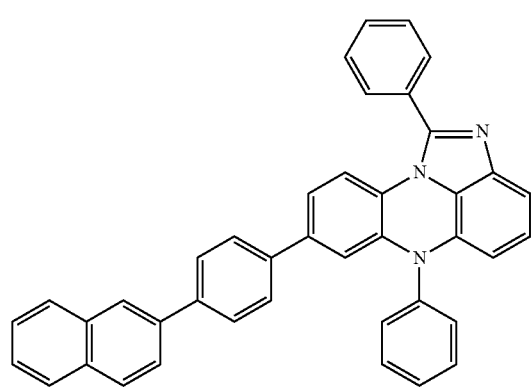
[Chemical Formula 4-29]
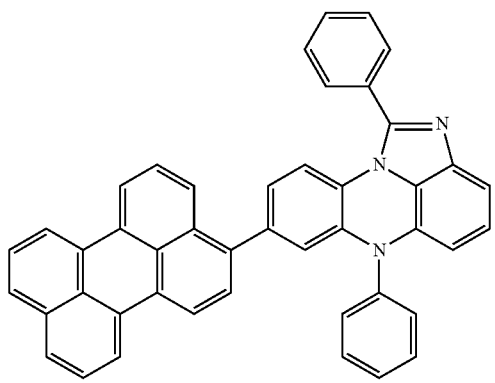

[Chemical Formula 4-30]
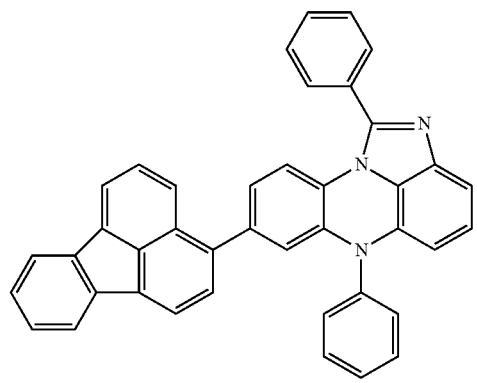
[Chemical Formula 4-31]
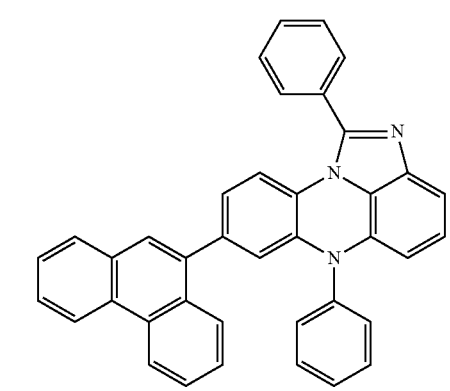
[Chemical Formula 4-32]
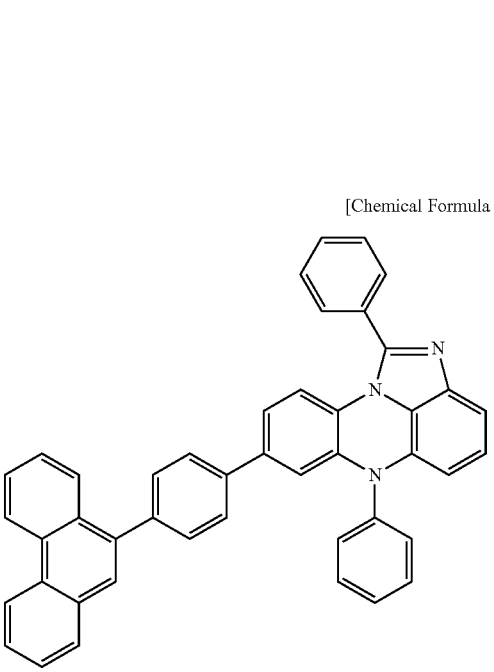
[Chemical Formula 4-33]
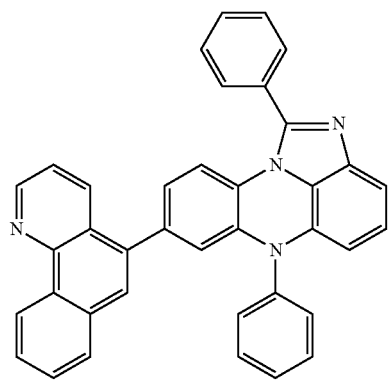
[Chemical Formula 4-34]
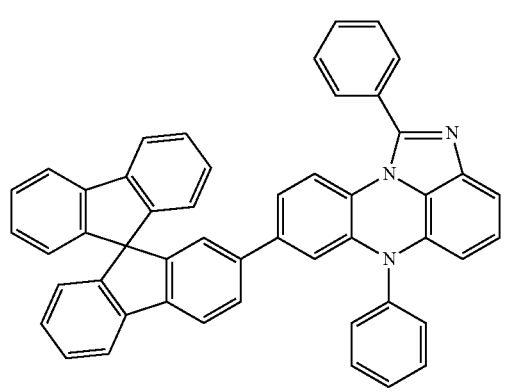
[Chemical Formula 4-35]
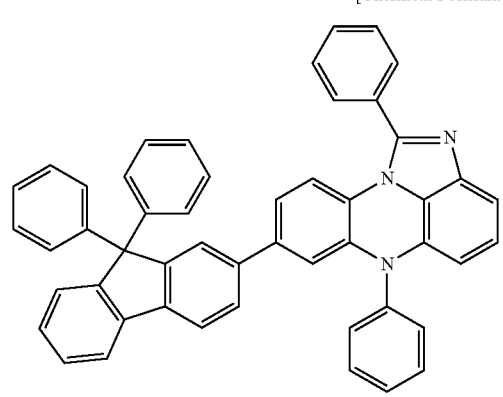
[Chemical Formula 4-36]
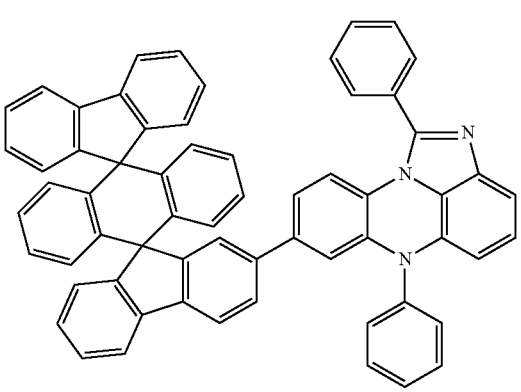

[Chemical Formula 4-37]
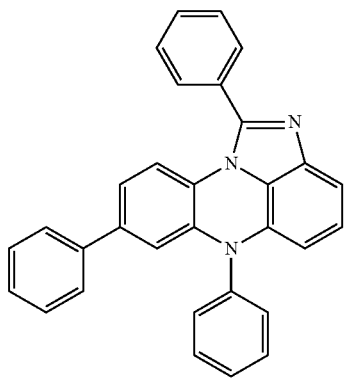
[Chemical Formula 4-38]
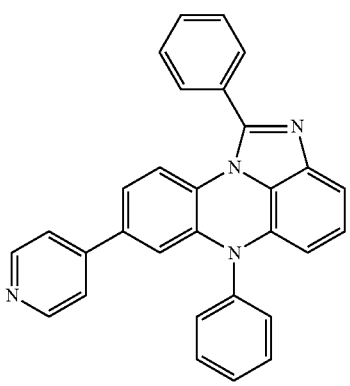
[Chemical Formula 4-39]
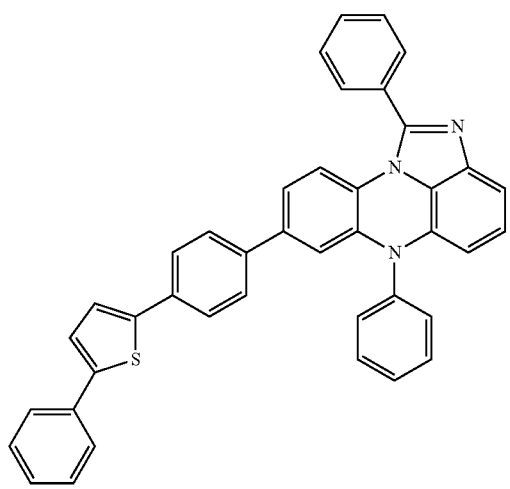
[Chemical Formula 4-40]
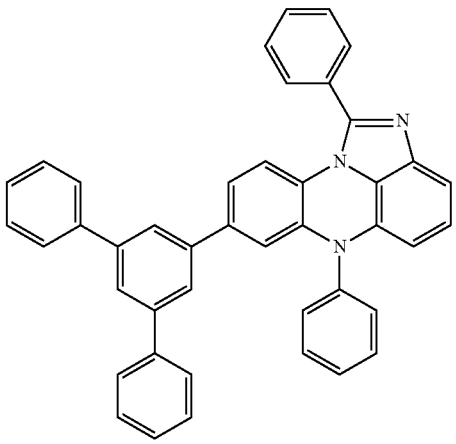
[Chemical Formula 4-41]
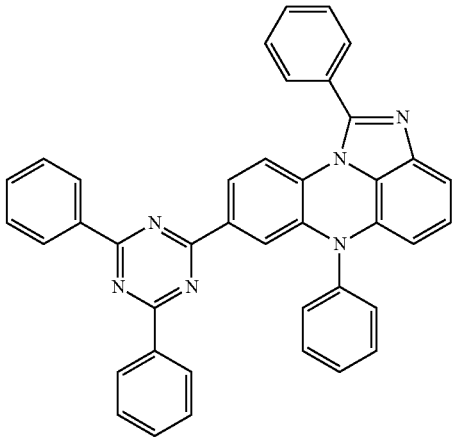
[Chemical Formula 4-42]
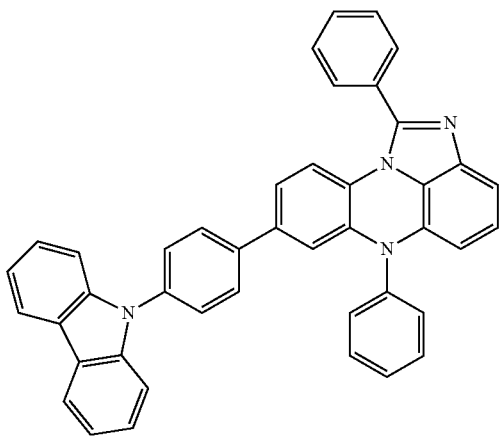

[Chemical Formula 4-43]
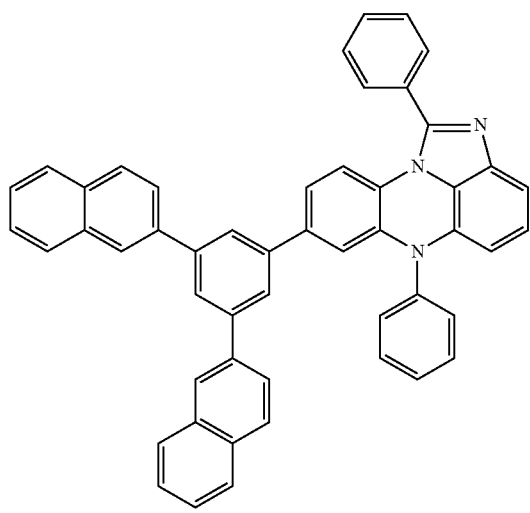
[Chemical Formula 4-44]
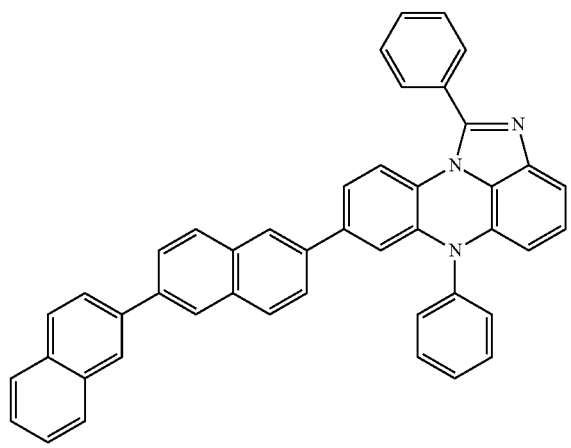
[Chemical Formula 4-45]
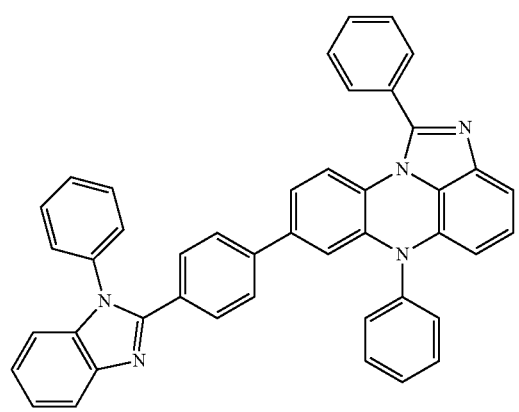
[Chemical Formula 4-46]
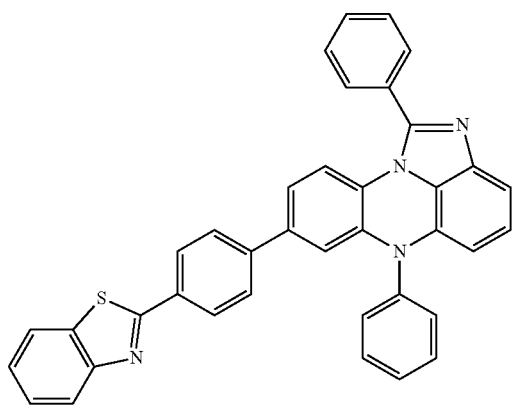
[Chemical Formula 4-47]
[Chemical Formula 4-48]
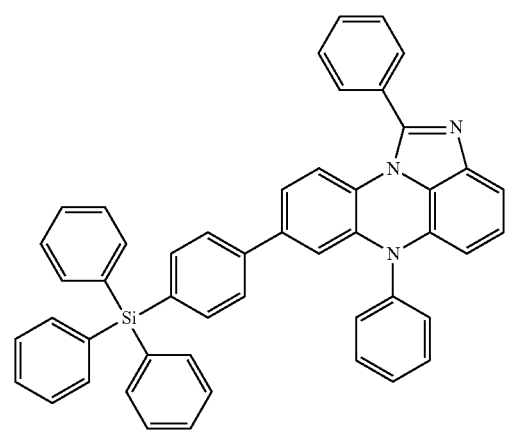

[Chemical Formula 4-49]
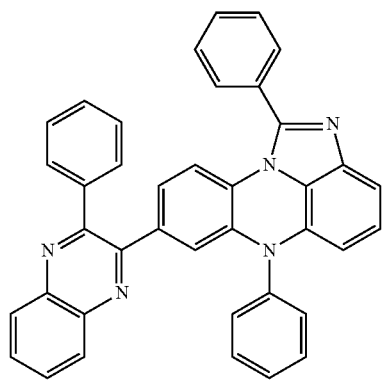
[Chemical Formula 4-50]
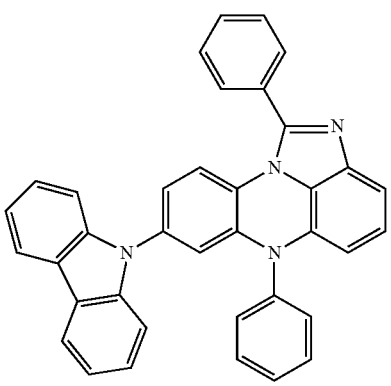
[Chemical Formula 4-51]
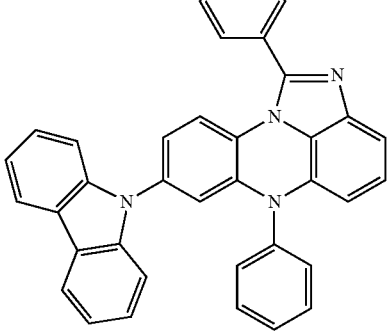
[Chemical Formula 4-52]
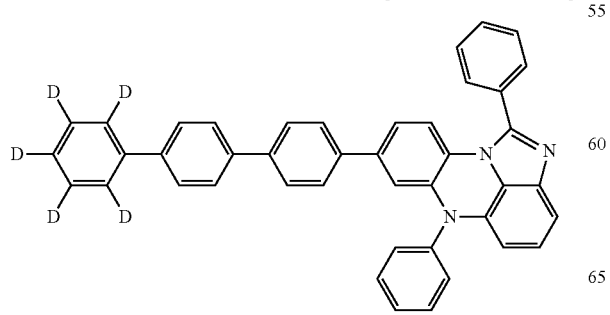
[Chemical Formula 4-53]
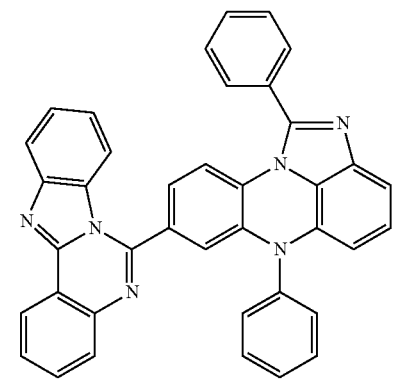
[Chemical Formula 4-54]
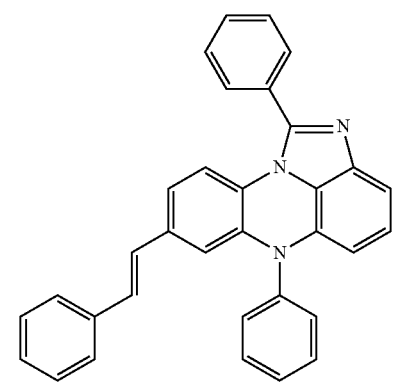
[Chemical Formula 5-1]
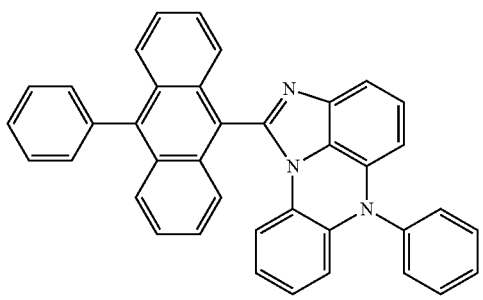
[Chemical Formula 5-2]
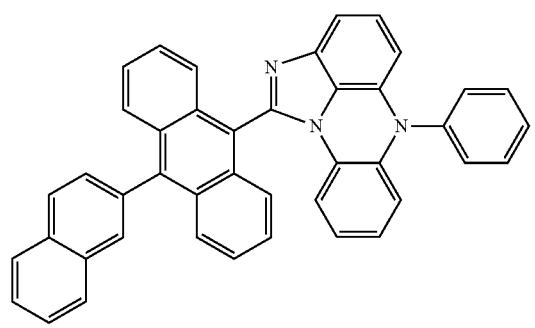

[Chemical Formula 5-3]
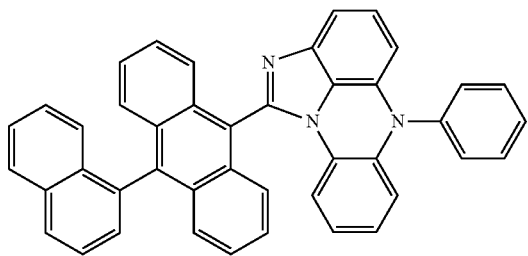
[Chemical Formula 5-4]
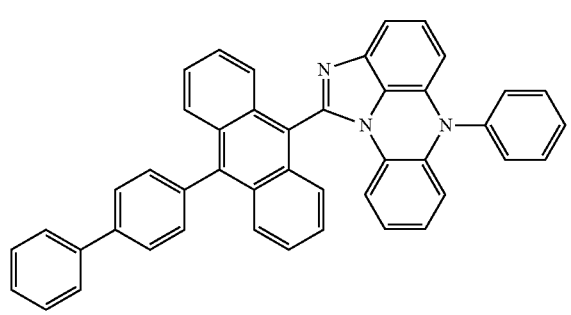
[Chemical Formula 5-5]
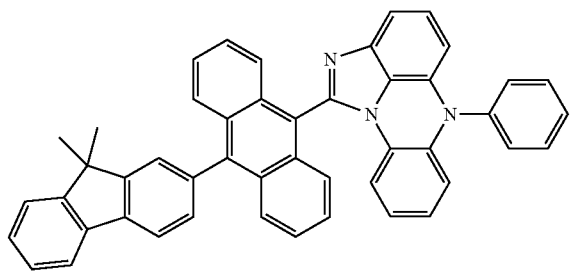
[Chemical Formula 5-6]
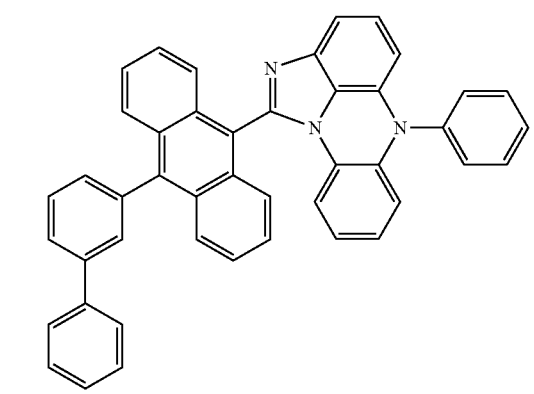
[Chemical Formula 5-7]
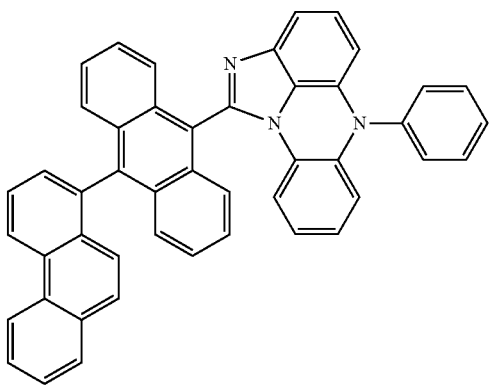
[Chemical Formula 5-8]
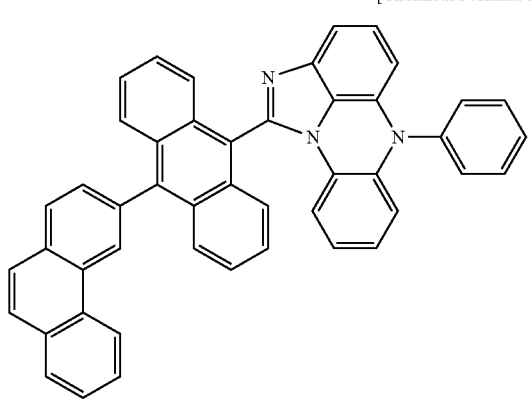
[Chemical Formula 5-9]
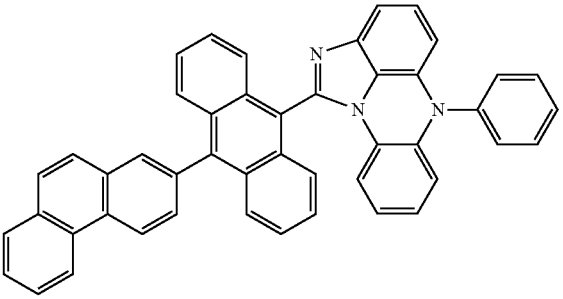
[Chemical Formula 5-10]
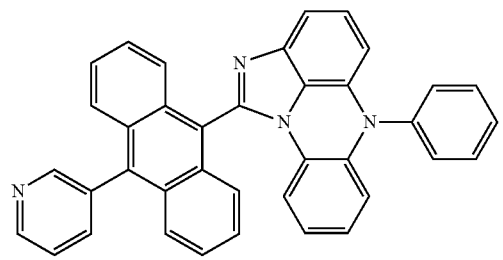

[Chemical Formula 5-11]
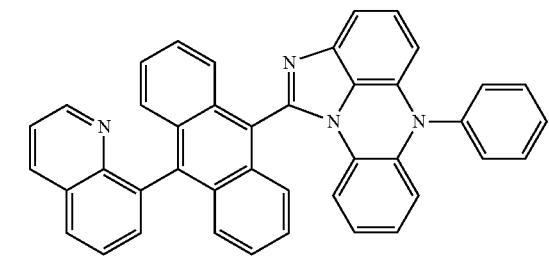
[Chemical Formula 5-12]
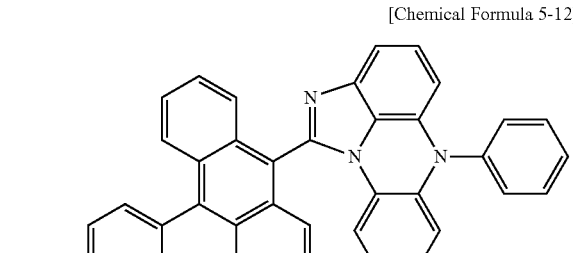
[Chemical Formula 5-13]
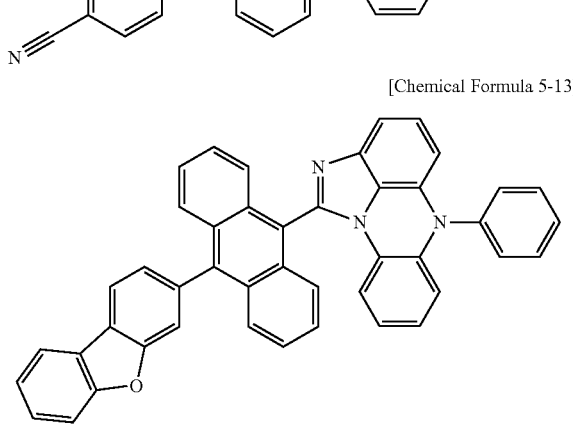
[Chemical Formula 5-14]
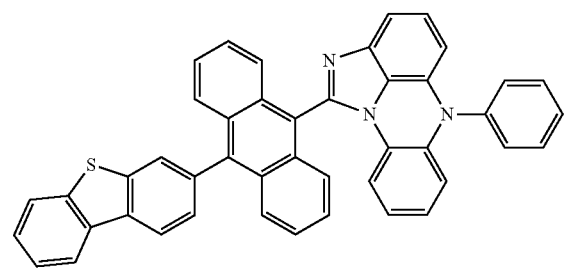
[Chemical Formula 5-15]
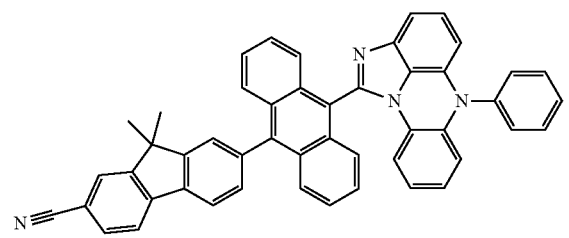
[Chemical Formula 5-16]
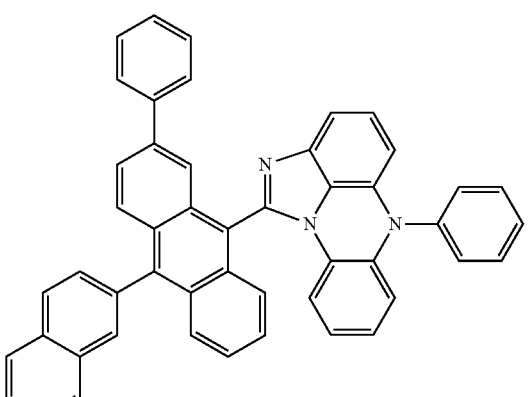
[Chemical Formula 5-17]
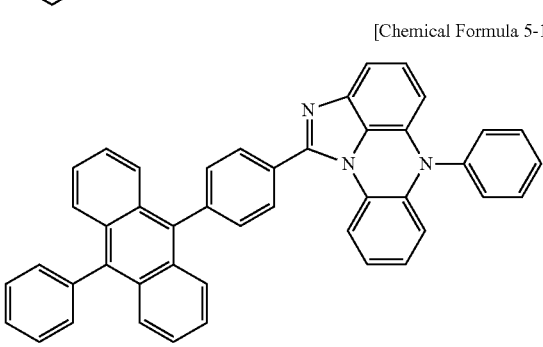
[Chemical Formula 5-18]
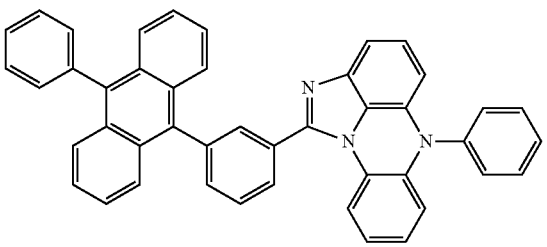
[Chemical Formula 5-19]
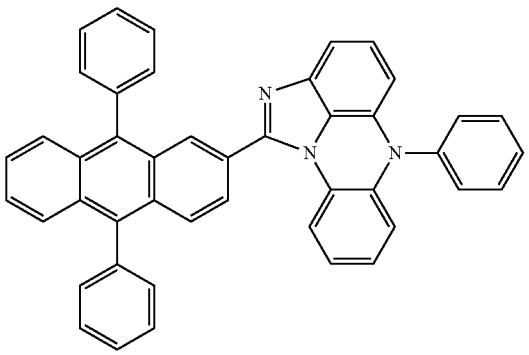

[Chemical Formula 5-20]
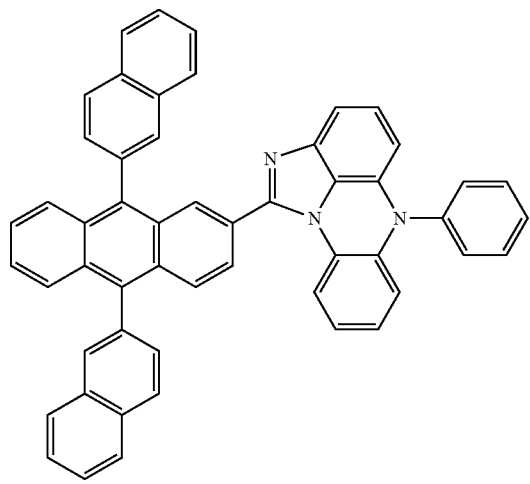
[Chemical Formula 5-21]
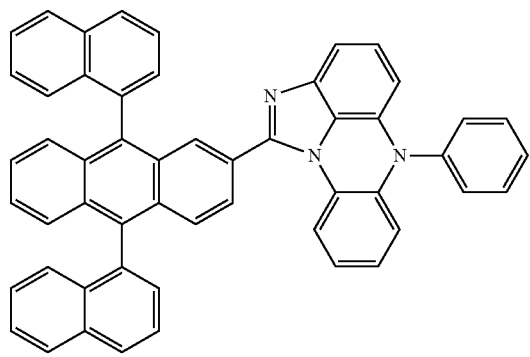
[Chemical Formula 5-22]
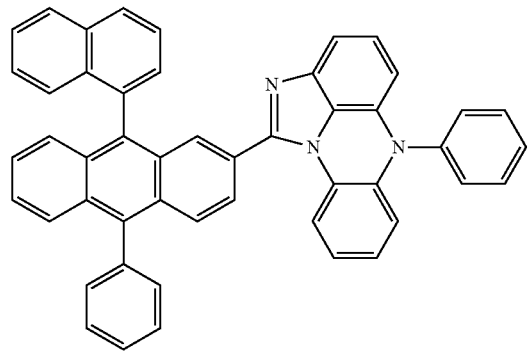
[Chemical Formula 5-23]
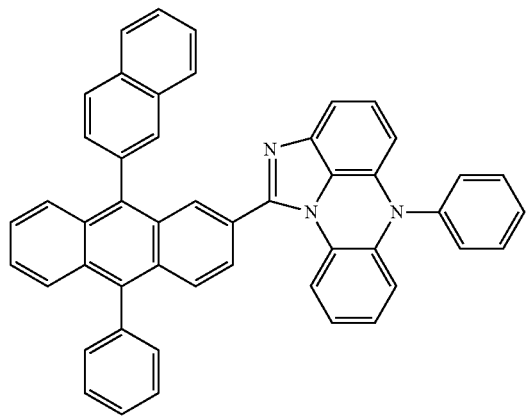
[Chemical Formula 5-24]
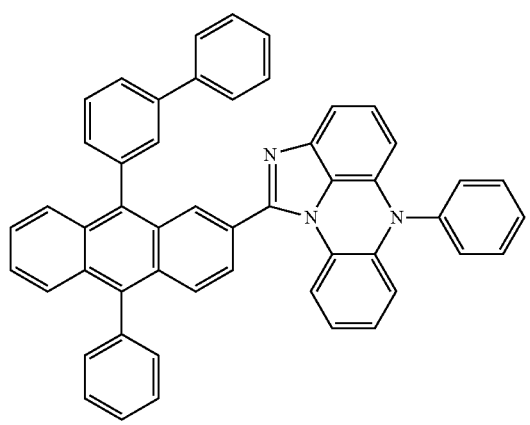
[Chemical Formula 5-25]
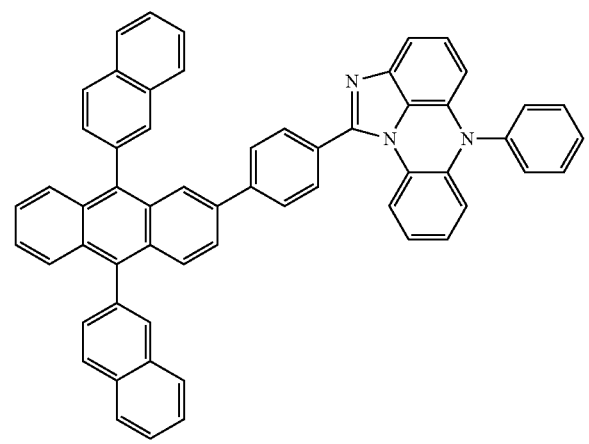
[Chemical Formula 5-26]
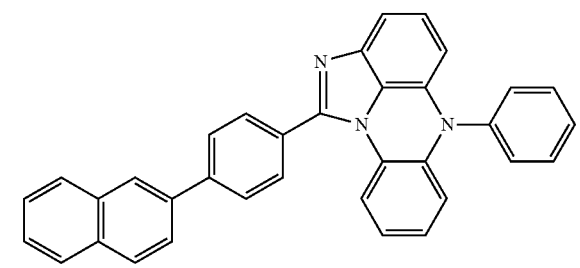

[Chemical Formula 5-27]
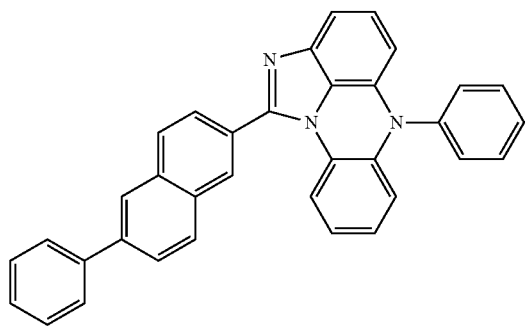
[Chemical Formula 5-28]
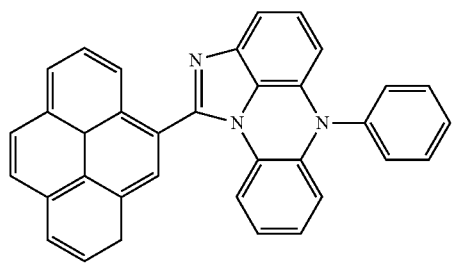
[Chemical Formula 5-29]
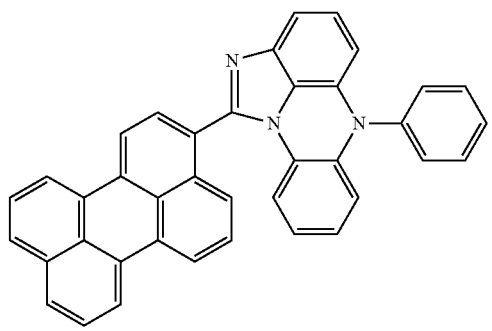
[Chemical Formula 5-30]
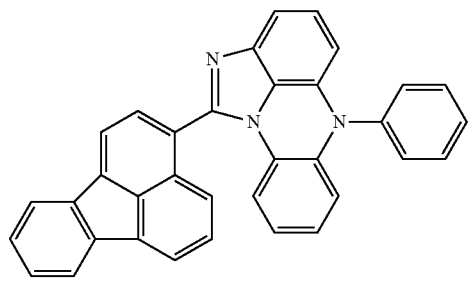
[Chemical Formula 5-31]
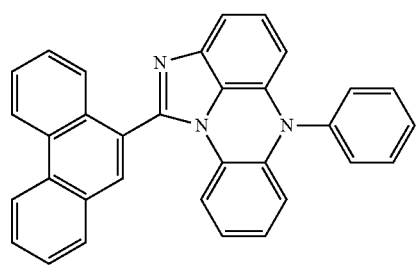
[Chemical Formula 5-32]
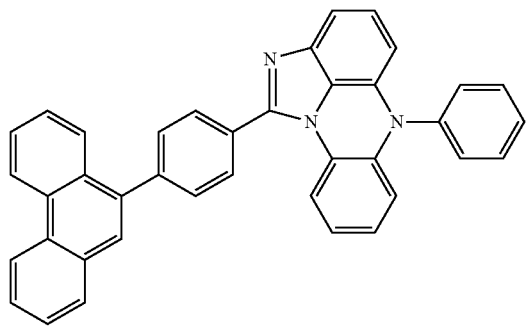
[Chemical Formula 5-33]
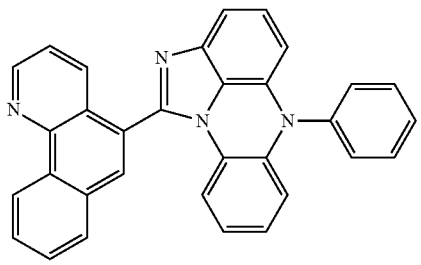
[Chemical Formula 5-34]
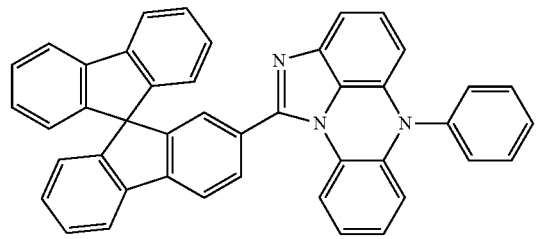
[Chemical Formula 5-35]
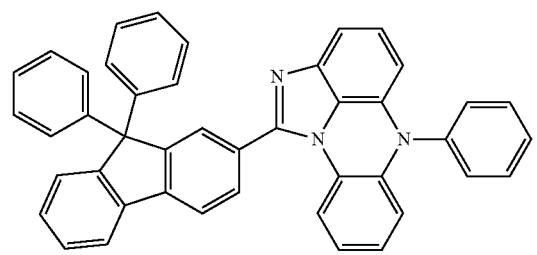
[Chemical Formula 5-36]
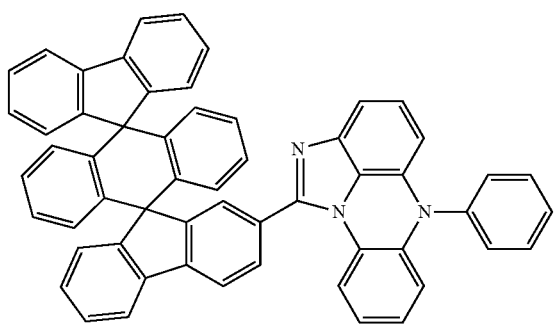

[Chemical Formula 5-37]
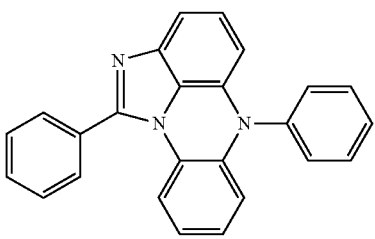
[Chemical Formula 5-38]
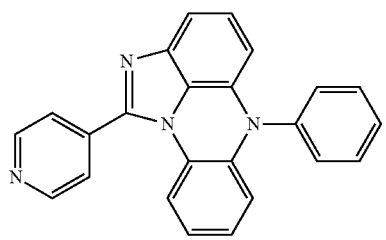
[Chemical Formula 5-39]
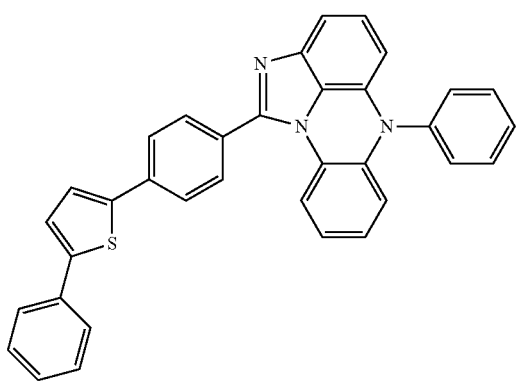
[Chemical Formula 5-40]
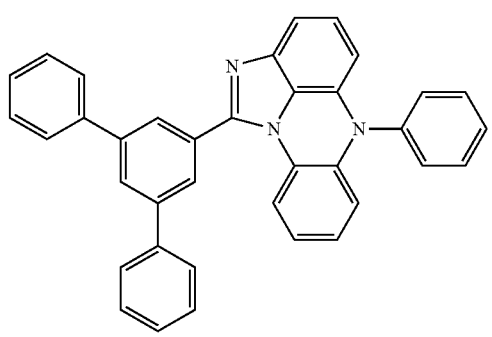
[Chemical Formula 5-41]
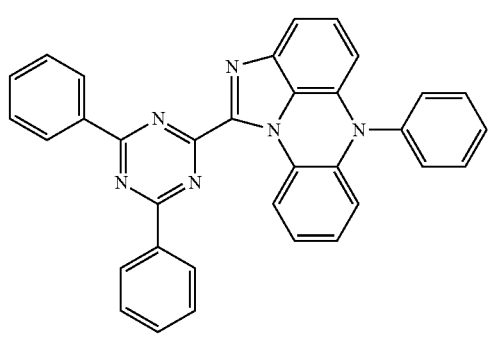
[Chemical Formula 5-42]
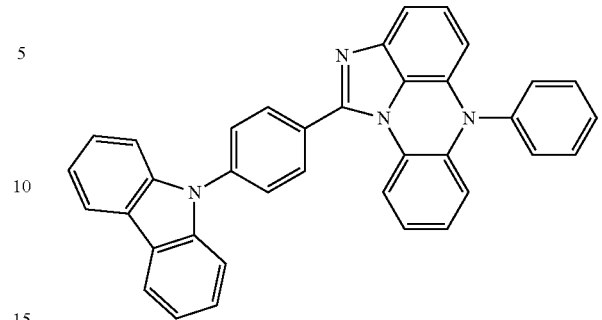
[Chemical Formula 5-43]
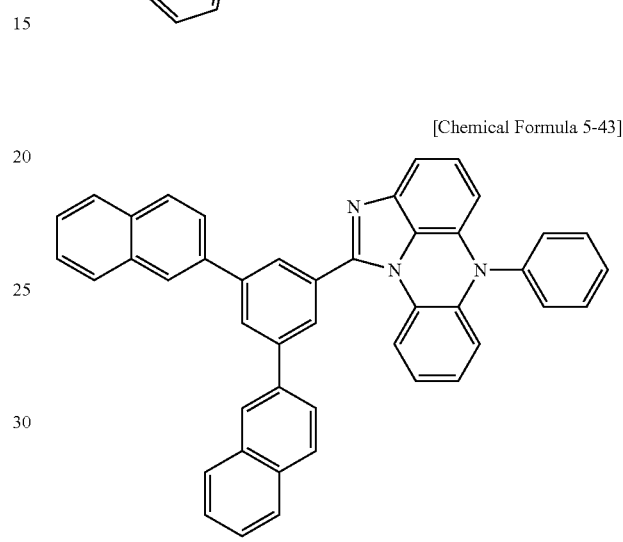
[Chemical Formula 5-44]
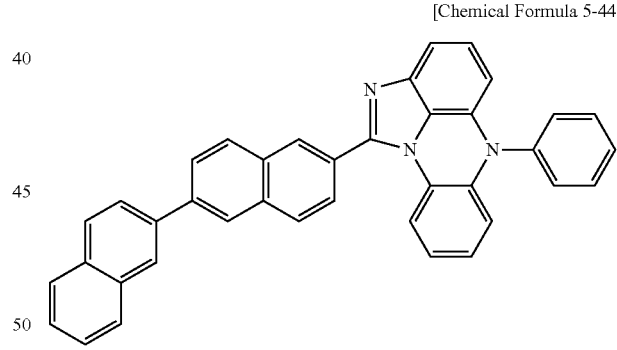
[Chemical Formula 5-45]
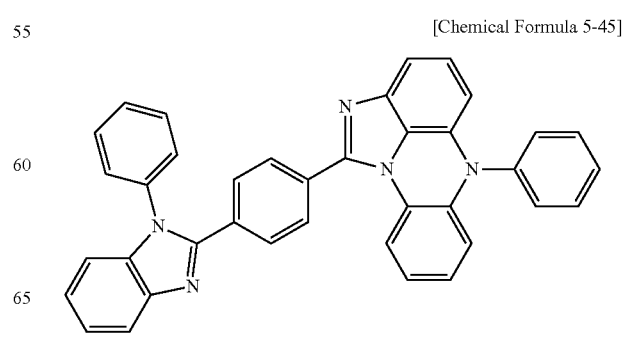

[Chemical Formula 5-46]
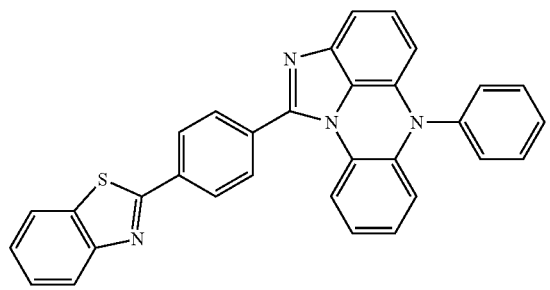
[Chemical Formula 5-47]
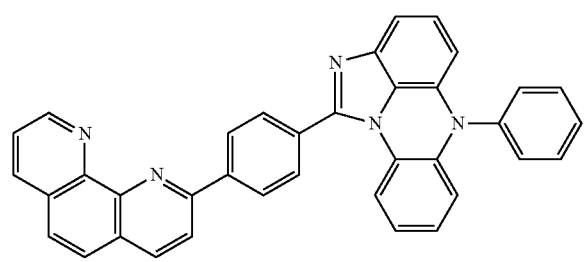
[Chemical Formula 5-48]
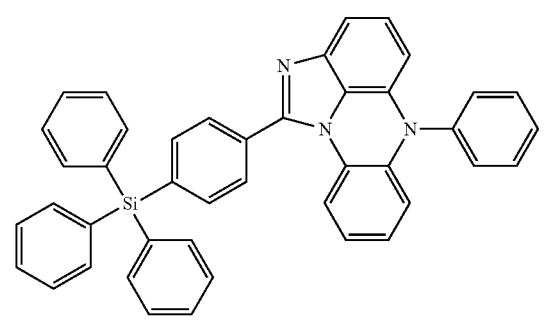
[Chemical Formula 5-49]
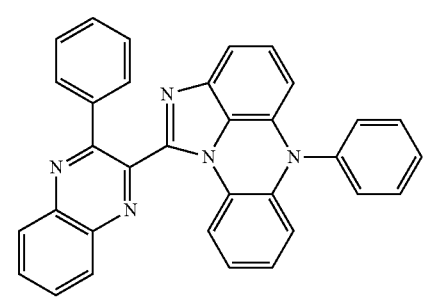
[Chemical Formula 5-50]
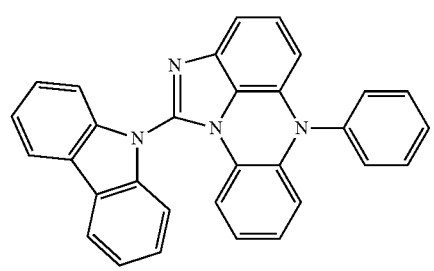
[Chemical Formula 5-51]
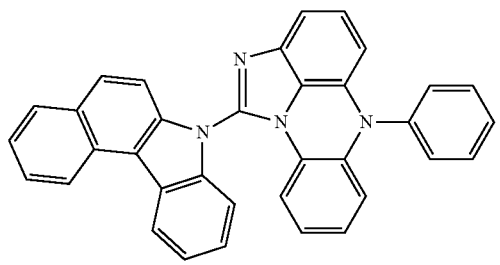
[Chemical Formula 5-52]
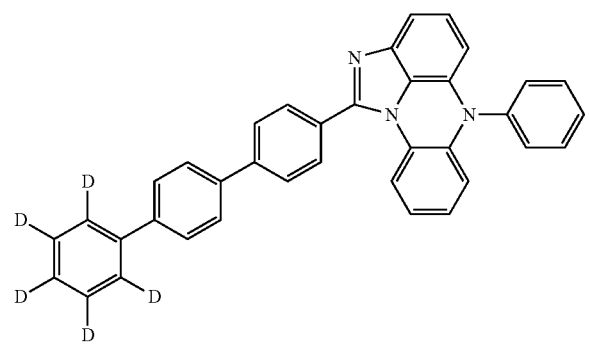
[Chemical Formula 5-53]
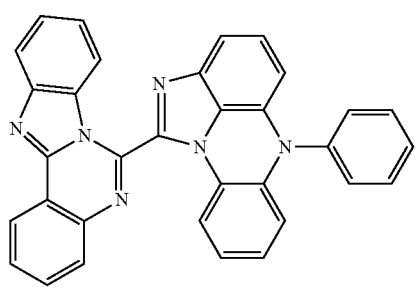
[Chemical Formula 5-54]
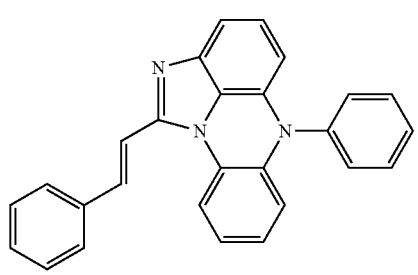
[Chemical Formula 6-1]
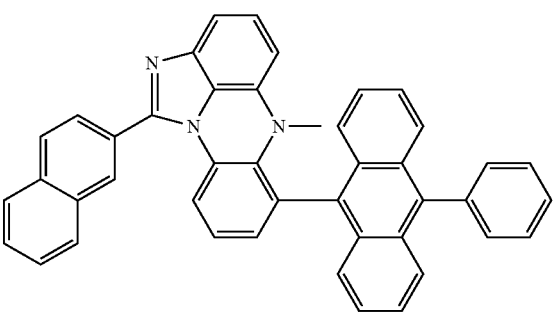

[Chemical Formula 6-2]
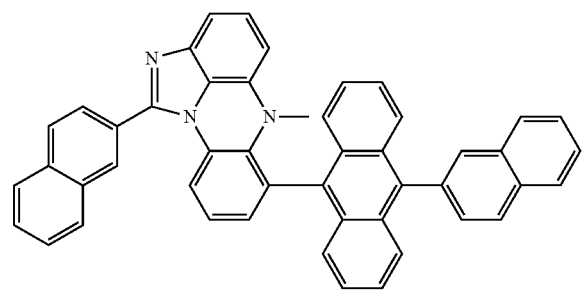
[Chemical Formula 6-3]
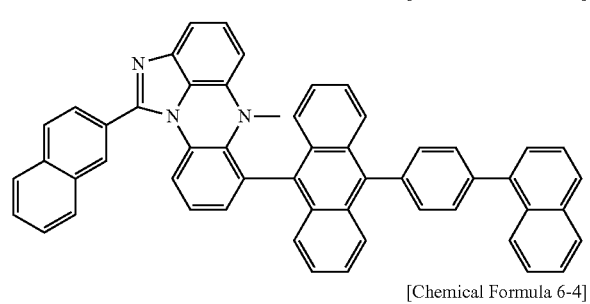
[Chemical Formula 6-4]
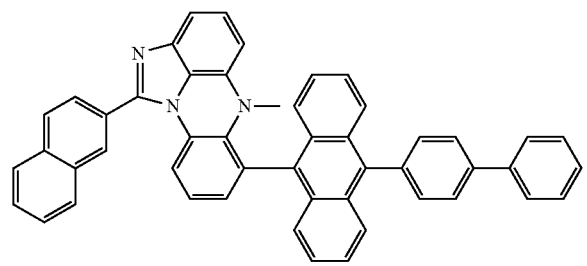
[Chemical Formula 6-5]
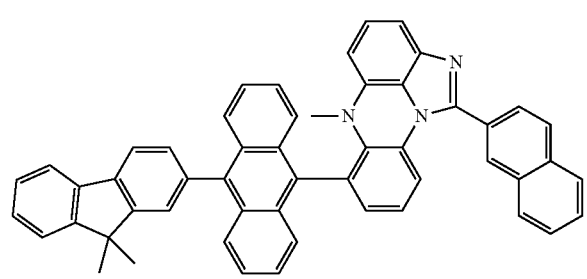
[Chemical Formula 6-6]
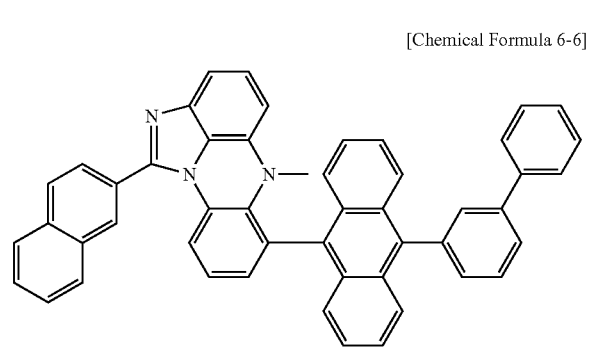
[Chemical Formula 6-7]
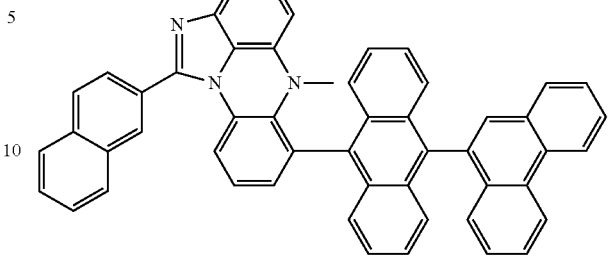
[Chemical Formula 6-8]
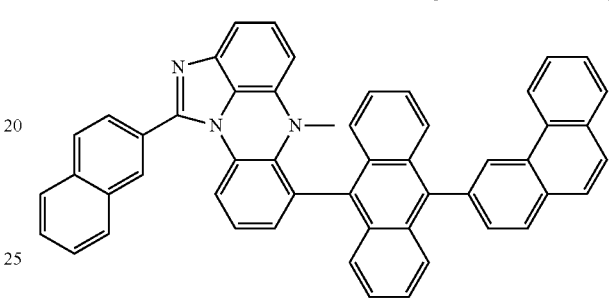
[Chemical Formula 6-9]
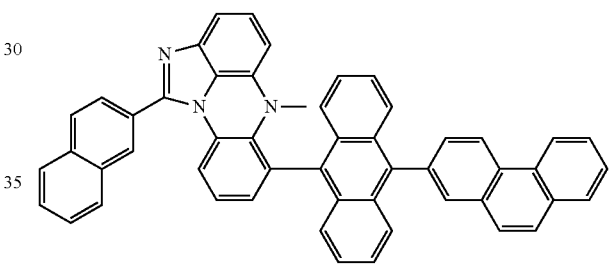
[Chemical Formula 6-10]
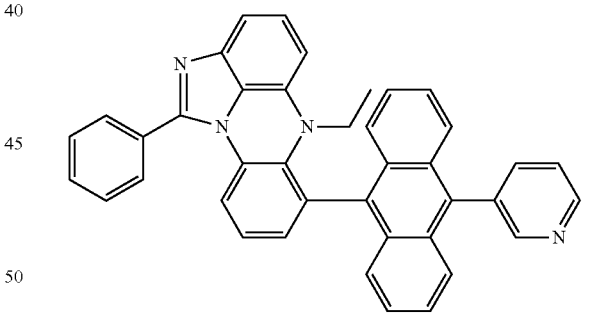
[Chemical Formula 6-11]
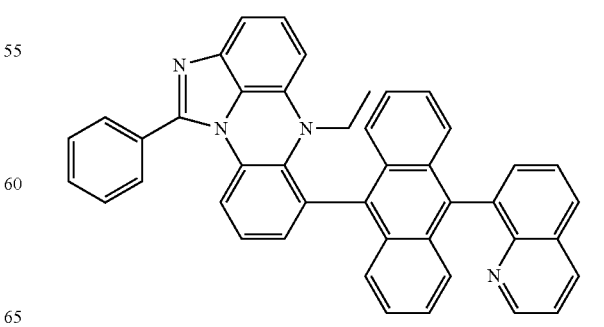

[Chemical Formula 6-12]
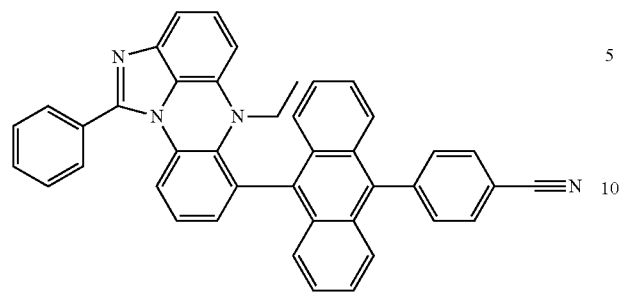
[Chemical Formula 6-13]
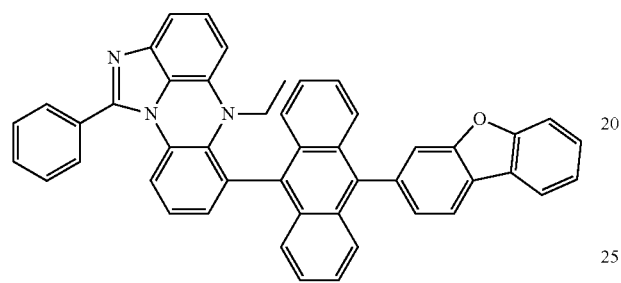
[Chemical Formula 6-14]
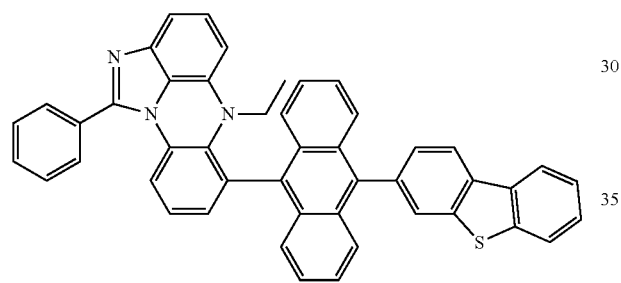
[Chemical Formula 6-15]
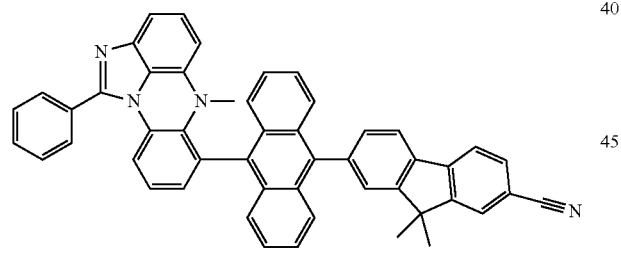
[Chemical Formula 6-16]
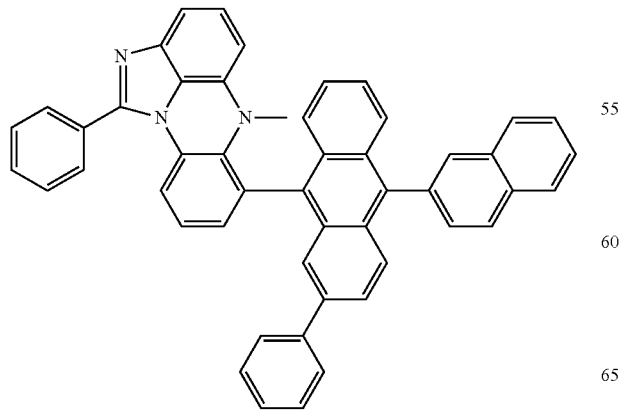
[Chemical Formula 6-17]
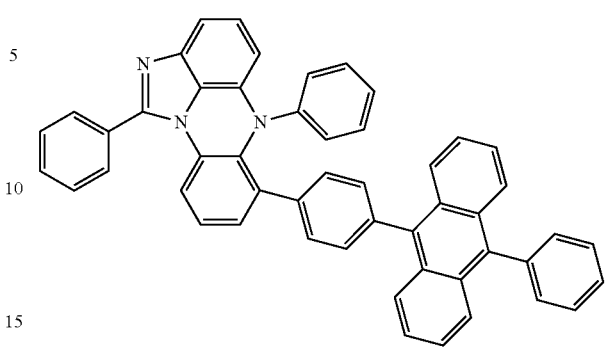
[Chemical Formula 6-18]
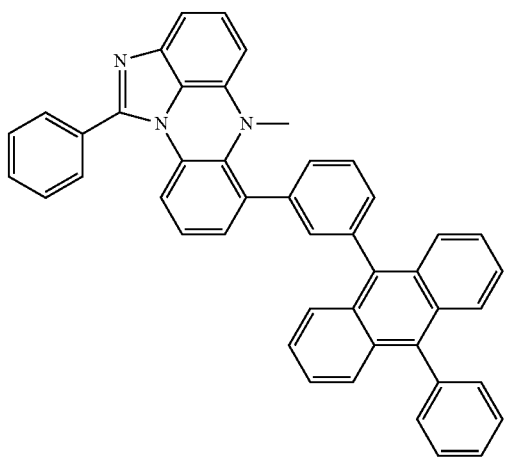
[Chemical Formula 6-19]
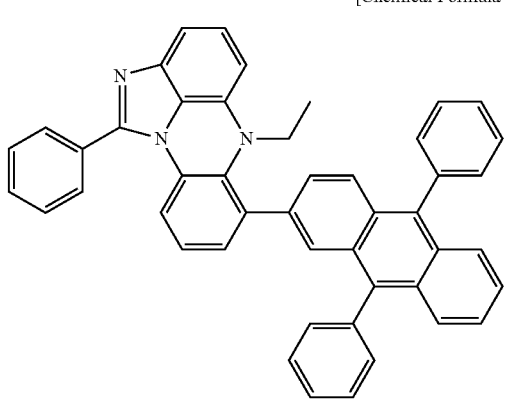

[Chemical Formula 6-20]
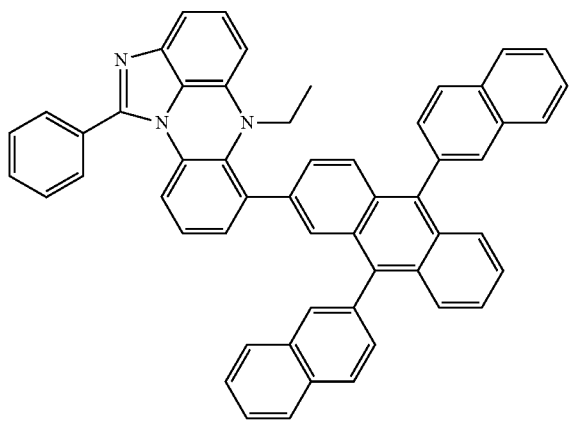
[Chemical Formula 6-21]
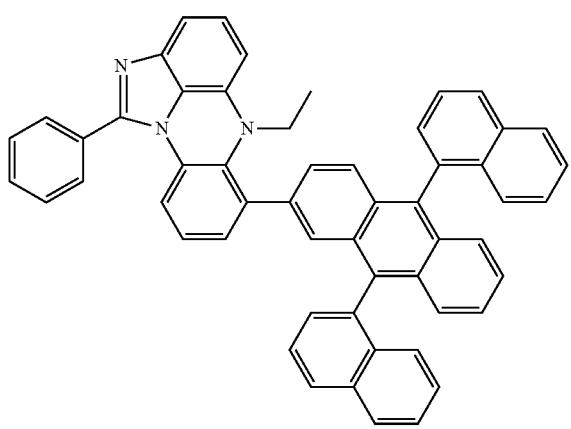
[Chemical Formula 6-22]
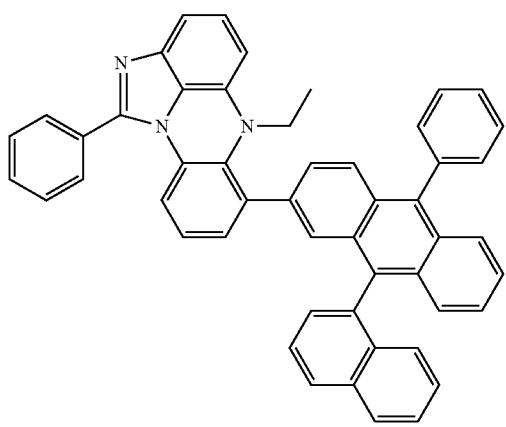
[Chemical Formula 6-23]
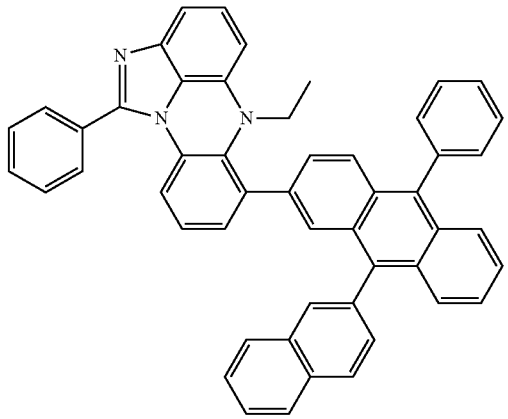
[Chemical Formula 6-24]
[Chemical Formula 6-25]
[Chemical Formula 6-26]
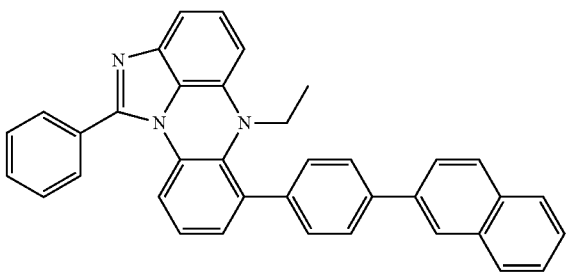

-continued
[Chemical Formula 6-27]
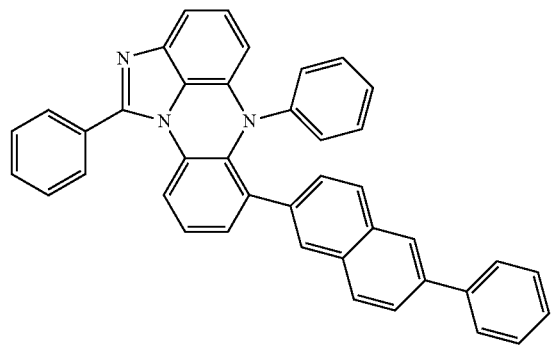
[Chemical Formula 6-28]
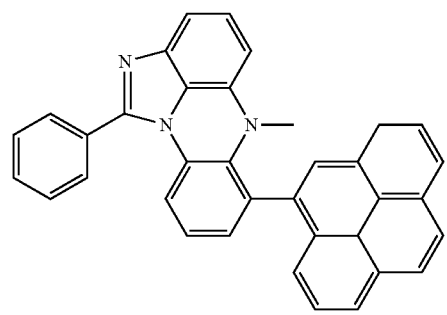
[Chemical Formula 6-29]
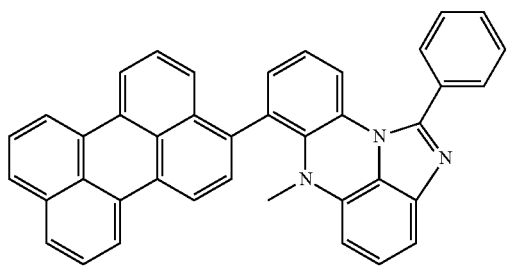
[Chemical Formula 6-30]
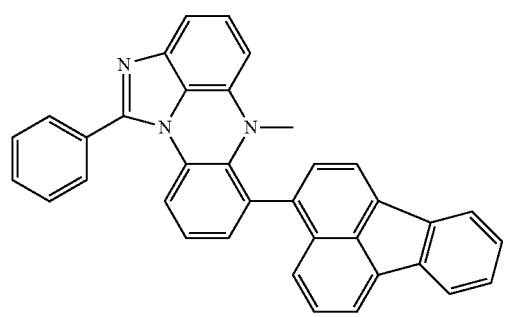
[Chemical Formula 6-31]
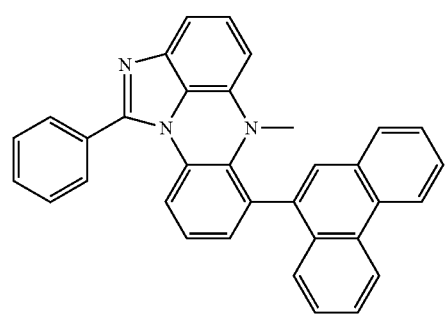
-continued
[Chemical Formula 6-32]
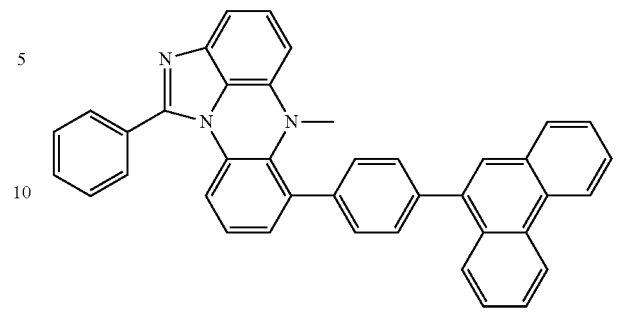
[Chemical Formula 6-33]
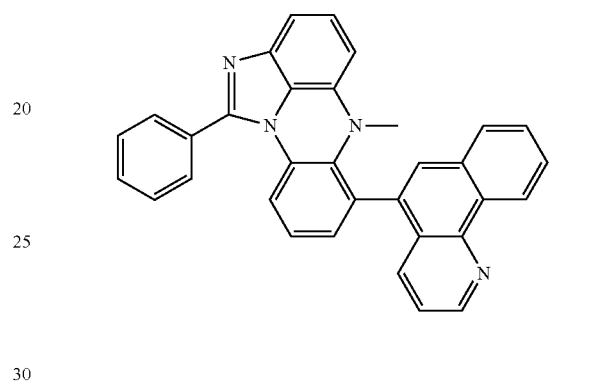
[Chemical Formula 6-34]
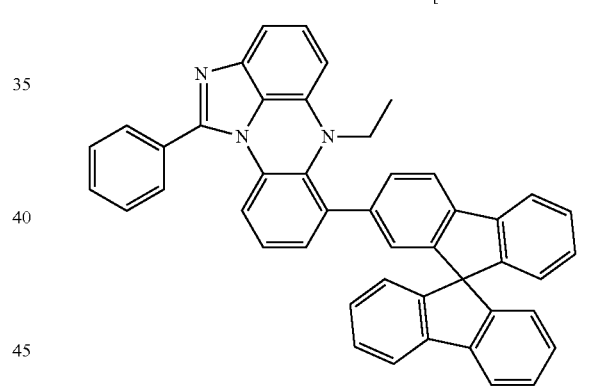
[Chemical Formula 6-35]
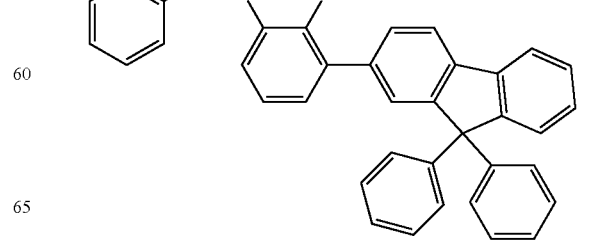

[Chemical Formula 6-36]
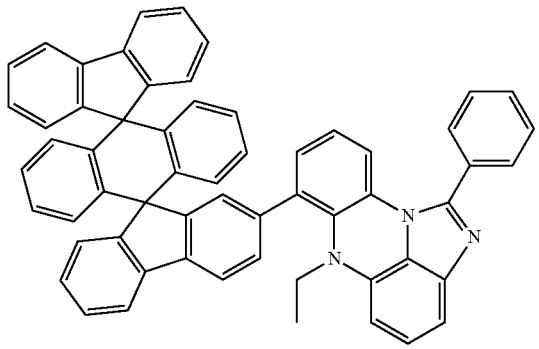
[Chemical Formula 6-37]
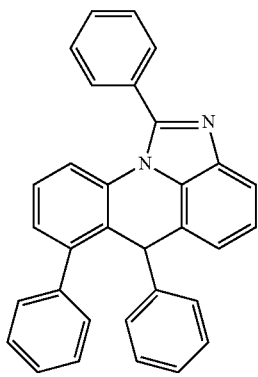
[Chemical Formula 6-38]
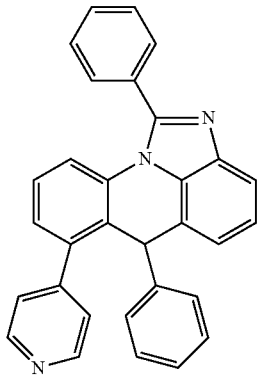
[Chemical Formula 6-39]
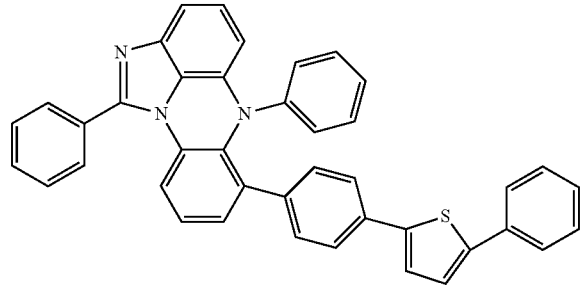
[Chemical Formula 6-40]
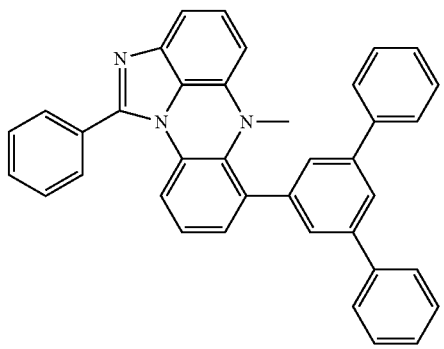
[Chemical Formula 6-41]
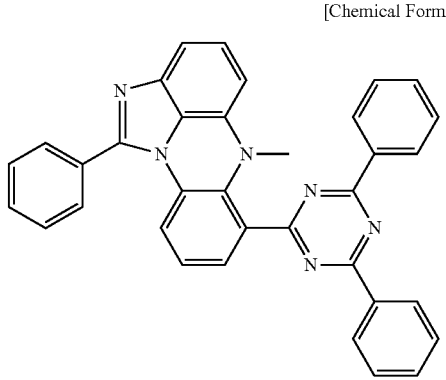
[Chemical Formula 6-42]
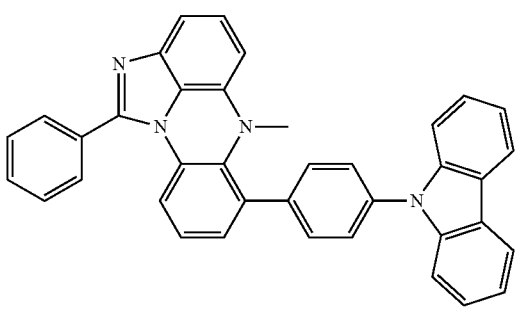
[Chemical Formula 6-43]
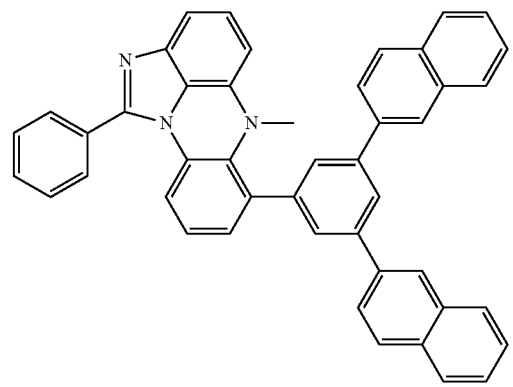

[Chemical Formula 6-44]
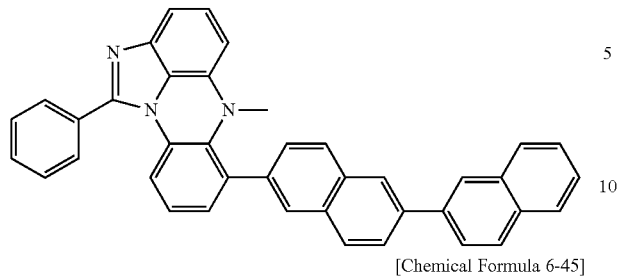
[Chemical Formula 6-45]
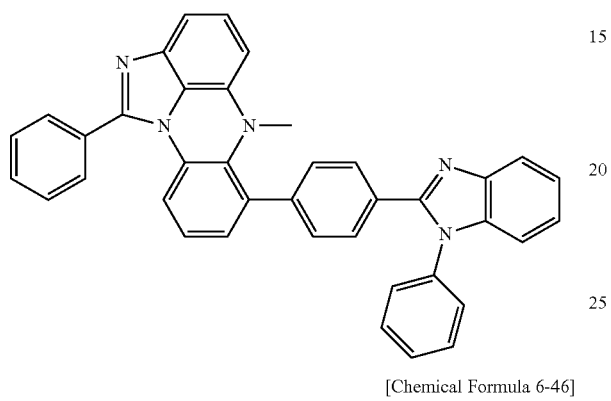
[Chemical Formula 6-46]
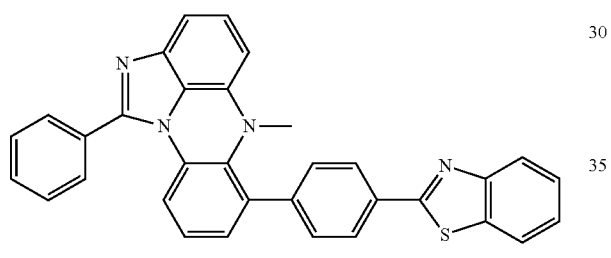
[Chemical Formula 6-47]
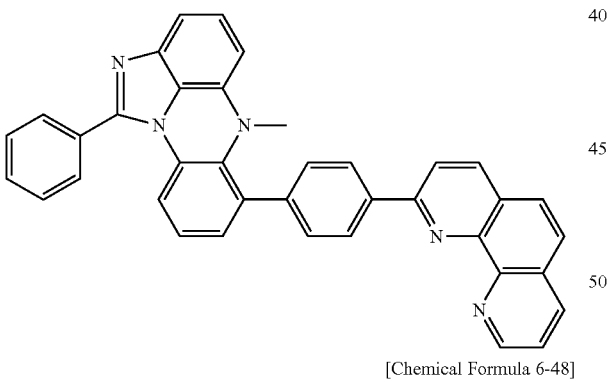
[Chemical Formula 6-48]
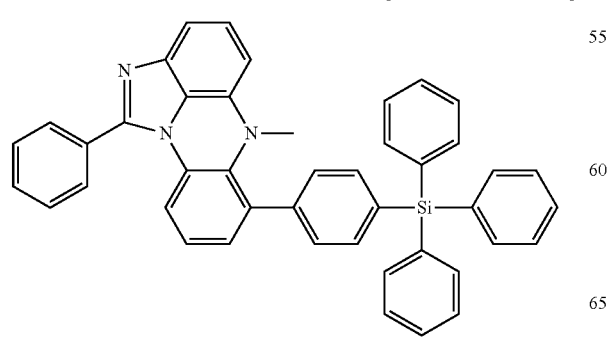
[Chemical Formula 6-49]
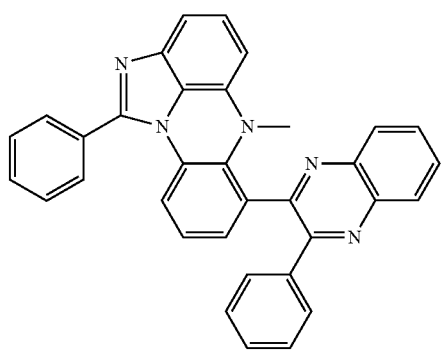
[Chemical Formula 6-50]
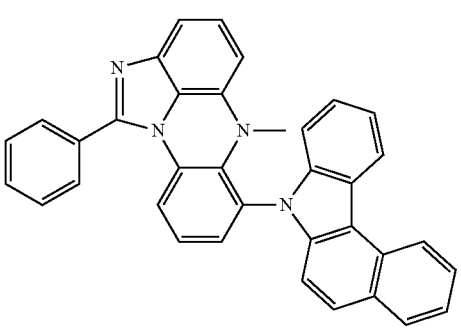
[Chemical Formula 6-51]
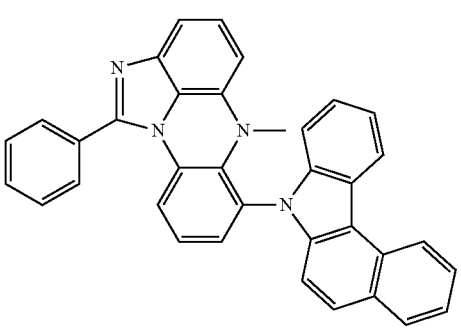
[Chemical Formula 6-52]
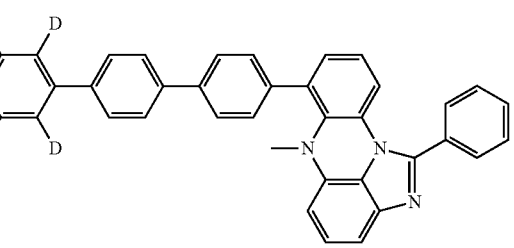

[Chemical Formula 6-53]
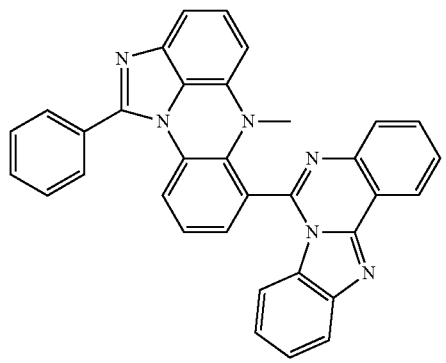
[Chemical Formula 6-54]
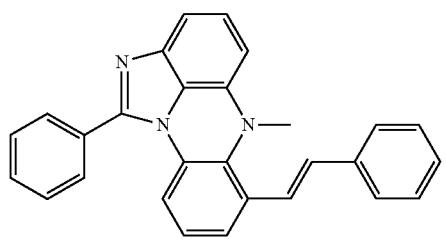
[Chemical Formula 7-1]
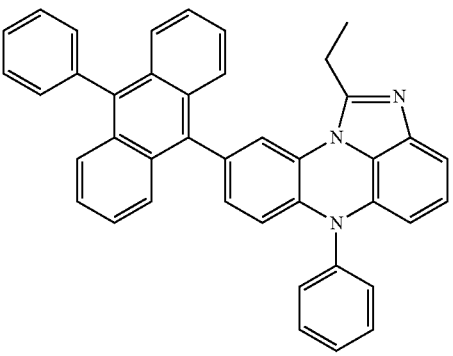
[Chemical Formula 7-2]
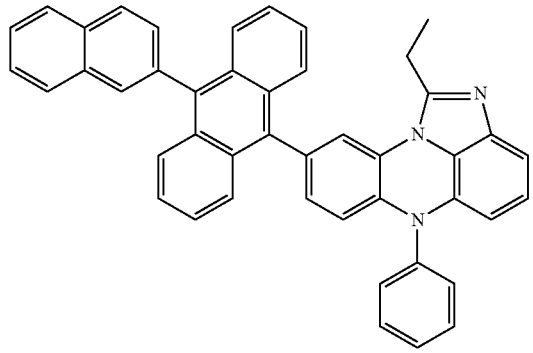
[Chemical Formula 7-3]
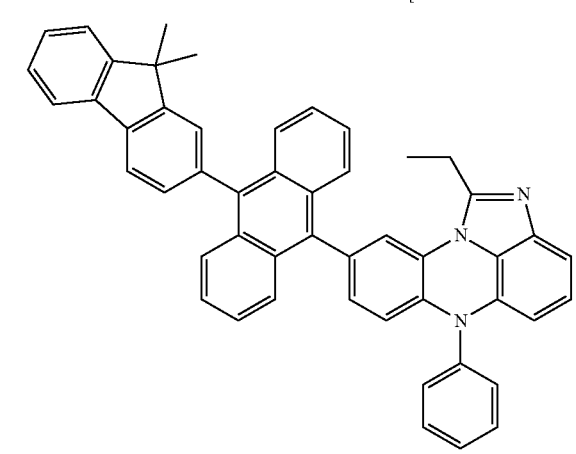
[Chemical Formula 7-4]
[Chemical Formula 7-5]

[Chemical Formula 7-6]
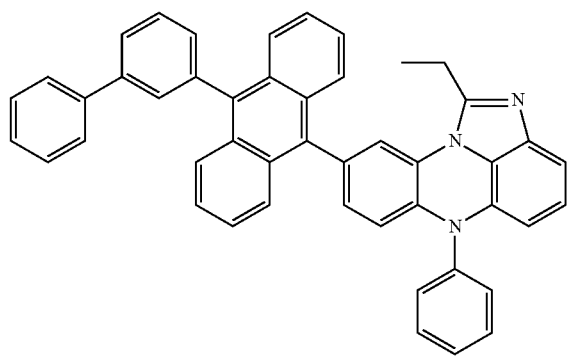
[Chemical Formula 7-7]
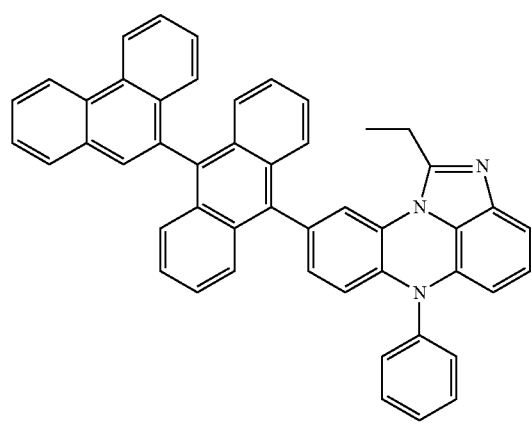
[Chemical Formula 7-8]
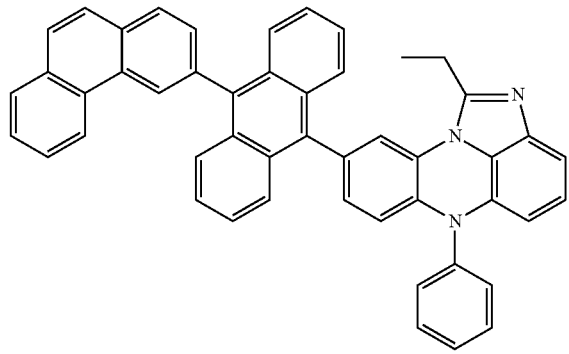
[Chemical Formula 7-9]
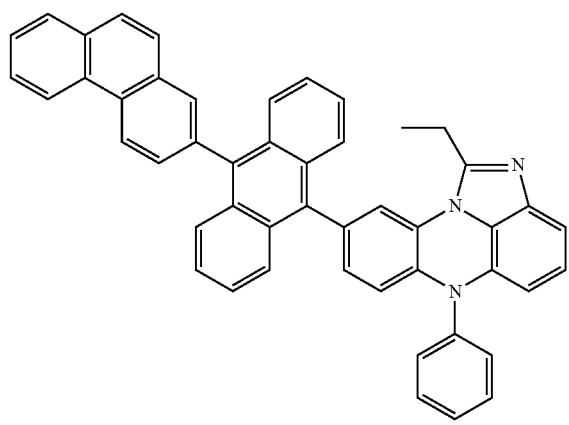
[Chemical Formula 7-10]
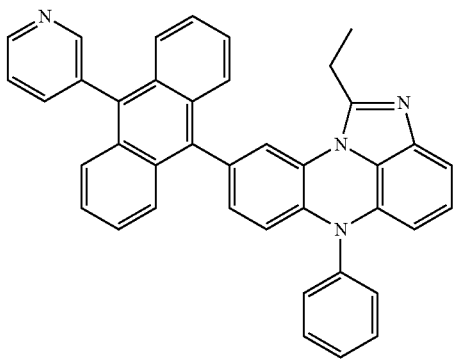
[Chemical Formula 7-11]
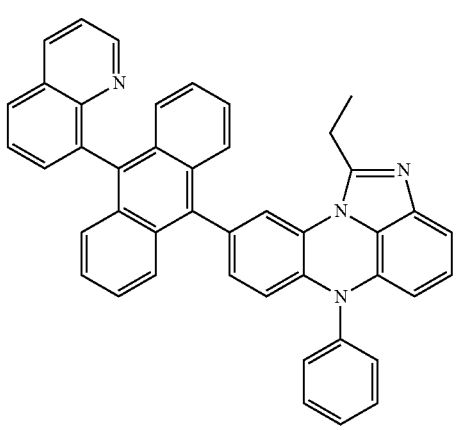
[Chemical Formula 7-12]
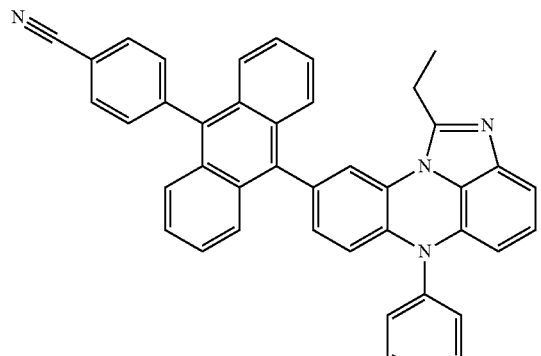
[Chemical Formula 7-13]
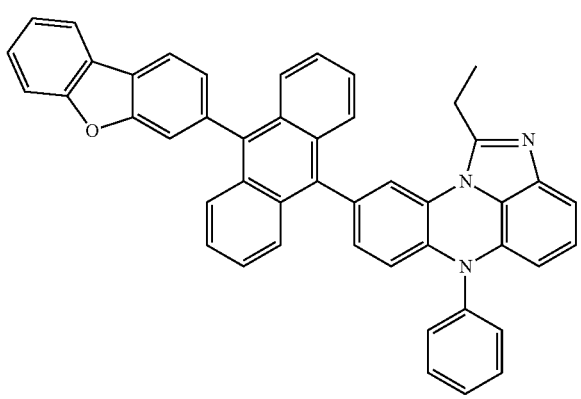

[Chemical Formula 7-14]
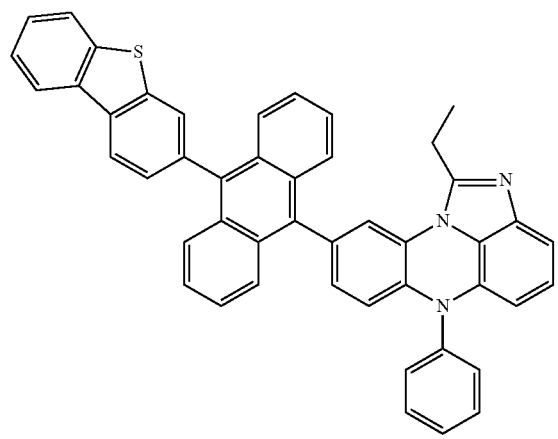
[Chemical Formula 7-15]
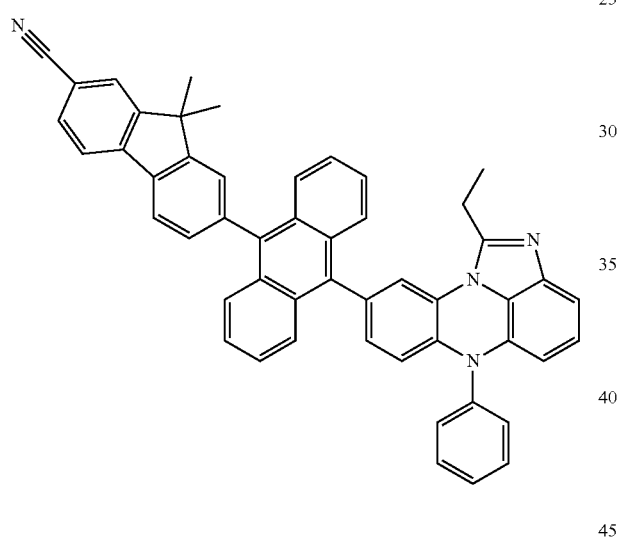
[Chemical Formula 7-16]
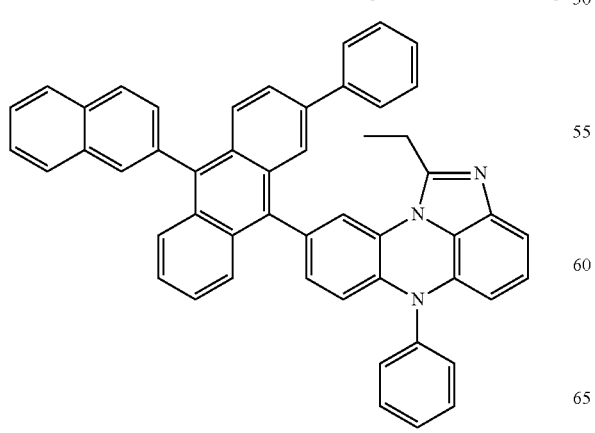
[Chemical Formula 7-17]
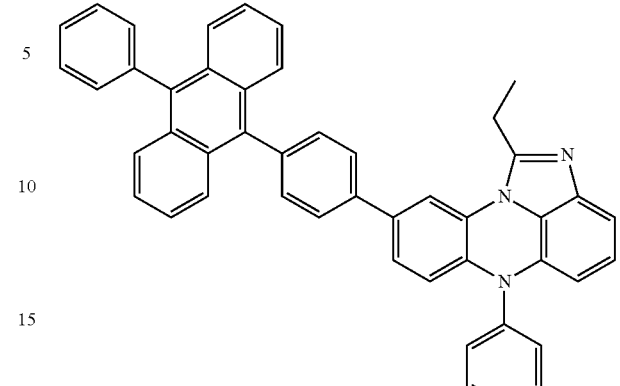
[Chemical Formula 7-18]
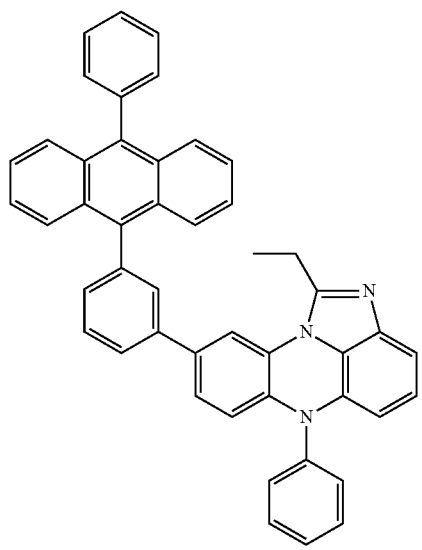
[Chemical Formula 7-19]
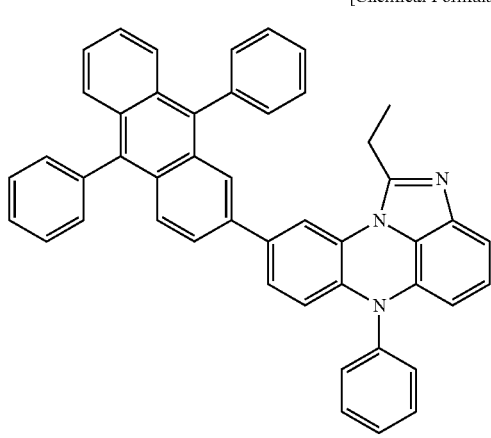

[Chemical Formula 7-20]
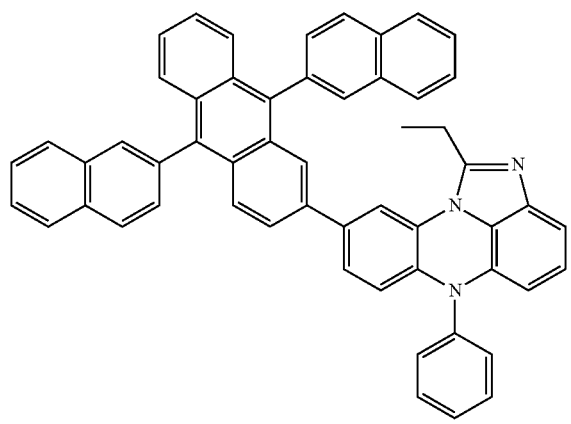
[Chemical Formula 7-21]
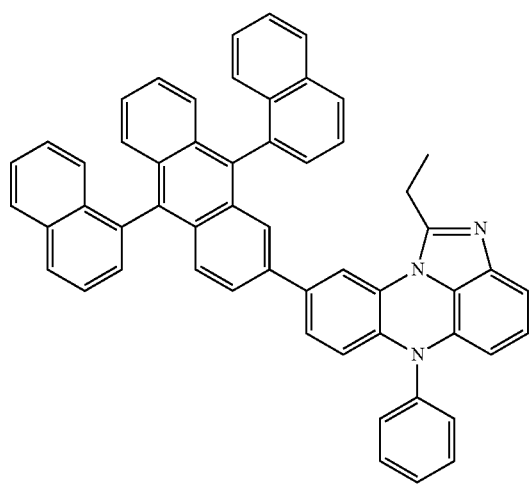
[Chemical Formula 7-22]
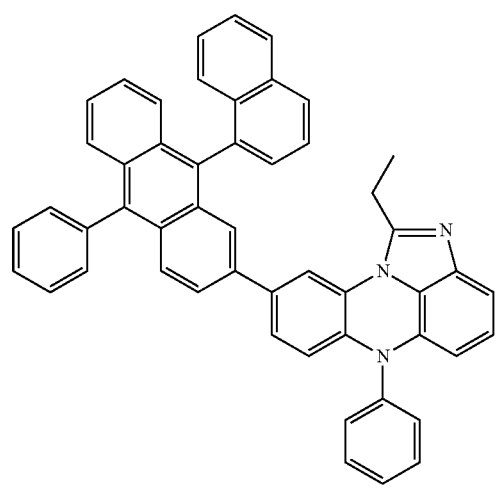
[Chemical Formula 7-23]
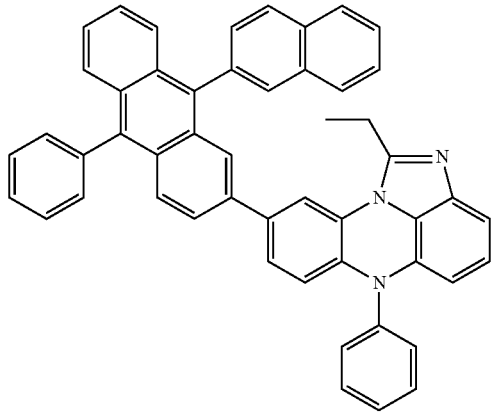
[Chemical Formula 7-24]
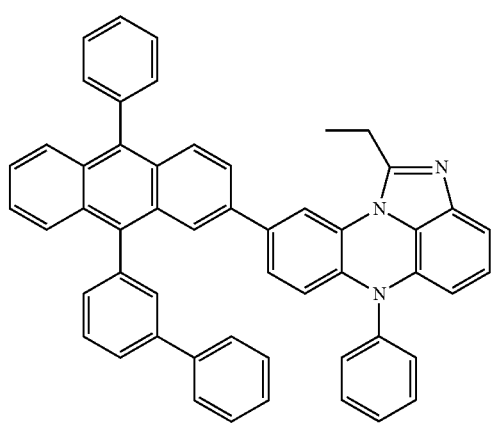
[Chemical Formula 7-25]
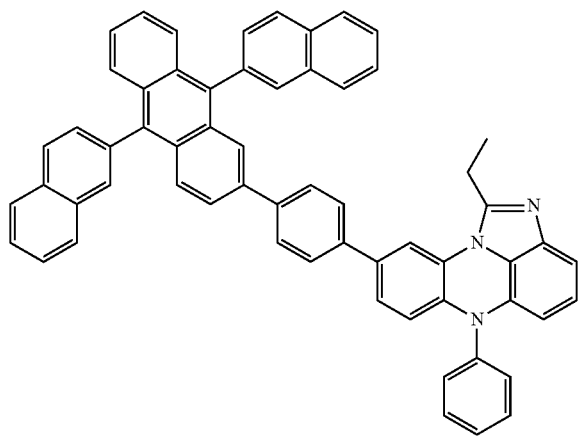

[Chemical Formula 7-26]
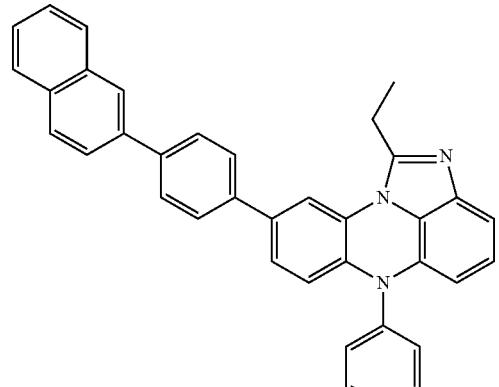
[Chemical Formula 7-27]
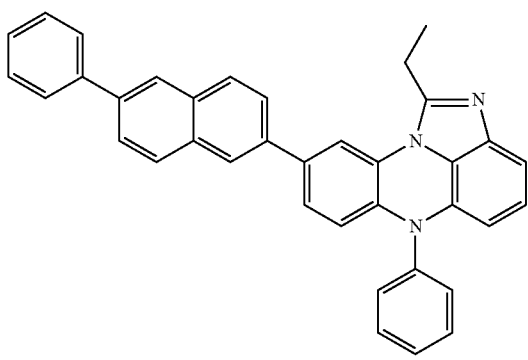
[Chemical Formula 7-28]
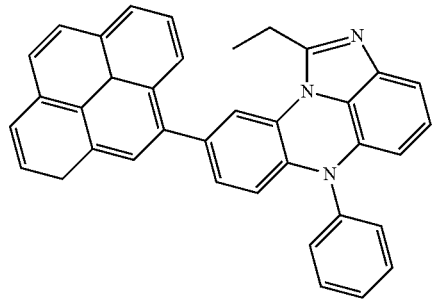
[Chemical Formula 7-29]
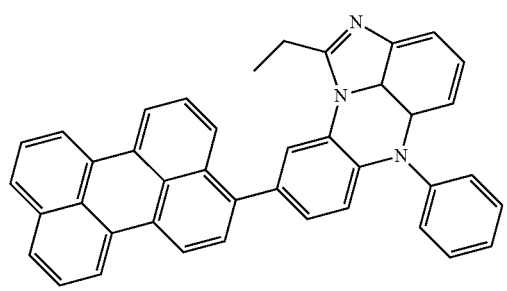
[Chemical Formula 7-30]
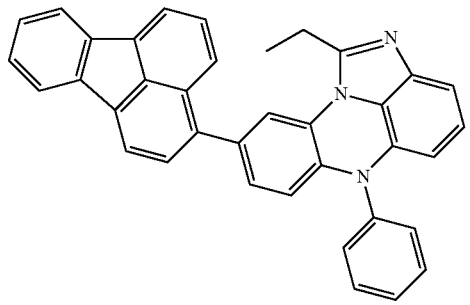
[Chemical Formula 7-31]
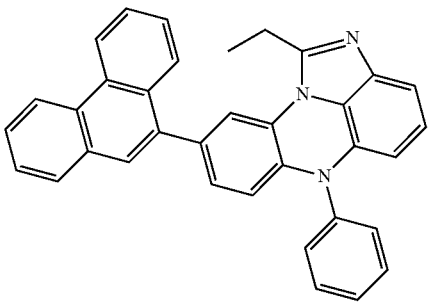
[Chemical Formula 7-32]
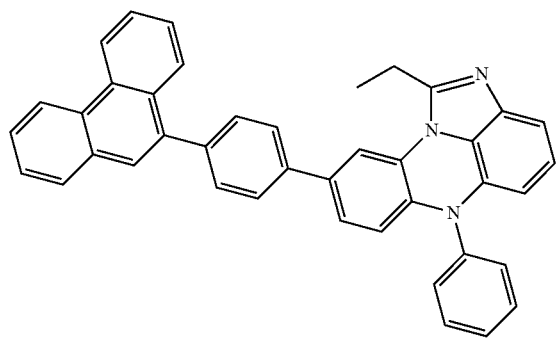
[Chemical Formula 7-33]
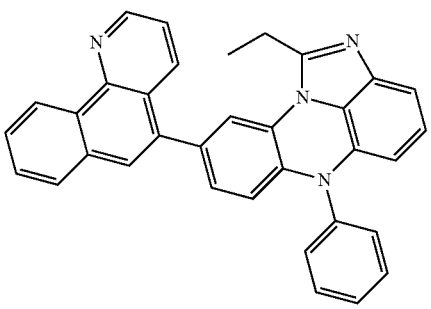

[Chemical Formula 7-34]
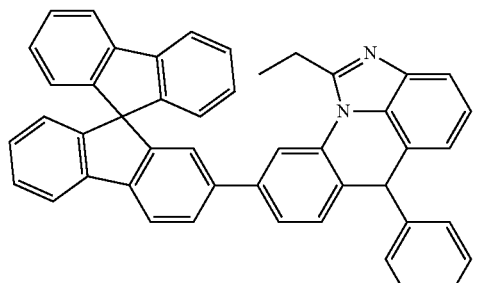
[Chemical Formula 7-35]
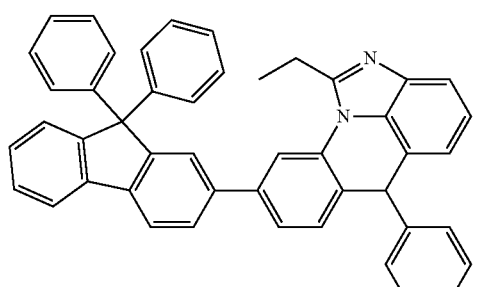
[Chemical Formula 7-36]
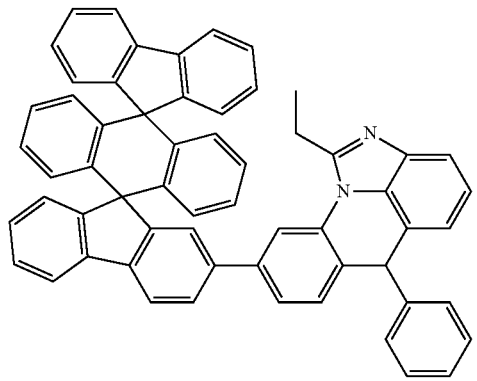
[Chemical Formula 7-37]
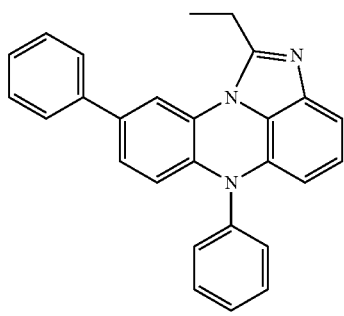
[Chemical Formula 7-38]
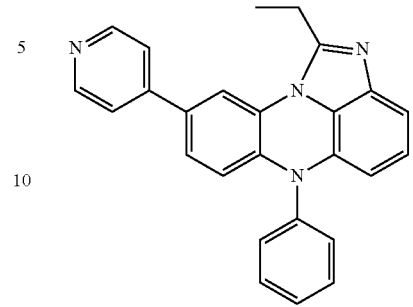
[Chemical Formula 7-39]
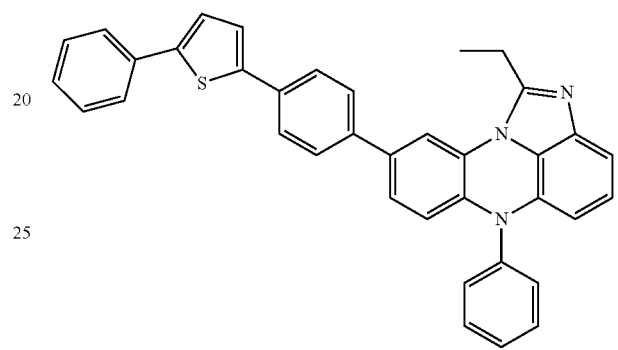
[Chemical Formula 7-40]
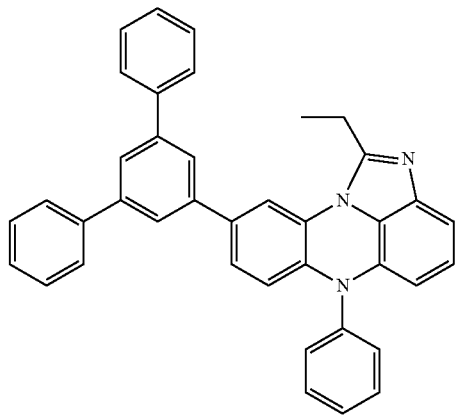
[Chemical Formula 7-41]
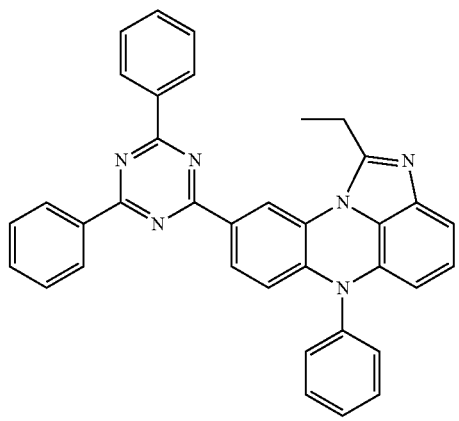

[Chemical Formula 7-42]
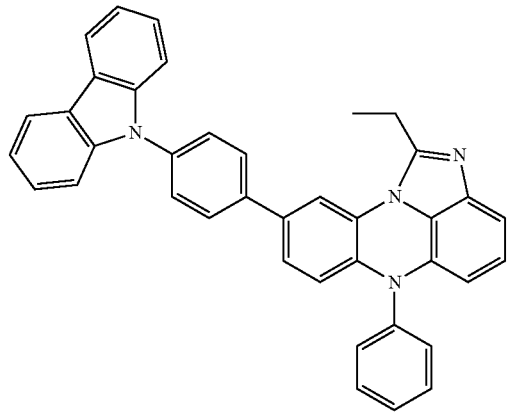
[Chemical Formula 7-43]
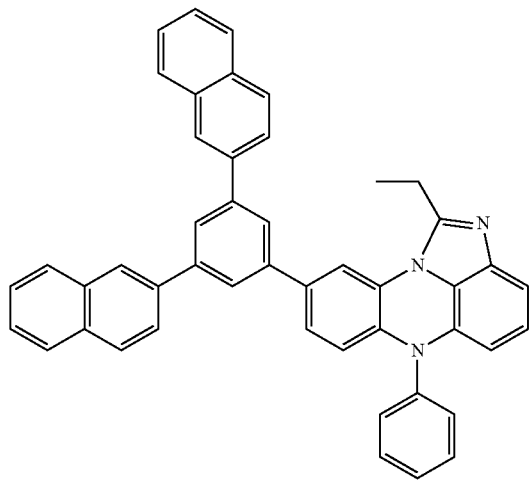
[Chemical Formula 7-44]
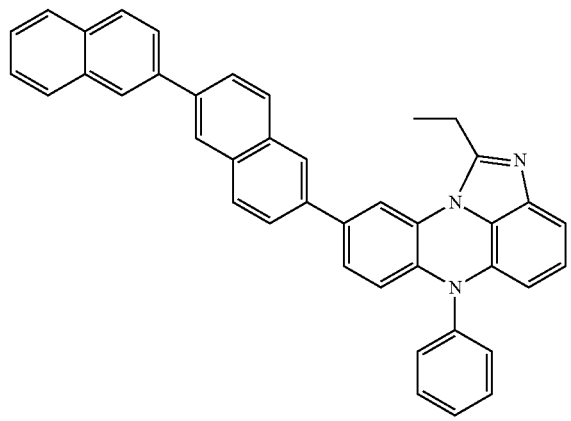
[Chemical Formula 7-45]
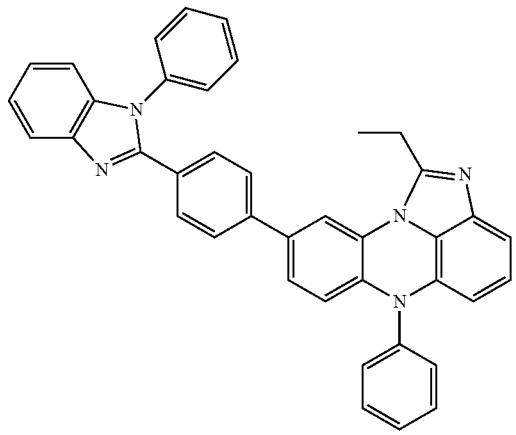
[Chemical Formula 7-46]
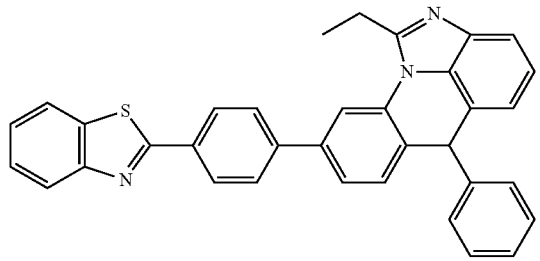
[Chemical Formula 7-47]
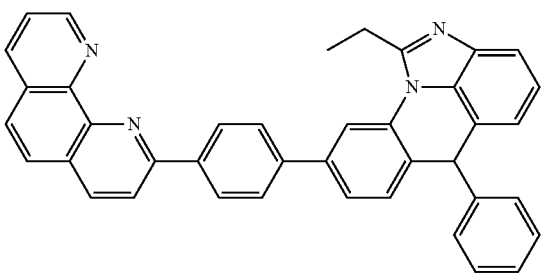
[Chemical Formula 7-48]
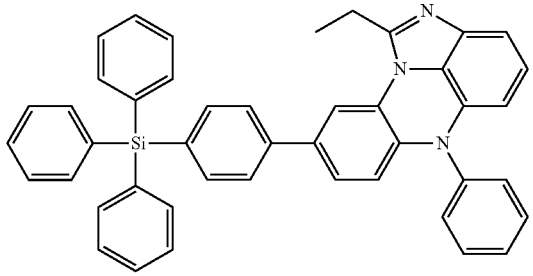

[Chemical Formula 7-49]
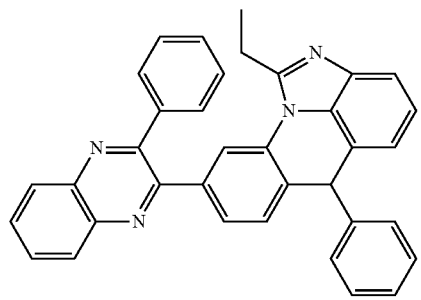
[Chemical Formula 7-50]
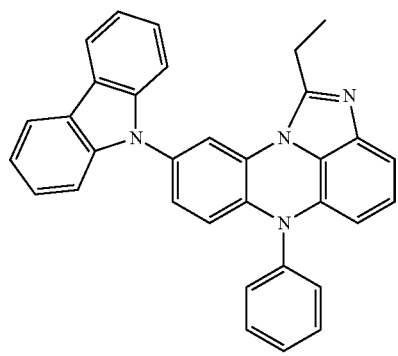
[Chemical Formula 7-51]
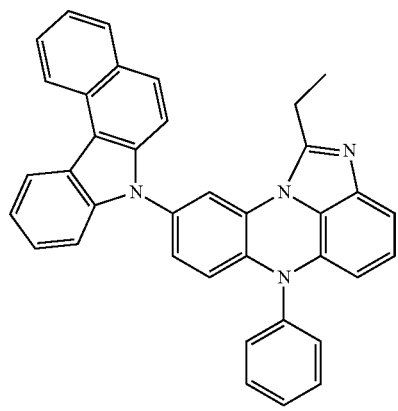
[Chemical Formula 7-52]
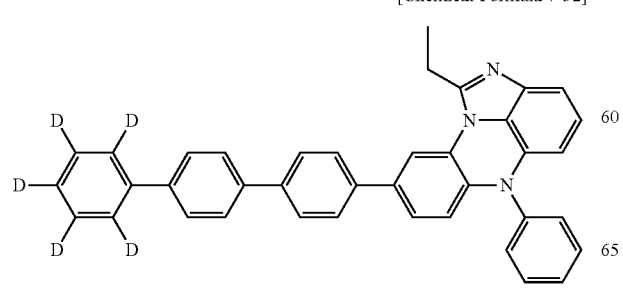
[Chemical Formula 7-53]
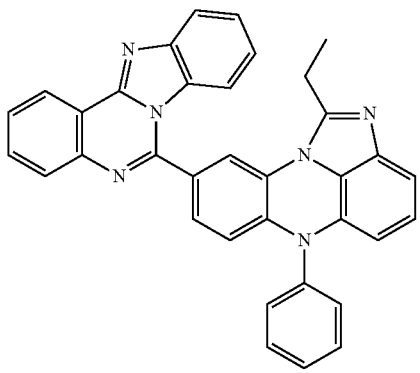
[Chemical Formula 7-54]
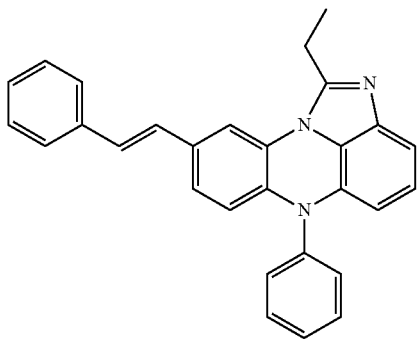
[Chemical Formula 8-1]
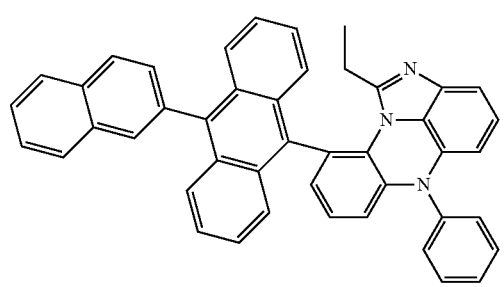
[Chemical Formula 8-2]

[Chemical Formula 8-3]
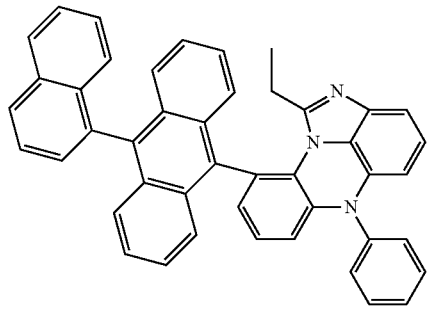
[Chemical Formula 8-4]
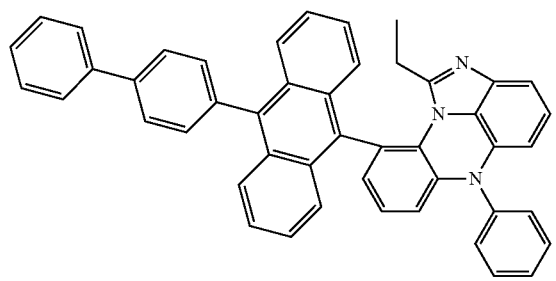
[Chemical Formula 8-5]
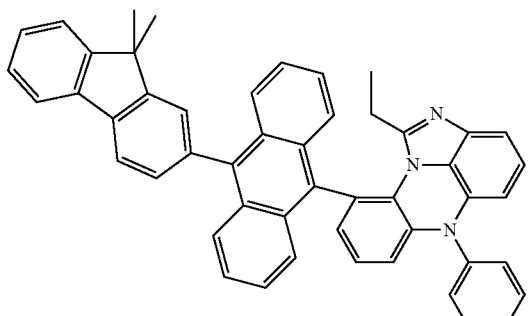
[Chemical Formula 8-6]
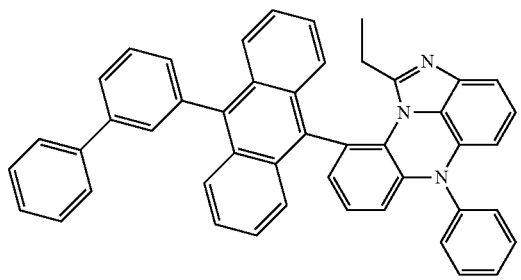
[Chemical Formula 8-7]
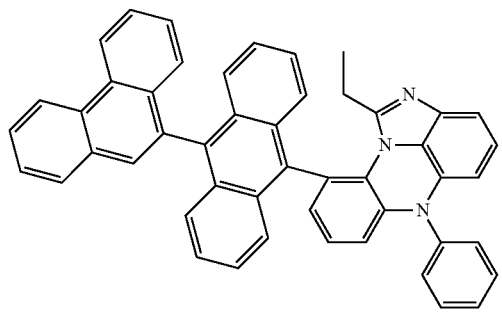
[Chemical Formula 8-8]
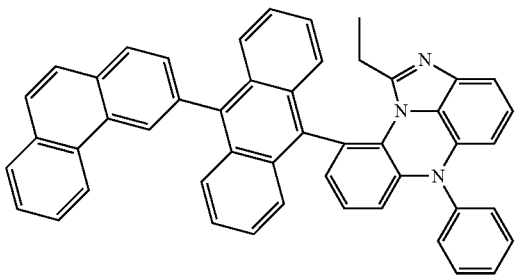
[Chemical Formula 8-9]
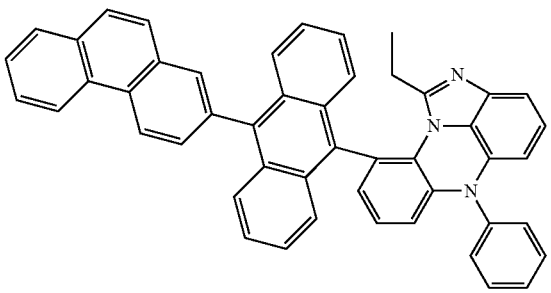
[Chemical Formula 8-10]
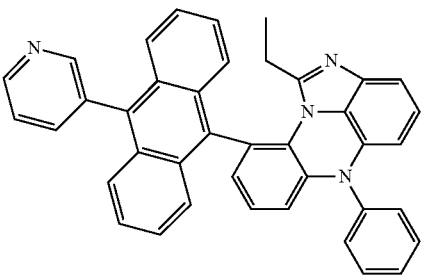
[Chemical Formula 8-11]
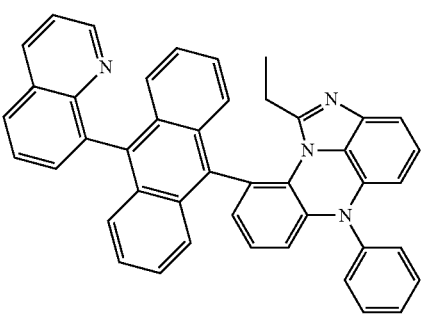
[Chemical Formula 8-12]
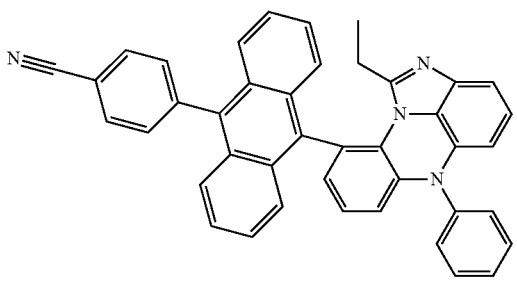

[Chemical Formula 8-13]
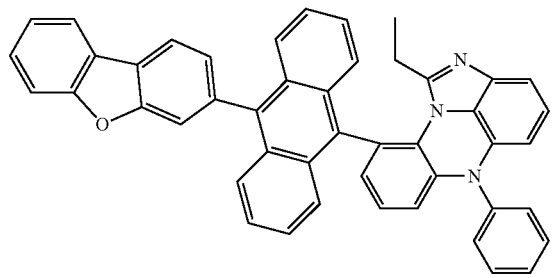
[Chemical Formula 8-14]
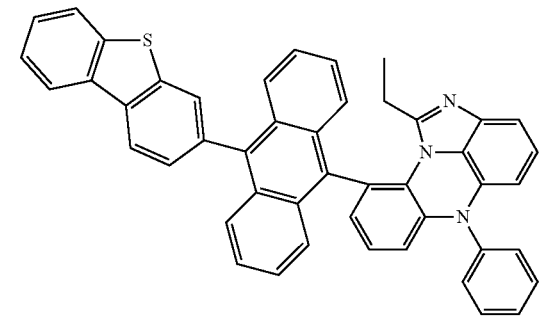
[Chemical Formula 8-15]
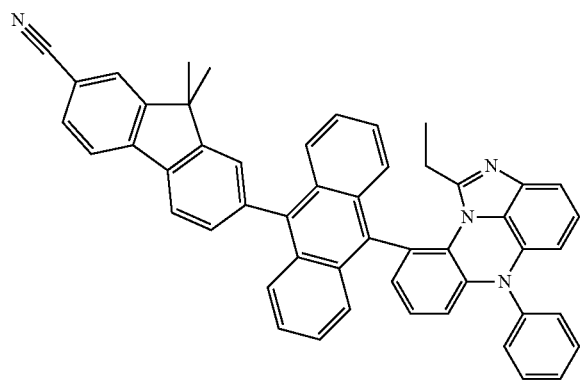
[Chemical Formula 8-16]
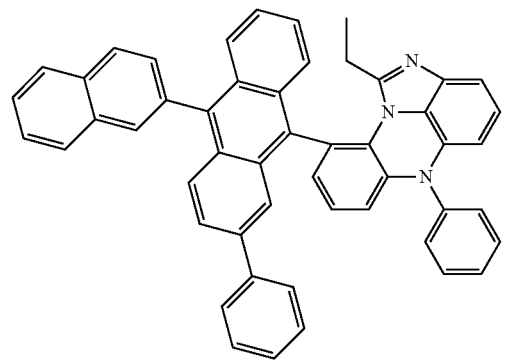
[Chemical Formula 8-17]
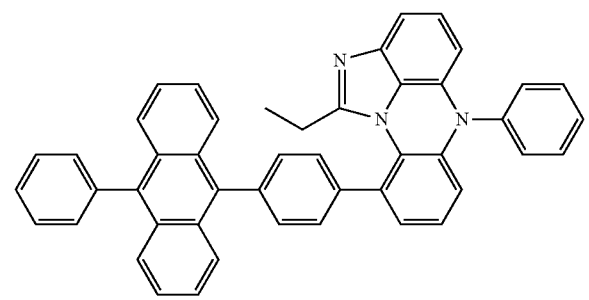
[Chemical Formula 8-18]
[Chemical Formula 8-19]
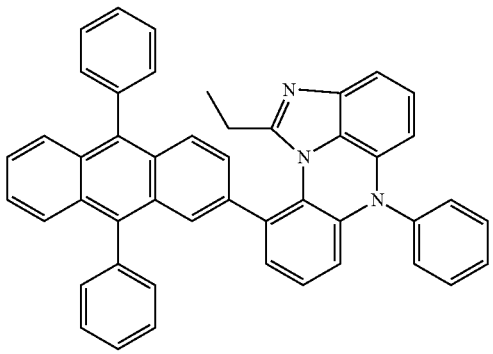
[Chemical Formula 8-20]
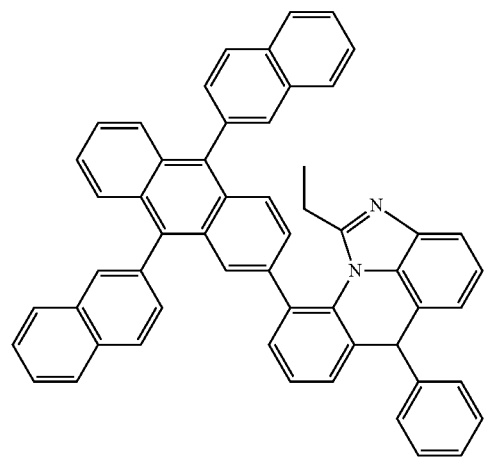

[Chemical Formula 8-21]
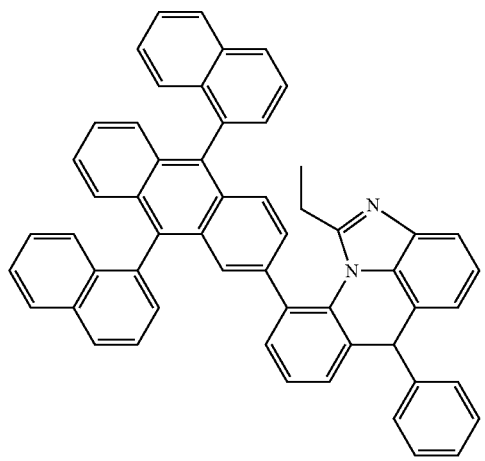
[Chemical Formula 8-22]
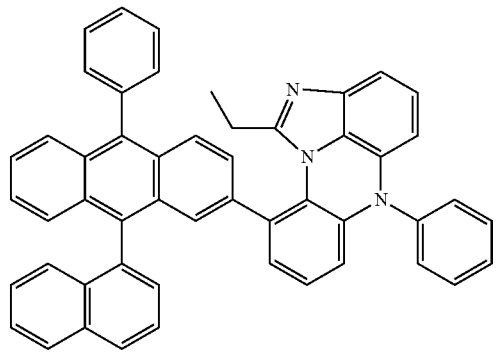
[Chemical Formula 8-23]
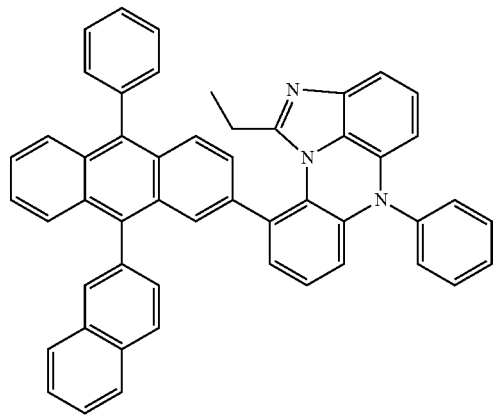
[Chemical Formula 8-24]
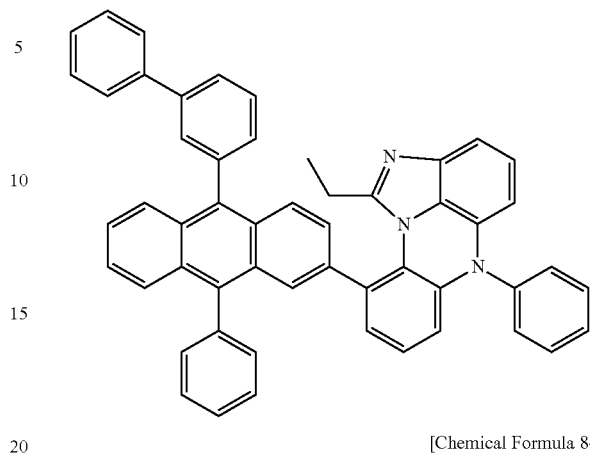
[Chemical Formula 8-25]
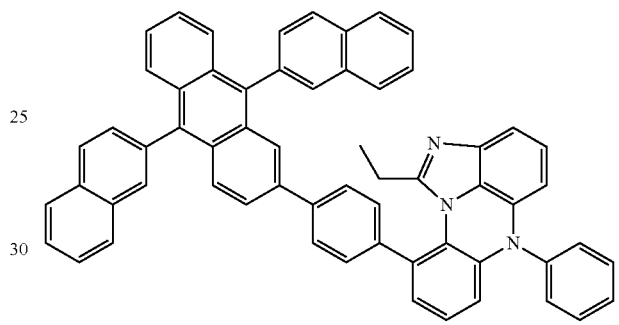
[Chemical Formula 8-26]
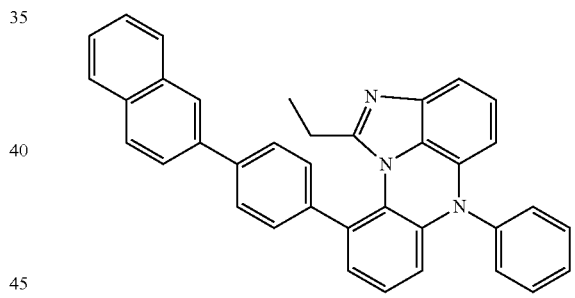
[Chemical Formula 8-27]
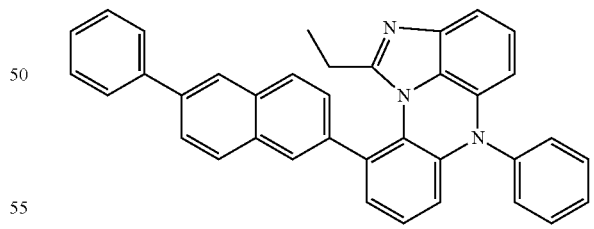
[Chemical Formula 8-28]
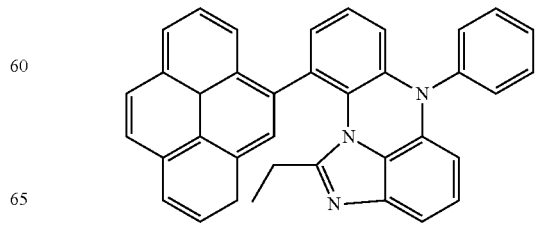

[Chemical Formula 8-29]
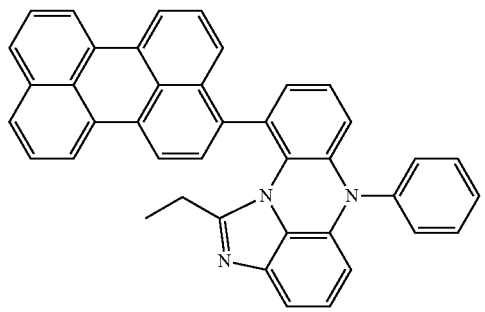
[Chemical Formula 8-30]
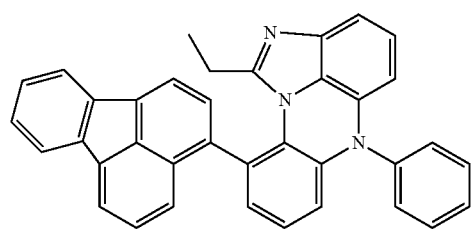
[Chemical Formula 8-31]
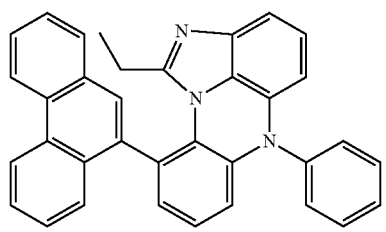
[Chemical Formula 8-32]
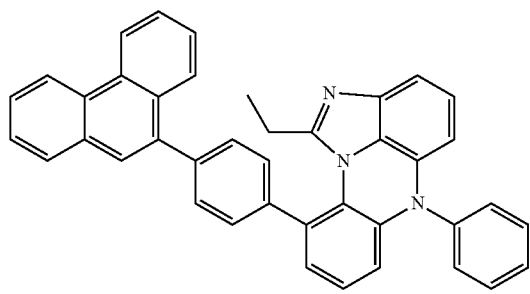
[Chemical Formula 8-33]
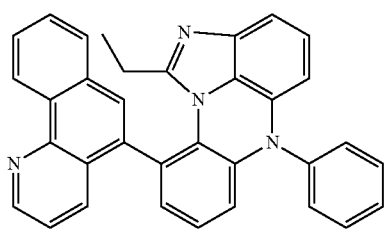
[Chemical Formula 8-34]
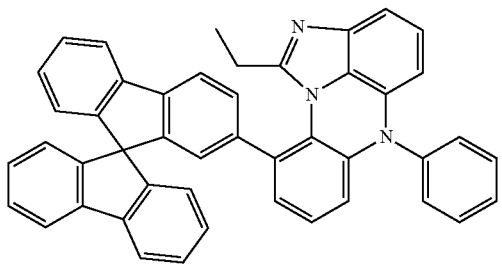
[Chemical Formula 8-35]
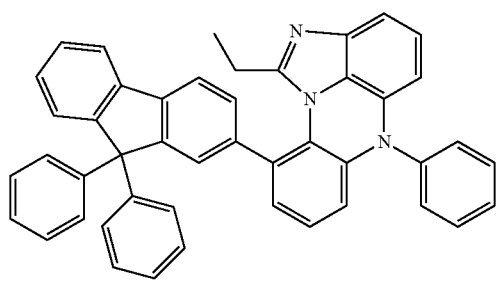
[Chemical Formula 8-36]
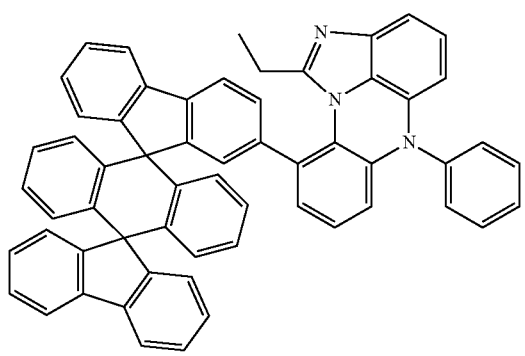
[Chemical Formula 9-1]
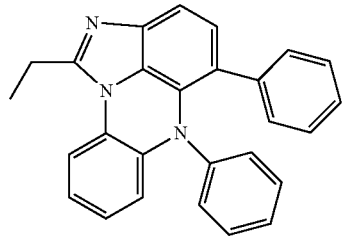
[Chemical Formula 9-2]
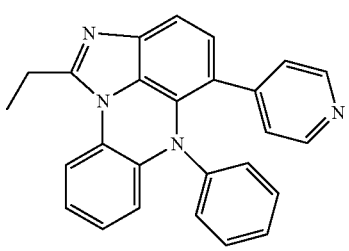

-continued
[Chemical Formula 9-3]
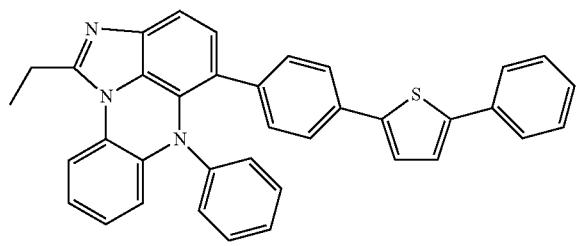
[Chemical Formula 9-4]
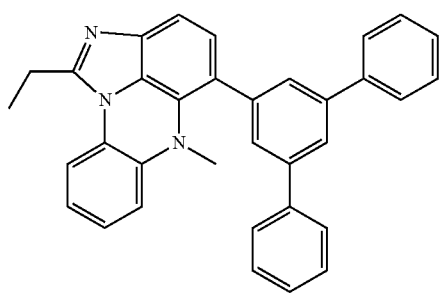
[Chemical Formula 9-5]
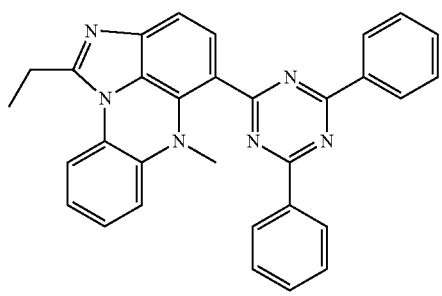
[Chemical Formula 9-6]
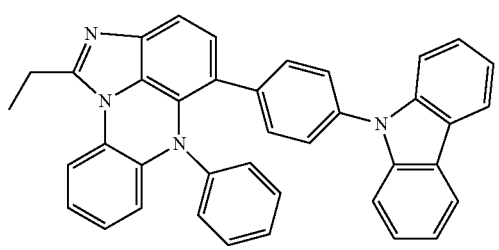
[Chemical Formula 9-7]
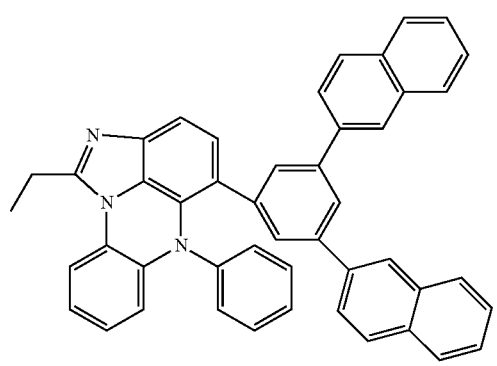
-continued
[Chemical Formula 9-8]
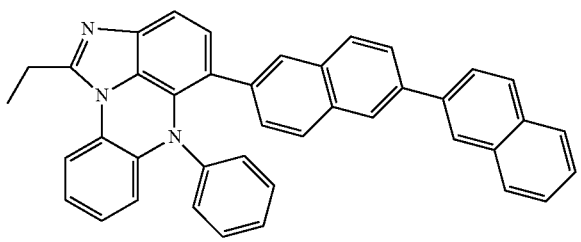
[Chemical Formula 9-9]
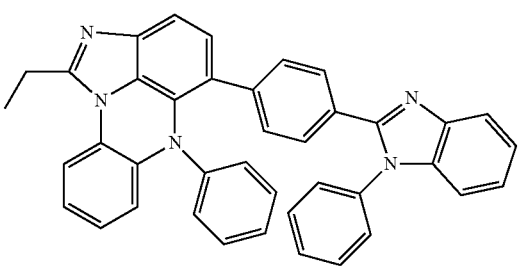
[Chemical Formula 9-10]
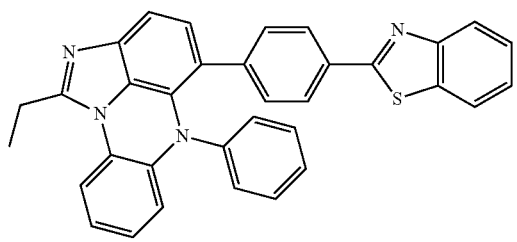
[Chemical Formula 9-11]
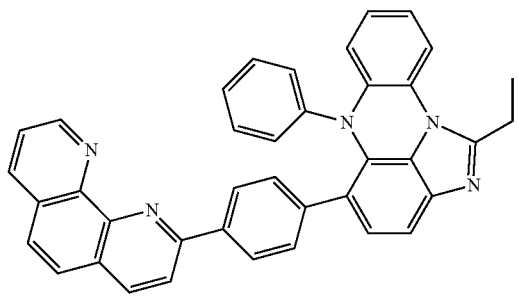
[Chemical Formula 9-12]
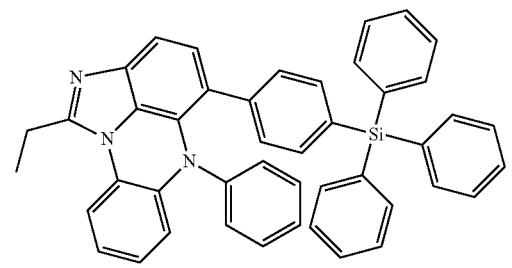

[Chemical Formula 9-13]
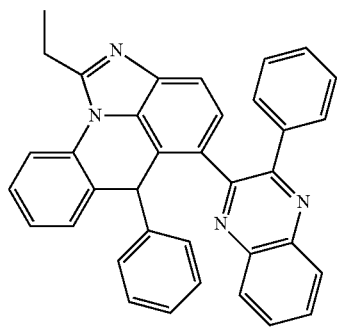
[Chemical Formula 9-14]
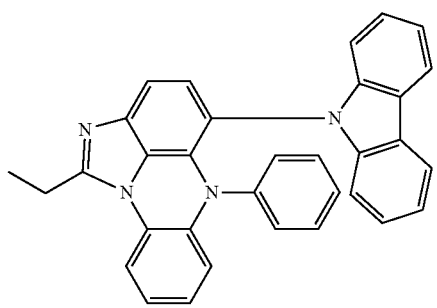
[Chemical Formula 9-15]
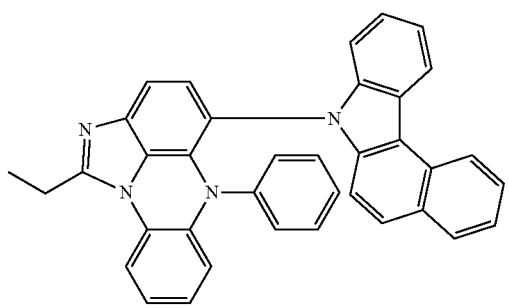
[Chemical Formula 9-16]
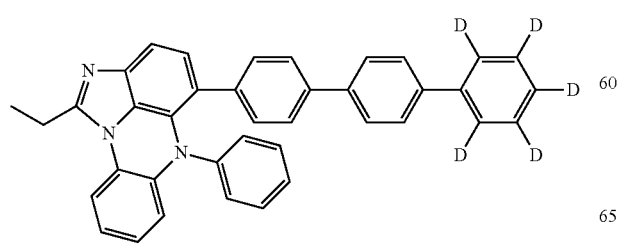
[Chemical Formula 9-17]
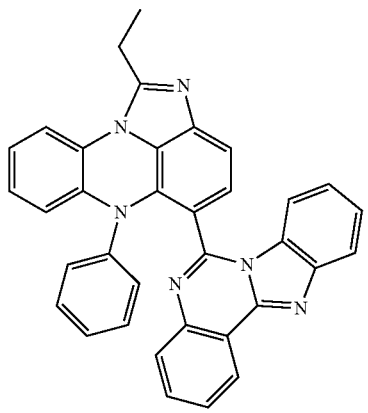
[Chemical Formula 9-18]
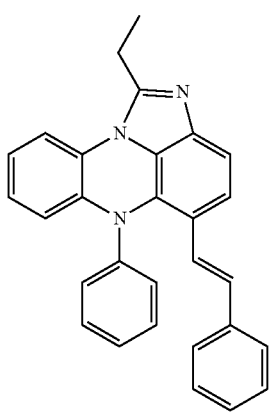
[Chemical Formula 10-1]
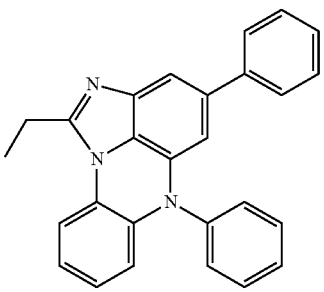
[Chemical Formula 10-2]
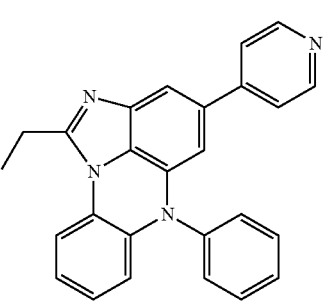

[Chemical Formula 10-3]
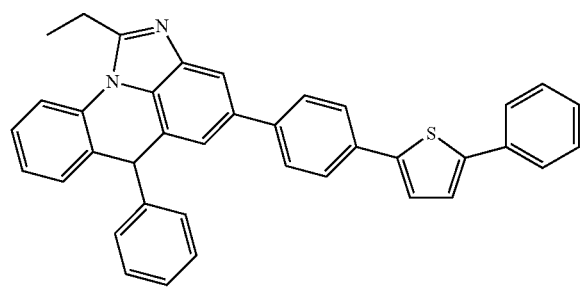
[Chemical Formula 10-4]
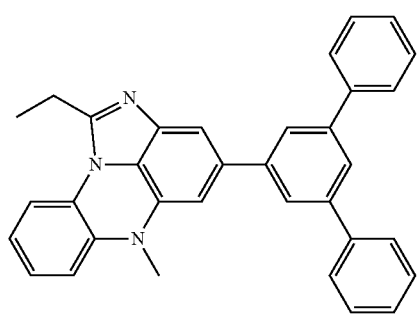
[Chemical Formula 10-5]
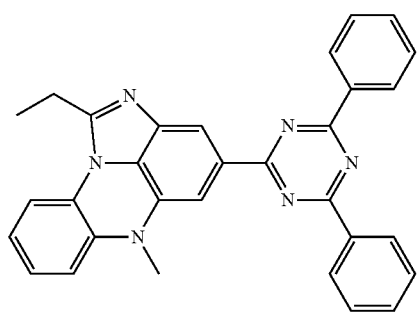
[Chemical Formula 10-6]
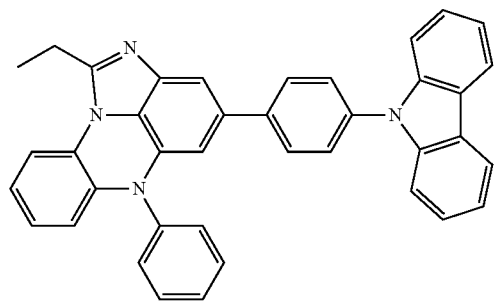
[Chemical Formula 10-7]
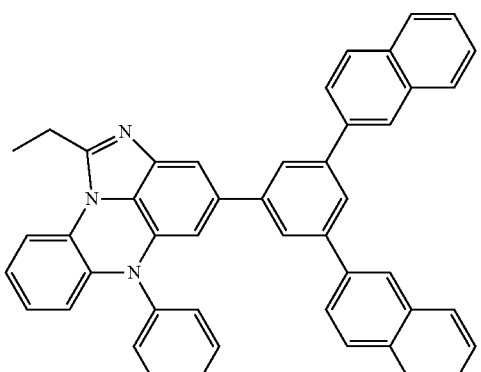
[Chemical Formula 10-8]
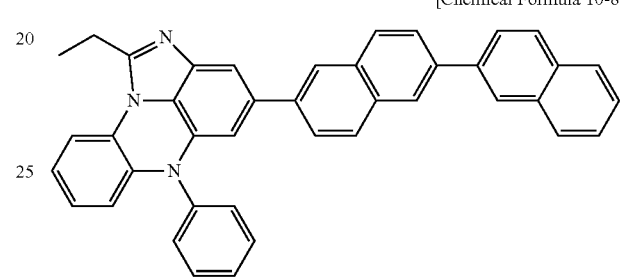
[Chemical Formula 10-9]
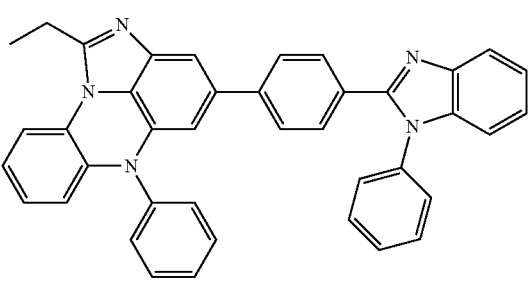
[Chemical Formula 10-10]
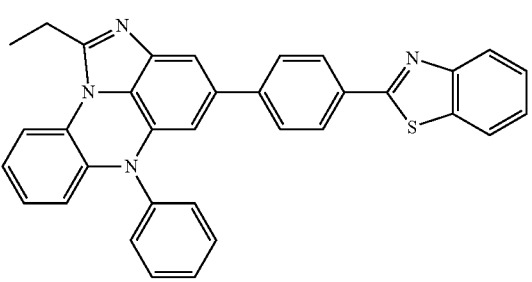
[Chemical Formula 10-11]
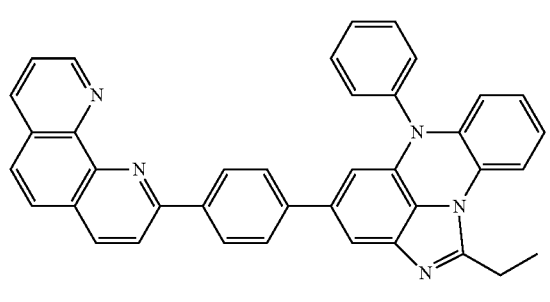

[Chemical Formula 10-12]
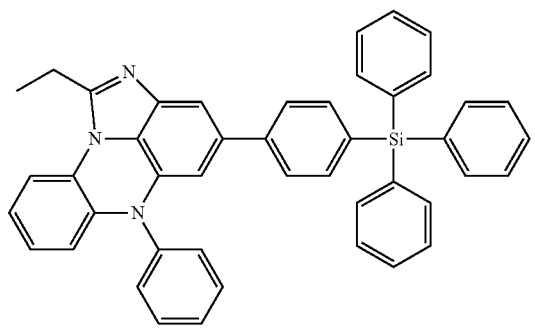
[Chemical Formula 10-16]
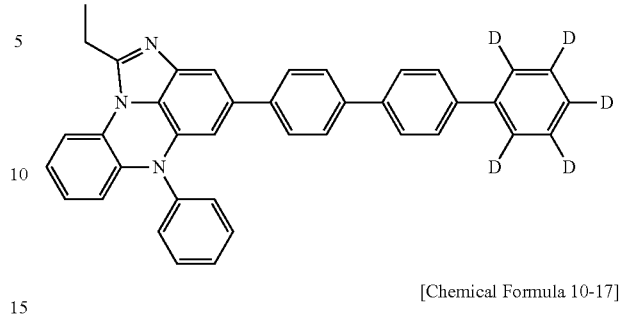
[Chemical Formula 10-13]
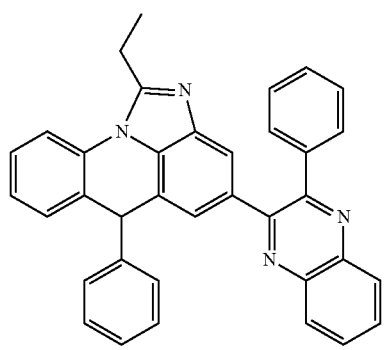
[Chemical Formula 10-17]
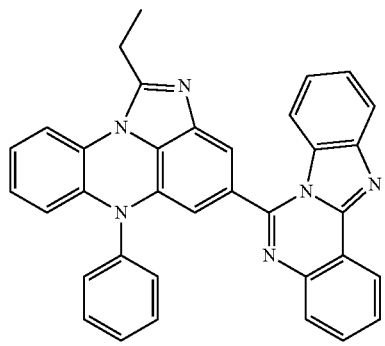
[Chemical Formula 10-14]
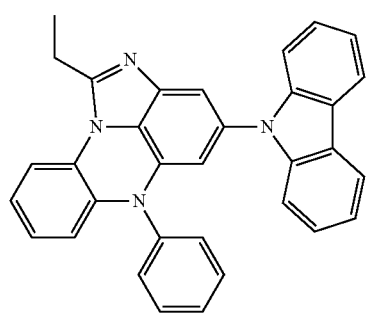
[Chemical Formula 10-18]
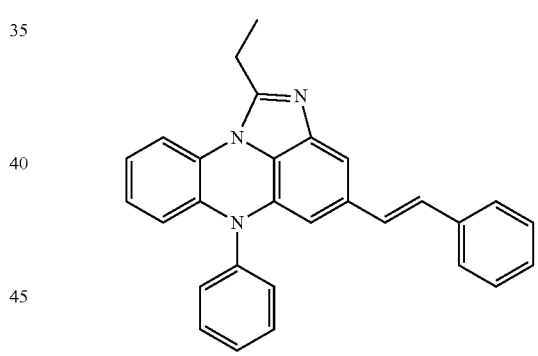
[Chemical Formula 10-15]
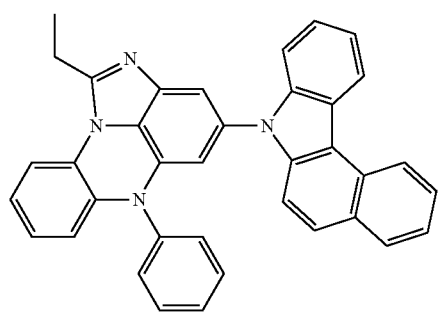
[Chemical Formula 11-1]
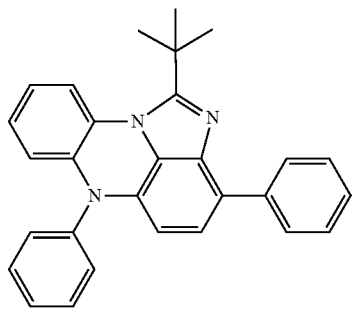

-continued
[Chemical Formula 11-2]
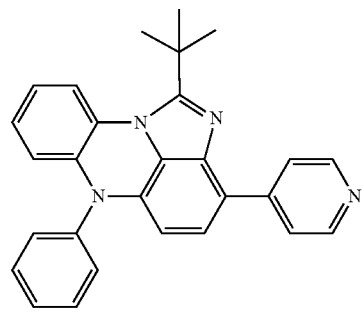
[Chemical Formula 11-3]
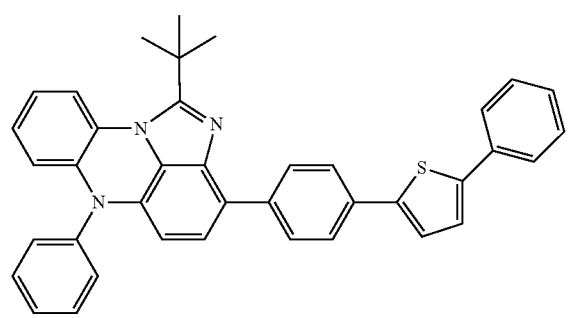
[Chemical Formula 11-4]
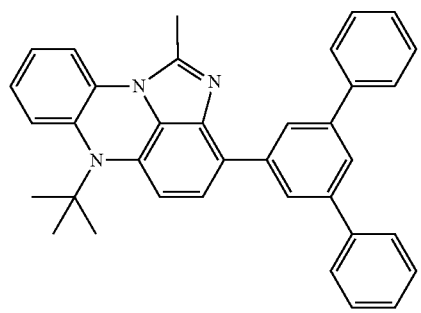
[Chemical Formula 11-5]
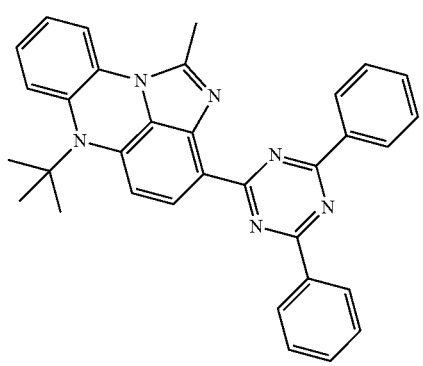
-continued
[Chemical Formula 11-6]
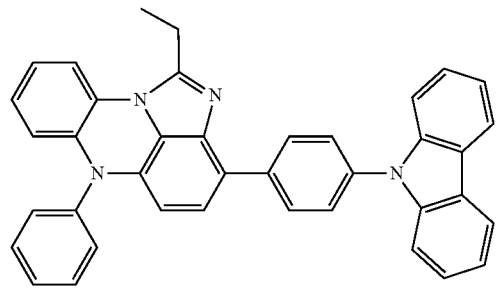
[Chemical Formula 11-7]
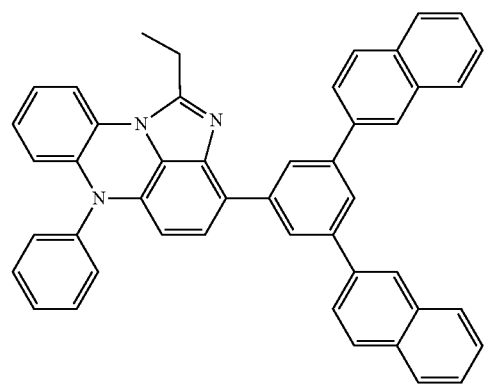
[Chemical Formula 11-8]
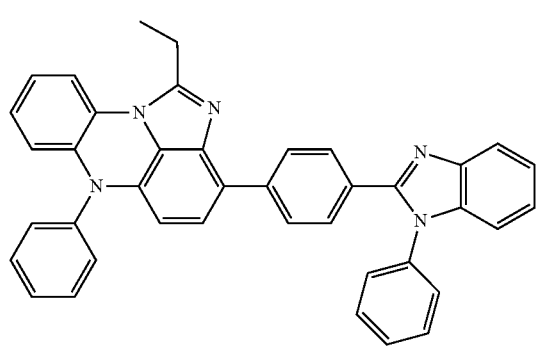
[Chemical Formula 11-9]

[Chemical Formula 11-10]
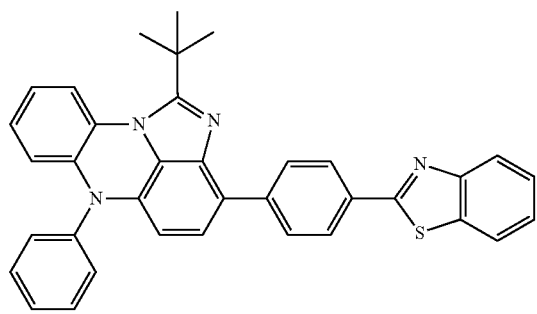
[Chemical Formula 11-11]
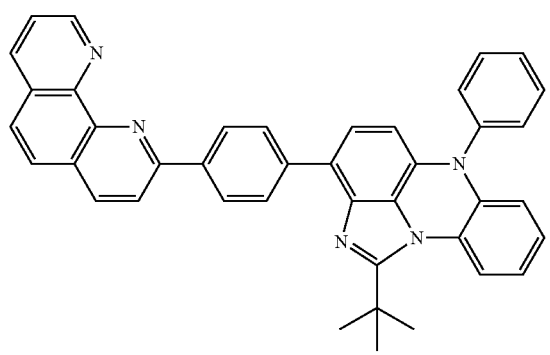
[Chemical Formula 11-12]
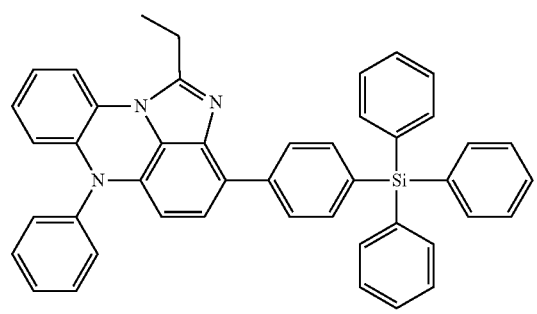
[Chemical Formula 11-13]
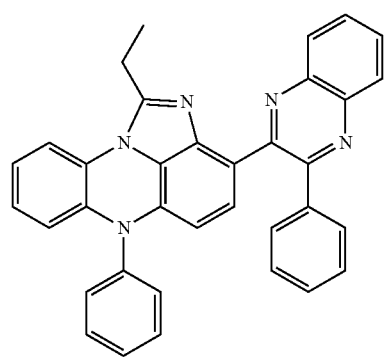
[Chemical Formula 11-14]
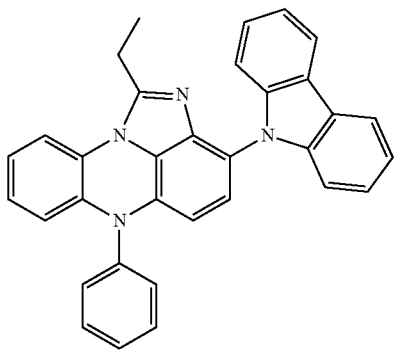
[Chemical Formula 11-15]
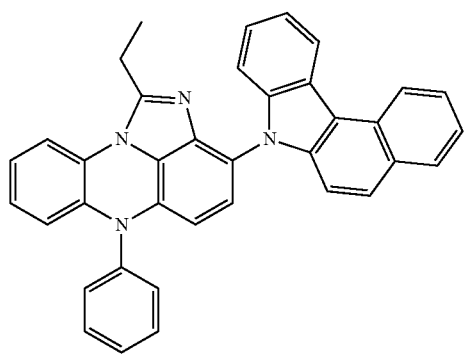
[Chemical Formula 11-16]
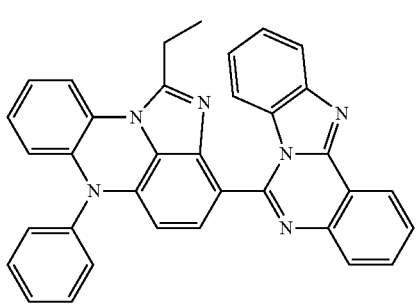
[Chemical Formula 11-17]

[Chemical Formula 11-18]
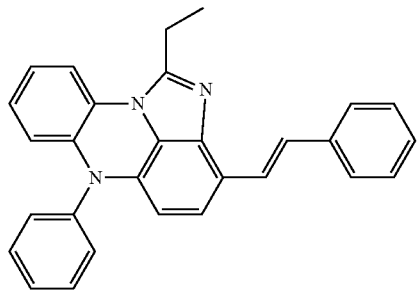
[Chemical Formula 12-1]
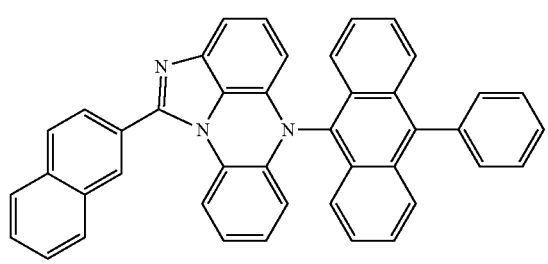
[Chemical Formula 12-2]
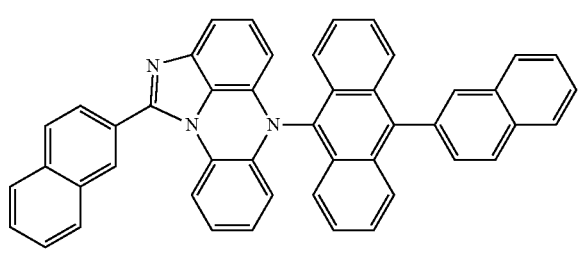
[Chemical Formula 12-3]
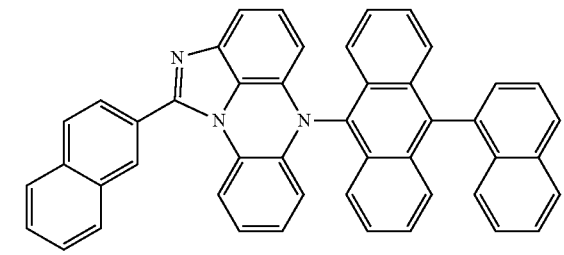
[Chemical Formula 12-4]
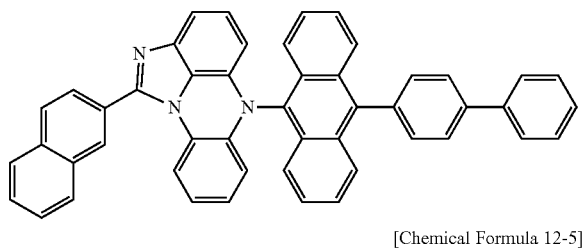
[Chemical Formula 12-5]
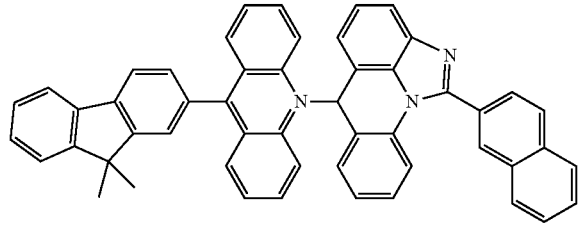
[Chemical Formula 12-6]
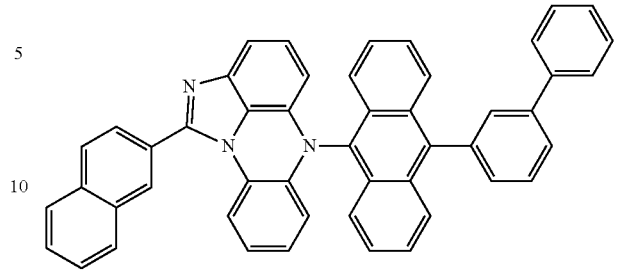
[Chemical Formula 12-7]
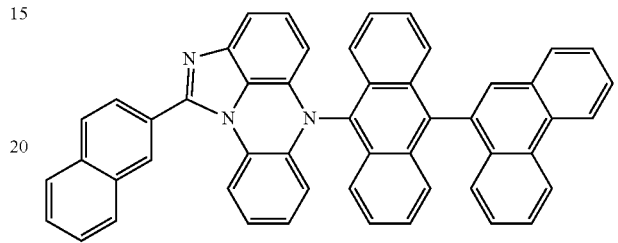
[Chemical Formula 12-8]
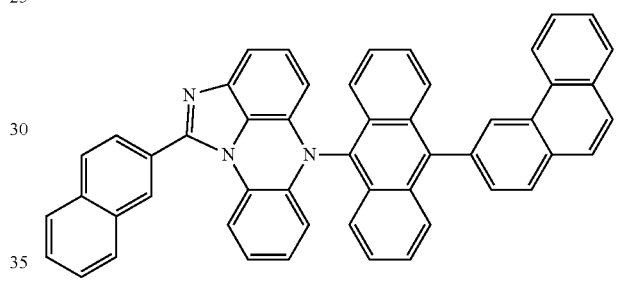
[Chemical Formula 12-9]
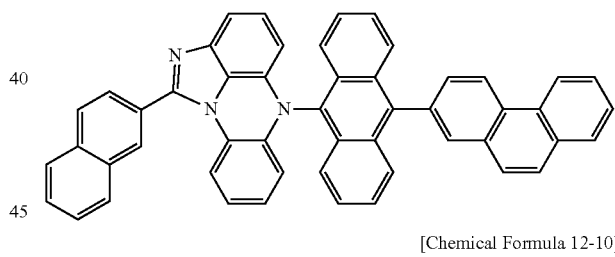
[Chemical Formula 12-10]
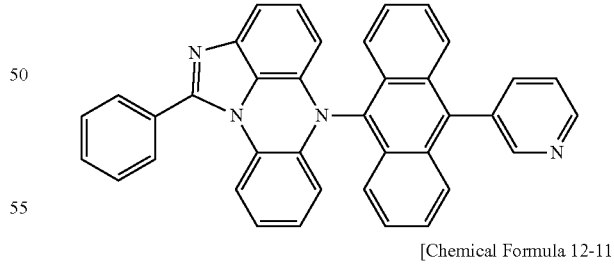
[Chemical Formula 12-11]
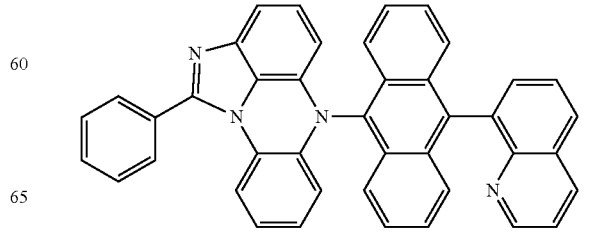

[Chemical Formula 12-12]
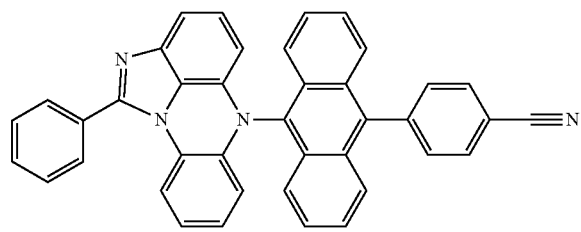
[Chemical Formula 12-13]
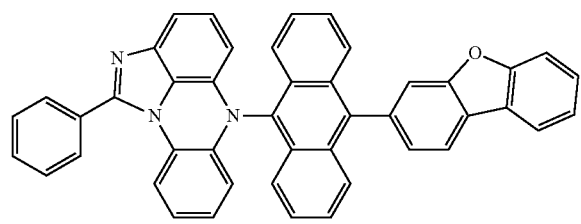
[Chemical Formula 12-14]
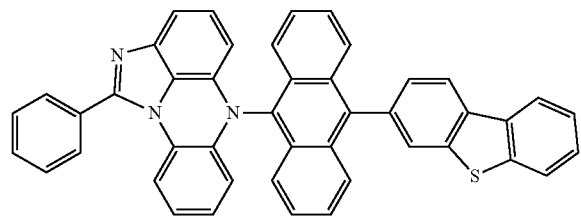
[Chemical Formula 12-15]
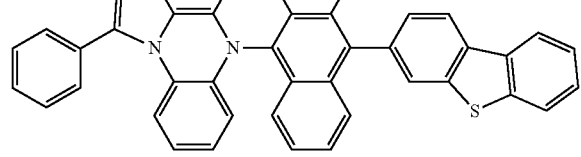
[Chemical Formula 12-16]
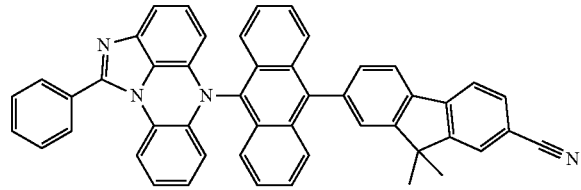
[Chemical Formula 12-17]
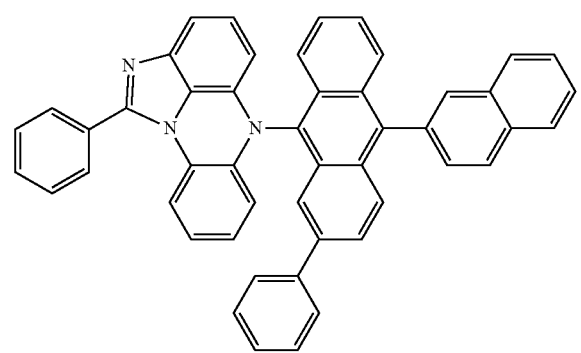
[Chemical Formula 12-18]
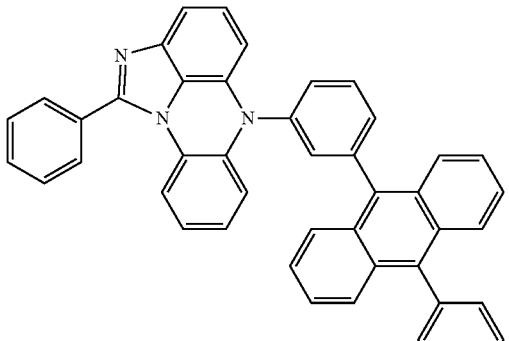
[Chemical Formula 12-19]
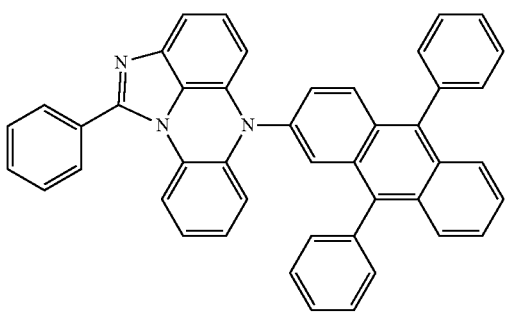
[Chemical Formula 12-20]
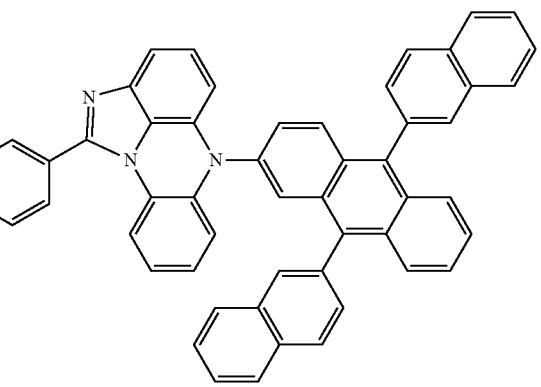
[Chemical Formula 12-21]
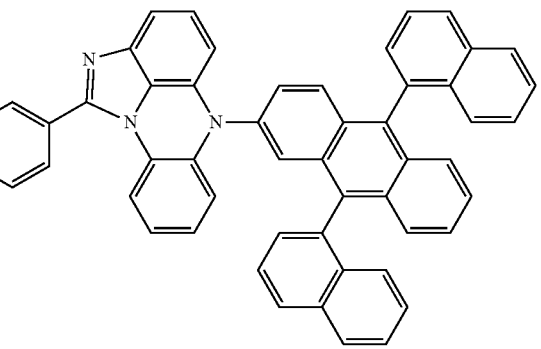

[Chemical Formula 12-22]
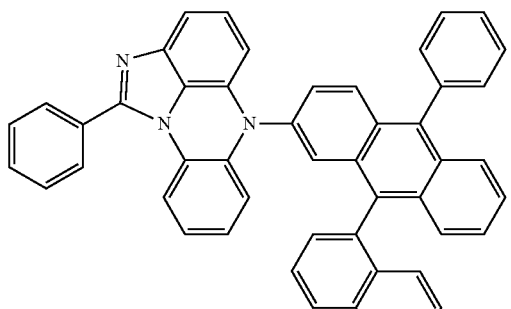
[Chemical Formula 12-23]
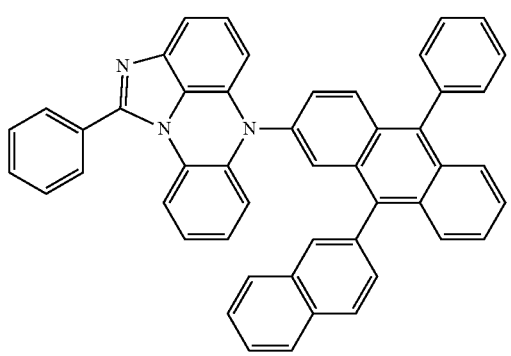
[Chemical Formula 12-24]
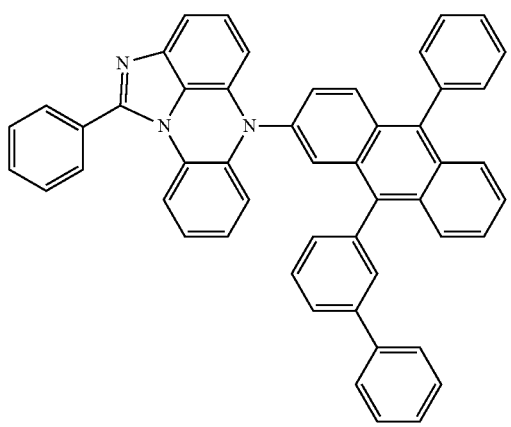
[Chemical Formula 12-25]
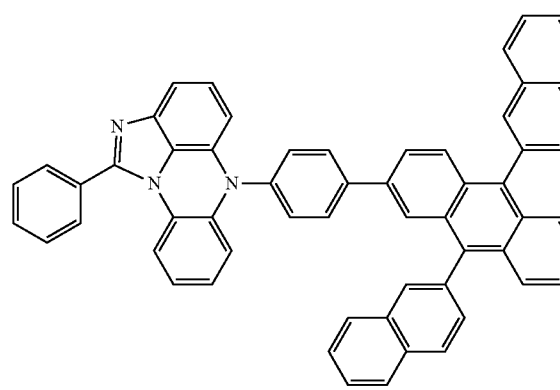
[Chemical Formula 12-26]
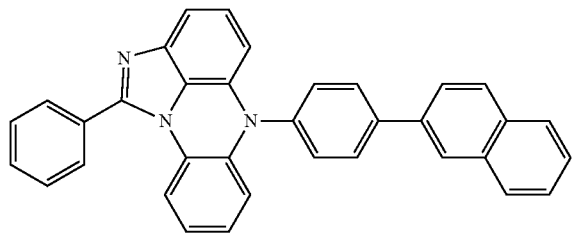
[Chemical Formula 12-27]
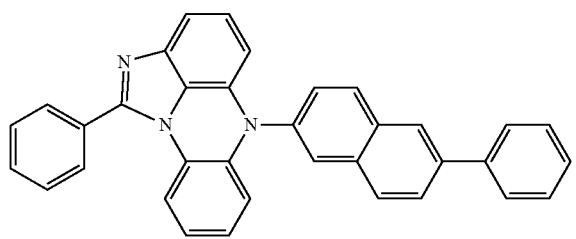
[Chemical Formula 12-28]
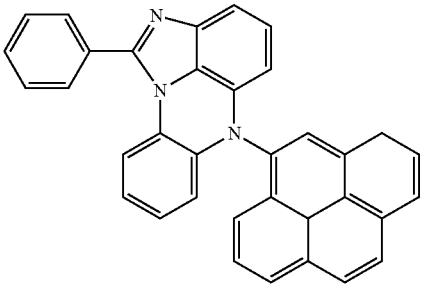
[Chemical Formula 12-29]
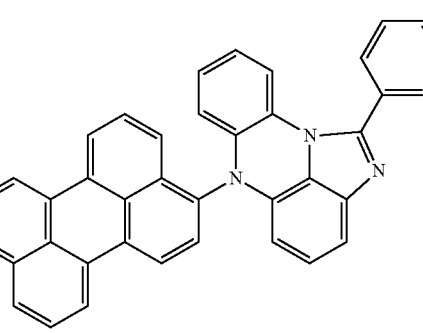
[Chemical Formula 12-30]
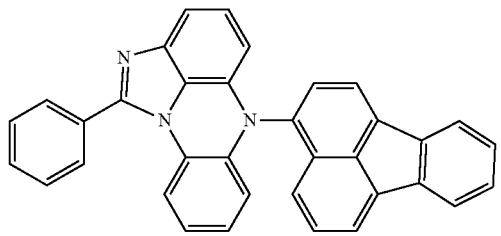

[Chemical Formula 12-31]
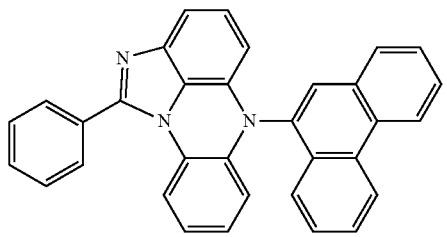
[Chemical Formula 12-32]
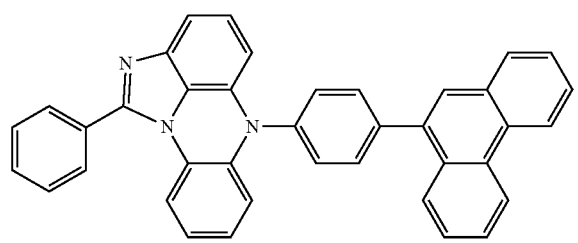
[Chemical Formula 12-33]
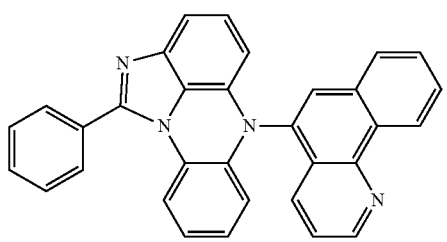
[Chemical Formula 12-34]
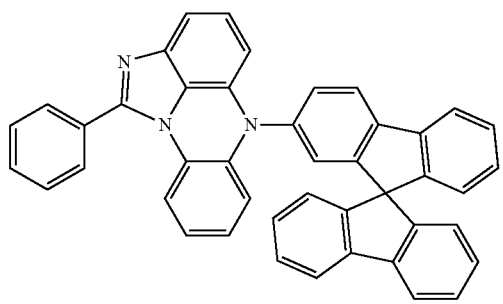
[Chemical Formula 12-35]
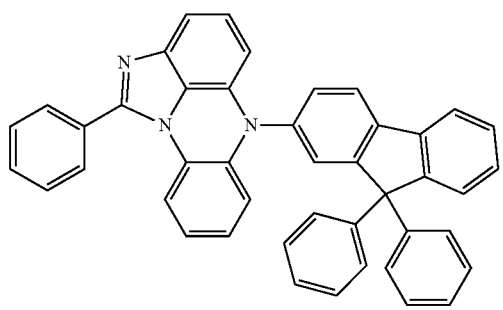
[Chemical Formula 12-36]
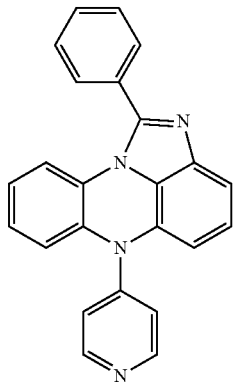
[Chemical Formula 12-37]
[Chemical Formula 12-38]
[Chemical Formula 12-39]
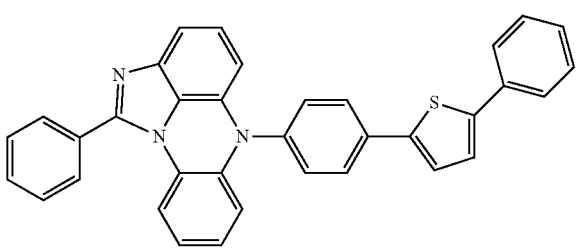

[Chemical Formula 12-40]
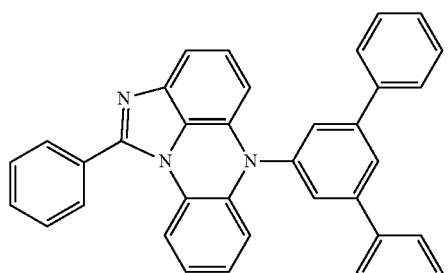
[Chemical Formula 12-41]
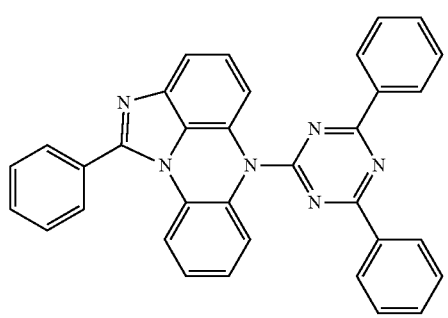
[Chemical Formula 12-42]
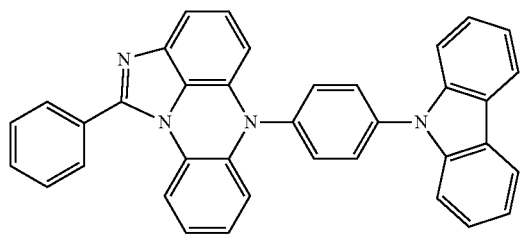
[Chemical Formula 12-43]
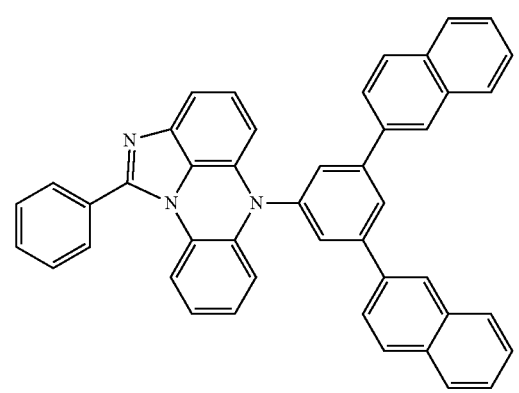
[Chemical Formula 12-44]
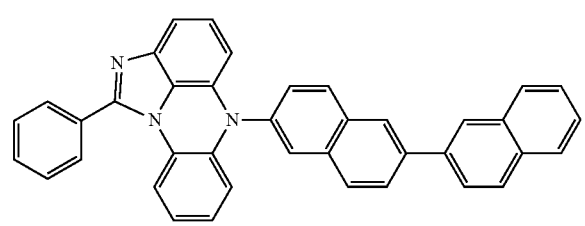
[Chemical Formula 12-45]
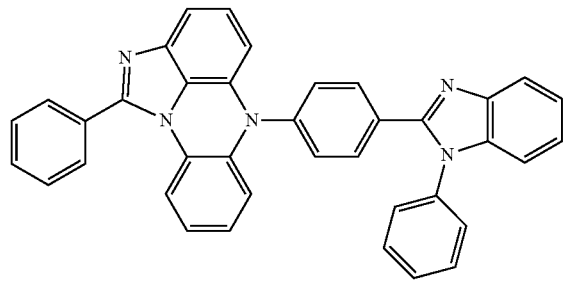
[Chemical Formula 12-46]
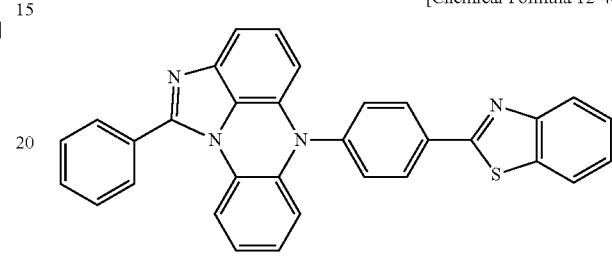
[Chemical Formula 12-47]
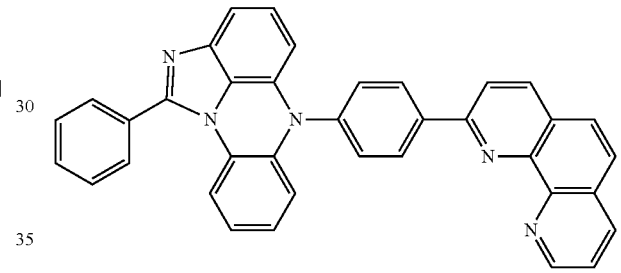
[Chemical Formula 12-48]
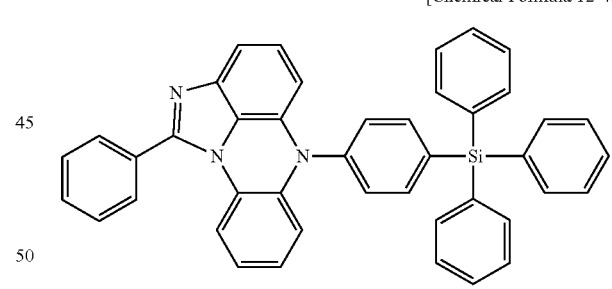
[Chemical Formula 12-49]
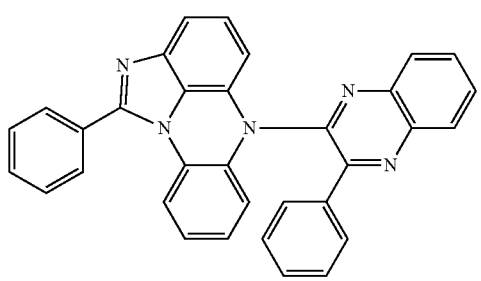

[Chemical Formula 12-50]
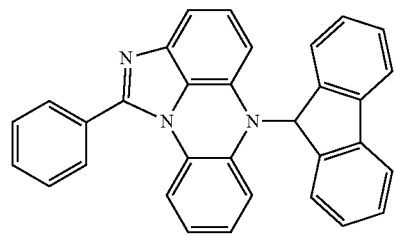
[Chemical Formula 12-51]
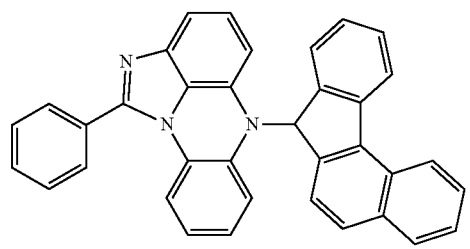
[Chemical Formula 12-52]
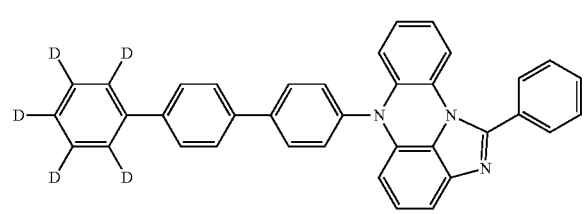
[Chemical Formula 12-53]
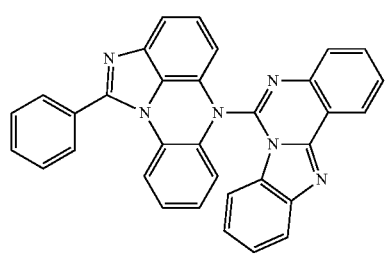
[Chemical Formula 12-54]
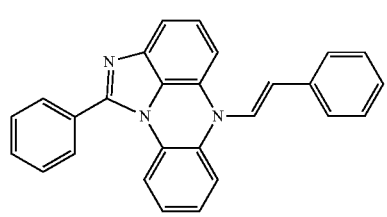
[Chemical Formula 13-1]
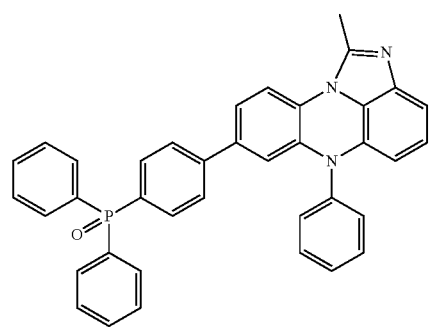
[Chemical Formula 13-2]
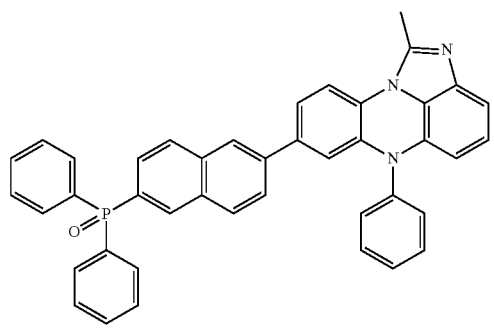
[Chemical Formula 13-3]
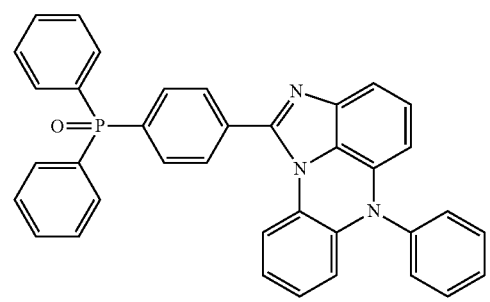
[Chemical Formula 13-4]
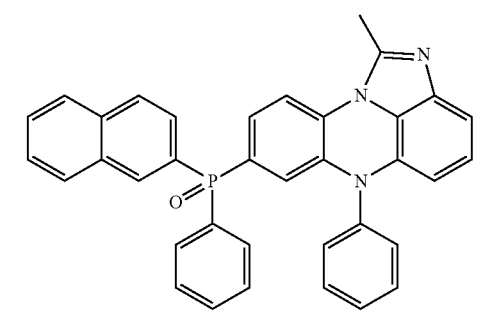
[Chemical Formula 13-5]
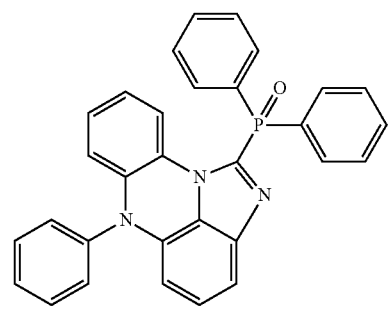
[Chemical Formula 13-6]
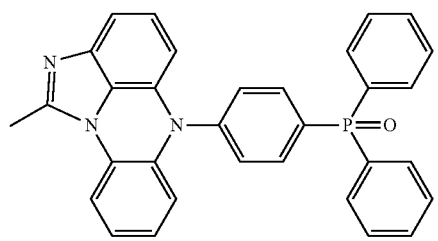

-continued

[Chemical Formula 13-7]

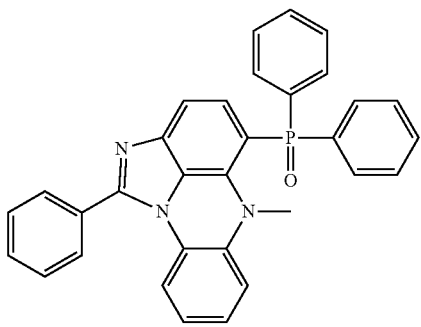

[Chemical Formula 13-8]

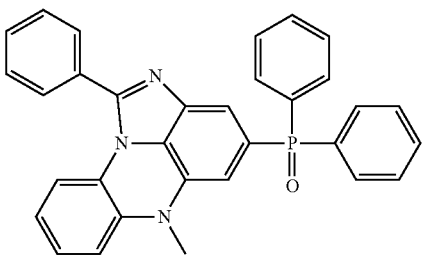

[Chemical Formula 13-9]

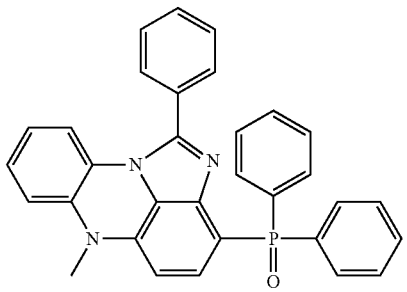

The compounds in the present specification may be prepared based on the preparation examples described below.

Specifically, according to one embodiment of the present specification, the heterocyclic compound of Chemical Formula 1 may be prepared through a cyclization reaction, and the heterocyclic compound represented by Chemical Formula 1 may be prepared by reacting R1 to R9 substituted with boronic acid or a dioxaborolane group, however, the preparation method is not limited thereto.

The present specification provides an organic light emitting device including the heterocyclic compound described above.

The present specification provides an organic light emitting device including a first electrode; a second electrode provided opposite to the first electrode; and one or more organic material layers including a light emitting layer provided between the first electrode and the second electrode, wherein one or more layers of the organic material layers include the heterocyclic compound described above.

In one embodiment of the present specification, the organic material layer includes an electron transfer layer, an electron injection layer or a layer carrying out electron transfer and electron injection at the same time, and the electron transfer layer, the electron injection layer or the layer carrying out electron transfer and electron injection at the same time includes the heterocyclic compound.

In one embodiment of the present specification, as an organic light emitting device including a first electrode; a second electrode provided opposite to the first electrode; a light emitting layer provided between the first electrode and the second electrode; and two or more organic material layers provided between the light emitting layer and the first electrode, or between the light emitting layer and the second electrode, at least one of the two or more organic material layers includes the heterocyclic compound. In one embodiment, as the two or more organic material layers, two or more may be selected from the group consisting of an electron transfer layer, an electron injection layer, a layer carrying out electron transfer and electron injection at the same time and a hole blocking layer.

In one embodiment of the present specification, the organic material layer includes two or more electron transfer layers, and at least one of the two or more electron transfer layers includes the heterocyclic compound. Specifically, in one embodiment of the present specification, the heterocyclic compound may be included in one layer of the two or more electron transfer layers, or in each of the two or more electron transfer layers.

In addition, in one embodiment of the present specification, when the heterocyclic compound is included in each of the two or more electron transfer layers, materials other than the heterocyclic compound may be the same as or different from each other.

In one embodiment of the present specification, the electron transfer layer, the electron injection layer or the layer carrying out electron transfer and electron injection at the same time is formed only with the heterocyclic compound.

In one embodiment of the present specification, the electron transfer layer, the electron injection layer or the layer carrying out electron transfer and electron injection at the same time includes the heterocyclic compound as a p-type host, and an n-type dopant as a dopant.

In one embodiment of the present specification, the n-type dopant includes alkali metals, alkali metal compounds, alkaline earth metals, alkaline earth metal compounds, or combinations thereof.

In one embodiment of the present specification, as the n-type dopant, one, two or more are selected from the group consisting of Li, Na, K, Rb, Cs, Mg, Ca, Sr, Ba, La, Nd, Sm, Eu, Tb, Yb, LiF, Li$_2$O, CsF or the following compounds.

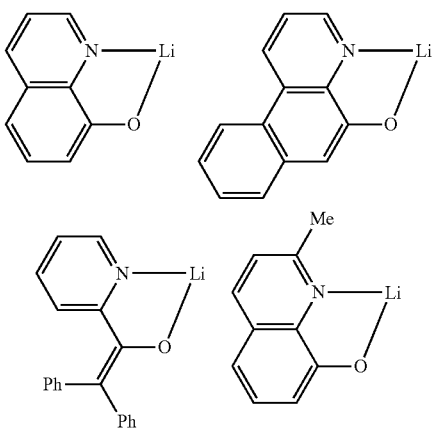

-continued

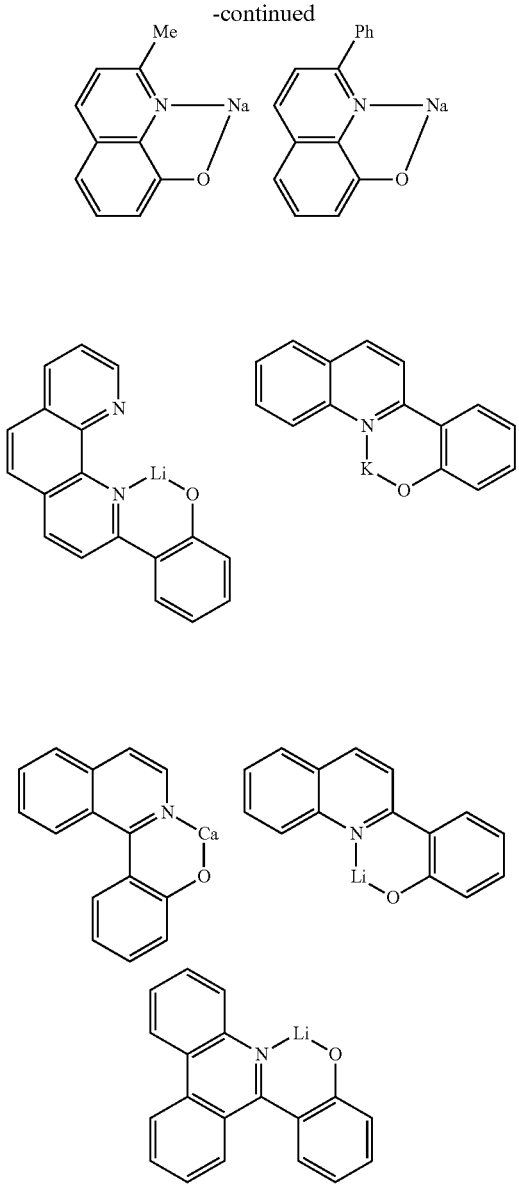

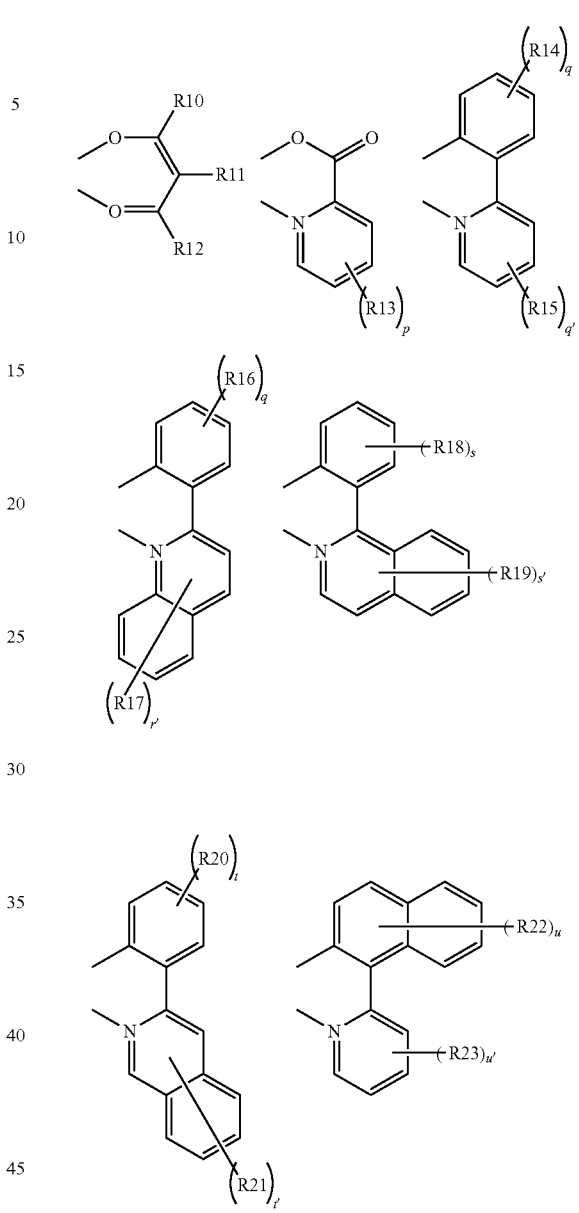

In one embodiment of the present specification, the light emitting layer includes the heterocyclic compound.

In one embodiment of the present specification, the light emitting layer includes the heterocyclic compound as a host, and includes a phosphorous dopant compound as a dopant.

In one embodiment of the present specification, the phosphorous dopant compound is represented by the following Chemical Formula 2.

[Chemical Formula 2]

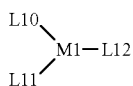

In Chemical Formula 2,

M1 is Ir or Os,

L10, L11 and L12 are the same as or different from each other, and each independently any one of the following structures,

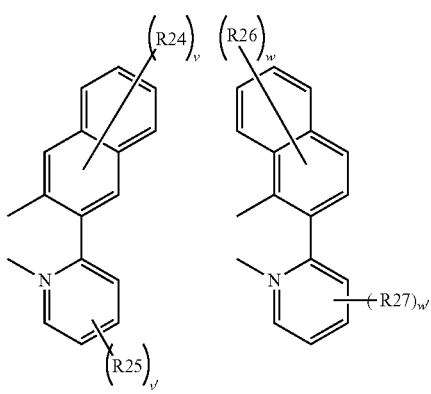

-continued

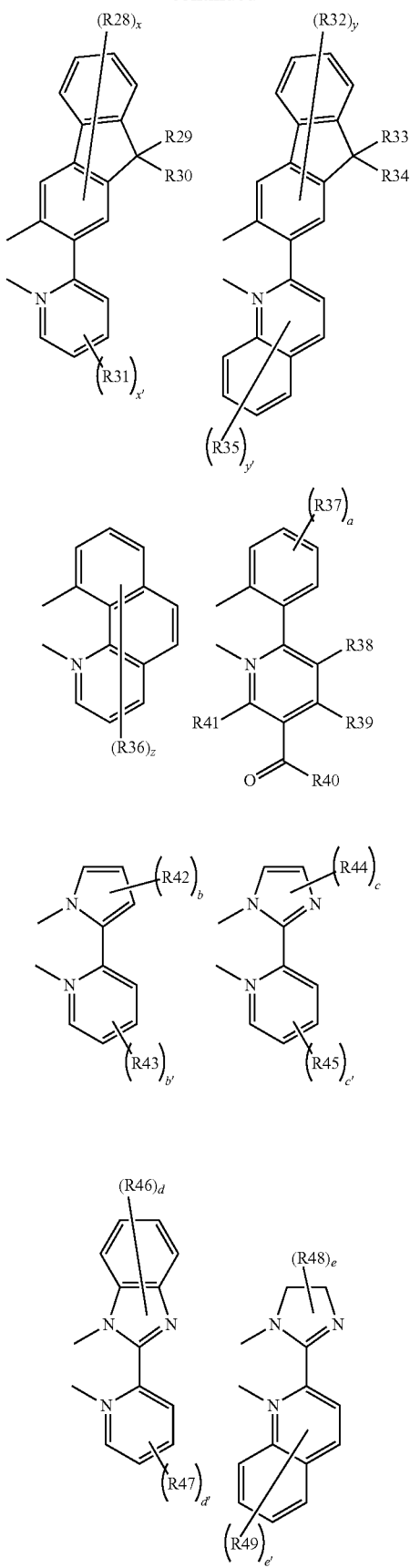

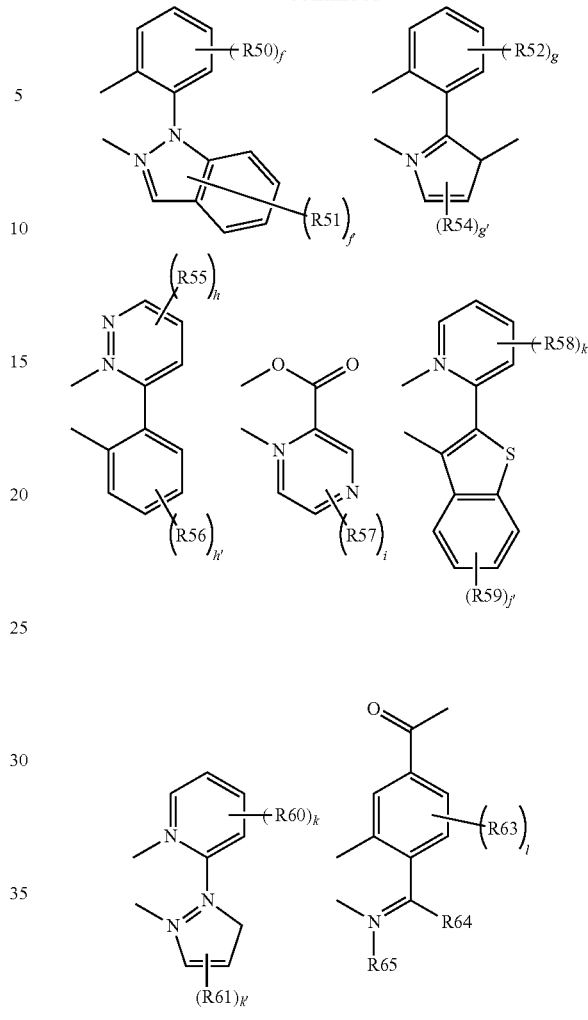

p, q, q', r, s, t, u', v', w', x', a, b', c', d, d', f, g, h', j, j' and k are each an integer of 0 to 4, r', s', t', u, v, w, x, y, y' and e' are each an integer of 0 to 6, b, e, h, i, k' and l are an integer of 0 to 3, c and g' are an integer of 0 to 2, f' is an integer of 0 to 5, z is an integer of 0 to 8, and R10 to R65 are the same as or different from each other, and each independently selected from the group consisting of hydrogen; deuterium; a halogen group; a cyano group; a substituted or unsubstituted $C_{2\sim10}$ alkylsilyl group; a substituted or unsubstituted $C_{6\sim30}$ arylsilyl group; a substituted or unsubstituted $C_{1\sim10}$ alkyl group; a substituted or unsubstituted $C_{2\sim10}$ alkenyl group; a substituted or unsubstituted $C_{1\sim10}$ alkoxy group; a substituted or unsubstituted $C_{6\sim20}$ aryl group; and a substituted or unsubstituted $C_{5\sim20}$ heteroring group, or adjacent groups form a monocyclic or multicyclic aliphatic, aromatic, heteroaliphatic or heteroaromatic fused ring.

In one embodiment of the present specification, the phosphorous dopant compound represented by Chemical Formula 2 is any one of the following compounds.

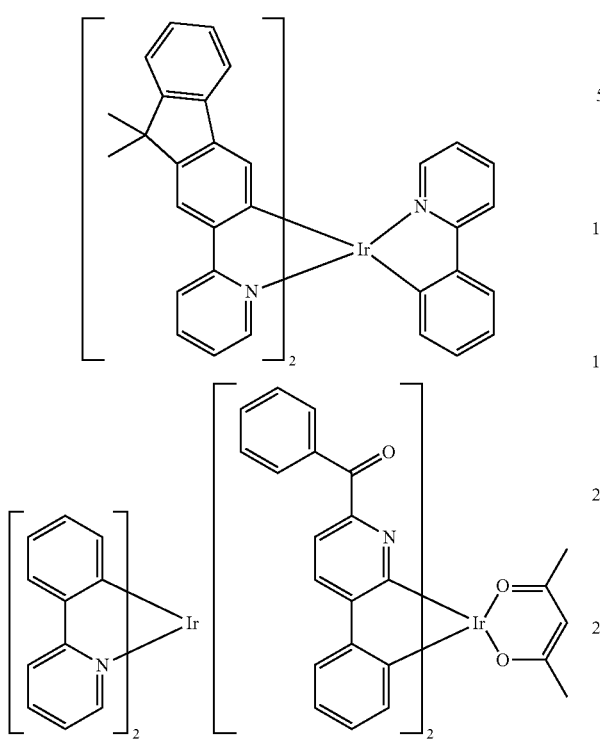
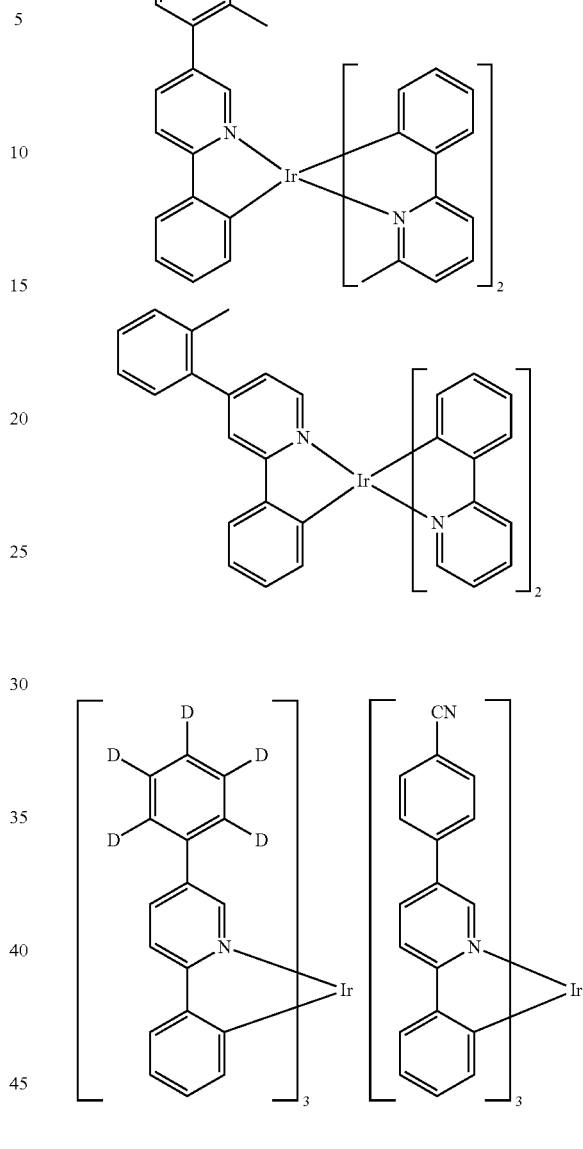
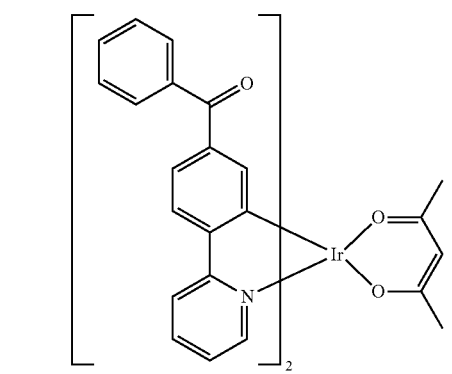
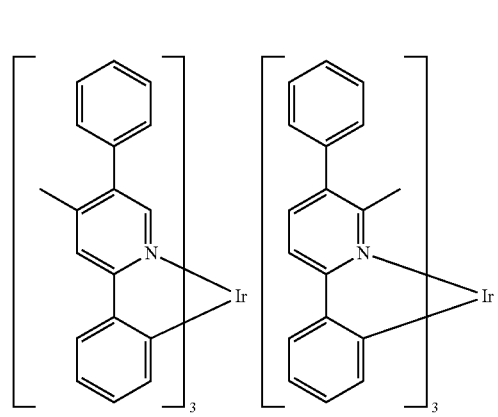
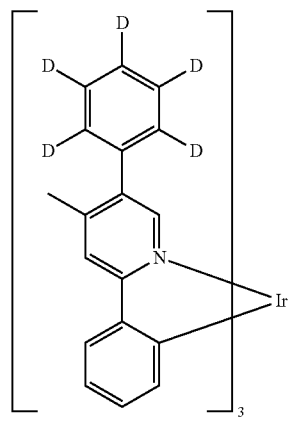

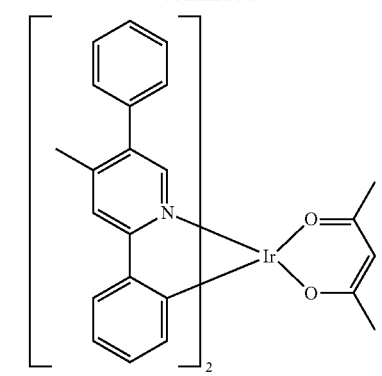
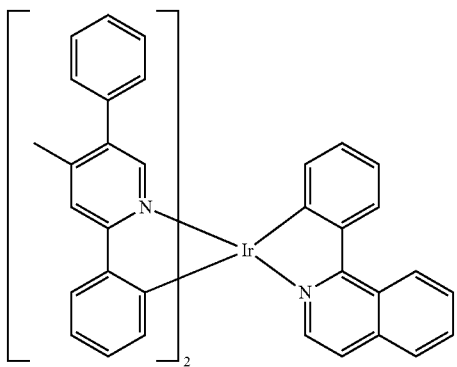
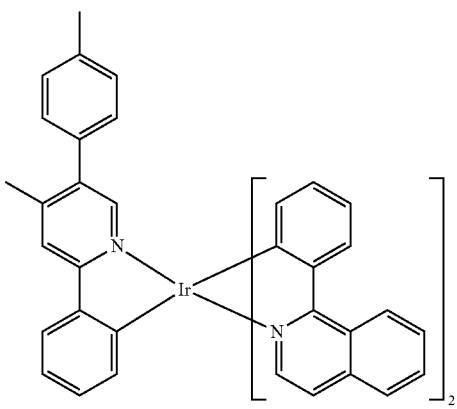
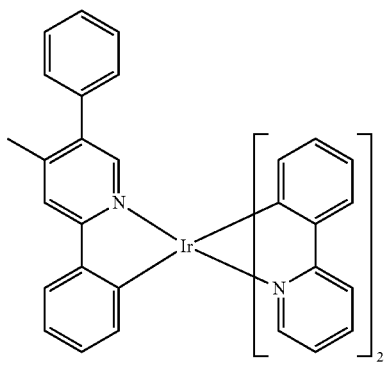
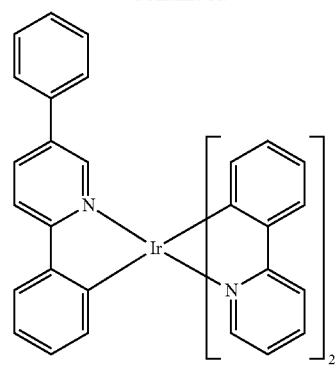
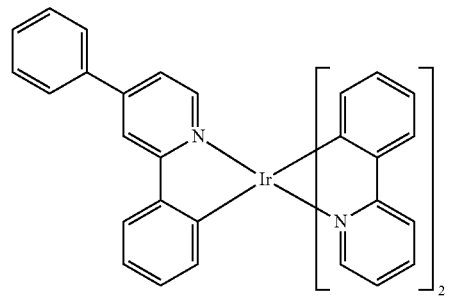
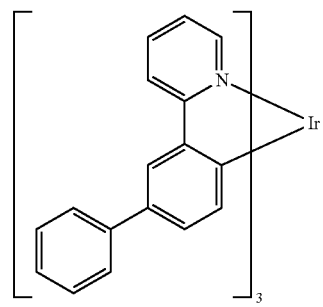
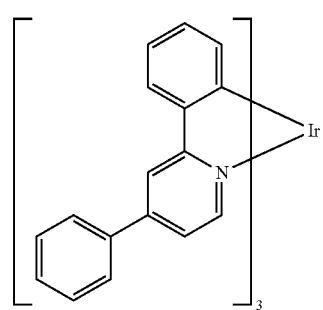
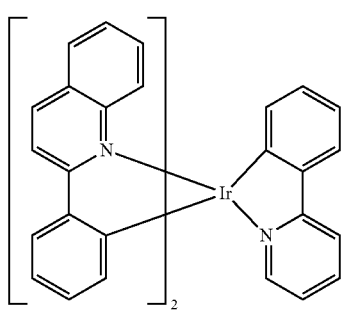

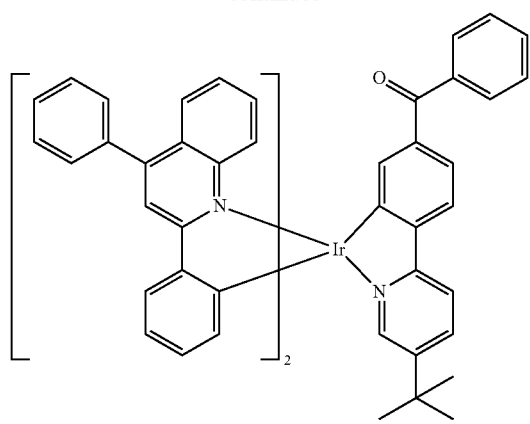
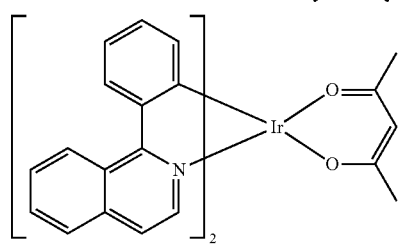
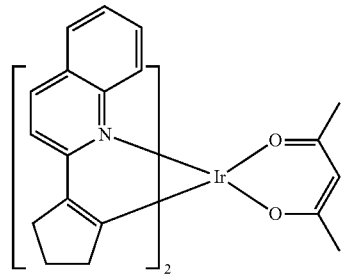
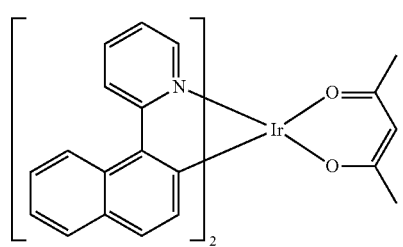
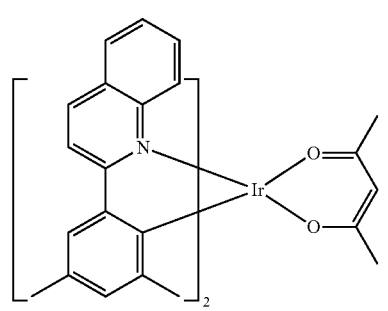
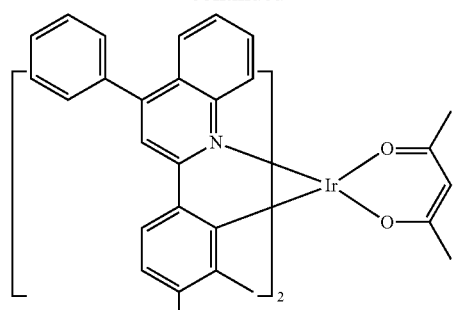
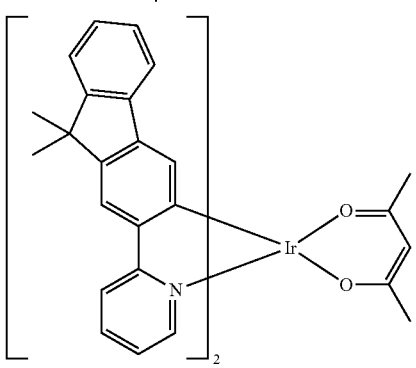
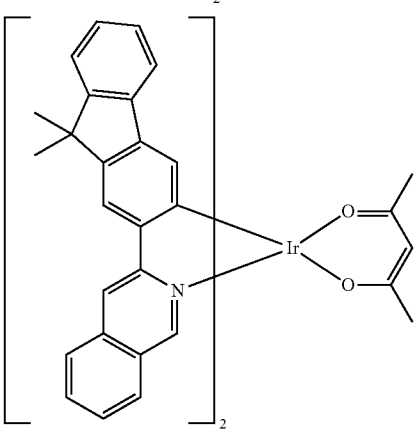
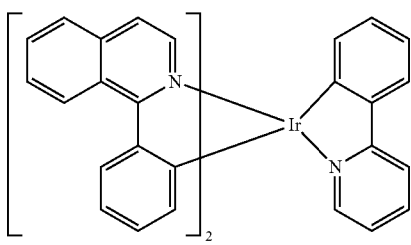
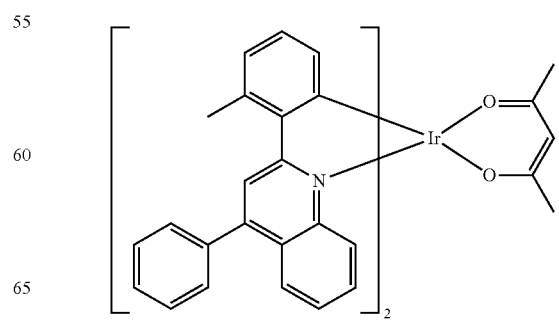

-continued

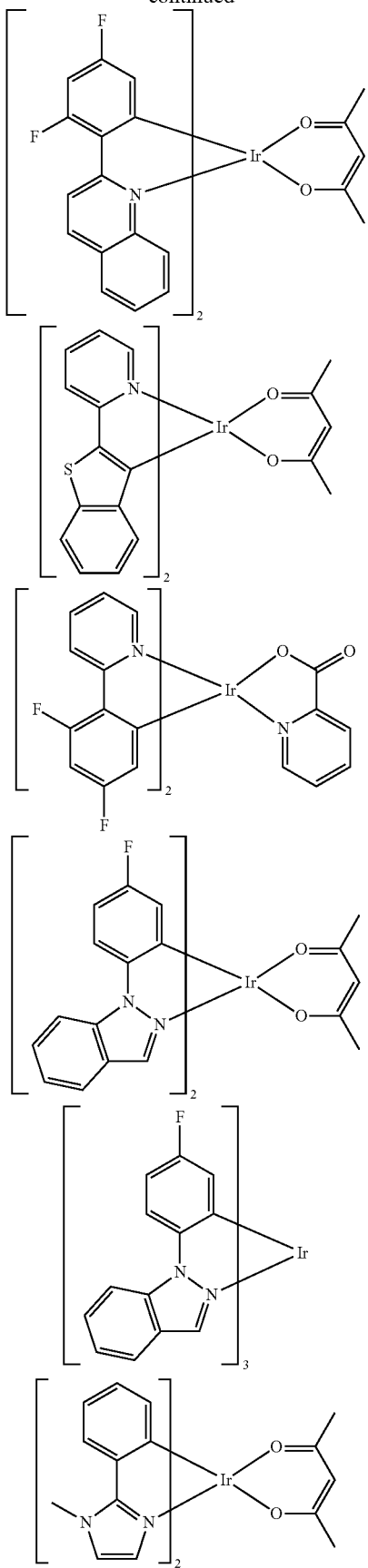

-continued

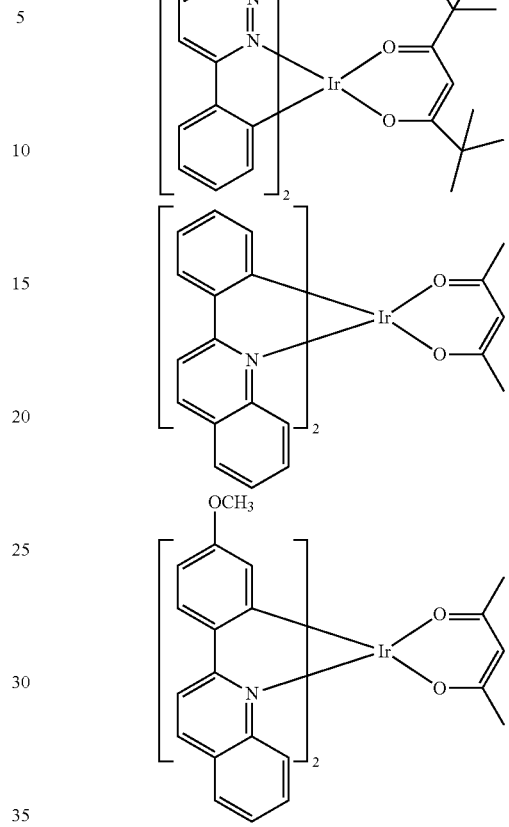

In one embodiment of the present specification, the organic material layer further includes one, two or more layers selected from the group consisting of a hole injection layer, a hole transfer layer, an electron transfer layer, an electron injection layer, an electron blocking layer and a hole blocking layer.

The organic material layer of the organic light emitting device in the present specification may be formed as a monolayer structure, but may also be formed as a multilayer structure in which two or more organic material layers are laminated. For example, the organic light emitting device of the present specification may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

In another embodiment, the organic light emitting device may be an organic light emitting device having a structure in which an anode, one or more organic material layers and a cathode are laminated in consecutive order on a substrate (normal type).

In another embodiment, the organic light emitting device may be an organic light emitting device having a structure in which a cathode, one or more organic material layers and an anode are laminated in consecutive order on a substrate (inverted type).

For example, the structures of an organic light emitting device according to the present invention are illustrated in FIGS. 1 to 5.

FIG. 1 illustrates the structure of an organic light emitting device in which an anode (2), a hole injection layer (3), a hole transfer layer (4), a light emitting layer (5), an electron transfer layer (6) and a cathode (7) are laminated in consecutive order on a substrate (1). In a structure such as this, the compound represented by Chemical Formula 1 may be included in the hole injection layer (3), the hole transfer layer (4), the light emitting layer (5) or the electron transfer layer (6).

FIG. 2 illustrates the structure of an organic light emitting device in which an anode (2), a hole injection layer (3), a hole transfer layer (4), a light emitting layer (5) and a cathode (7) are laminated in consecutive order on a substrate (1). In a structure such as this, the compound represented by Chemical Formula 1 may be included in the hole injection layer (3), the hole transfer layer (4) or the light emitting layer (5).

FIG. 3 illustrates the structure of an organic light emitting device in which an anode (2), a hole transfer layer (4), a light emitting layer (5), an electron transfer layer (6) and a cathode (7) are laminated in consecutive order on a substrate (1). In a structure such as this, the compound represented by Chemical Formula 1 may be included in the hole transfer layer (4), the light emitting layer (5) or the electron transfer layer (6).

FIG. 4 illustrates the structure of an organic light emitting device in which an anode (2), a light emitting layer (5), an electron transfer layer (6) and a cathode (7) are laminated in consecutive order on a substrate (1). In a structure such as this, the compound represented by Chemical Formula 1 may be included in the light emitting layer (5) or the electron transfer layer (6).

FIG. 5 illustrates the structure of an organic light emitting device in which an anode (2), a light emitting layer (5) and a cathode (7) are laminated in consecutive order on a substrate (1). In a structure such as this, the compound represented by Chemical Formula 1 may be included in the light emitting layer (5).

The organic light emitting device of the present specification may be prepared using materials and methods known in the art, except that one or more layers of the organic material layers include the compound of the present specification, that is, the heterocyclic compound.

For example, the organic light emitting device of the present specification may be prepared by laminating a first electrode, an organic material layer and a second electrode in consecutive order on a substrate. Herein, the organic light emitting device may be prepared by forming an anode on the substrate by depositing a metal, a metal oxide having a conductivity, or alloys thereof using a physical vapor deposition (PVD) method such as a sputtering method or an e-beam evaporation method, forming the organic material layer including a hole injection layer, a hole transfer layer, a light emitting layer and an electron transfer layer thereon, and then depositing a material capable of being used as a cathode thereon. In addition to this method, the organic light emitting device may be prepared by depositing a cathode material, an organic material layer and an anode material in consecutive order on a substrate.

In addition, the heterocyclic compound may be formed as the organic material layer using a solution coating method as well as a vacuum deposition method when the organic light emitting device is prepared. Herein, the solution coating method means spin coating, dip coating, doctor blading, ink jet printing, screen printing, a spray method, roll coating and the like, but is not limited thereto.

In one embodiment of the present specification, the first electrode is a cathode, and the second electrode is an anode.

In one embodiment of the present specification, the first electrode is an anode, and the second electrode is a cathode.

The substrate may be selected considering optical properties and physical properties as necessary. For example, the substrate is preferably transparent. The substrate may be formed with hard materials, but may also be formed with flexible materials such as plastic.

The substrate material may include, in addition to glass and a quartz plate, polyethyleneterephthalate (PET), polyethylene naphthalate (PEN), polypropylene (PP), polyimide (PI), polycarbonate (PC), polystyrene (PS), polyoxymethylene (POM), an acrylonitrile styrene copolymer (AS) resin, an acrylonitrile butadiene styrene copolymer (ABS) resin, triacetyl cellulose (TAC) and polyarylate (PAR) and the like, but is not limited thereto.

As the cathode material, a material having small work function is normally preferable so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the anode material, a material having large work function is normally preferable so that hole injection to the organic material layer is smooth. Specific examples of the anode material capable of being used in the present specification include metals such as vanadium, chromium, copper, zinc and gold, or alloys thereof; metal oxides such as zinc oxides, indium oxides, indium tin oxides (ITO) and indium zinc oxide (IZO); combinations of metals and oxides such as ZnO:Al or $SnO_2$:Sb; conductive polymers such as poly(3-methylthiophene), poly[3,4-(ethylen-1,2-dioxy)thiophene] (PEDOT), polypyrrole and polyaniline, and the like, but are not limited thereto.

The hole transfer layer is a layer that receives holes from a hole injection layer and transfers the holes to a light emitting layer, and as the hole transfer material, a material capable of receiving the holes from an anode or a hole injection layer, moving the holes to a light emitting layer, and having high mobility for the holes, is suitable. Specific examples thereof include an arylamin-based organic material, a conductive polymer, a block copolymer having conjugated parts and non-conjugated parts together, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include a metal porphyrin, oligothiophene, an arylamin-based organic material, a phthalocyanine derivative, a hexanitrile hexazatriphenylen-based organic material, a quinacridon-based organic material, a perylen-based organic material, anthraquinone, and a polyanilin- and a polythiophen-based conductive polymer, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include a 8-hydroxy-quinoline aluminum complex (Alq$_3$); a carbazole-based compound; a dimerized styryl compound; BAlq; a 10-hydroxybenzo quinolin-metal compound; a benzoxazole-, a benzthiazole- and a benzimidazole-based compound; a poly(p-phenylenevinylene) (PPV)-based polymer; a spiro compound; polyfluorene, rubrene, and the like, but are not limited thereto.

The light emitting layer may include a host material and a dopant material. The host material includes a fused aromatic ring derivative, a heteroring-containing compound or the like. Specifically, the fused aromatic ring derivative includes an anthracene derivative, a pyrene derivative, a naphthalene derivative, a pentacene derivative, a phenanthrene compound, a fluoranthene compound and the like, and the heteroring-containing compound includes a carbazole derivative, a dibenzofuran derivative, a ladder-type furan compound, a pyrimidine derivative and the like, but the material is not limited thereto.

The dopant material includes an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group and includes arylamino group-including pyrene, anthracene, crycene, periflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes an iridium complex, a platinum complex or the like, but is not limited thereto.

The electron transfer layer is a layer that receives electrons from an electron injection layer and transfers the electrons to a light emitting layer, and as the electron transfer material, a material capable of favorably receiving electrons from a cathode, moving the electrons to a light emitting layer, and having high mobility for the electrons, is suitable. Specific examples thereof include an Al complex of 8-hydroxyquinoline; a complex including Alq3; an organic radical compound; a hydroxyflavon-metal complex and the like, but are not limited thereto. The electron transfer layer may be used together with any desired cathode material as used according to existing technologies. Particularly, examples of the suitable cathode material include common materials that have small work function, and in which an aluminum layer or a silver layer follows. Specifically the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode and has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, a metal complex compound, a nitrogen-containing 5-membered ring derivative, and the like, but are not limited thereto.

The metal complex compound may include 8-hydroxy-quinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium, and the like, but is not limited thereto.

The hole blocking layer is a layer that blocks holes from reaching a cathode, and may generally be formed under the same condition as the hole injection layer. Specific examples thereof include an oxadiazole derivative or a triazole derivative, a phenanthroline derivative, BCP, an aluminum complex and the like, but are not limited thereto.

In one embodiment of the present specification, the organic light emitting device according to the present specification may be a top-emission type, a bottom-emission type or a dual-emission type depending on the materials used.

In one embodiment of the present specification, the heterocyclic compound may be included in an organic solar cell or an organic transistor in addition to an organic light emitting device.

The preparation of the heterocyclic compound represented by Chemical Formula 1 and the organic light emitting device including the heterocyclic compound will be described in detail in the following examples. However, the following examples are for illustrative purposes only, and the scope of the present specification is not limited thereto.

SYNTHESIS EXAMPLE

<Synthesis Example 1> Synthesis of Chemical Formula 2-1

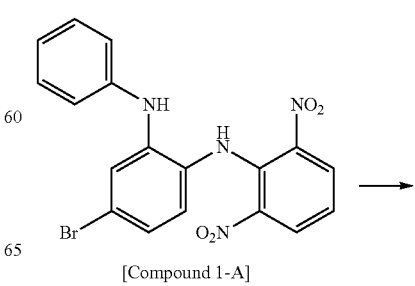

[Compound 1-A]

-continued

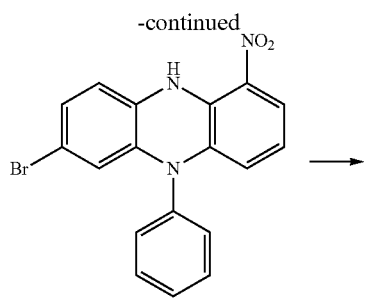

[Compound 1-B]

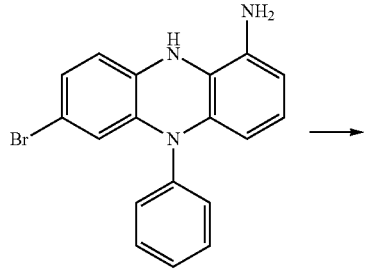

[Compound 1-C]

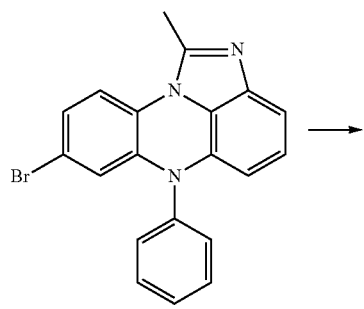

[Compound 1-B]

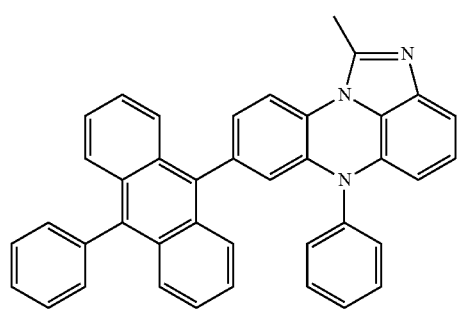

[Chemical Formula 2-1]

<Synthesis Example 1-1> Synthesis of Compound 1-A

After 2-chloro-1,3-dinitrobenzene (30 g, 148.1 mmol) was dissolved in anhydrous ethanol (200 ml), the mixture was stirred under nitrogen. 5-Bromo-$N^1$-phenylbenzene-1, 2-diamine (50.7 g, 192.5 mmol) and anhydrous sodium acetate (21.0 g, 255.8 mmol) were added thereto. The above solution was refluxed for 2 hours, and then cooled to room temperature when the reaction was complete. The precipitated solids were washed until the filtrate became colorless, and dried to obtain Compound 1-A (44.5 g, yield 70%; MS:$[M+H]^+$=429).

<Synthesis Example 1-2> Synthesis of Compound 1-B

Compound 1-A (44.5 g, 103.7 mmol) was placed in an aqueous 1% sodium hydroxide (NaOH) solution (685 ml), and the mixture was refluxed for 1 hour. After the result was cooled to room temperature, the produced solids were filtered under reduced pressure while being washed with hot water until the solids became neutral, and then the solids were dried to obtain Compound 1-B (35.2 g, yield 89%; MS:$[M+H]^+$=381).

<Synthesis Example 1-3> Synthesis of Compound 1-C

After Compound 1-B (35.2 g, 92.3 mmol) was dissolved in ethanol (26 ml), 10% Pd—C (0.98 g, 9.2 mmol) was added and dispersed thereto, and the mixture was cooled to 0° C. Hydrazine monohydrate (22 ml) was slowly added dropwise thereto. The mixture was heated for 30 minutes at 50° C. After the reaction was complete, the reaction product was cooled to room temperature, filtered using ethanol, and the filtrate was vacuum distilled to obtain Compound 1-C (32.2 g, yield 99.0%; MS:$[M+H]^+$=352).

<Synthesis Example 1-4> Synthesis of Compound 1-D

Compound 1-C (31.7 g, 90.0 mmol) and acetaldehyde (5.0 ml, 90.0 mmol) were refluxed for 1 hour in ethyl acetate (150 ml). After the ethyl acetate was removed under reduced pressure, the result was dissolved in chloroform (250 ml), and 2,3-dichloro-5,6-dicyano-1,4-benzoquinone (DDQ) (22.5 g, 99.1 mmol) was added thereto. The mixture was stirred for 1 hour at room temperature. The black solids obtained by vacuum distilling the mixture was columned using a tetrahydrofuran/hexane (THF/Hexane:1/3) solution to obtain Compound 1-D (21.0 g, yield 62.0%; MS:$[M+H]^+$=376).

<Synthesis Example 1-5> Synthesis of Chemical Formula 2-1

Compound 1-D (18.8 g, 50.0 mmol) and (10-phenylanthracen-9-yl)boronic acid (14.9 g, 50.0 mmol) were dissolved in tetrahydrofuran (THF). A 2 M potassium carbonate ($K_2CO_3$) solution (72 mL) and tetrakis(triphenylphosphine) palladium(0) (1.10 g, 1.91 mmol) were added thereto, and the result was refluxed for 6 hours. After the reaction was complete, the result was cooled to room temperature, filtered, and then washed several times with water and ethanol. The filtered solid product was recrystallized three times using chloroform and ethyl acetate to obtain a compound of Chemical Formula 2-1 (11.8 g, yield 43%; MS:$[M+H]^+$=550).

\<Synthesis Example 2\> Synthesis of Chemical Formula 3-1

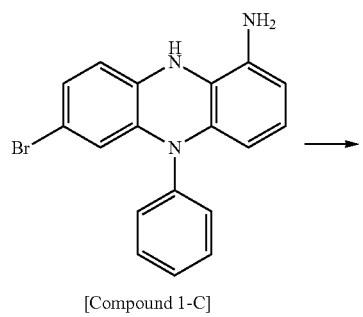

[Compound 1-C]

↓

[Compound 2-A]

↓

[Chemical Formula 3-1]

\<Synthesis Example 2-1\> Synthesis of Compound 2-A

Compound 2-A (31.3 g, yield 89.0%; MS:[M+H]$^+$=390) was obtained in the same manner as in Synthesis Example 1-4 except that propionaldehyde (6.5 ml, 90.0 mmol) was used instead of acetaldehyde.

\<Synthesis Example 2-2\> Synthesis of Chemical Formula 3-1

A compound of Chemical Formula 3-1 (18.0 g, yield 64%; MS:[M+H]$^+$=564) was obtained in the same manner as in Synthesis Example 1-5 except that Compound 2-A (19.5 g, 50.0 mmol) was used instead of Compound 1-D.

\<Synthesis Example 3\> Synthesis of Chemical Formula 3-4

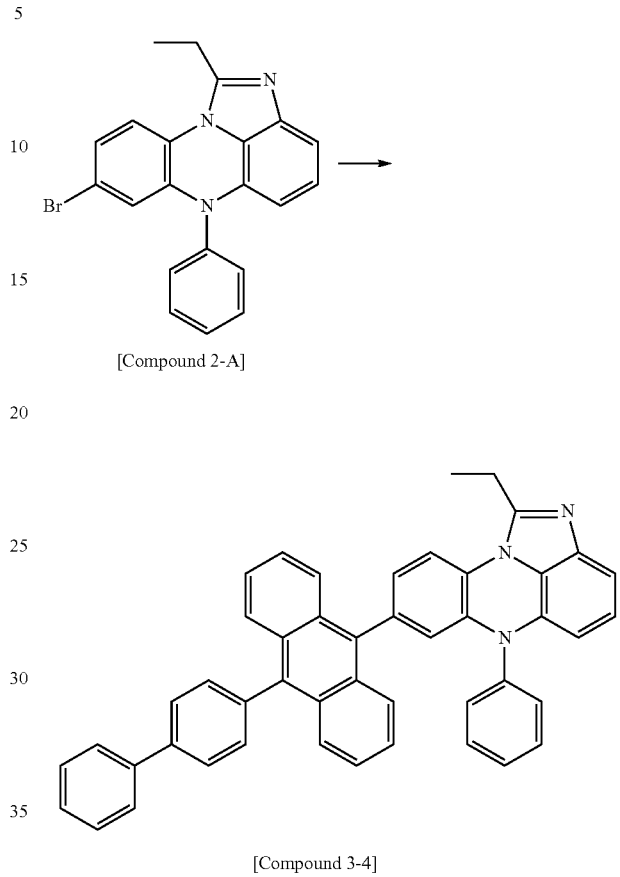

[Compound 2-A]

↓

[Compound 3-4]

A compound of Chemical Formula 3-4 (22.7 g, yield 71%; MS:[M+H]$^+$=640) was obtained in the same manner as in Synthesis Example 1-5 except that Compound 2-A (19.5 g, 50.0 mmol) was used instead of Compound 1-D, and (10-([1,1'-biphenyl]-4-yl)anthracen-9-yl)boronic acid (18.7 g, 50.0 mmol) was used instead of (10-phenylanthracen-9-yl)boronic acid.

\<Synthesis Example 4\> Synthesis of Chemical Formula 3-5

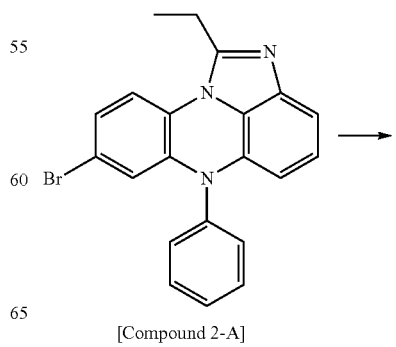

[Compound 2-A]

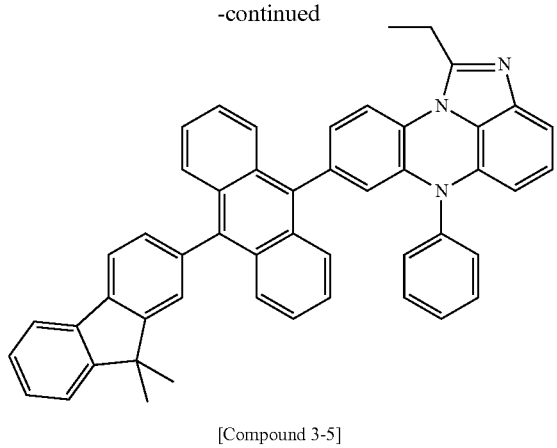

[Compound 3-5]

A compound of Chemical Formula 3-5 (23.5 g, yield 69%; MS:[M+H]⁺=680) was obtained in the same manner as in Synthesis Example 1-5 except that Compound 2-A (19.5 g, 50.0 mmol) was used instead of Compound 1-D, and (10-(9,9-dimethyl-9H-fluoren-2-yl)anthracen-9-yl)boronic acid (20.7 g, 50.0 mmol) was used instead of (10-phenylanthracen-9-yl)boronic acid.

<Synthesis Example 5> Synthesis of Chemical Formula 3-6

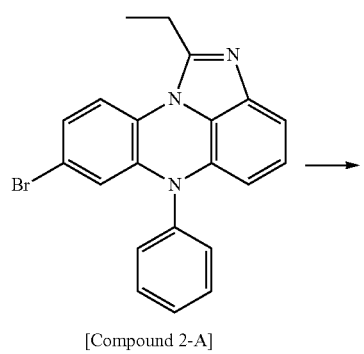

[Compound 2-A]

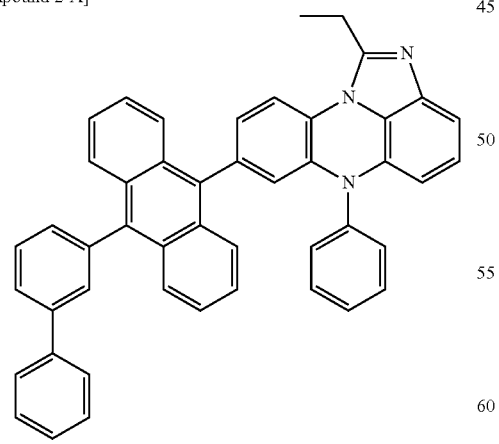

[Chemical Formula 3-6]

A compound of Chemical Formula 3-6 (18.2 g, yield 57%; MS:[M+H]⁺=640) was obtained in the same manner as in Synthesis Example 1-5 except that Compound 2-A (19.5 g, 50.0 mmol) was used instead of Compound 1-D, and (10-([1,1'-biphenyl]-3-yl)anthracen-9-yl)boronic acid (18.7 g, 50.0 mmol) was used instead of (10-phenylanthracen-9-yl)boronic acid.

<Synthesis Example 6> Synthesis of Chemical Formula 3-12

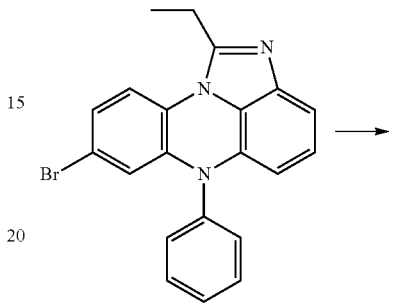

[Compound 2-A]

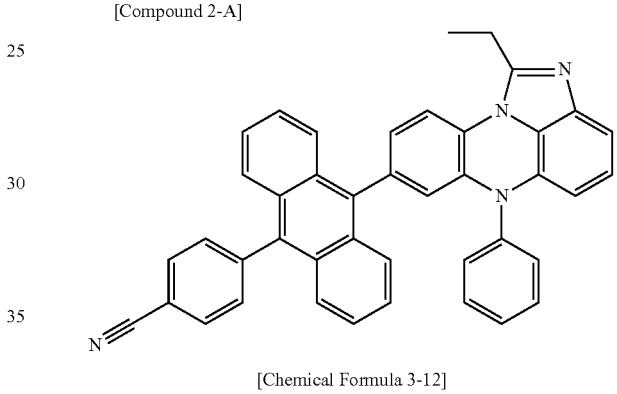

[Chemical Formula 3-12]

A compound of Chemical Formula 3-12 (15.6 g, yield 53%; MS:[M+H]⁺=514) was obtained in the same manner as in Synthesis Example 1-5 except that Compound 2-A (19.5 g, 50.0 mmol) was used instead of Compound 1-D, and (10-(4-cyanophenyl)anthracen-9-yl)boronic acid (16.2 g, 50.0 mmol) was used instead of (10-phenylanthracen-9-yl)boronic acid.

<Synthesis Example 7> Synthesis of Chemical Formula 3-18

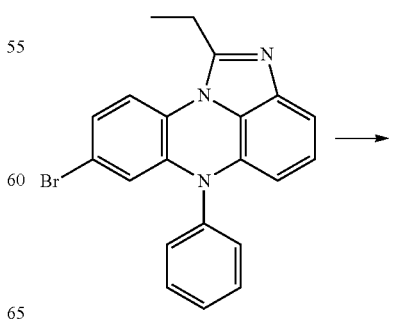

[Compound 2-A]

-continued

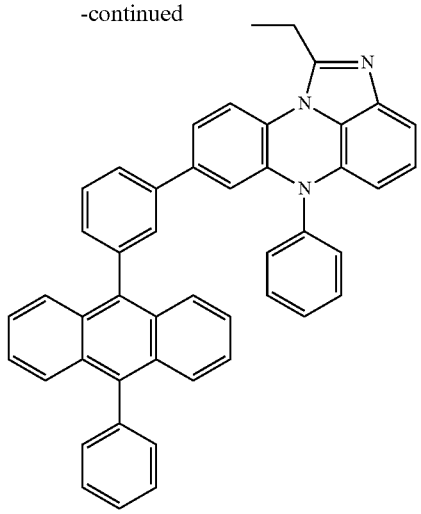

[Chemical Formula 3-18]

A compound of Chemical Formula 3-18 (18.9 g, yield 59%; MS:[M+H]⁺=640) was obtained in the same manner as in Synthesis Example 1-5 except that Compound 2-A (19.5 g, 50.0 mmol) was used instead of Compound 1-D, and (3-(10-phenylanthracen-9-yl)phenyl)boronic acid (18.7 g, 50.0 mmol) was used instead of (10-phenylanthracen-9-yl)boronic acid.

<Synthesis Example 8> Synthesis of Chemical Formula 3-19

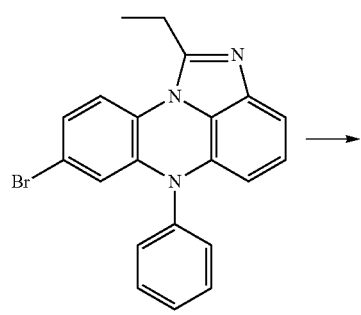

[Compound 2-A]

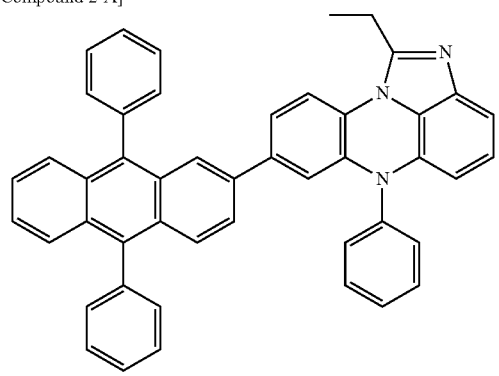

[Chemical Formula 3-19]

A compound of Chemical Formula 3-19 (20.8 g, yield 65%; MS:[M+H]⁺=640) was obtained in the same manner as in Synthesis Example 1-5 except that Compound 2-A (19.5 g, 50.0 mmol) was used instead of Compound 1-D, and 2-(9,10-diphenylanthracen-2-yl)-4,4,5,5-tetramethyl-1,3,2-dioxaborolane (22.8 g, 50.0 mmol) was used instead of (10-phenylanthracen-9-yl)boronic acid.

<Synthesis Example 9> Synthesis of Chemical Formula 3-26

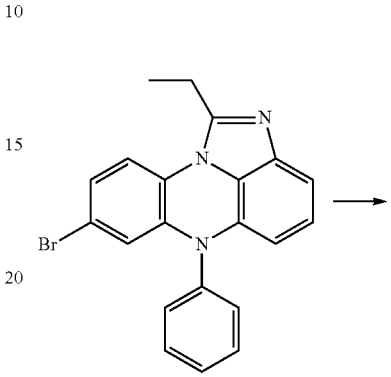

[Compound 2-A]

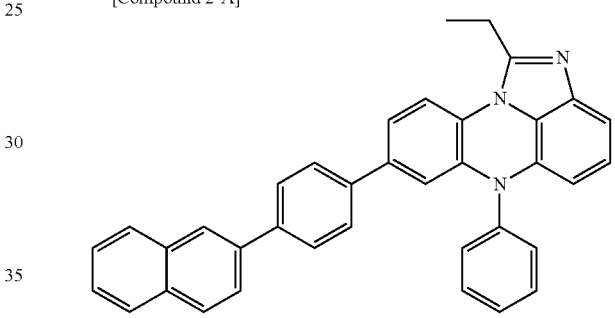

[Chemical Formula 3-26]

A compound of Chemical Formula 3-26 (18.7 g, yield 73%; MS:[M+H]⁺=514) was obtained in the same manner as in Synthesis Example 1-5 except that Compound 2-A (19.5 g, 50.0 mmol) was used instead of Compound 1-D, and (4-(naphthalen-2-yl)phenyl)boronic acid (12.4 g, 50.0 mmol) was used instead of (10-phenylanthracen-9-yl)boronic acid.

<Synthesis Example 10> Synthesis of Chemical Formula 3-28

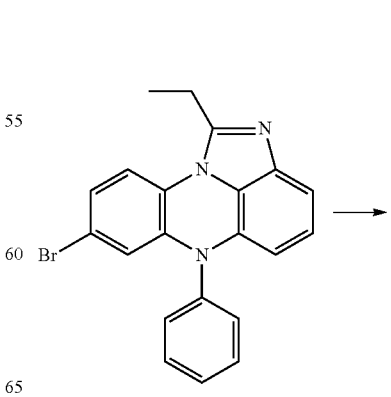

[Compound 2-A]

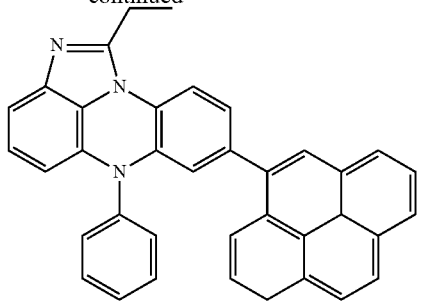

[Chemical Formula 3-28]

A compound of Chemical Formula 3-28 (20.0 g, yield 78%; MS:[M+H]$^+$=514) was obtained in the same manner as in Synthesis Example 1-5 except that Compound 2-A (19.5 g, 50.0 mmol) was used instead of Compound 1-D, and (3,8-dihydropyren-4-yl)boronic acid (12.4 g, 50.0 mmol) was used instead of (10-phenylanthracen-9-yl)boronic acid.

<Synthesis Example 11> Synthesis of Chemical Formula 3-29

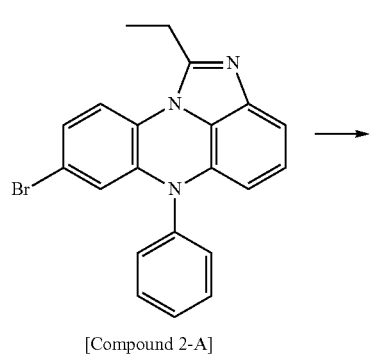

[Compound 2-A]

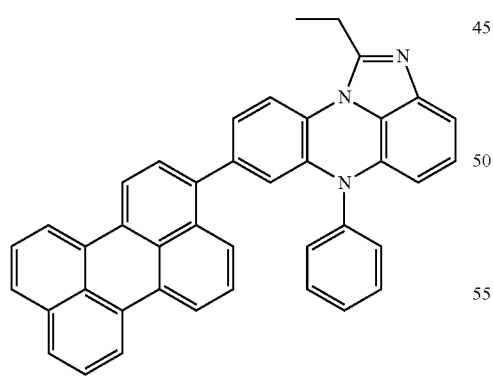

[Chemical Formula 3-29]

A compound of Chemical Formula 3-29 (18.8 g, yield 67%; MS:[M+H]$^+$=562) was obtained in the same manner as in Synthesis Example 1-5 except that Compound 2-A (19.5 g, 50.0 mmol) was used instead of Compound 1-D, and perylen-3-ylboronic acid (14.8 g, 50.0 mmol) was used instead of (10-phenylanthracen-9-yl)boronic acid.

<Synthesis Example 12> Synthesis of Chemical Formula 3-30

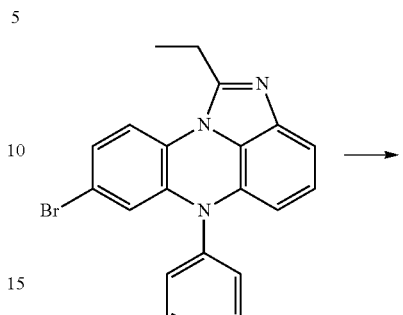

[Compound 2-A]

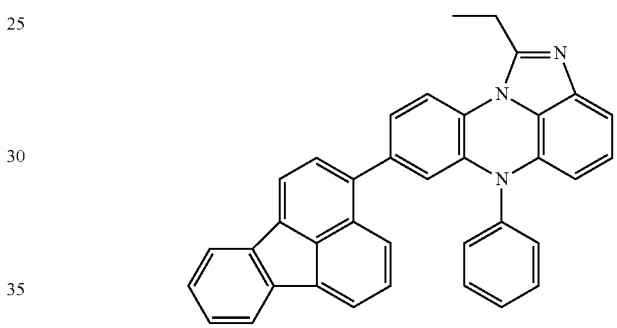

[Chemical Formula 3-30]

A compound of Chemical Formula 3-30 (15.6 g, yield 61%; MS:[M+H]$^+$=512) was obtained in the same manner as in Synthesis Example 1-5 except that Compound 2-A (19.5 g, 50.0 mmol) was used instead of Compound 1-D, and fluoranthen-3-ylboronic acid (12.3 g, 50.0 mmol) was used instead of (10-phenylanthracen-9-yl)boronic acid.

<Synthesis Example 13> Synthesis of Chemical Formula 3-34

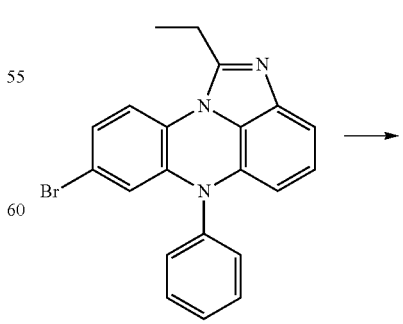

[Compound 2-A]

167
-continued

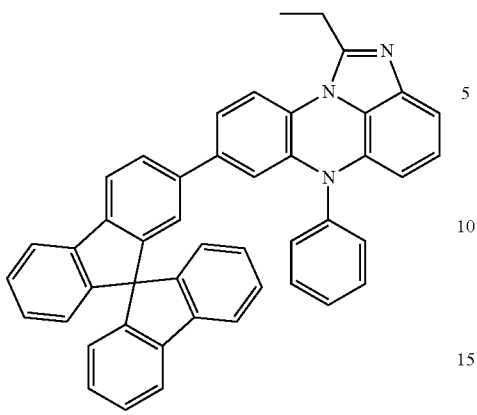

[Chemical Formula 3-34]

A compound of Chemical Formula 3-34 (17.8 g, yield 57%; MS:[M+H]$^+$=626) was obtained in the same manner as in Synthesis Example 1-5 except that Compound 2-A (19.5 g, 50.0 mmol) was used instead of Compound 1-D, and 9,9'-spirobi[fluoren]-2-ylboronic acid (18.0 g, 50.0 mmol) was used instead of (10-phenylanthracen-9-yl)boronic acid.

<Synthesis Example 14> Synthesis of Chemical Formula 4-1

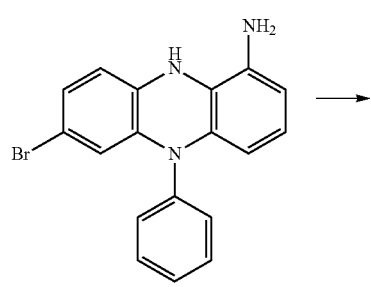

[Compound 1-C]

168
-continued

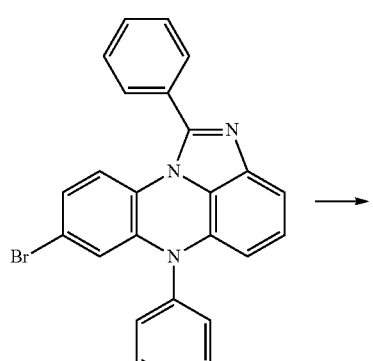

[Chemical Formula 4-1]

<Synthesis Example 14-1> Synthesis of Compound 14-A

Compound 14-A (35.5 g, yield 90%; MS:[M+H]$^+$=438) was obtained in the same manner as in Synthesis Example 1-4 except that benzaldehyde (95.4 g, 90.0 mmol) was used instead of acetaldehyde.

<Synthesis Example 14-2> Synthesis of Chemical Formula 4-1

A compound of Chemical Formula 4-1 (24.8 g, yield 81%; MS:[M+H]$^+$=612) was obtained in the same manner as in Synthesis Example 1-5 except that Compound 14-A (18.2 g, 50.0 mmol) was used instead of Compound 1-D.

<Synthesis Example 15> Synthesis of Chemical Formula 4-26

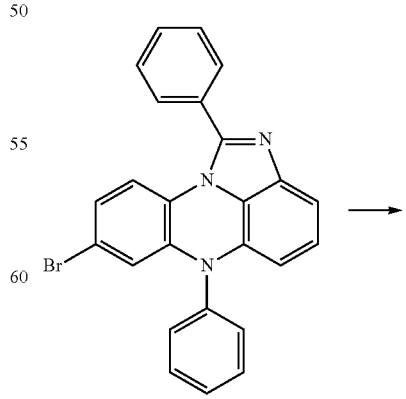

[Compound 14-A]

[Compound 14-A]

-continued

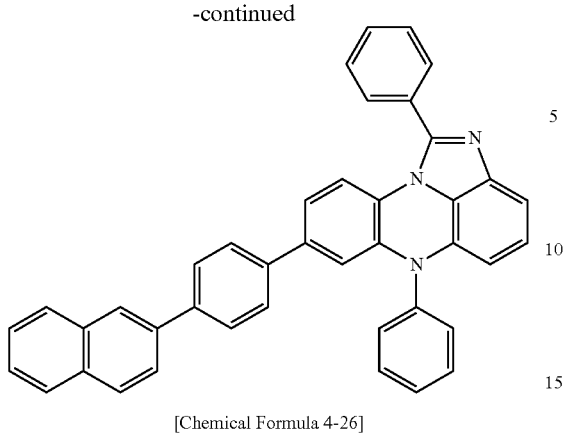

[Chemical Formula 4-26]

A compound of Chemical Formula 4-26 (22.2 g, yield 79%; MS:[M+H]$^+$=562) was obtained in the same manner as in Synthesis Example 1-5 except that Compound 14-A (18.2 g, 50.0 mmol) was used instead of Compound 1-D, and (4-(naphthalen-2-yl)phenyl)boronic acid (12.4 g, 50.0 mmol) was used instead of (10-phenylanthracen-9-yl)boronic acid.

<Synthesis Example 16> Synthesis of Chemical Formula 4-40

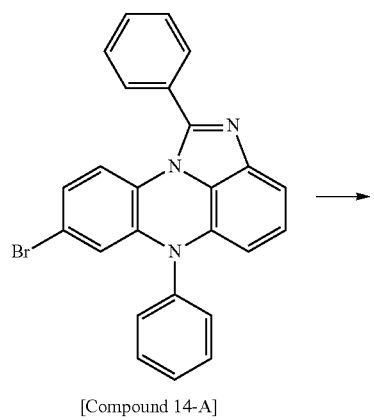

[Compound 14-A]

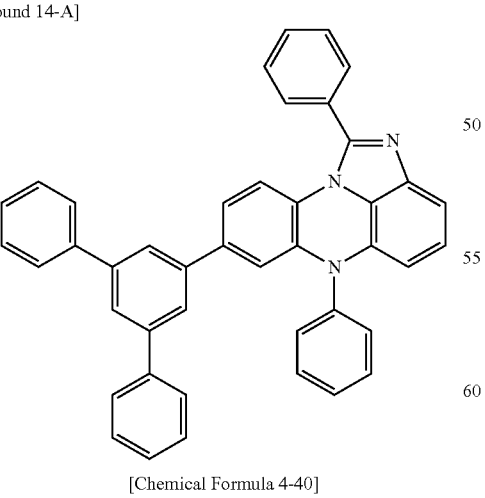

[Chemical Formula 4-40]

A compound of Chemical Formula 4-40 (19.1 g, yield 65%; MS:[M+H]$^+$=588) was obtained in the same manner as in Synthesis Example 1-5 except that Compound 14-A (18.2 g, 50.0 mmol) was used instead of Compound 1-D, and [1,1':3',1''-terphenyl]-5'-ylboronic acid (13.7 g, 50.0 mmol) was used instead of (10-phenylanthracen-9-yl)boronic acid.

<Synthesis Example 17> Synthesis of Chemical Formula 4-41

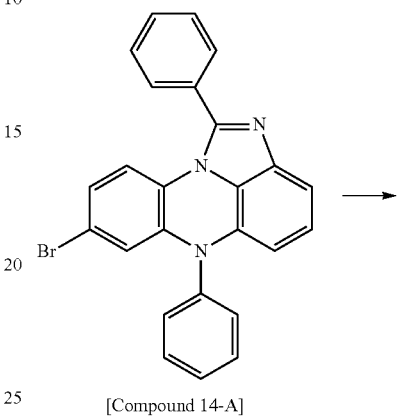

[Compound 14-A]

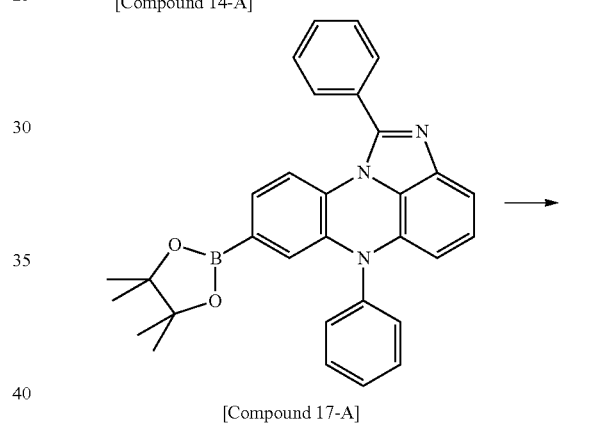

[Compound 17-A]

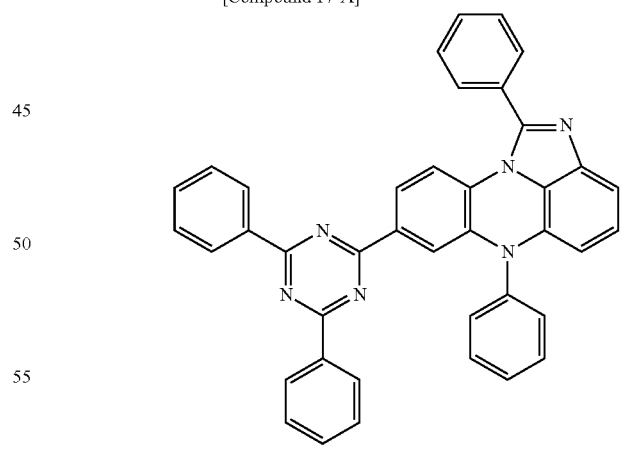

[Chemical Formula 4-41]

<Synthesis Example 17-1> Synthesis of Compound 17-A

Compound 14-A (30.7 g, 70.0 mmol), bis(pinacolato)diborone (19.6 g, 77.0 mmol), potassium acetate (20.6 g, 210 mmol), [1,1'-bis(diphenylphosphino)ferrocene]dichloropalladium(II) (1.2 g, 2.1 mmol) and tricyclohexylphosphine (1.2 g, 2.4 mmol) were placed in dioxane (350 ml), and the mixture was refluxed for 12 hours. After the reaction was complete, the result was cooled to room temperature, and vacuum distilled to remove the solvent. The result was dissolved in chloroform, washed three times with water, and the organic layer was separated and dried using magnesium sulfate. The resulting organic layer was vacuum distilled to obtain Compound 17-A (27.2 g, yield 80%; MS:[M+H]$^+$=486).

<Synthesis Example 17-2> Synthesis of Chemical Formula 4-41

Compound 17-A (24.3 g, 50 mmol) and 2-chloro-4,6-diphenyl-1,3,5-triazine (13.4 g, 50 mmol) were dissolved in tetrahydrofuran (THF). A 2M potassium carbonate (K$_2$CO$_3$) solution (72 mL) and tetrakis(triphenylphosphine) palladium(0) (1.10 g, 1.91 mmol) were added thereto, and the result was refluxed for 1 hour. After the reaction was complete, the result was cooled to room temperature, filtered, and then washed with water and ethanol. The filtered solid product was purified by column chromatography using tetrahydrofuran/hexane (THF/Hexane:1/5) to obtain a compound of Chemical Formula 4-41 (12.7 g, yield 43%; MS:[M+H]$^+$=591).

<Synthesis Example 18> Synthesis of Chemical Formula 5-17

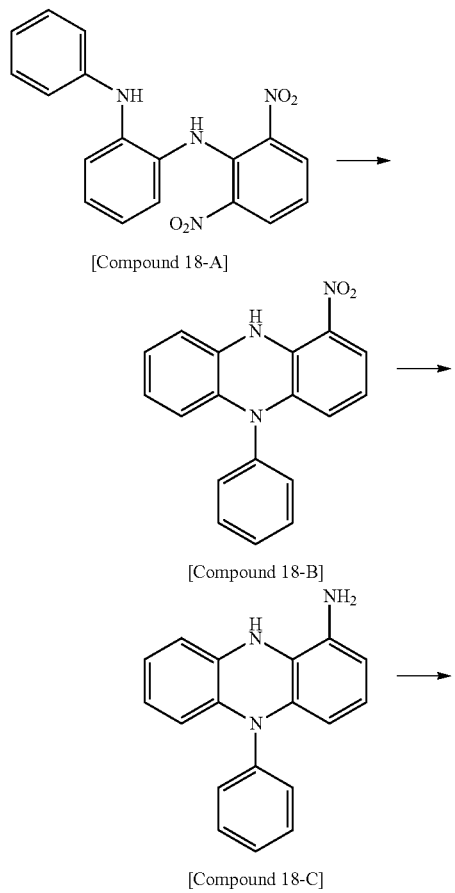

[Compound 18-A]

[Compound 18-B]

[Compound 18-C]

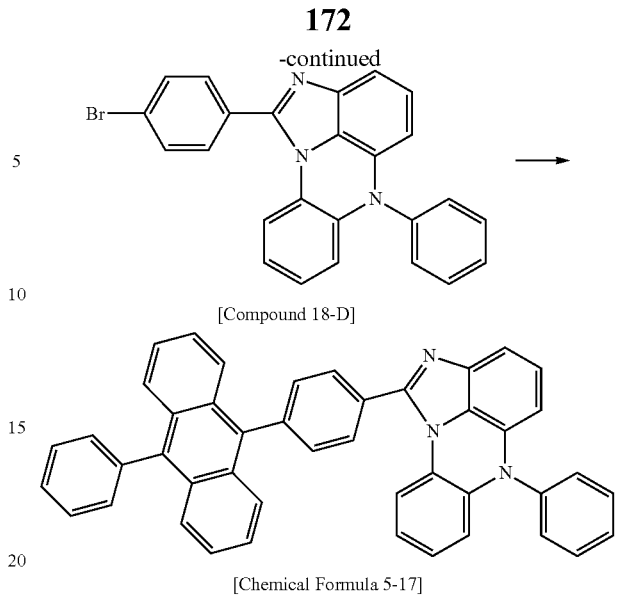

[Compound 18-D]

[Chemical Formula 5-17]

<Synthesis Example 18-1> Synthesis of Compound 18-A

After 2-chloro-1,3-dinitrobenzene (30 g, 148.1 mmol) was dissolved in anhydrous ethanol (200 ml), the mixture was stirred under nitrogen. N$^1$-phenylbenzene-1,2-diamine (35.5 g, 192.5 mmol) and anhydrous sodium acetate (21.0 g, 255.8 mmol) were added thereto. The above solution was refluxed for 2 hours, and then cooled to room temperature when the reaction was complete. The precipitated solids were washed until the filtrate became colorless, and dried to obtain Compound 18-A (37.9 g, yield 73%; MS:[M+H]$^+$=351).

<Synthesis Example 18-2> Synthesis of Compound 18-B

Compound 18-A (37.9 g, 108.1 mmol) was placed in an aqueous 1% sodium hydroxide solution (715 ml), and the mixture was refluxed for 1 hour. After the result was cooled to room temperature, the produced solids were filtered under reduced pressure while being washed with hot water until the solids became neutral, and then the solids were dried to obtain Compound 18-B (27.5 g, yield 84%; MS:[M+H]$^+$=304).

<Synthesis Example 18-3> Synthesis of Compound 18-C

After Compound 18-B (27.5 g, 90.8 mmol) was dissolved in ethanol (25 ml), 10% Pd—C (0.96 g, 9.1 mmol) was added and dispersed thereto, and the mixture was cooled to 0° C. Hydrazine monohydrate (22 ml) was slowly added dropwise thereto. The mixture was heated for 30 minutes at 50° C. After the reaction was complete, the reaction product was cooled to room temperature, filtered using ethanol, and the filtrate was vacuum distilled to obtain Compound 18-C (24.6 g, yield 99.0%; MS:[M+H]$^+$=274).

<Synthesis Example 18-4> Synthesis of Compound 18-D

Compound 18-C (23.2 g, 85.0 mmol) and 4-bromobenzaldehyde (15.7 g, 85.0 mmol) were refluxed for 1 hour in ethyl acetate (150 ml). After the ethyl acetate was removed under reduced pressure, the result was dissolved in chloroform (250 ml), and 2,3-dichloro-5,6-dicyano-1,4-benzoquinone (DDQ) (21.3 g, 94.0 mmol) was added thereto. The mixture was stirred for 1 hour at room temperature. The black solids obtained by vacuum distilling the mixture was columned using a tetrahydrofuran/hexane (THF/Hexane:1/4) solution to obtain Compound 18-D (24.2 g, yield 65.0%; MS:[M+H]$^+$=438).

<Synthesis Example 18-5> Synthesis of Chemical Formula 5-17

Compound 18-D (21.9 g, 50.0 mmol) and (10-phenylanthracen-9-yl)boronic acid (14.9 g, 50.0 mmol) were dissolved in tetrahydrofuran (THF). A 2 M potassium carbonate ($K_2CO_3$) solution (72 mL) and tetrakis(triphenylphosphine)palladium(0) (1.10 g, 1.91 mmol) were added thereto, and the result was refluxed for 3 hours. After the reaction was complete, the result was cooled to room temperature, filtered, and then washed several times with water and ethanol. The filtered solid product was recrystallized three times using chloroform and ethyl acetate to obtain a compound of Chemical Formula 5-17 (14.7 g, yield 48%; MS:[M+H]$^+$=184).

<Synthesis Example 19> Synthesis of Chemical Formula 6-17

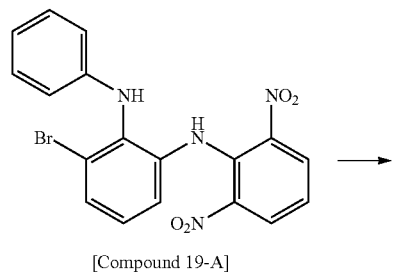

[Compound 19-A]

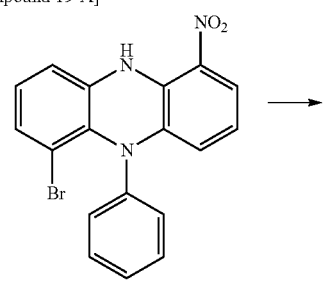

[Compound 19-B]

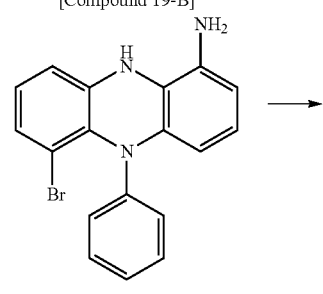

[Compound 19-C]

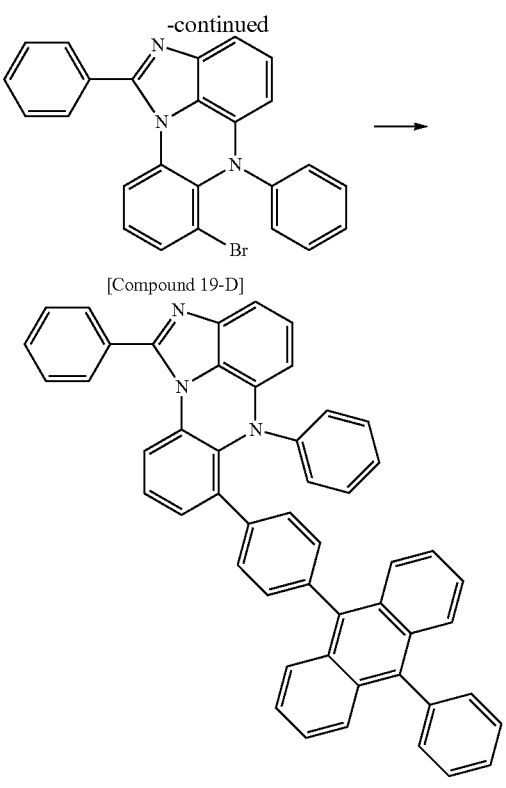

[Chemical Formula 6-17]

<Synthesis Example 19-1> Synthesis of Compound 19-A

Compound 19-A (33.1 g, yield 52%; MS:[M+H]$^+$=429) was obtained in the same manner as in Synthesis Example 1-1 except that 6-bromo-N$^1$-phenylbenzene-1,2-diamine (50.7 g, 192.5 mmol) was used instead of 5-bromo-N$^1$-phenylbenzene-1,2-diamine.

<Synthesis Example 19-2> Synthesis of Compound 19-B

Compound 19-B (14.1 g, yield 48%; MS:[M+H]$^+$=382) was obtained in the same manner as in Synthesis Example 1-2 except that Compound 19-A (33.1 g, 77.0 mmol) was used instead of Compound 1-A, and an aqueous 1% sodium hydroxide solution (510 ml) was used.

<Synthesis Example 19-3> Synthesis of Compound 19-C

After Compound 19-B (14.1 g, 37.0 mmol) was dissolved in ethanol (15 ml), 10% Pd—C (0.39 g, 3.7 mmol) was added and dispersed thereto, and the mixture was cooled to 0° C. Hydrazine monohydrate (10 ml) was slowly added dropwise thereto. The mixture was heated for 30 minutes at 50° C. After the reaction was complete, the reaction product was cooled to room temperature, filtered using ethanol, and the filtrate was vacuum distilled to obtain Compound 19-C (12.6 g, yield 97.0%; MS:[M+H]$^+$=352).

<Synthesis Example 19-4> Synthesis of Compound 19-D

Compound 19-D (11.2 g, yield 71.0%; MS:[M+H]$^+$=438) was obtained in the same manner as in Synthesis Example 1-4 except that Compound 19-C (12.6 g, 35.9 mmol) was used instead of Compound 1-C, benzaldehyde (3.8 g, 35.9 mmol) was used instead of acetaldehyde, and 2,3-dichloro-5,6-dicyano-1,4-benzoquinone (DDQ) (9.0 g, 39.5 mmol) was used.

<Synthesis Example 19-5> Synthesis of Chemical Formula 6-17

A compound of Chemical Formula 6-17 (7.4 g, yield 42%; MS:[M+H]$^+$=688) was obtained in the same manner as in Synthesis Example 1-5 except that Compound 19-D (11.2 g, 25.5 mmol) was used instead of Compound 1-D, (4-(10-phenylanthracen-9-yl)phenyl)boronic acid (9.6 g, 25.5 mmol) was used instead of (10-phenylanthracen-9-yl)boronic acid, and a 2 M potassium carbonate ($K_2CO_3$) solution (37 ml) and tetrakis(triphenylphosphine)palladium(0) (0.5 g, 0.97 mmol) were used.

<Synthesis Example 20> Synthesis of Chemical Formula 7-17

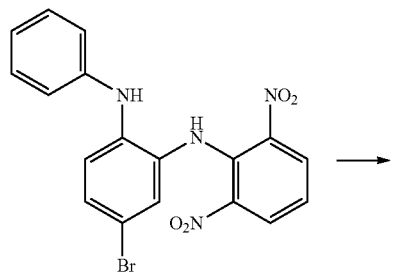

[Compound 20-A]

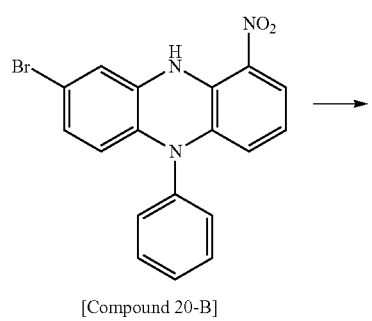

[Compound 20-B]

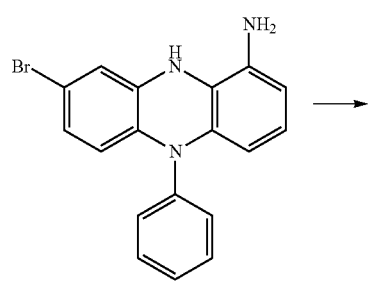

[Compound 20-C]

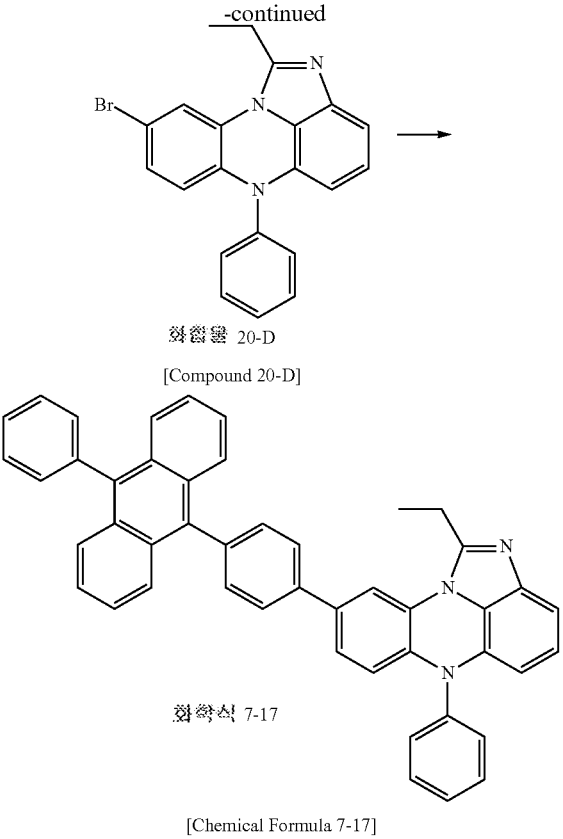

[Chemical Formula 7-17]

<Synthesis Example 20-1> Synthesis of Compound 20-A

Compound 20-A (40.7 g, yield 64%; MS:[M+H]$^+$=429) was obtained in the same manner as in Synthesis Example 1-1 except that 2-($\lambda^2$-azanyl)-4-bromo-N-phenylaniline (50.5 g, 192.5 mmol) was used instead of 5-bromo-N$^1$-phenylbenzene-1,2-diamine.

<Synthesis Example 20-2> Synthesis of Compound 20-B

Compound 20-B (25.7 g, yield 71%; MS:[M+H]$^+$=382) was obtained in the same manner as in Synthesis Example 1-2 except that Compound 20-A (40.7 g, 94.8 mmol) was used instead of Compound 1-A, and an aqueous 1% sodium hydroxide solution (625 ml) was used.

<Synthesis Example 20-3> Synthesis of Compound 20-C

Compound 20-C (23.5 g, yield 99.0%; MS:[M+H]$^+$=352) was obtained in the same manner as in Synthesis Example 1-3 except that Compound 20-B (25.7 g, 67.3 mmol) was used instead of Compound 1-B, and Pd—C (0.9 g, 8.7 mmol) and hydrazine monohydrate (20 ml) were used.

<Synthesis Example 20-4> Synthesis of Compound 20-D

Compound 20-D (21.3 g, yield 82%; MS:[M+H]$^+$=390) was obtained in the same manner as in Synthesis Example 1-4 except that Compound 20-C (23.5 g, 66.6 mmol) was used instead of Compound 1-C, propionaldehyde (3.9 g, 66.6 mmol) was used instead of acetaldehyde, and 2,3-dichloro-5,6-dicyano-1,4-benzoquinone (DDQ) (16.7 g, 73.3 mmol) was used.

<Synthesis Example 20-5> Synthesis of Chemical Formula 7-17

A compound of Chemical Formula 7-17 (12.5 g, yield 39%; MS:[M+H]$^+$=640) was obtained in the same manner as in Synthesis Example 1-5 except that Compound 20-D (19.5 g, 50.0 mmol) was used instead of Compound 1-D, (4-(10-phenylanthracen-9-yl)phenyl)boronic acid (18.7 g, 50.0 mmol) was used instead of (10-phenylanthracen-9-yl)boronic acid, and a 2 M potassium carbonate ($K_2CO_3$) solution (73 ml) and tetrakis(triphenylphosphine)palladium(0) (1.1 g, 1.90 mmol) were used.

EXPERIMENTAL EXAMPLE

Experimental Example 1-1

A glass substrate on which indium tin oxide (ITO) was coated as a thin film to a thickness of 500 Å was placed in distilled water, in which a detergent is dissolved, and ultrasonic cleaned. As the detergent, a product of Fischer Corporation was used, and as the distilled water, distilled water filtered twice with a filter manufactured by Millipore Corporation was used. After the ITO was cleaned for 30 minutes, ultrasonic cleaning was repeated twice for 10 minutes using distilled water. After the cleaning with distilled water was finished, the substrate was ultrasonic cleaned with isopropyl alcohol, acetone and methanol solvents, and dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed to a thickness of 100 Å by thermal vacuum depositing hexanitrile hexaazatriphenylene (HAT) of the following Chemical Formula.

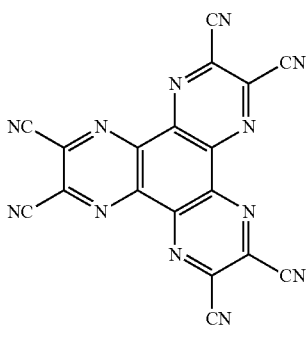

[HAT]

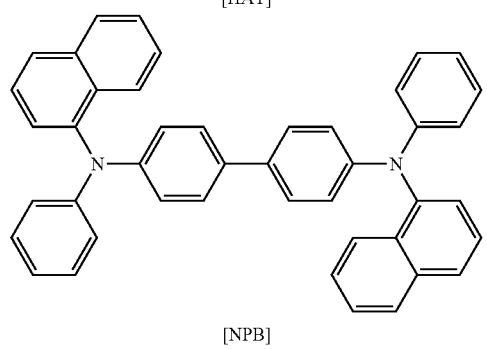

[NPB]

A hole transfer layer was formed on the hole injection layer by vacuum depositing 4,4'-bis[N-(1-naphthyl)-N-phenylamino]biphenyl (NPB) (1,000 Å) of the Chemical Formula shown above.

Subsequently, a light emitting layer was formed on the hole transfer layer to a film thickness of 230 Å by vacuum depositing GH and GD shown below in a weight ratio of 10:1.

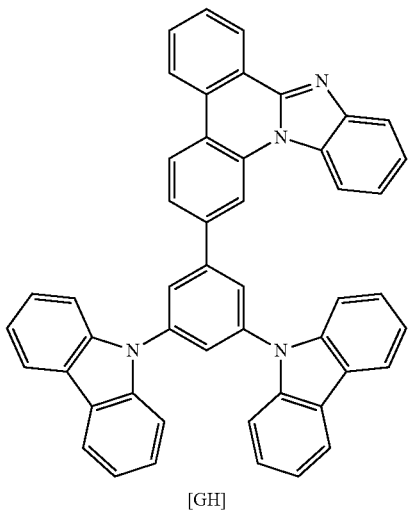

[GH]

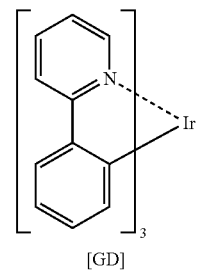

[GD]

An electron injection and transfer layer was formed on the light emitting layer to a thickness of 350 Å by vacuum depositing the compound of Chemical Formula 2-1.

A cathode was formed on the electron injection and transfer layer by depositing lithium fluoride (LiF) to a thickness of 15 Å and aluminum to a thickness of 2,000 Å in consecutive order.

In the above process, the deposition rates of the organic materials were maintained at 0.4 to 0.7 Å/sec, the deposition rates of the lithium fluoride and the aluminum of the cathode were maintained at 0.3 Å/sec and 2 Å/sec, respectively, and the degree of vacuum when being deposited was maintained at $2\times10^{-7}$ to $5\times10^{-6}$ torr, and as a result, an organic light emitting device was manufactured.

Comparative Example 1

An organic light emitting device was manufactured in the same manner as in Experimental Example 1-1 except that a compound of the following Chemical Formula ET-A was used instead of the compound of Chemical Formula 2-1.

[ET-A]

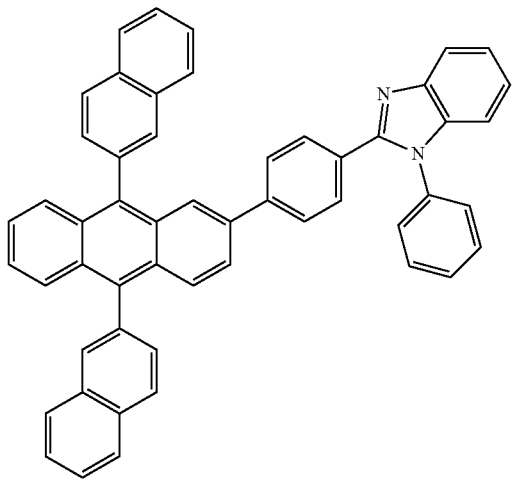

Experimental Examples 1-2 to 1-12

Organic light emitting devices of Experimental Examples 1-2 to 1-12 were manufactured in the same manner as in Experimental Example 1-1 except that each compound shown in Table 1 was used instead of the compound of Chemical Formula 2-1.

Current (10 mA/cm²) was applied to the organic light emitting devices manufactured in Experimental Examples 1-1 to 1-12 and Comparative Example 1, and the results are shown in Table 1.

TABLE 1

|  | Compound | Voltage (V) | Efficiency (dc/A) | Color Coordinate (x, y) |
| --- | --- | --- | --- | --- |
| Experimental Example 1-1 | 2-1 | 3.82 | 41.22 | (0.374, 0.619) |
| Experimental Example 1-2 | 3-1 | 3.73 | 41.68 | (0.373, 0.620) |
| Experimental Example 1-3 | 3-4 | 3.88 | 42.11 | (0.372, 0.622) |
| Experimental Example 1-4 | 3-5 | 3.85 | 41.80 | (0.373, 0.621) |
| Experimental Example 1-5 | 3-6 | 3.79 | 41.98 | (0.371, 0.622) |
| Experimental Example 1-6 | 3-12 | 3.89 | 42.10 | (0.372, 0.622) |
| Experimental Example 1-7 | 3-18 | 3.99 | 41.27 | (0.372, 0.619) |
| Experimental Example 1-8 | 3-19 | 3.76 | 40.24 | (0.373, 0.620) |
| Experimental Example 1-9 | 4-1 | 3.89 | 41.35 | (0.374, 0.620) |
| Experimental Example 1-10 | 5-17 | 3.88 | 42.34 | (0.374, 0.623) |
| Experimental Example 1-11 | 6-17 | 3.78 | 41.58 | (0.372, 0.624) |
| Experimental Example 1-12 | 7-17 | 3.96 | 42.15 | (0.373, 0.620) |
| Comparative Example 1 | ET-A | 3.98 | 39.99 | (0.373, 0.621) |

As seen from the results of Table 1, it was shown that the heterocyclic compound according to one embodiment of the present specification may be used as an organic material layer material of an organic light emitting device, and particularly when the heterocyclic compound was used in an electron injection and transfer layer among the organic material layers, the organic light emitting device exhibited superior properties in efficiency, driving voltage, stability and the like. In particular, it was demonstrated that the compound exhibited superior properties due to excellent thermal stability, a deep HOMO level, and hole stability. The compound has an advantage in that it improves the efficiency of an organic light emitting device, and may improve the stability of a device due to the thermal stability of the compound.

Experimental Example 2-1

On the transparent ITO electrode prepared as in Experimental Example 1-1, a hole injection layer was formed to a thickness of 100 Å by thermal vacuum depositing hexanitrile hexaazatriphenylene (HAT) of the Chemical Formula shown above.

A hole transfer layer was formed on the hole injection layer by vacuum depositing 4,4'-bis[N-(1-naphthyl)-N-phenylamino]biphenyl (NPB) (700 Å), hexanitrile hexaazatriphenylene (HAT) (50 Å) and 4,4'-bis[N-(1-naphthyl)-N-phenylamino]biphenyl (NPB) (700 Å) of the chemical formulae shown above in consecutive order.

Subsequently, a light emitting layer was formed on the hole transfer layer to a film thickness of 200 Å by vacuum depositing BH and BD shown below in a weight ratio of 25:1.

[BH]

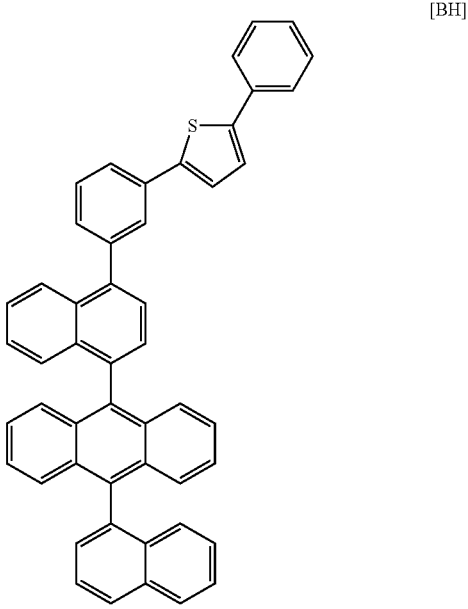

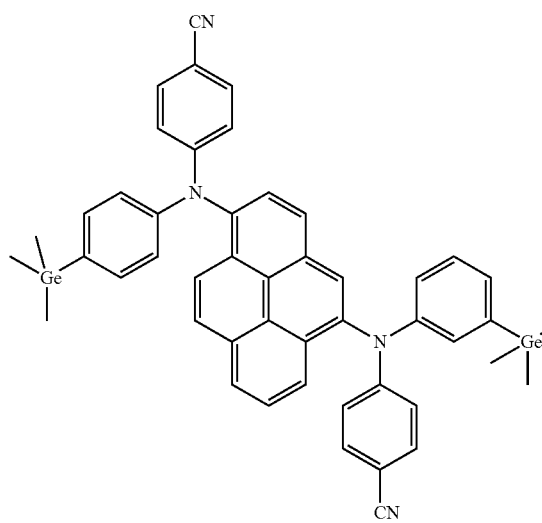

[BD]

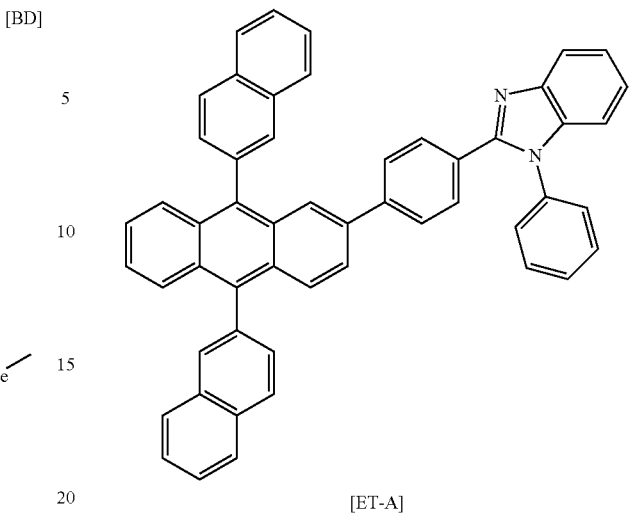

[ET-A]

An electron injection and transfer layer was formed on the light emitting layer to a thickness of 300 Å by vacuum depositing the compound of Chemical Formula 2-1 and lithium quinalate (LiQ) of the following Chemical Formula in a weight ratio of 1:1.

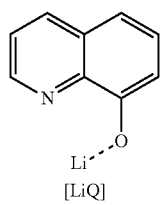

[LiQ]

A cathode was formed on the electron injection and transfer layer by depositing lithium fluoride (LiF) to a thickness of 15 Å and aluminum to a thickness of 2,000 Å in consecutive order.

In the above process, the deposition rates of the organic materials were maintained at 0.4 to 0.7 Å/sec, the deposition rates of the lithium fluoride and the aluminum of the cathode were maintained at 0.3 Å/sec and 2 Å/sec, respectively, and the degree of vacuum when being deposited was maintained at $2\times10^{-7}$ to $5\times10^{-6}$ torr, and as a result, an organic light emitting device was manufactured.

Comparative Example 2

An organic light emitting device was manufactured in the same manner as in Experimental Example 2-1 except that a compound of the following Chemical Formula ET-A was used instead of the compound of Chemical Formula 2-1.

Experimental Examples 2-2 to 2-12

Organic light emitting devices of Experimental Examples 2-2 to 2-12 were manufactured in the same manner as in Experimental Example 2-1 except that each compound shown in Table 2 was used instead of the compound of Chemical Formula 2-1.

Current (10 mA/cm$^2$) was applied to the organic light emitting devices manufactured in Experimental Examples 2-1 to 2-12 and Comparative Example 2, and the results are shown in Table 2.

TABLE 2

| | Compound | Voltage (V) | Efficiency (dc/A) | Color Coordinate (x, y) |
|---|---|---|---|---|
| Experimental Example 2-1 | 2-1 | 3.92 | 5.21 | (0.140, 0.131) |
| Experimental Example 2-2 | 3-1 | 3.89 | 5.22 | (0.141, 0.129) |
| Experimental Example 2-3 | 3-26 | 3.88 | 5.19 | (0.141, 0.130) |
| Experimental Example 2-4 | 3-28 | 3.86 | 5.20 | (0.139, 0.131) |
| Experimental Example 2-5 | 3-29 | 3.98 | 5.12 | (0.140, 0.130) |
| Experimental Example 2-6 | 3-30 | 3.96 | 4.99 | (0.142, 0.132) |
| Experimental Example 2-7 | 3-34 | 3.89 | 5.18 | (0.139, 0.133) |
| Experimental Example 2-8 | 4-1 | 3.82 | 5.23 | (0.141, 0.132) |
| Experimental Example 2-9 | 4-26 | 3.93 | 4.98 | (0.140, 0.130) |
| Experimental Example 2-10 | 4-40 | 3.94 | 5.26 | (0.141, 0.131) |
| Experimental Example 2-11 | 4-41 | 3.92 | 5.22 | (0.140, 0.130) |
| Experimental Example 2-12 | 5-17 | 3.96 | 5.13 | (0.140, 0.130) |
| Comparative Example 2 | ET-A | 4.05 | 4.75 | (0.141, 0.129) |

As seen from the results of Table 2, it was shown that the heterocyclic compound according to one embodiment of the present specification may be used as an organic material layer material of an organic light emitting device, and particularly when the heterocyclic compound was used in an electron injection and transfer layer among the organic material layers, the organic light emitting device exhibited superior properties in efficiency, driving voltage, stability and the like. In particular, it was demonstrated that the compound exhibited superior properties due to excellent thermal stability, a deep HOMO level, and hole stability. The compound may be used either alone or as a mixture with an n-type dopant such as LiQ in an organic electronic device including an organic light emitting device. The compound has an advantage in that it improves the efficiency of an organic light emitting device, and may improve the stability of a device due to the thermal stability of the compound.

The invention claimed is:

1. A heterocyclic compound represented by the following Chemical Formula 1:

[Chemical Formula 1]

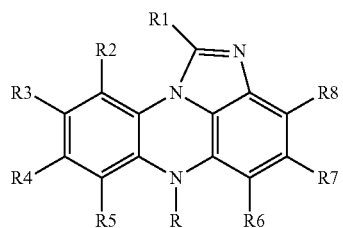

wherein, in Chemical Formula 1,
R is a substituted or unsubstituted aryl group,
R1 is a substituted or unsubstituted alkyl group; or a substituted or unsubstituted aryl group,
R2 to R8 are the same as or different from each other, and each dependently hydrogen; deuterium; a substituted or unsubstituted aryl group; or a substituted or unsubstituted heterring group including one or more of N, O and S atoms,
wherein when R1 is a substituted or unsubstituted aryl group, at least one of R2 to R8 is a substituted or unsubstituted aryl group; or a substituted or unsubstituted heterring group including one or more of N, O and S atoms.

2. The heterocyclic compound of claim 1, wherein at least one of R2 to R8 is any one of the following structures:

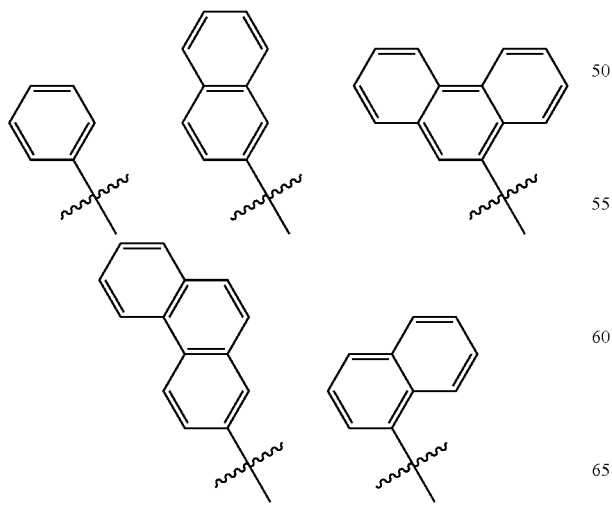

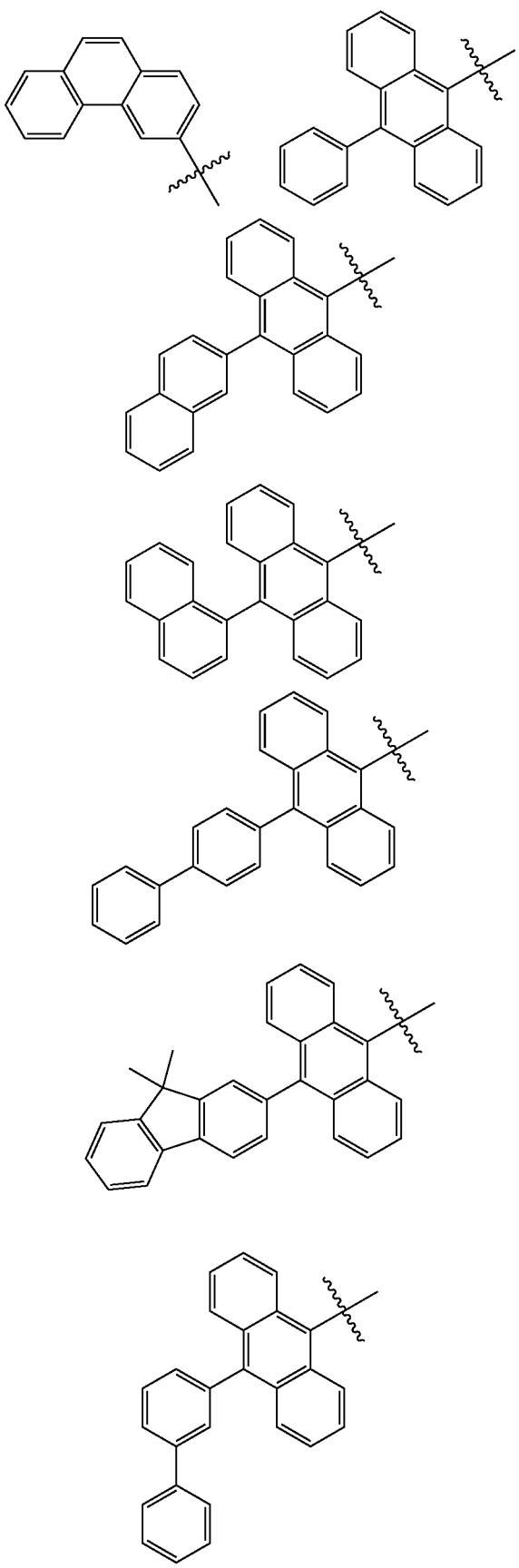

-continued
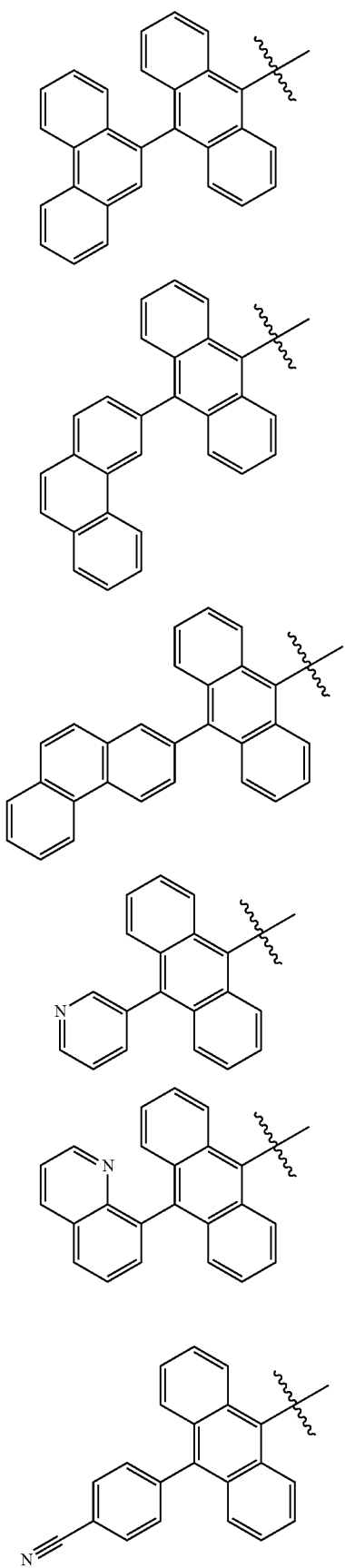
-continued
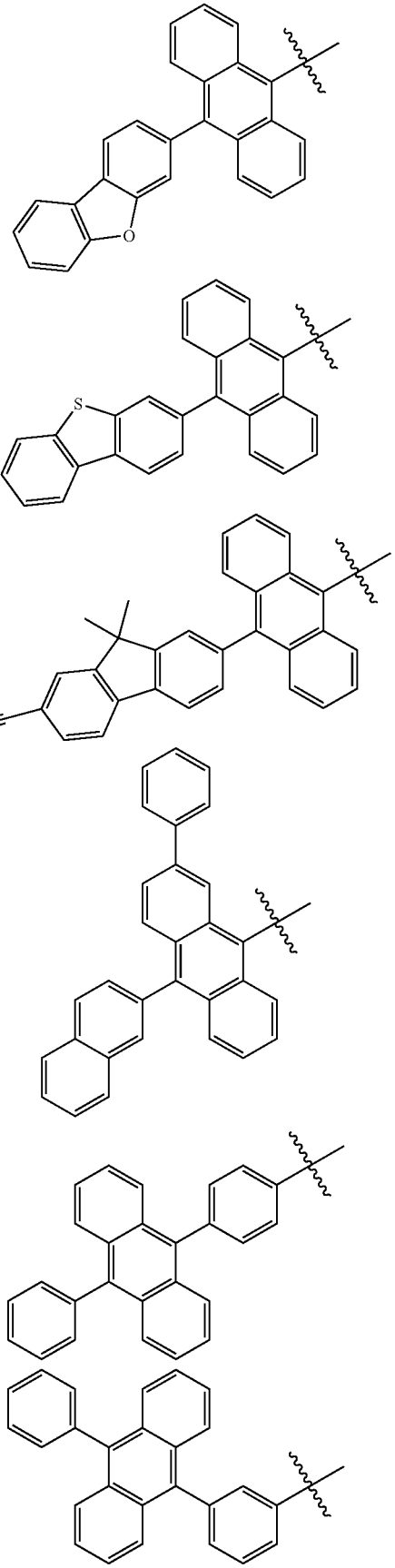

187
-continued
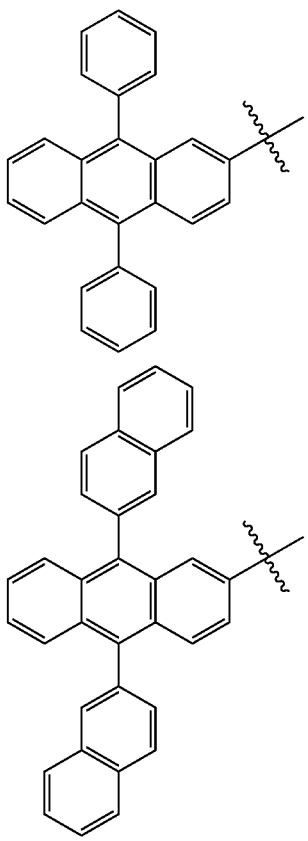
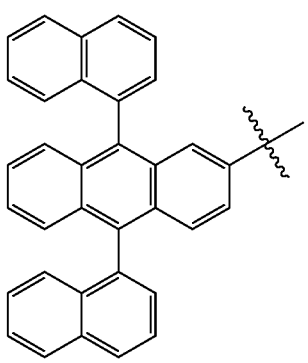
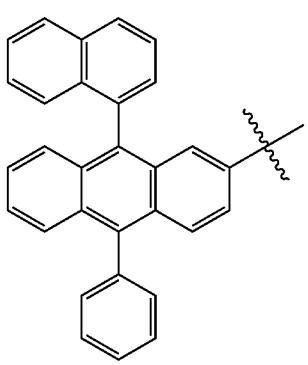
188
-continued
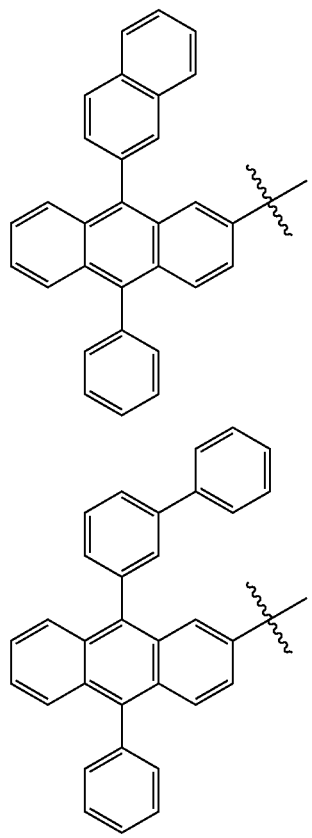
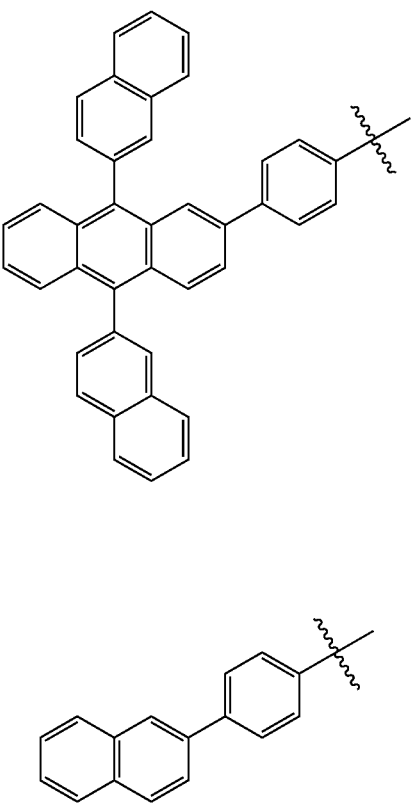

189
-continued
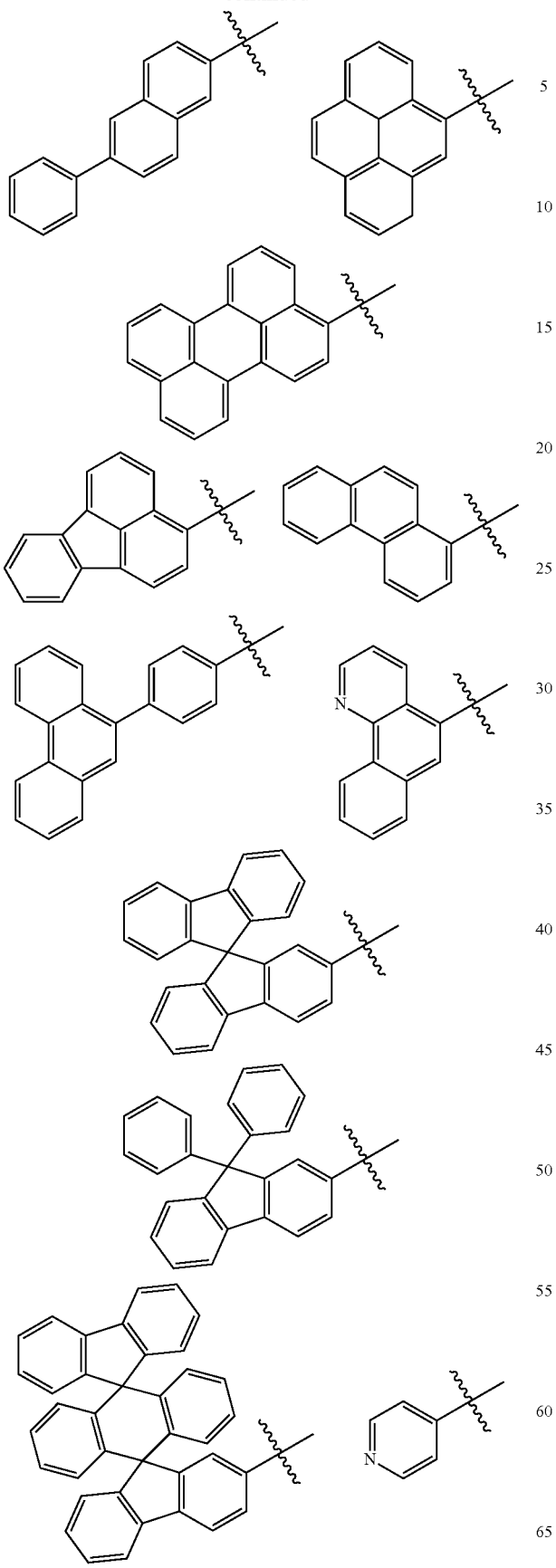
190
-continued
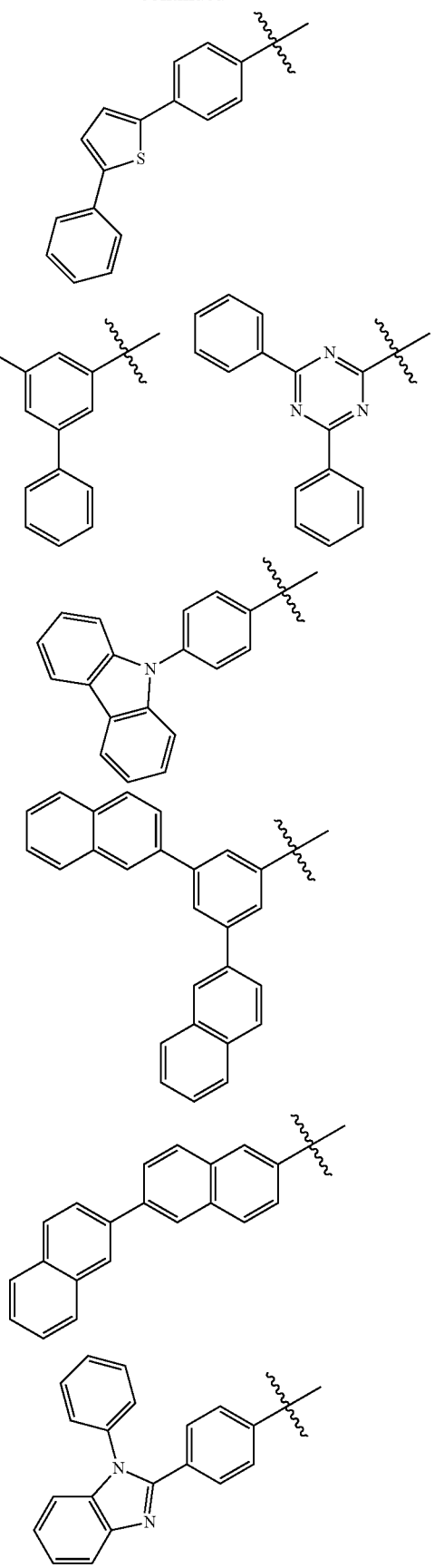

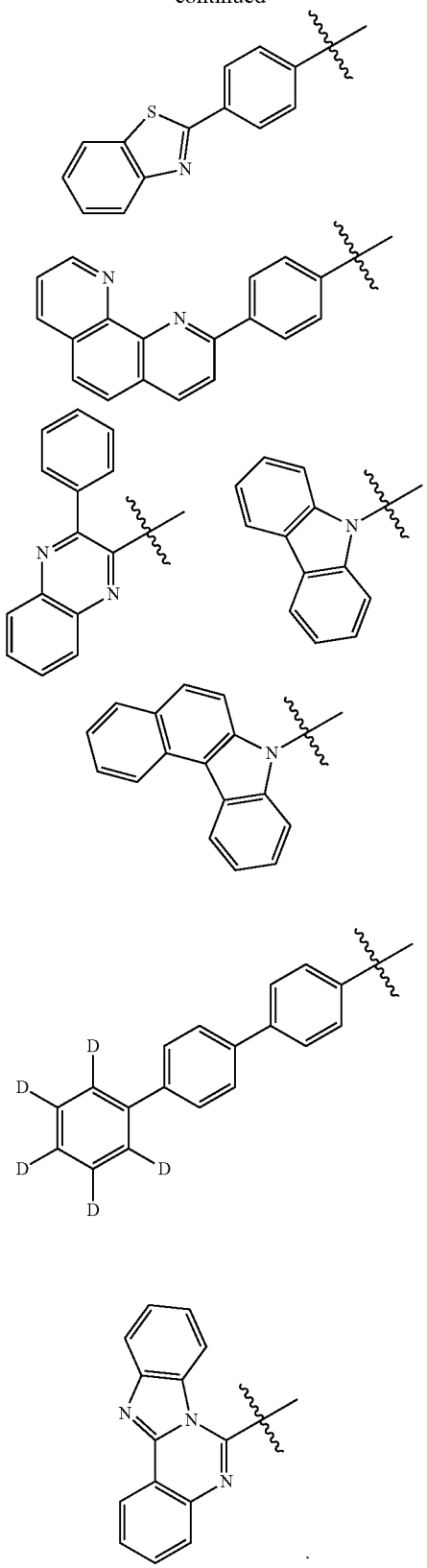
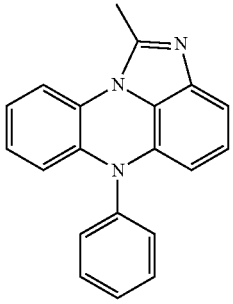
[Chemical Formula 1-1]
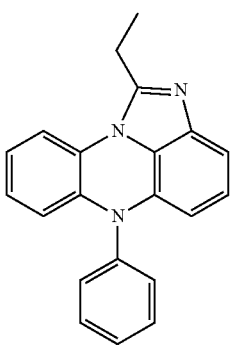
[Chemical Formula 1-2]
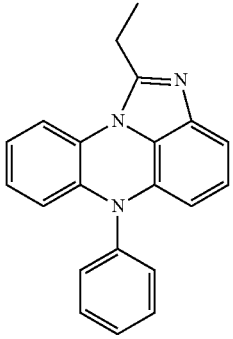
[Chemical Formula 1-4]
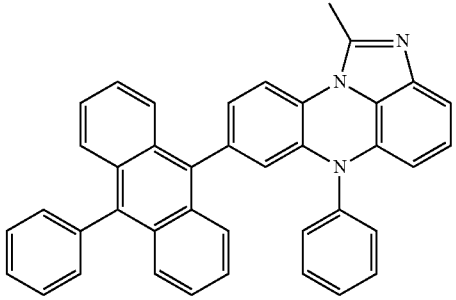
[Chemical Formula 2-1]
3. The heterocyclic compound of claim 1, wherein the heterocyclic compound represented by Chemical Formula 1 is represented by any one of the following structures:

[Chemical Formula 2-2]
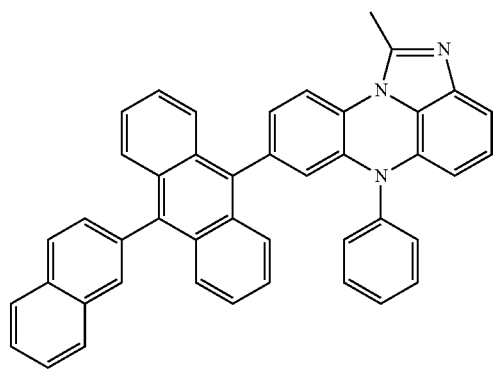
[Chemical Formula 2-3]
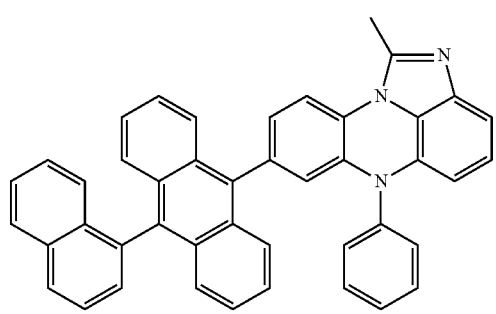
[Chemical Formula 2-4]
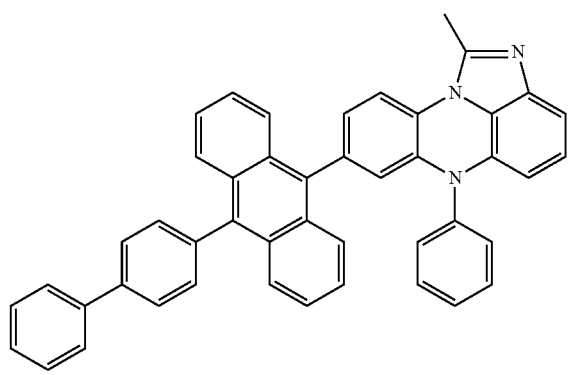
[Chemical Formula 2-5]
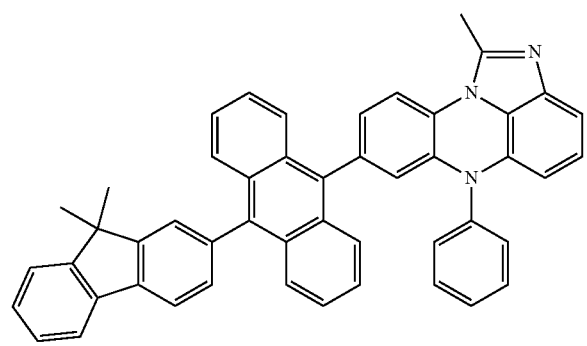
[Chemical Formula 2-6]
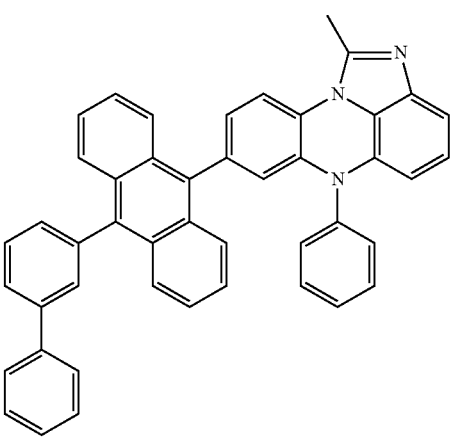
[Chemical Formula 2-7]
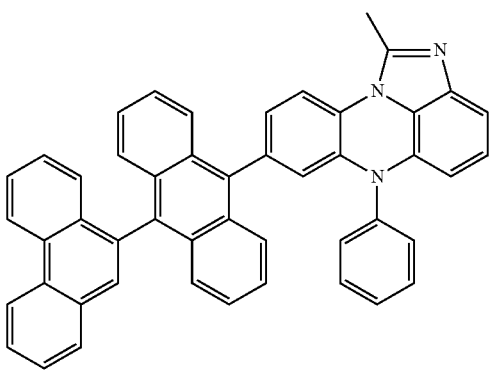
[Chemical Formula 2-8]
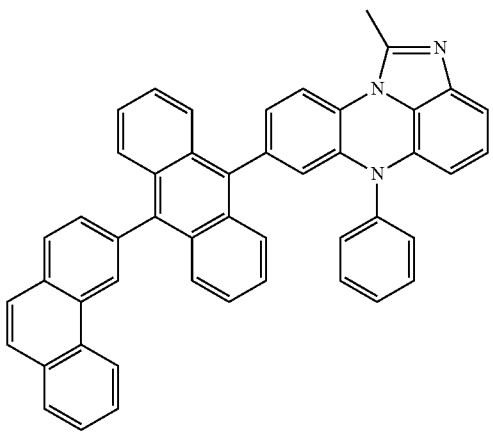

[Chemical Formula 2-9]
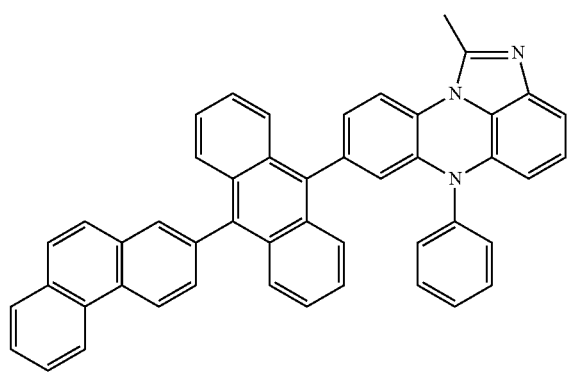
[Chemical Formula 2-10]
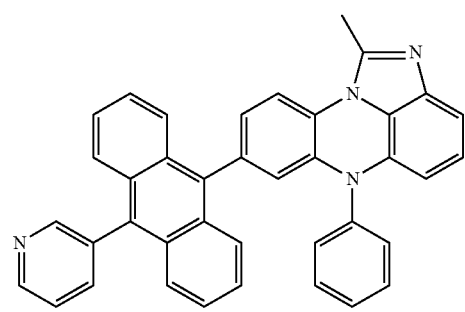
[Chemical Formula 2-11]
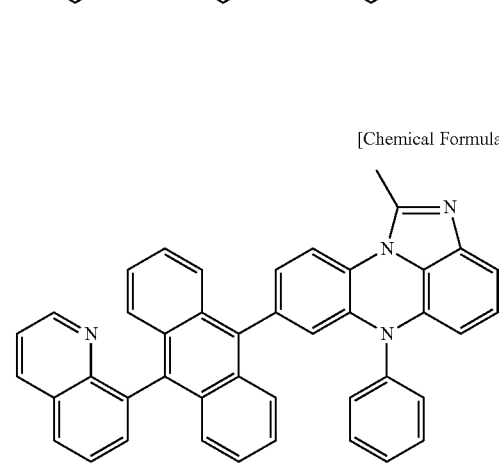
[Chemical Formula 2-12]
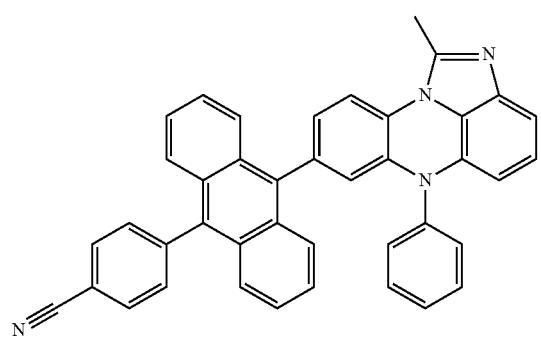
[Chemical Formula 2-13]
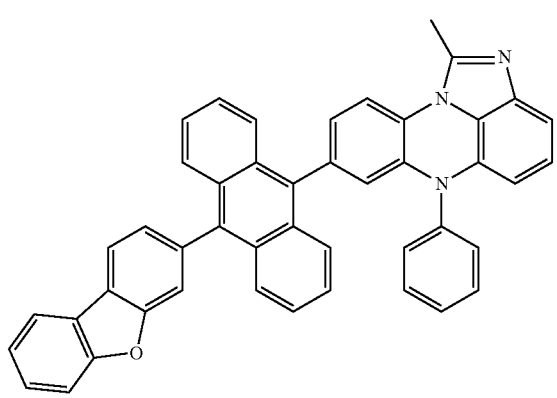
[Chemical Formula 2-14]
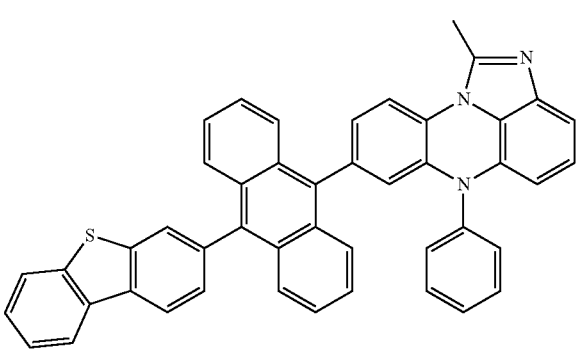
[Chemical Formula 2-15]
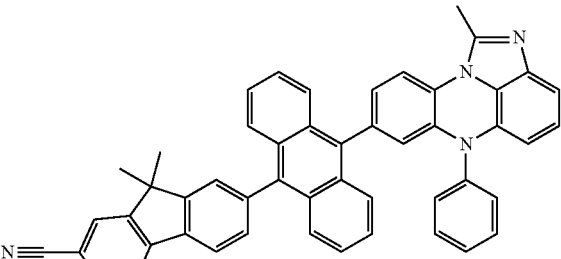
[Chemical Formula 2-16]
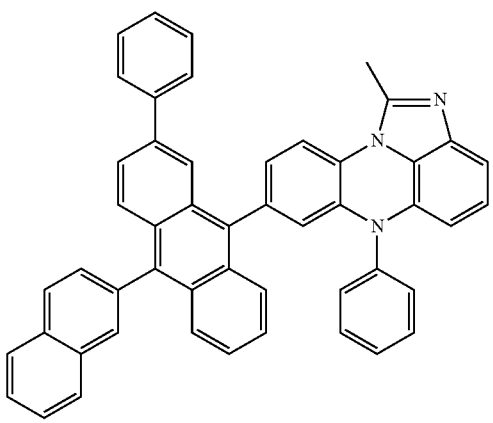

[Chemical Formula 2-17]
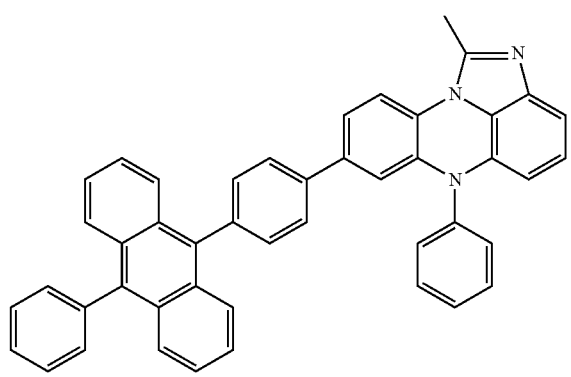
[Chemical Formula 2-18]
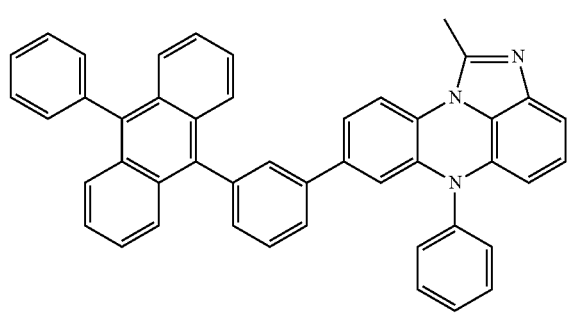
[Chemical Formula 2-19]
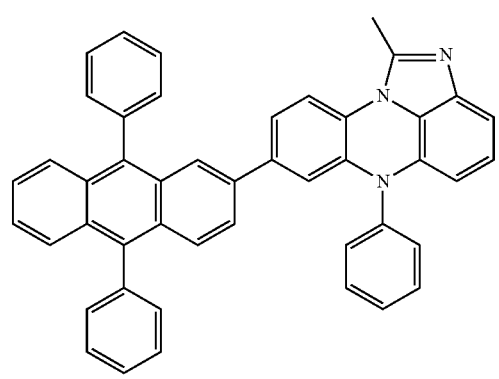
[Chemical Formula 2-20]
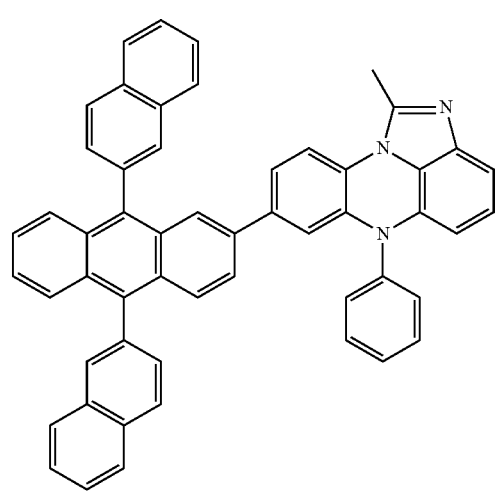
[Chemical Formula 2-21]
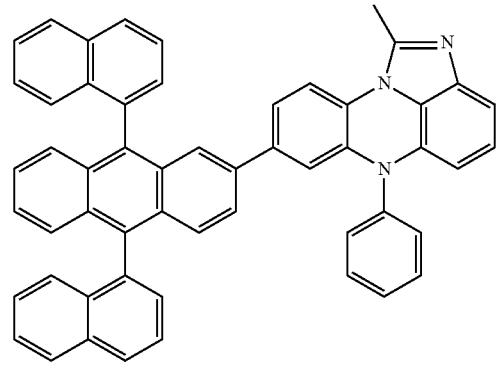
[Chemical Formula 2-22]
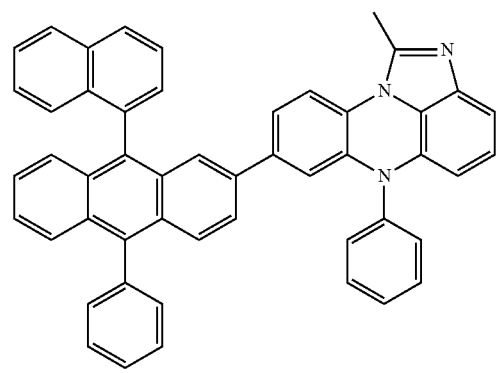
[Chemical Formula 2-23]
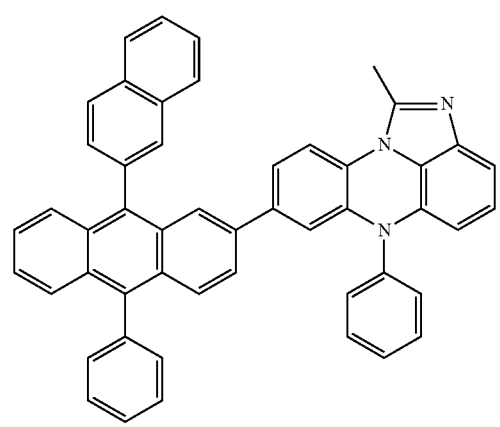
[Chemical Formula 2-24]
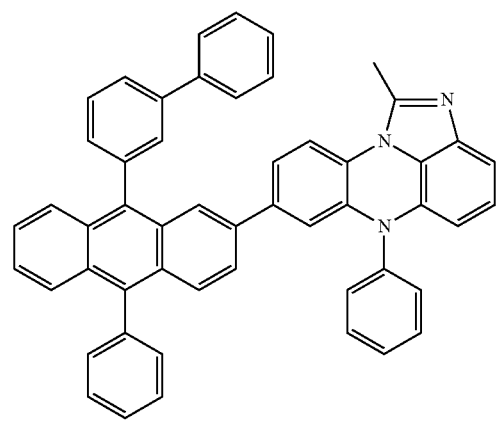

[Chemical Formula 2-25]
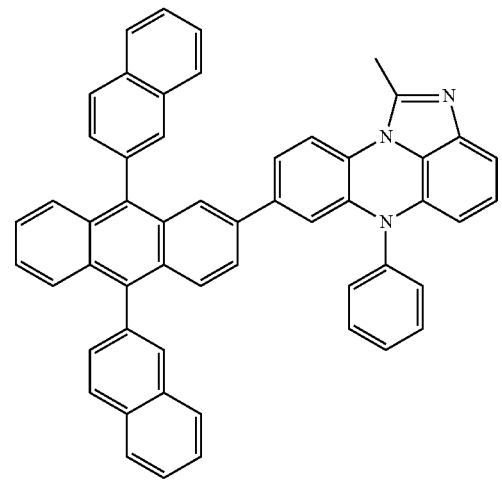
[Chemical Formula 2-26]
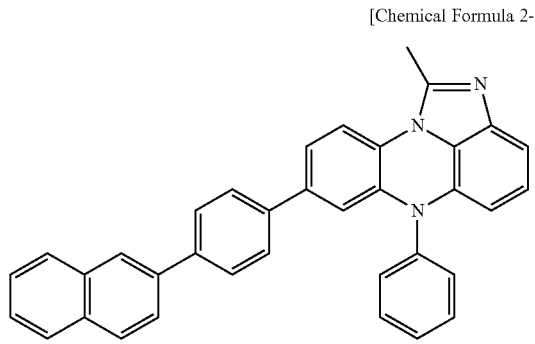
[Chemical Formula 2-27]
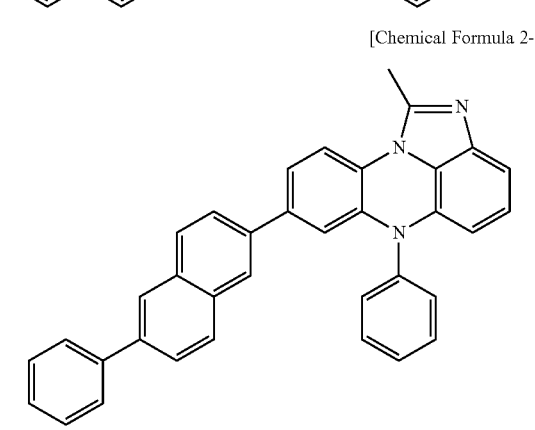
[Chemical Formula 2-28]
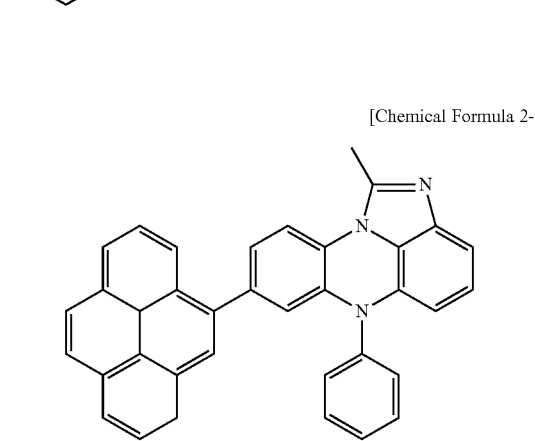
[Chemical Formula 2-29]
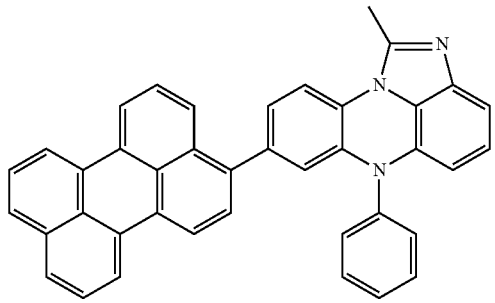
[Chemical Formula 2-30]
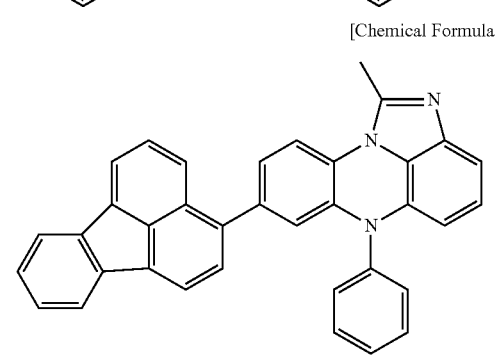
[Chemical Formula 2-31]
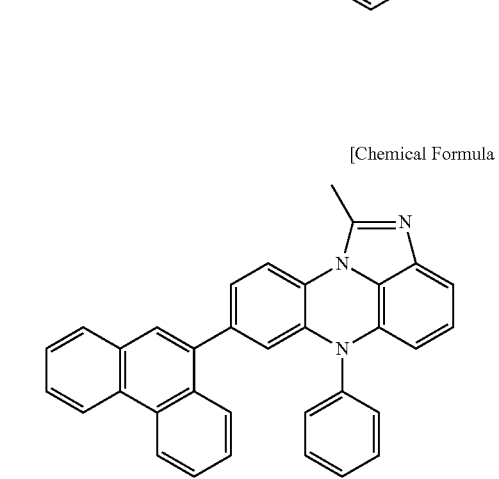
[Chemical Formula 2-32]
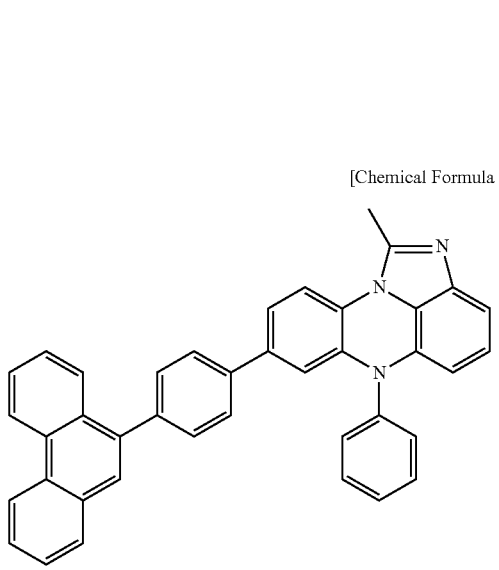

[Chemical Formula 2-33]
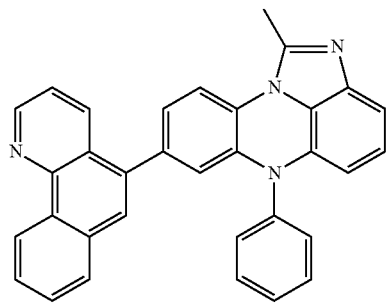
[Chemical Formula 2-34]
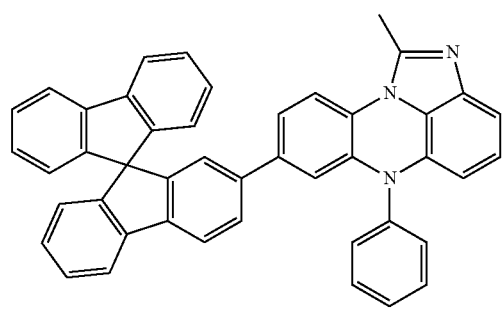
[Chemical Formula 2-35]
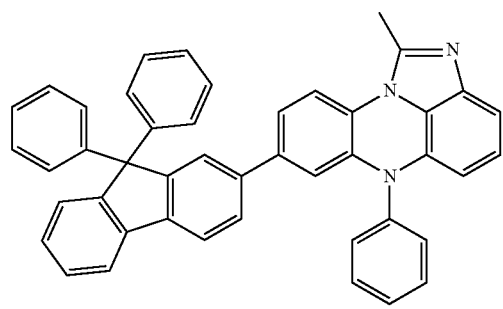
[Chemical Formula 2-36]
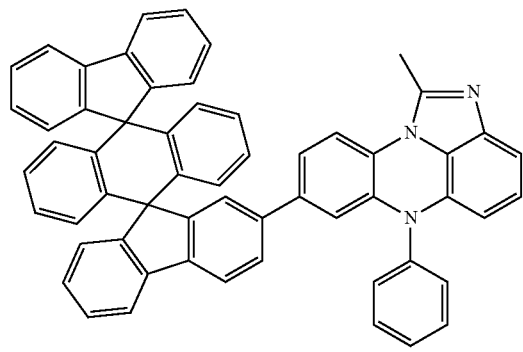
[Chemical Formula 2-37]
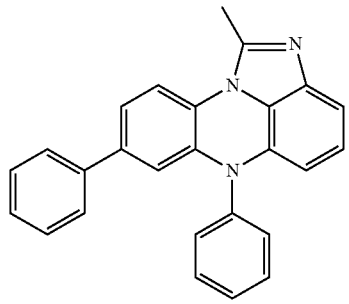
[Chemical Formula 2-38]
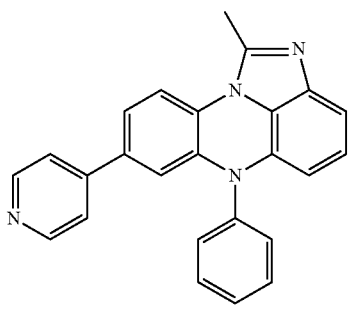
[Chemical Formula 2-39]
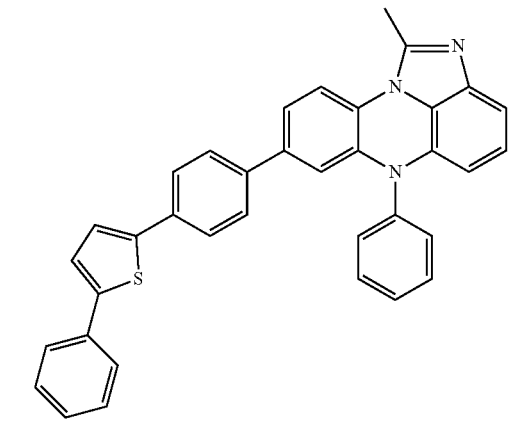
[Chemical Formula 2-40]
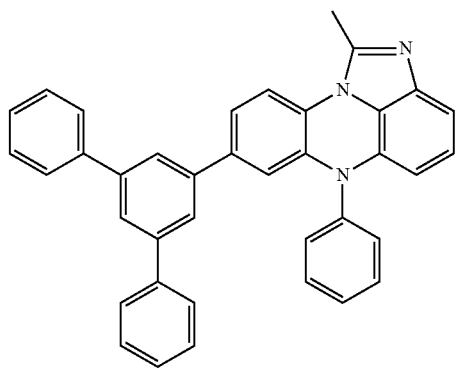

[Chemical Formula 2-41]
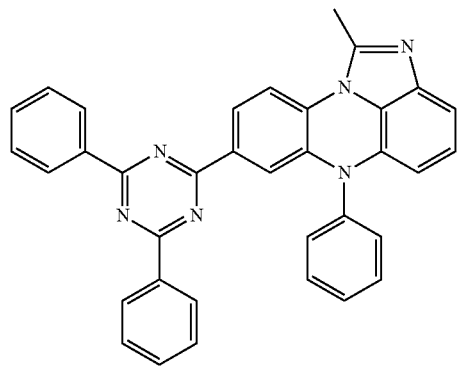
[Chemical Formula 2-42]
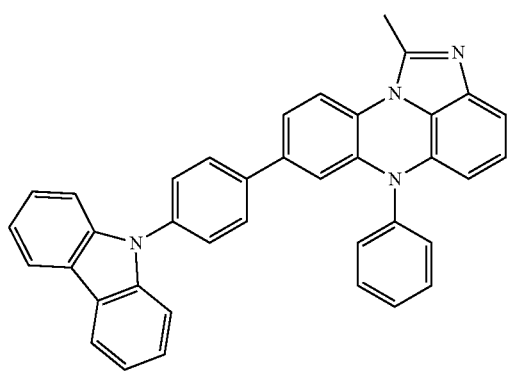
[Chemical Formula 2-43]
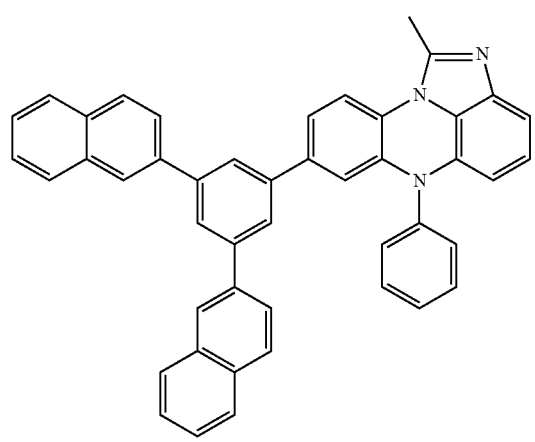
[Chemical Formula 2-44]
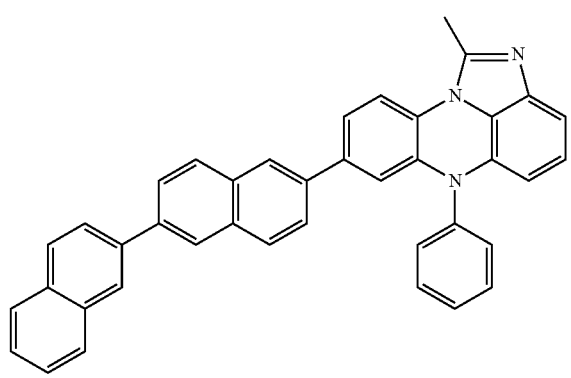
[Chemical Formula 2-45]
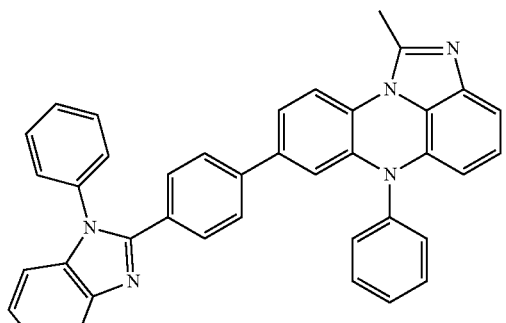
[Chemical Formula 2-46]
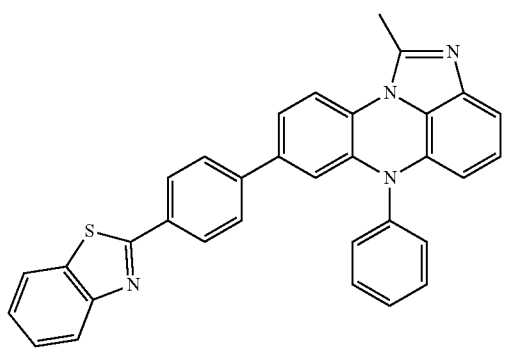
[Chemical Formula 2-47]
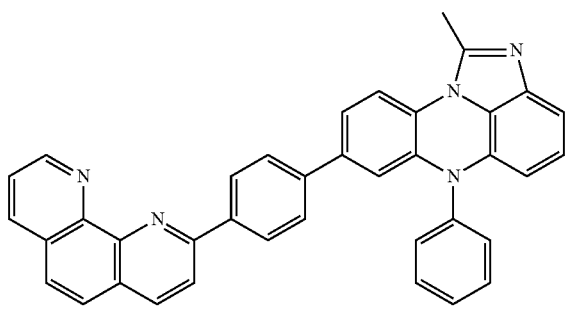
[Chemical Formula 2-49]
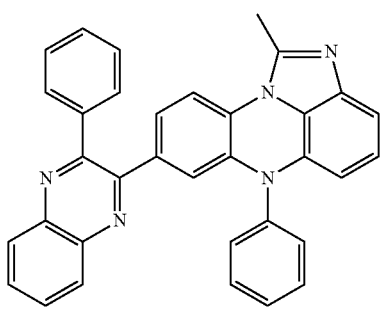

[Chemical Formula 2-50]
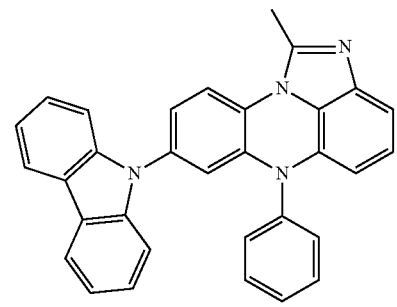
[Chemical Formula 2-51]
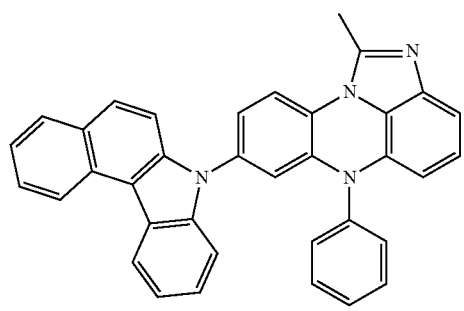
[Chemical Formula 2-52]
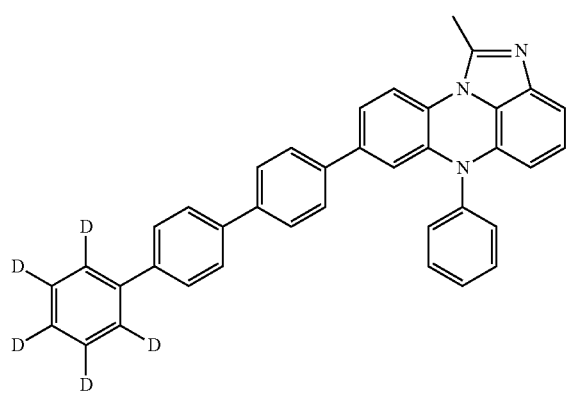
[Chemical Formula 2-53]
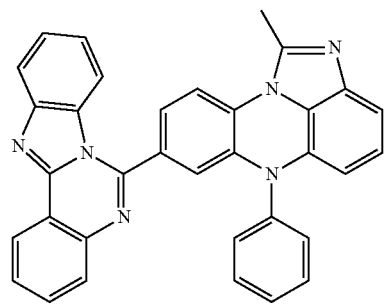
[Chemical Formula 3-1]
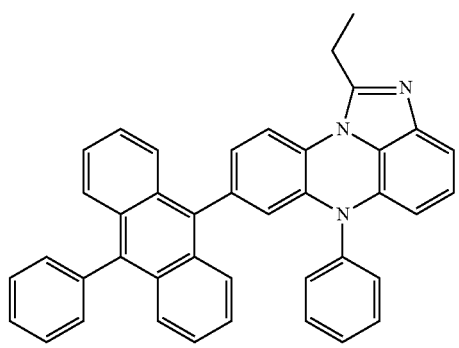
[Chemical Formula 3-2]
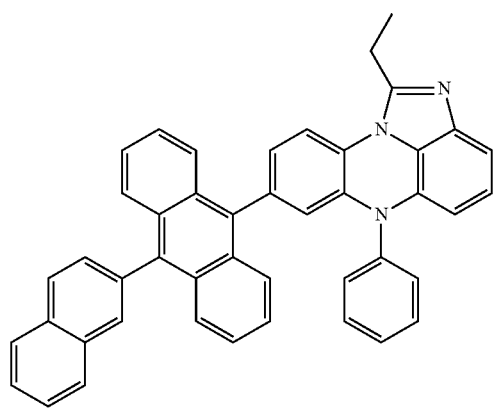
[Chemical Formula 3-3]
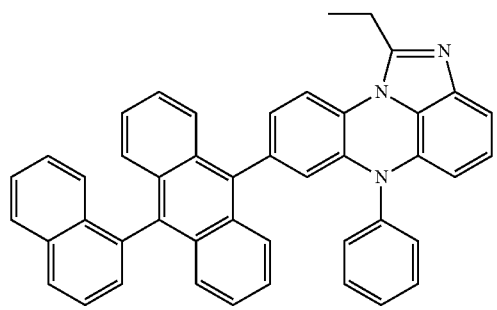
[Chemical Formula 3-4]
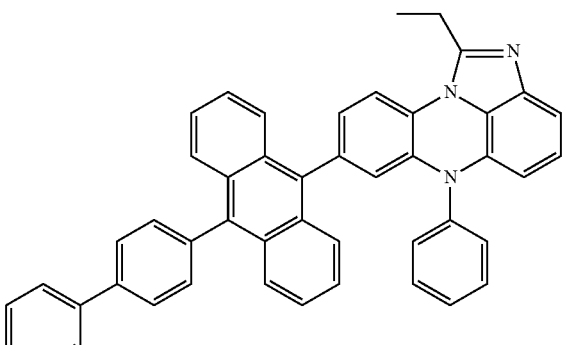

207
-continued
[Chemical Formula 3-5]
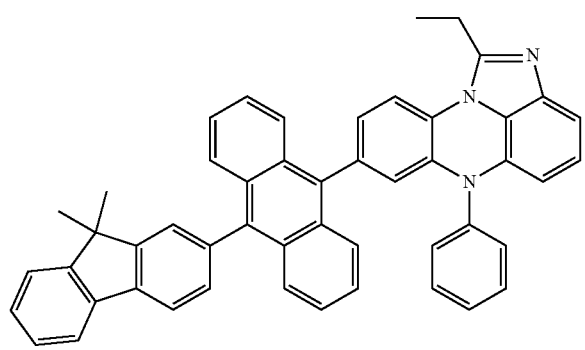
[Chemical Formula 3-6]
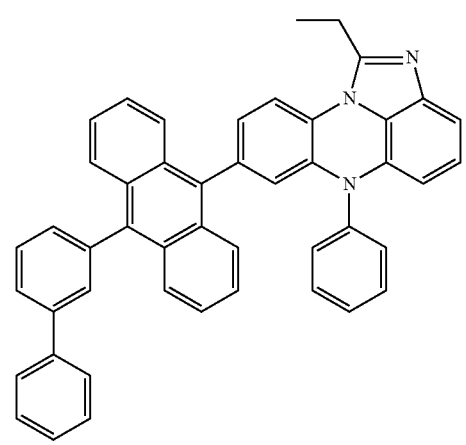
[Chemical Formula 3-7]
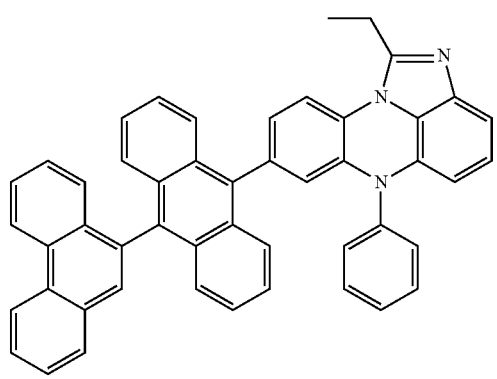
[Chemical Formula 3-8]
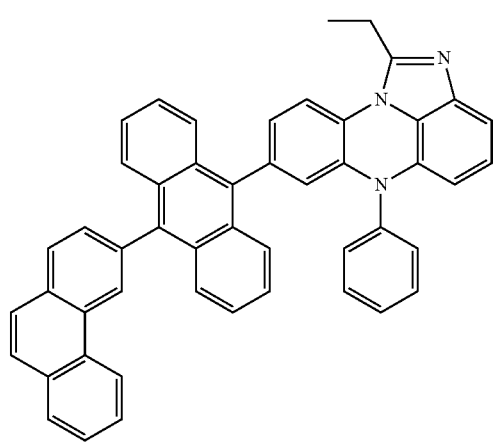
208
-continued
[Chemical Formula 3-9]
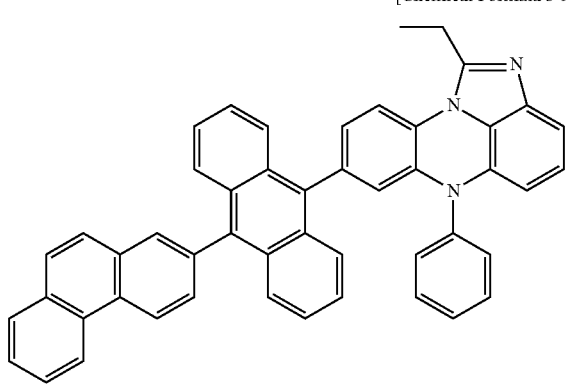
[Chemical Formula 3-10]
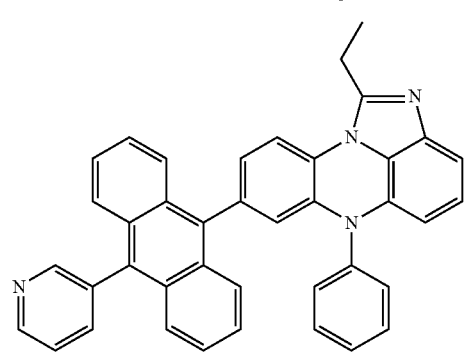
[Chemical Formula 3-11]
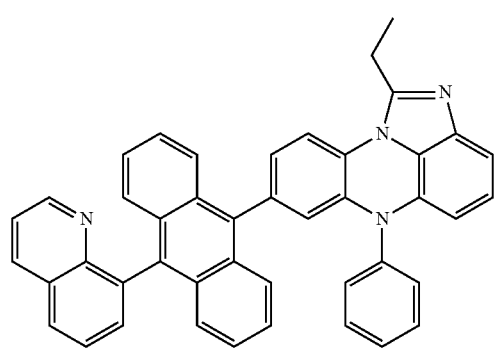
[Chemical Formula 3-12]
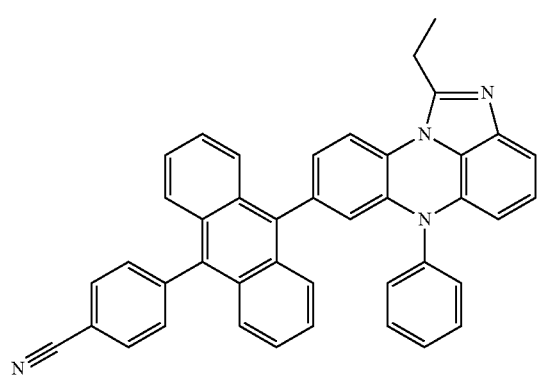

209
-continued
[Chemical Formula 3-13]
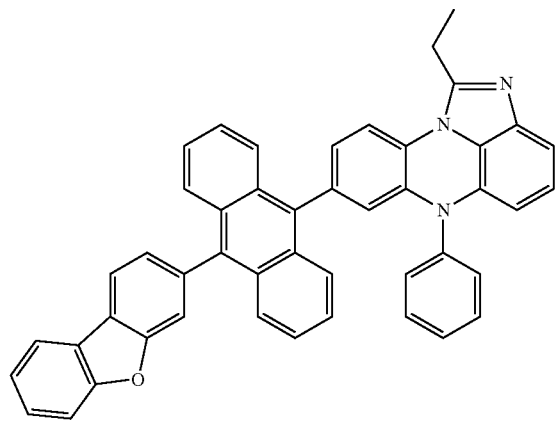
[Chemical Formula 3-14]
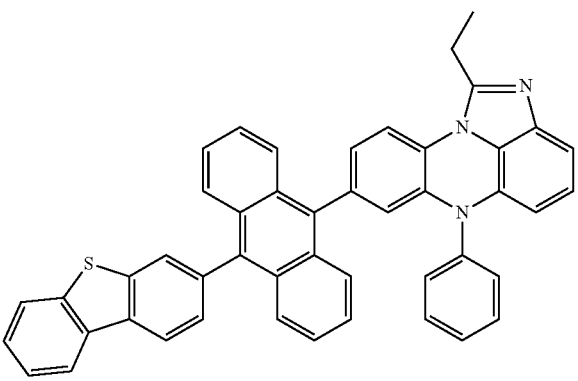
[Chemical Formula 3-15]
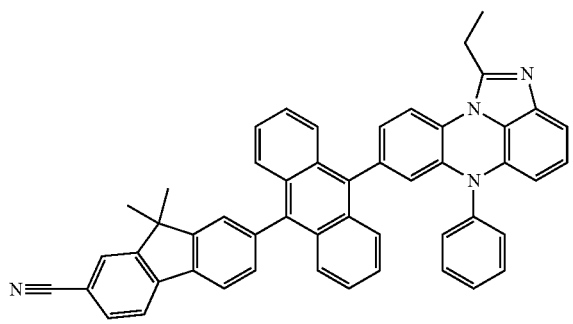
[Chemical Formula 3-16]
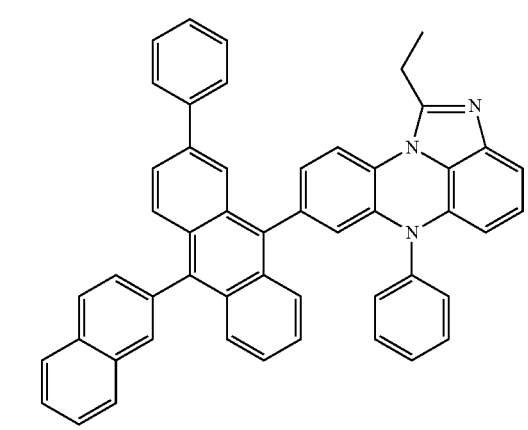
210
-continued
[Chemical Formula 3-17]
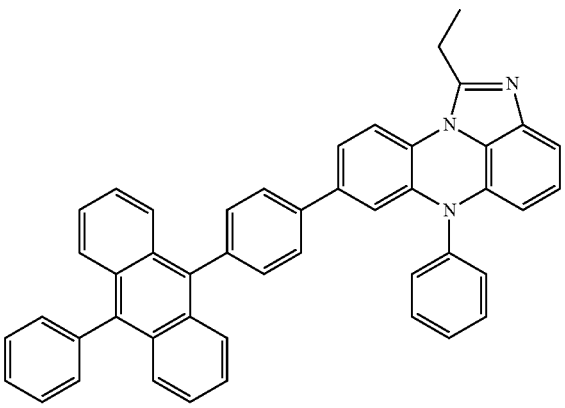
[Chemical Formula 3-18]
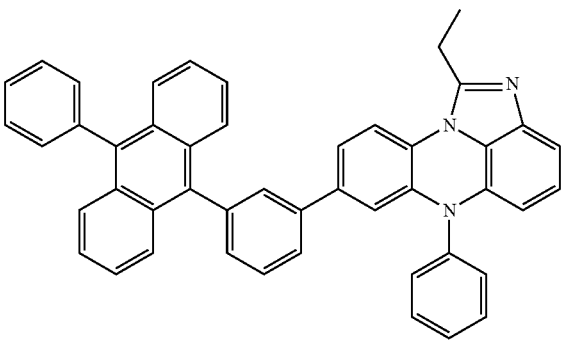
[Chemical Formula 3-19]
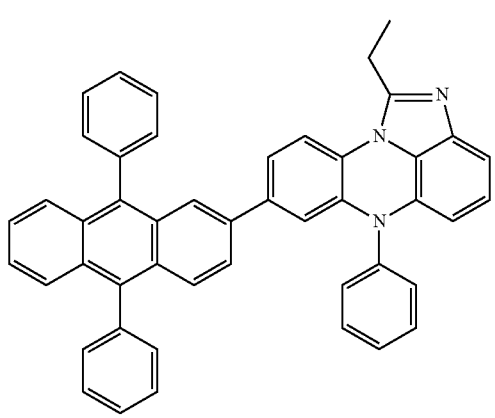

211
-continued
[Chemical Formula 3-20]
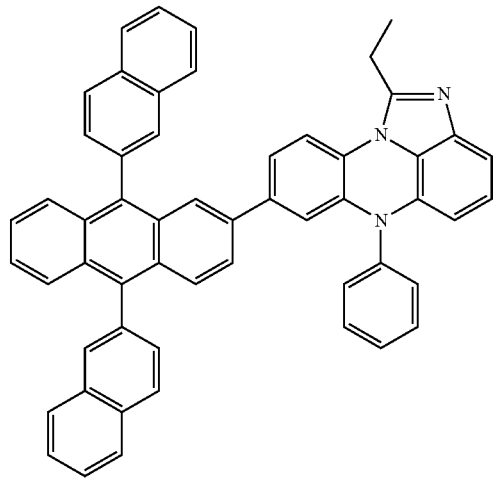
[Chemical Formula 3-21]
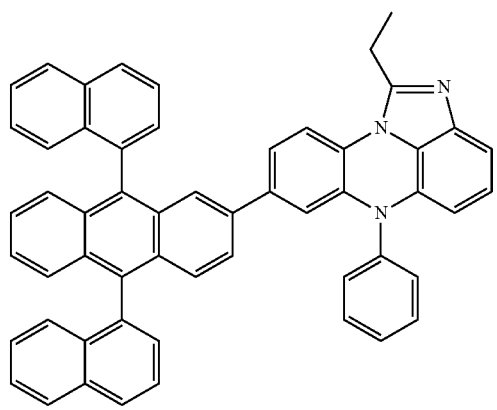
[Chemical Formula 3-22]
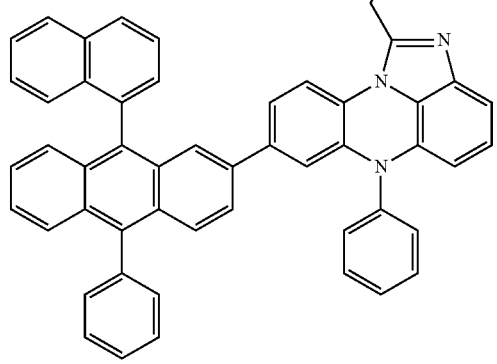
212
-continued
[Chemical Formula 3-23]
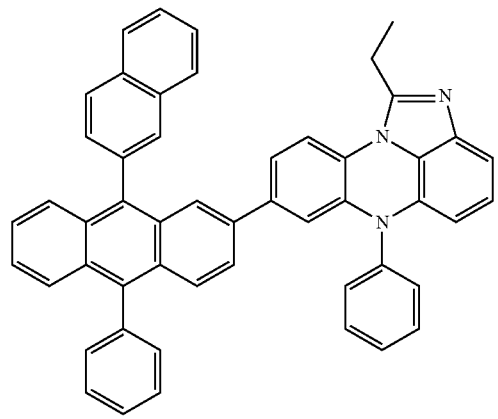
[Chemical Formula 3-24]
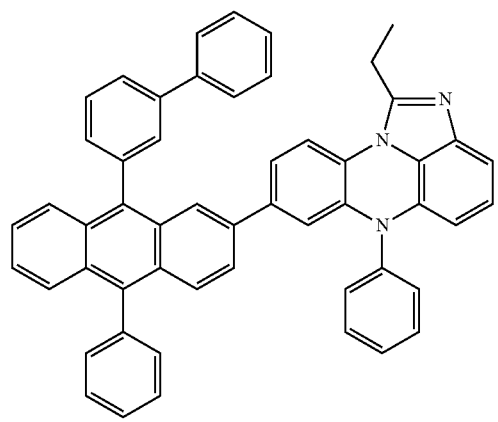
[Chemical Formula 3-25]
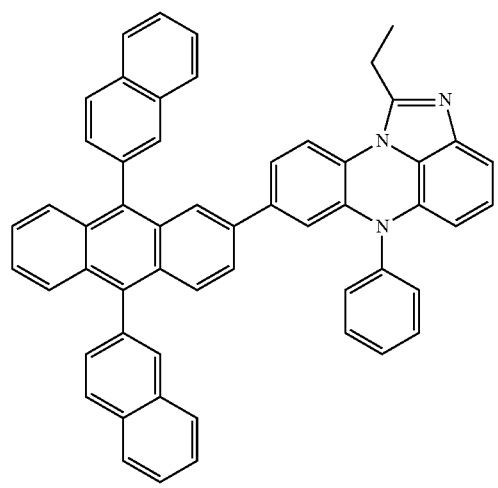

[Chemical Formula 3-26]
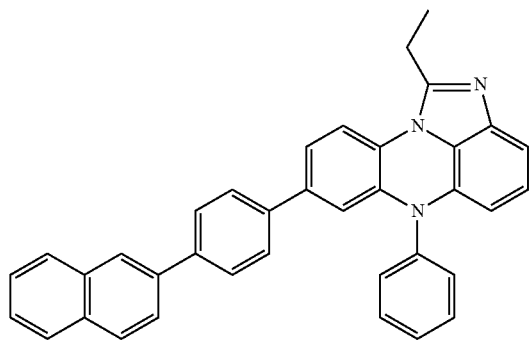
[Chemical Formula 3-27]
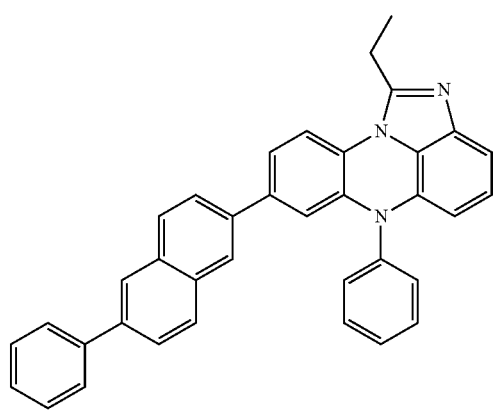
[Chemical Formula 3-28]
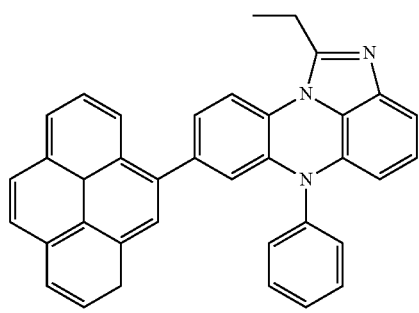
[Chemical Formula 3-29]
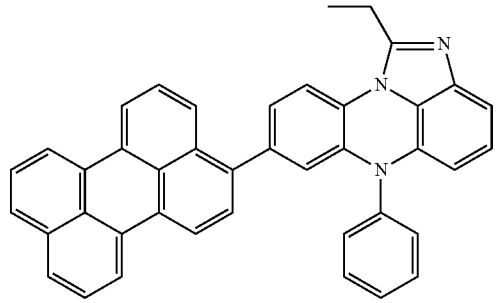
[Chemical Formula 3-30]
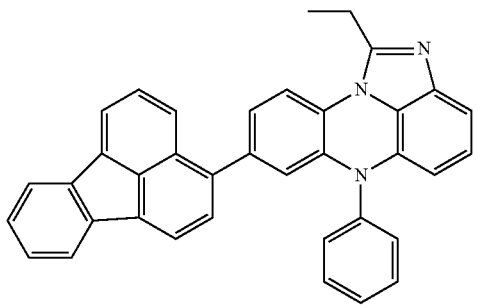
[Chemical Formula 3-31]
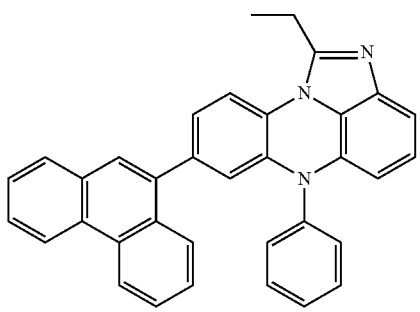
[Chemical Formula 3-32]
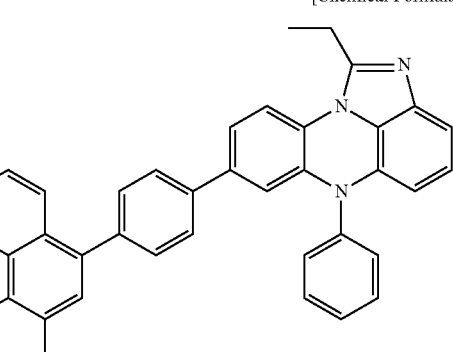
[Chemical Formula 3-33]
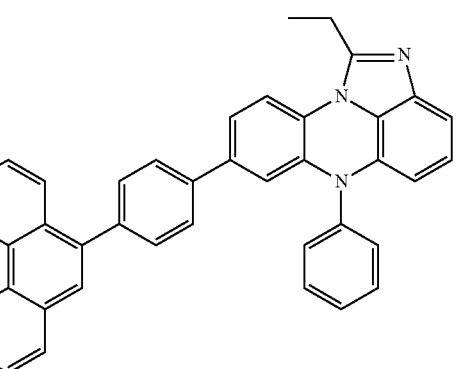

[Chemical Formula 3-34]
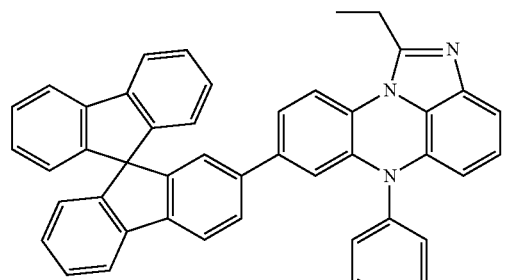
[Chemical Formula 3-35]
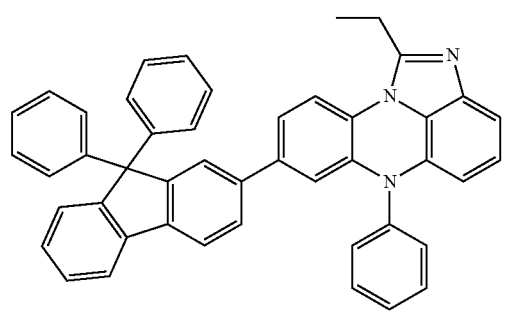
[Chemical Formula 3-36]
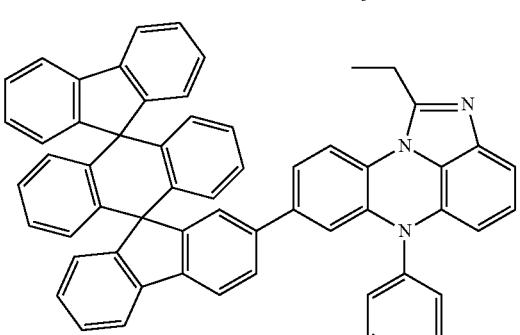
[Chemical Formula 3-37]
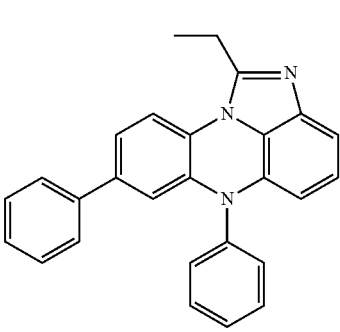
[Chemical Formula 3-38]
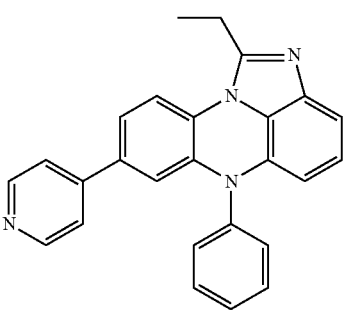
[Chemical Formula 3-39]
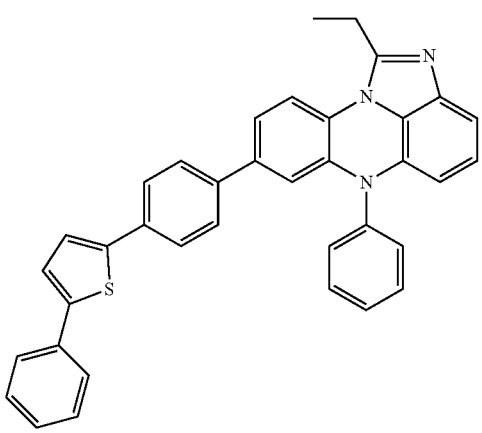
[Chemical Formula 3-40]
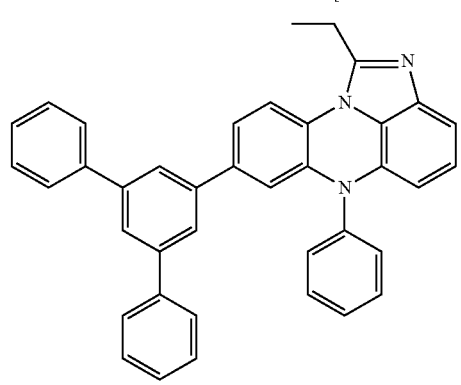
[Chemical Formula 3-41]
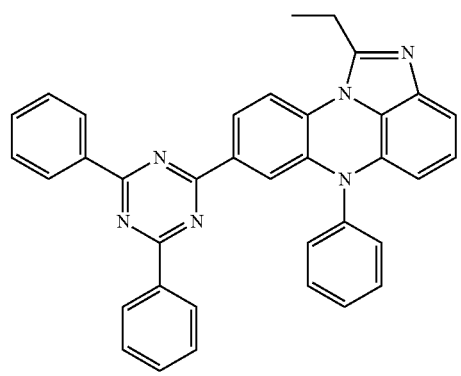
[Chemical Formula 3-42]
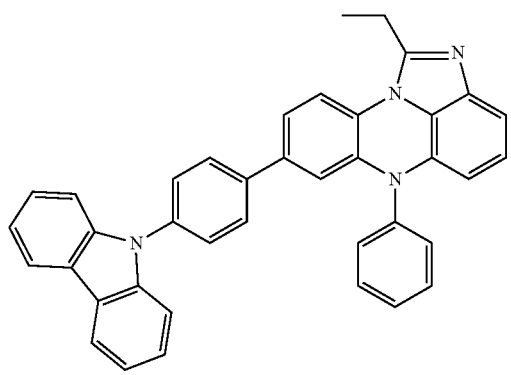

[Chemical Formula 3-43]
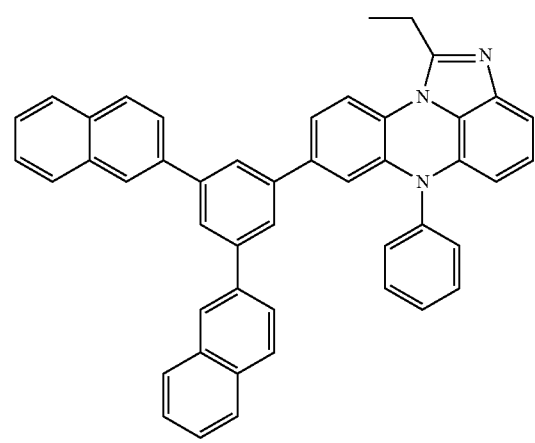
[Chemical Formula 3-44]
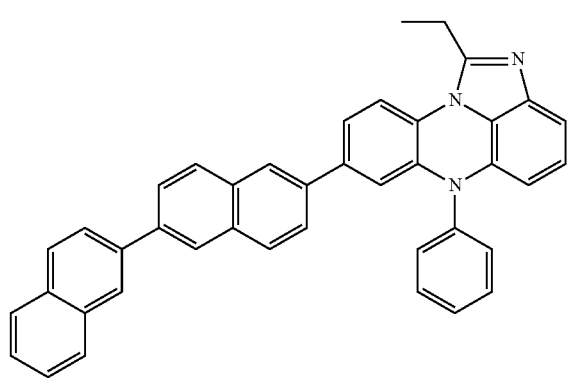
[Chemical Formula 3-45]
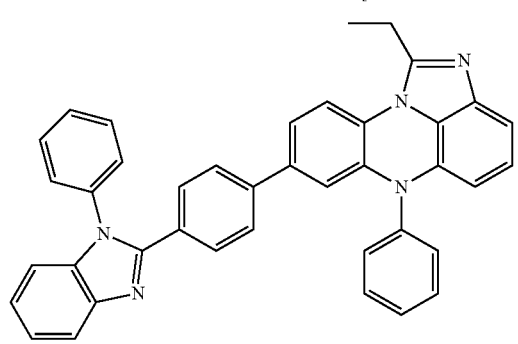
[Chemical Formula 3-46]
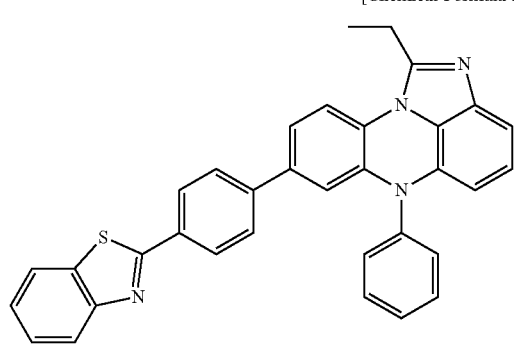
[Chemical Formula 3-47]
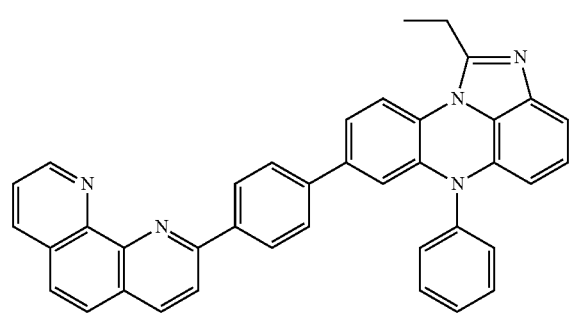
[Chemical Formula 3-49]
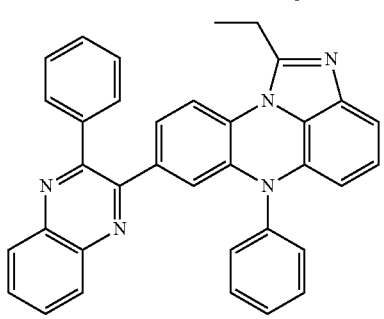
[Chemical Formula 3-50]
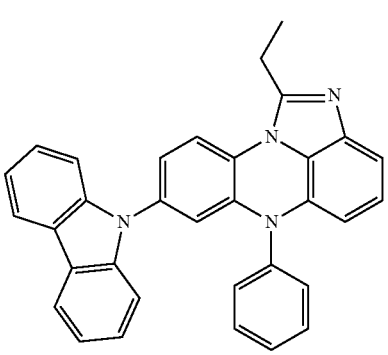
[Chemical Formula 3-51]
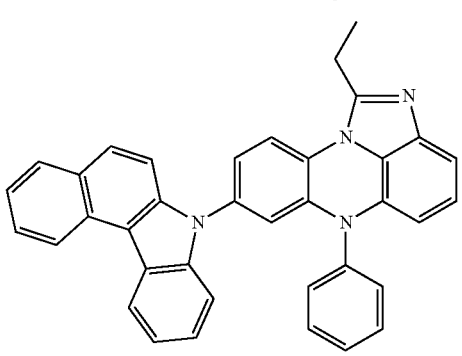

219
-continued
[Chemical Formula 3-52]
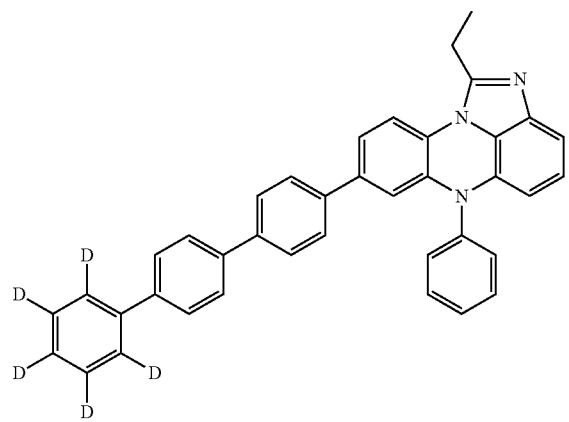
[Chemical Formula 3-53]
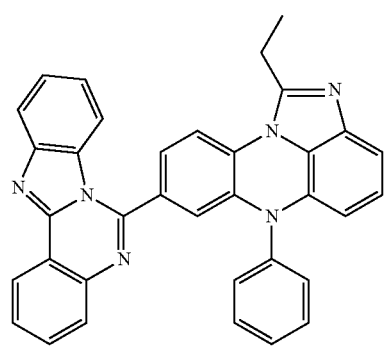
[Chemical Formula 4-1]
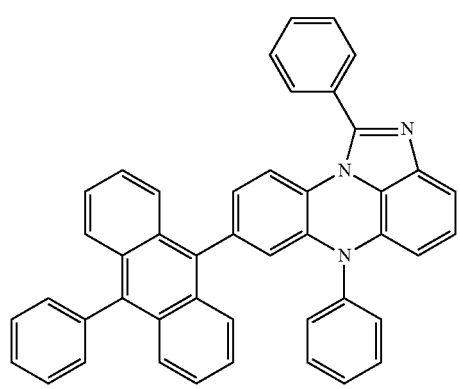
220
-continued
[Chemical Formula 4-2]
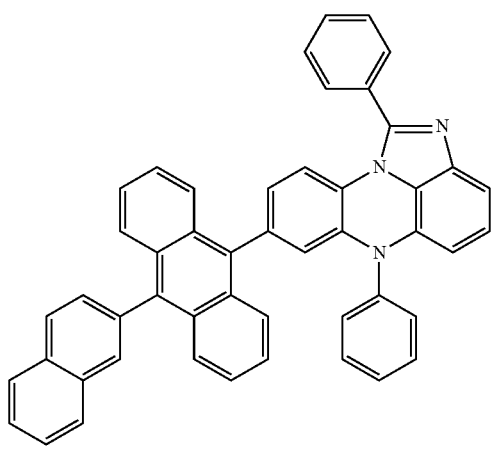
[Chemical Formula 4-3]
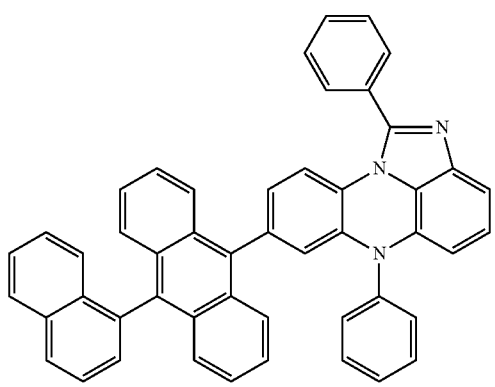
[Chemical Formula 4-4]
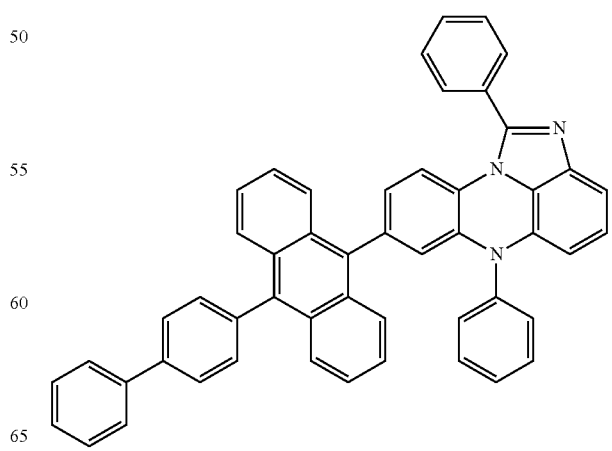

[Chemical Formula 4-5]
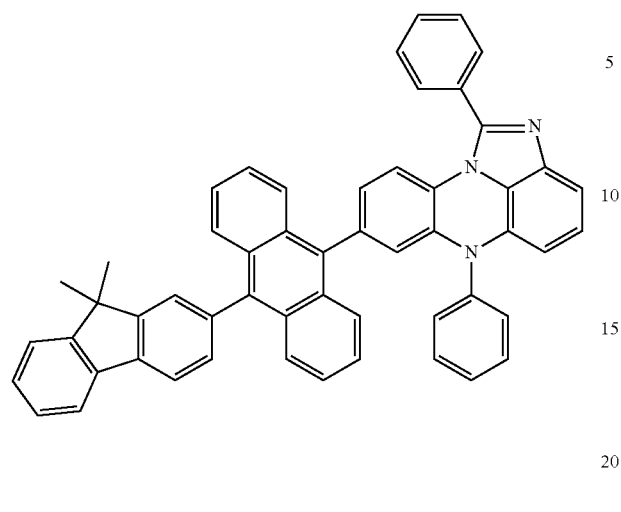
[Chemical Formula 4-6]
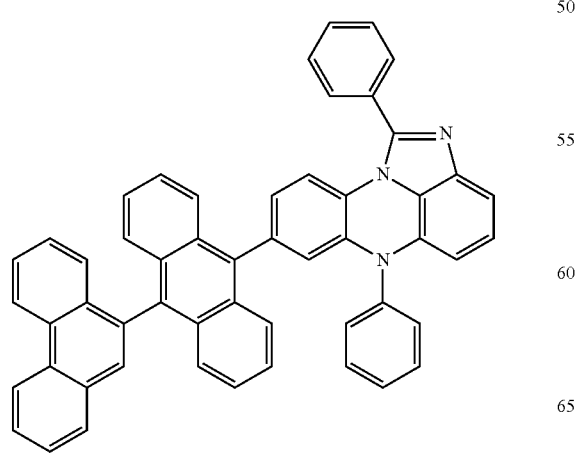
[Chemical Formula 4-7]
[Chemical Formula 4-8]
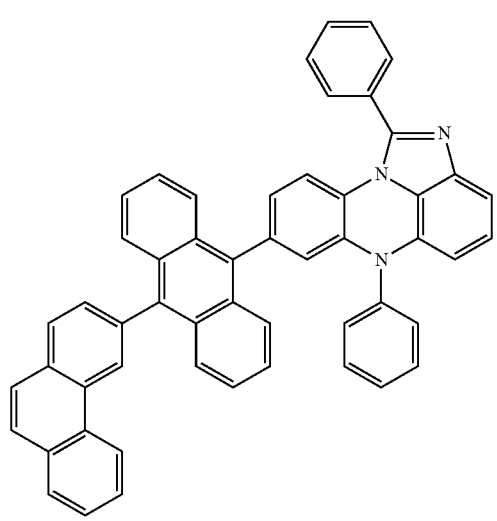
[Chemical Formula 4-9]
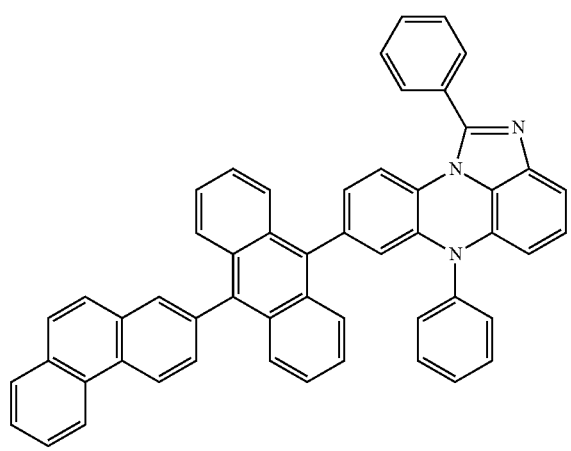
[Chemical Formula 4-10]
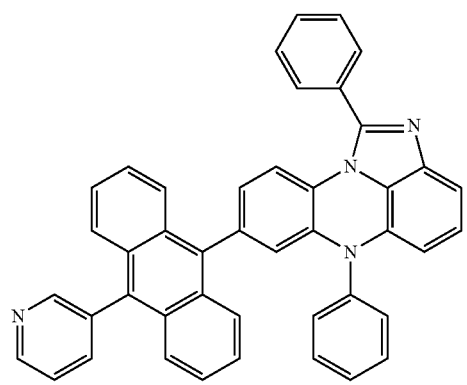

[Chemical Formula 4-11]
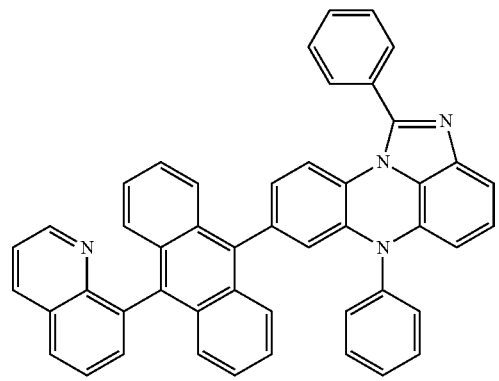
[Chemical Formula 4-12]
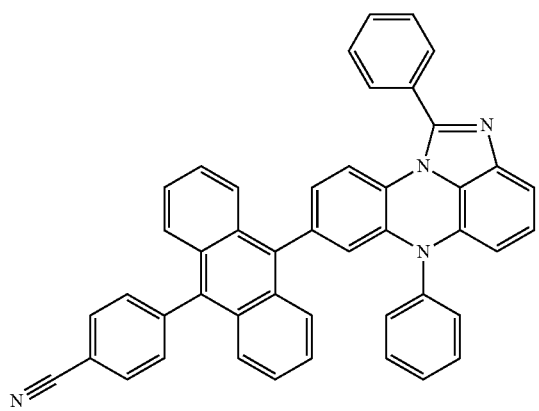
[Chemical Formula 4-13]
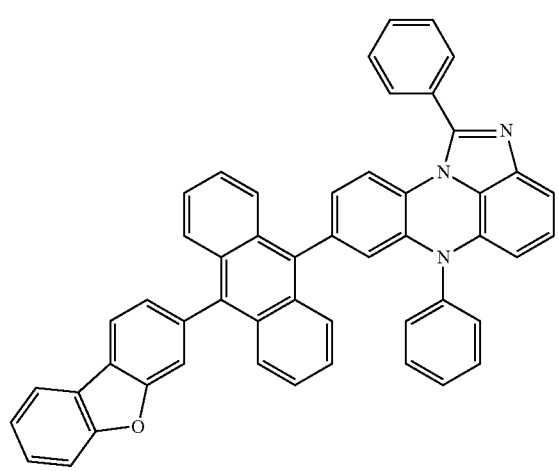
[Chemical Formula 4-14]
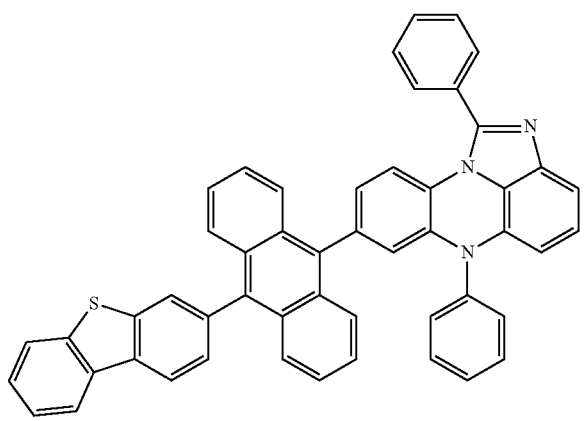
[Chemical Formula 4-15]
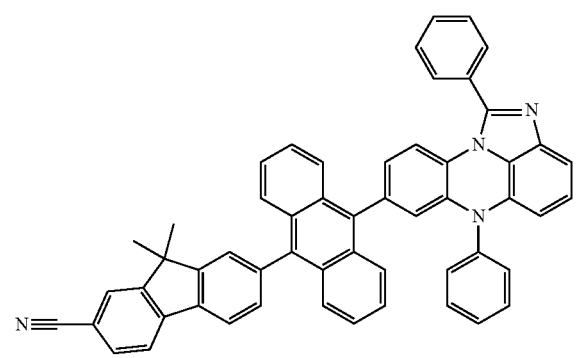
[Chemical Formula 4-16]
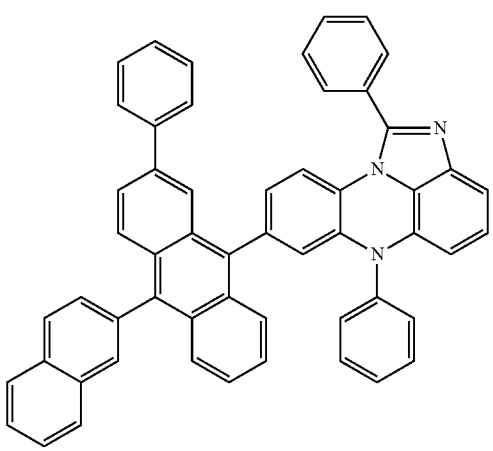

[Chemical Formula 4-17]
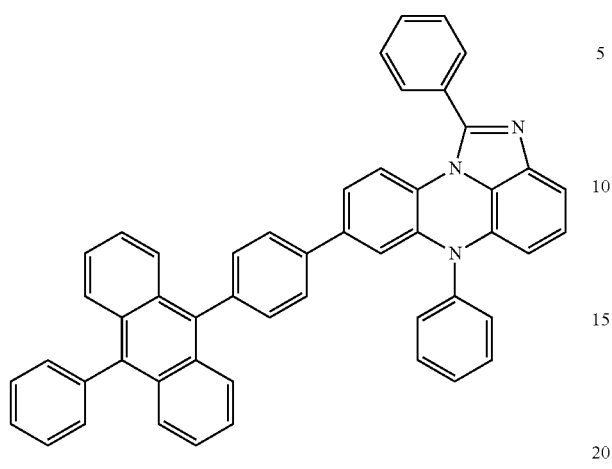
[Chemical Formula 4-18]
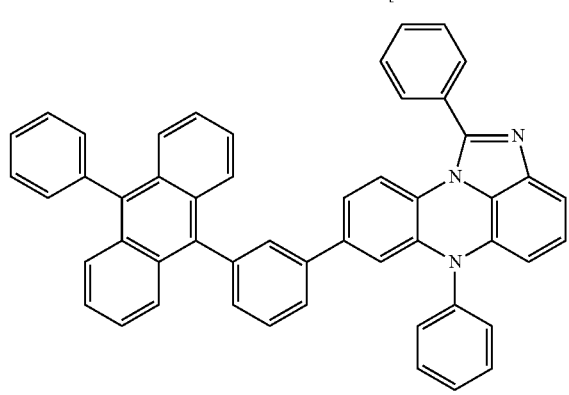
[Chemical Formula 4-19]
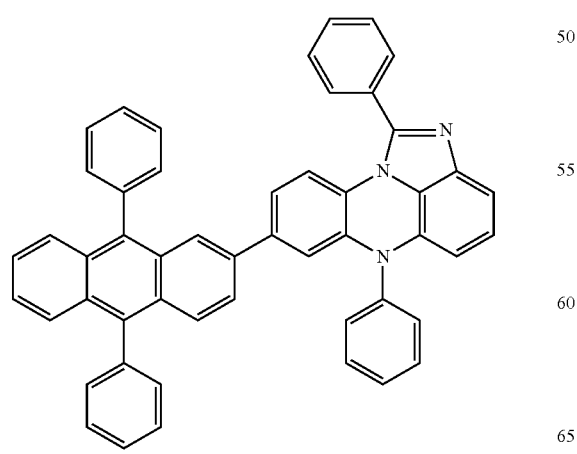
[Chemical Formula 4-20]
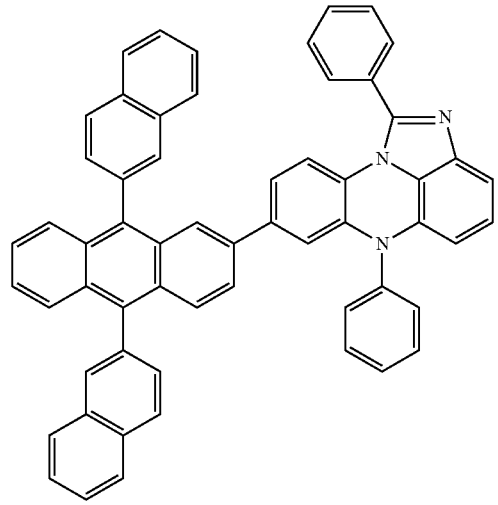
[Chemical Formula 4-21]
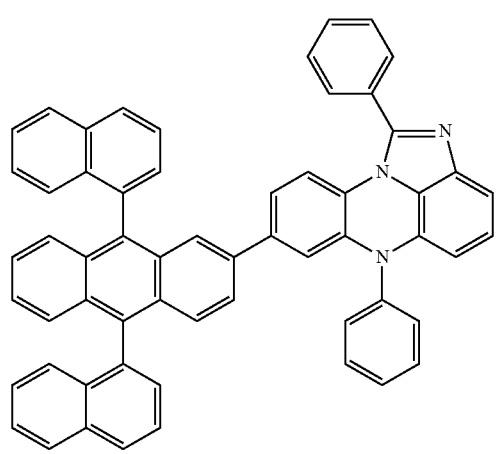
[Chemical Formula 4-22]
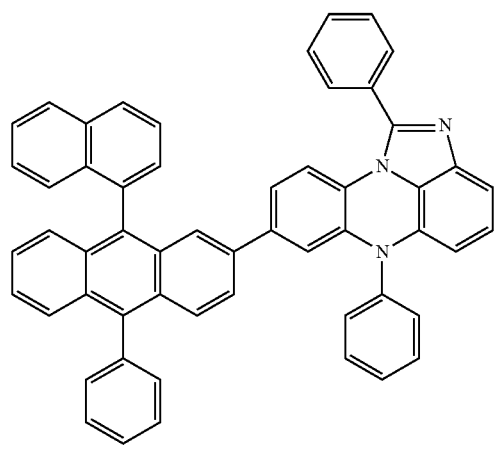

[Chemical Formula 4-23]
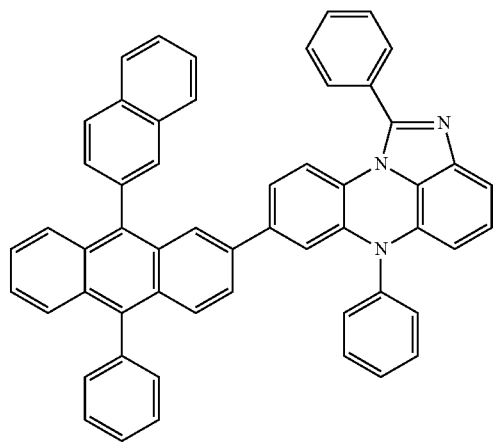
[Chemical Formula 4-24]
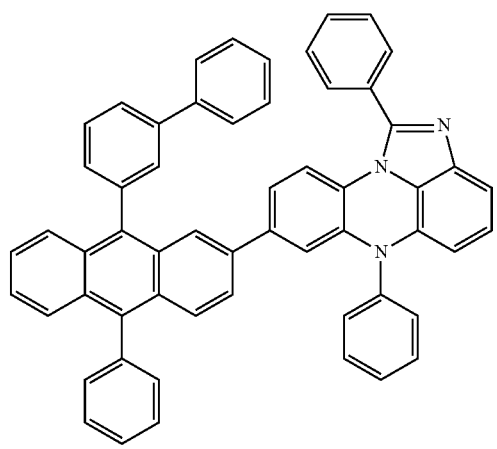
[Chemical Formula 4-25]
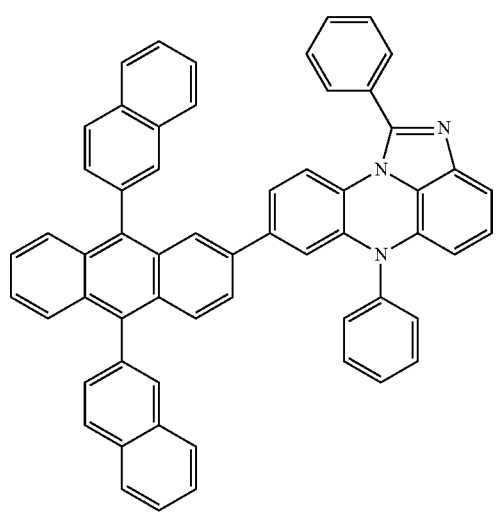
[Chemical Formula 4-26]
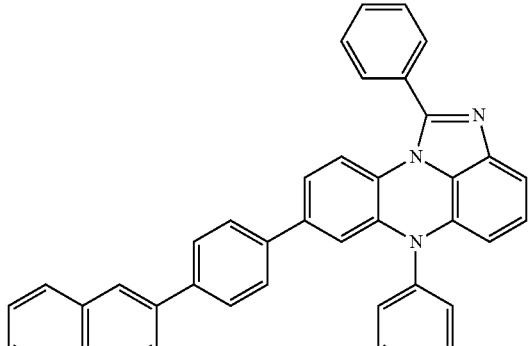
[Chemical Formula 4-27]
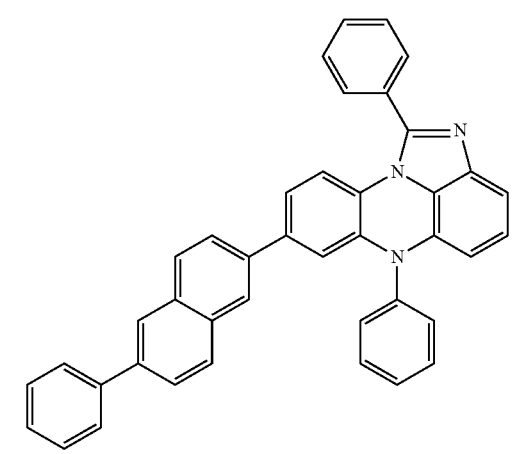
[Chemical Formula 4-28]
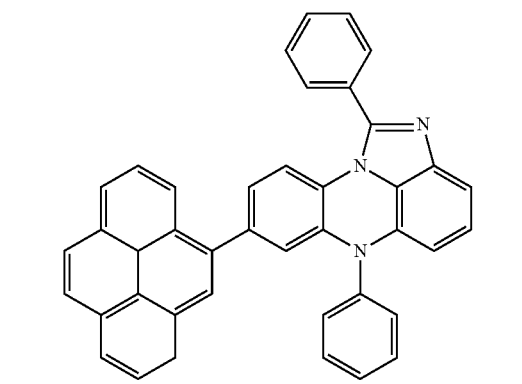
[Chemical Formula 4-29]
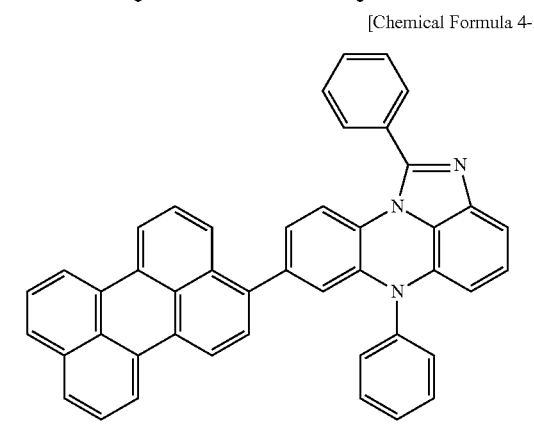

[Chemical Formula 4-30]
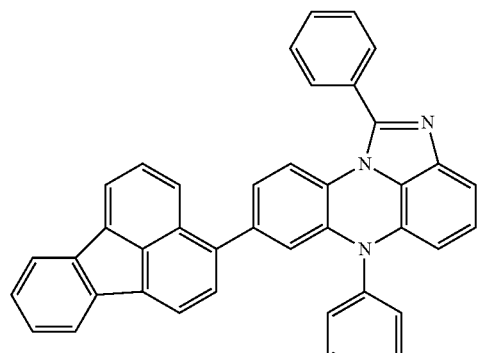
[Chemical Formula 4-31]
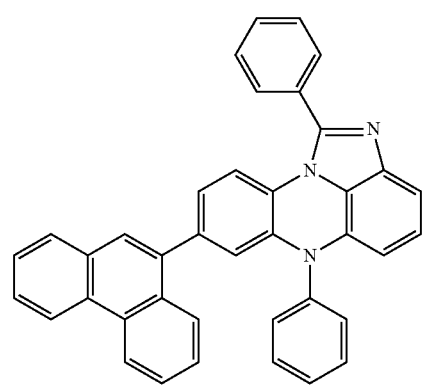
[Chemical Formula 4-32]
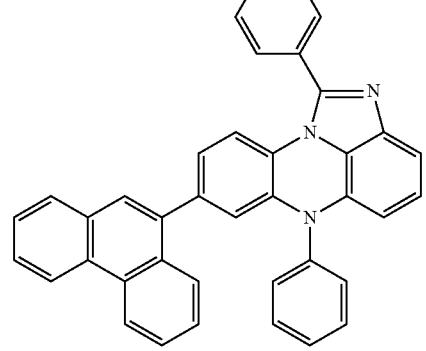
[Chemical Formula 4-33]
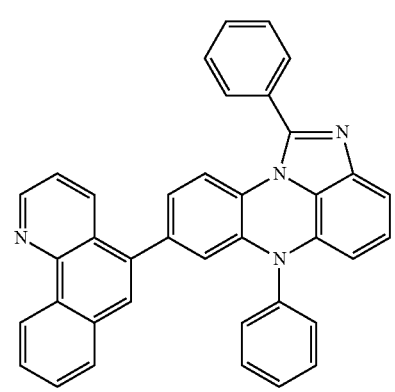
[Chemical Formula 4-34]
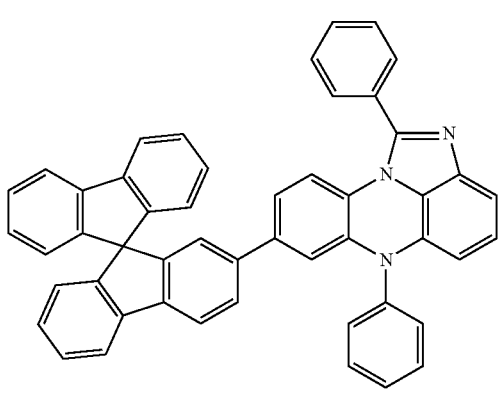
[Chemical Formula 4-35]
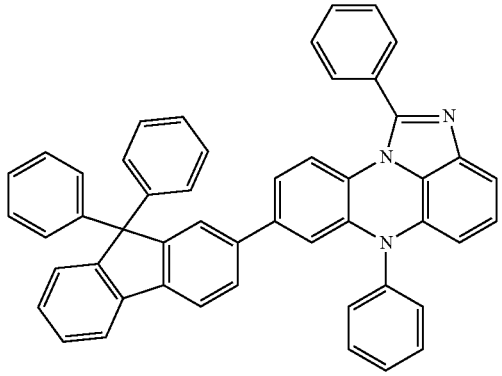
[Chemical Formula 4-36]
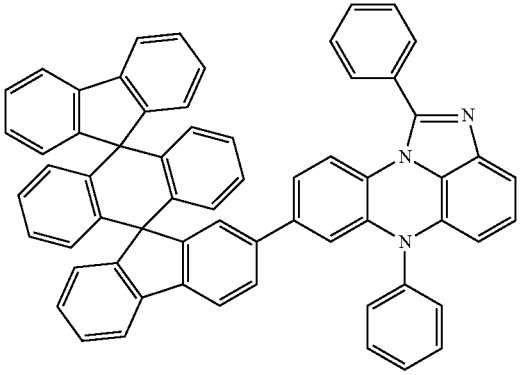
[Chemical Formula 4-37]
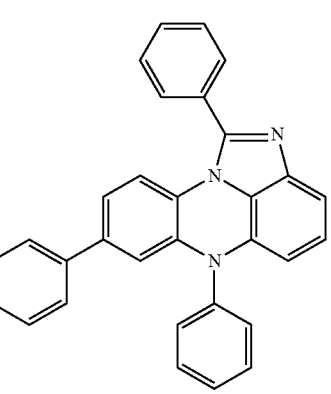

[Chemical Formula 4-38]
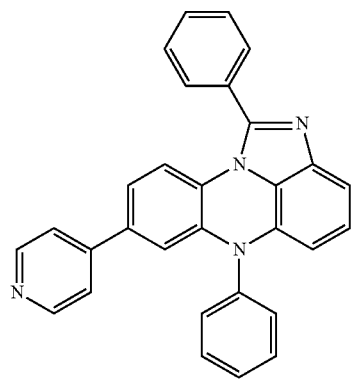
[Chemical Formula 4-39]
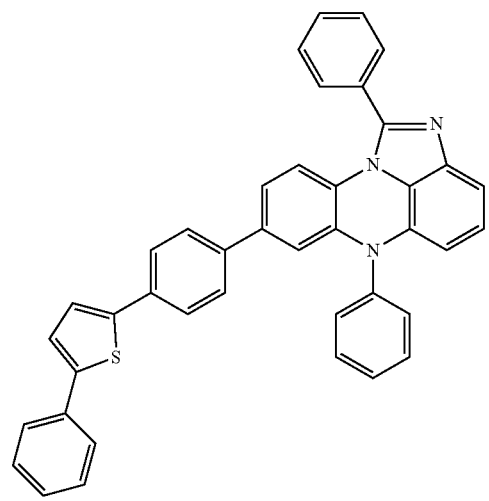
[Chemical Formula 4-40]
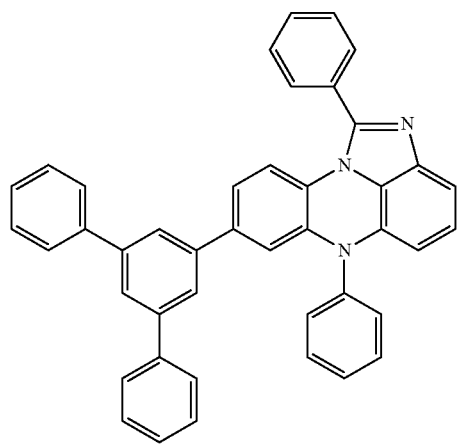
[Chemical Formula 4-41]
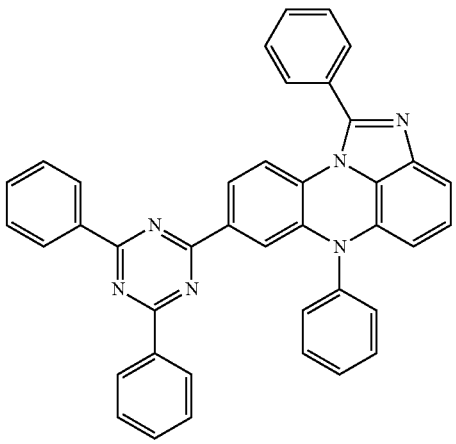
[Chemical Formula 4-42]
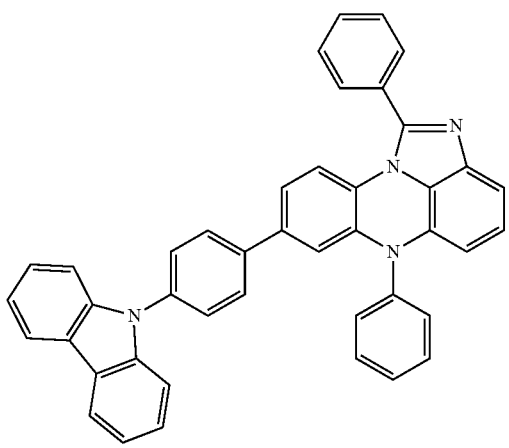
[Chemical Formula 4-43]
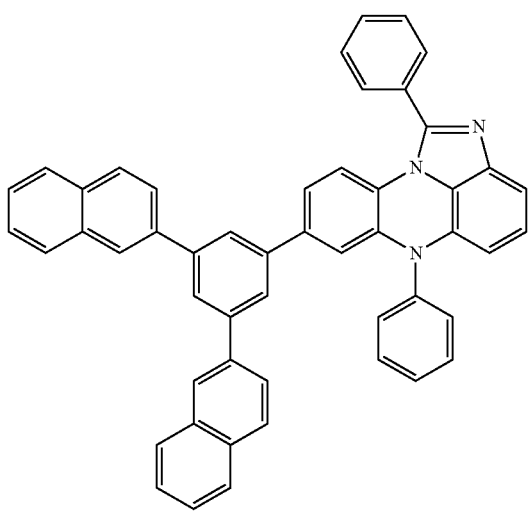

[Chemical Formula 4-44]
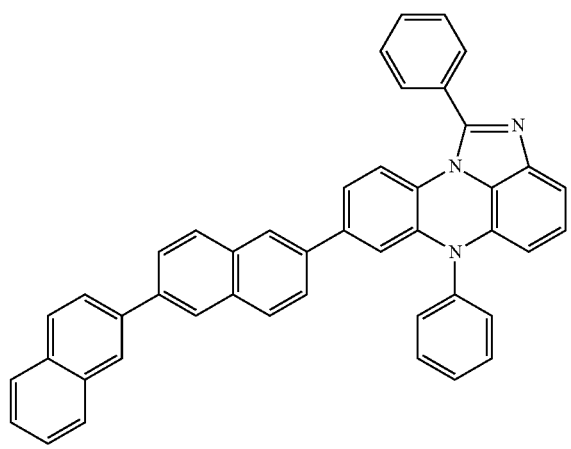
[Chemical Formula 4-45]
[Chemical Formula 4-46]
[Chemical Formula 4-47]
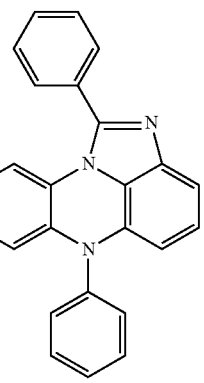
[Chemical Formula 4-49]
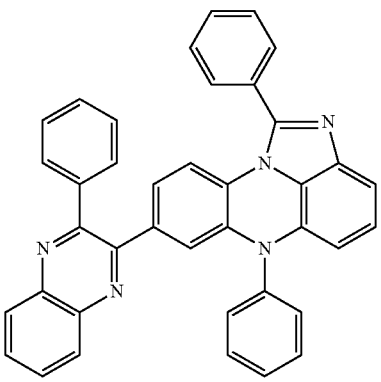
[Chemical Formula 4-50]
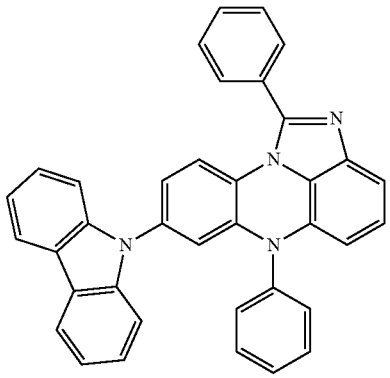
[Chemical Formula 4-51]
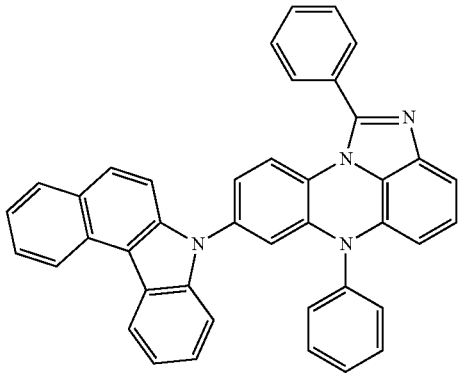

-continued
[Chemical Formula 4-52]
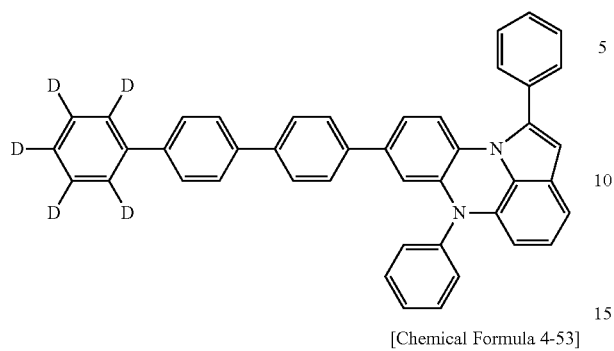
[Chemical Formula 4-53]
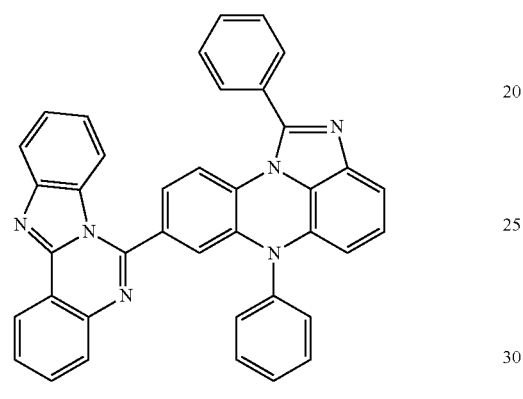
[Chemical Formula 6-17]
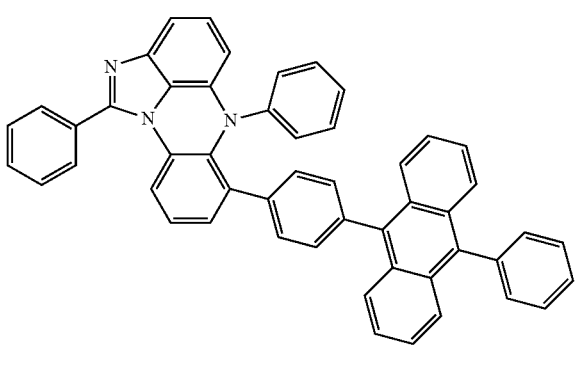
[Chemical Formula 6-27]
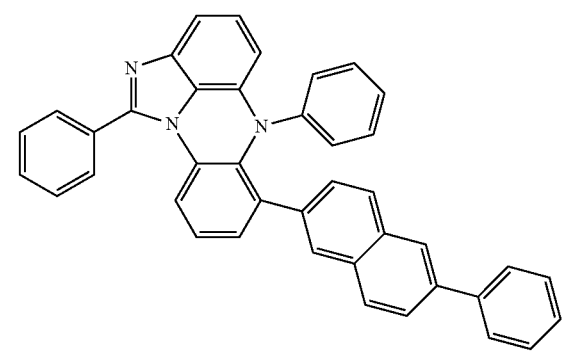
-continued
[Chemical Formula 6-37]
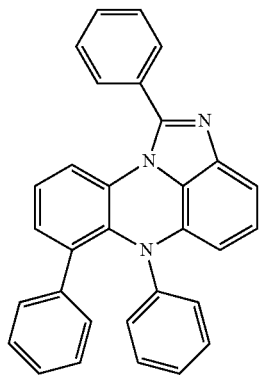
[Chemical Formula 6-38]
[Chemical Formula 6-39]
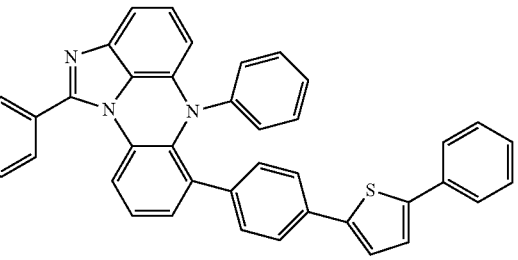
[Chemical Formula 7-1]
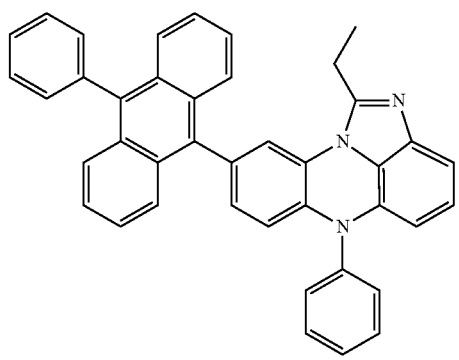

[Chemical Formula 7-2]
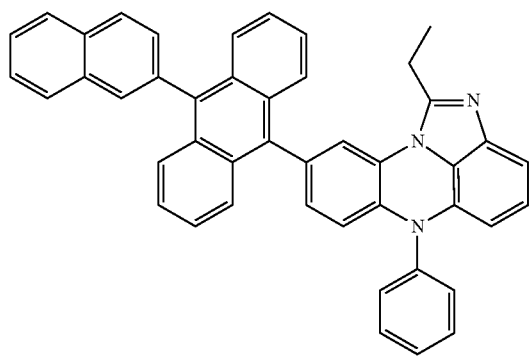
[Chemical Formula 7-3]
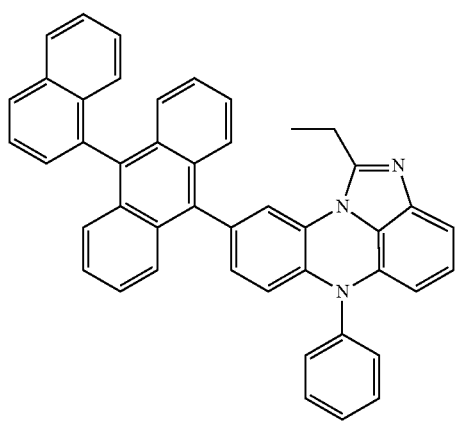
[Chemical Formula 7-4]
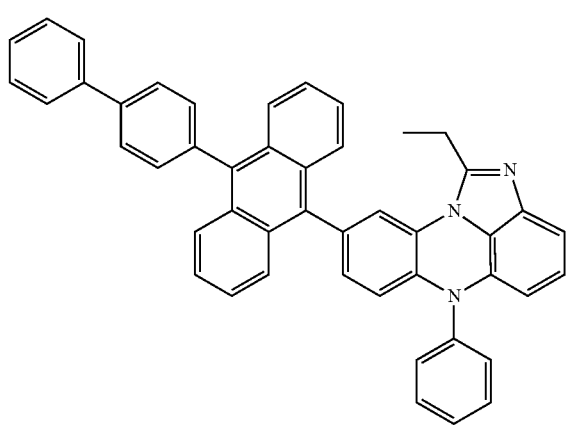
[Chemical Formula 7-5]
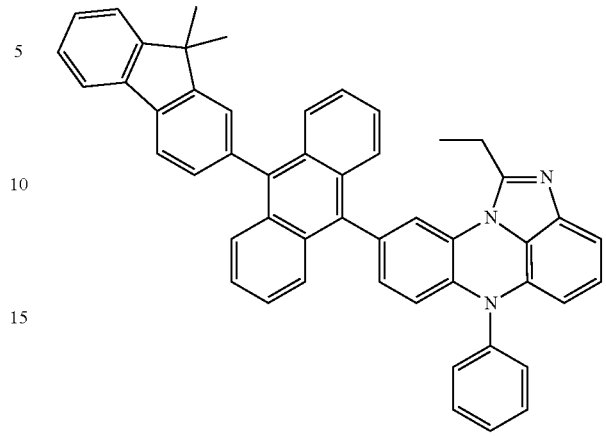
[Chemical Formula 7-6]
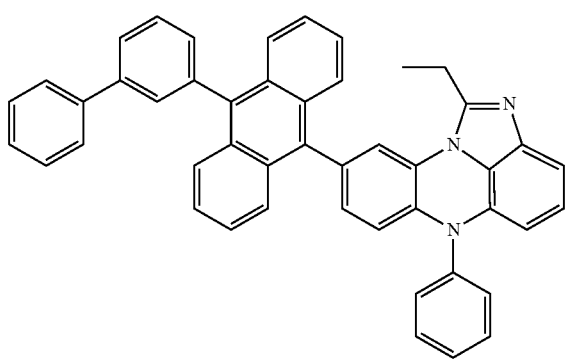
[Chemical Formula 7-7]
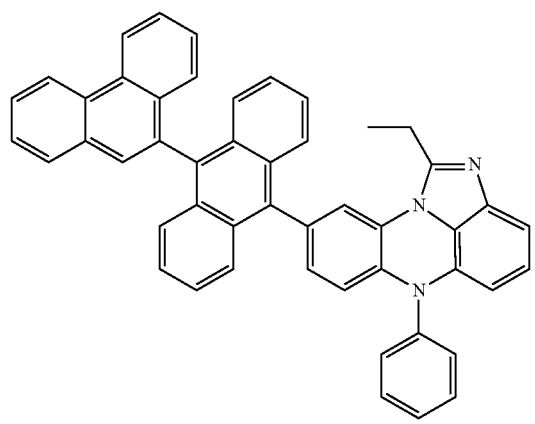
[Chemical Formula 7-8]

239
-continued
[Chemical Formula 7-9]
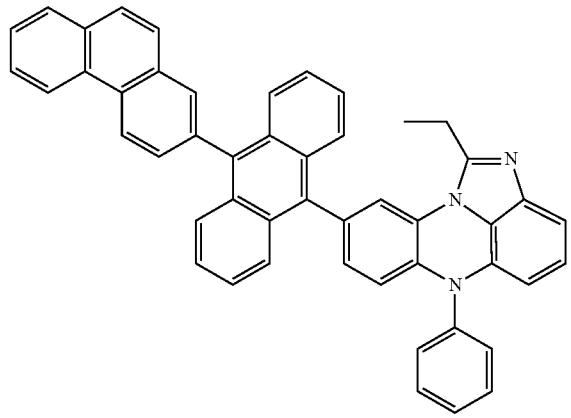
[Chemical Formula 7-10]
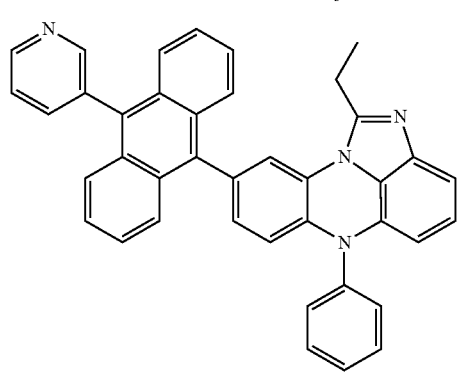
[Chemical Formula 7-11]
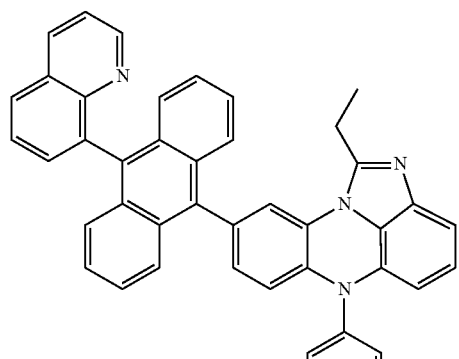
[Chemical Formula 7-12]
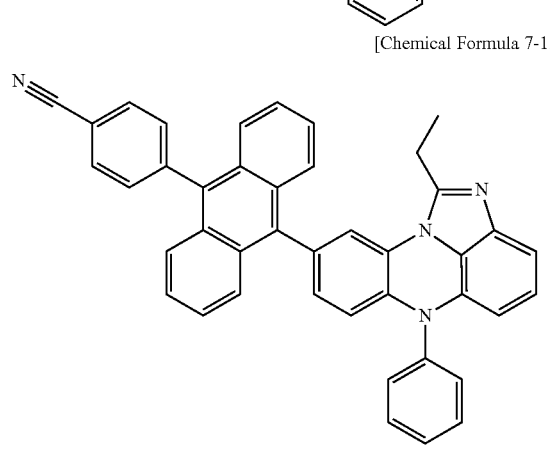
240
-continued
[Chemical Formula 7-13]
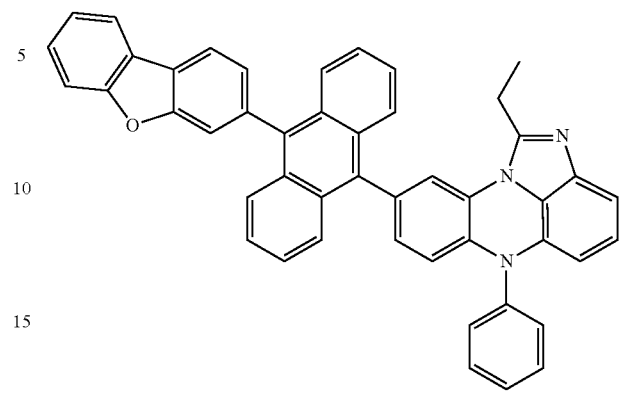
[Chemical Formula 7-14]
[Chemical Formula 7-15]
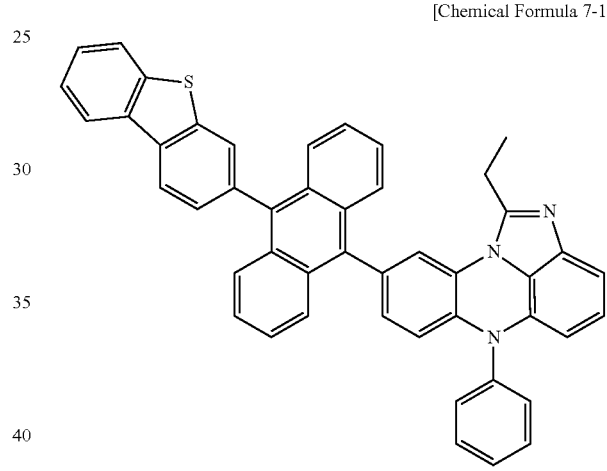

[Chemical Formula 7-16]
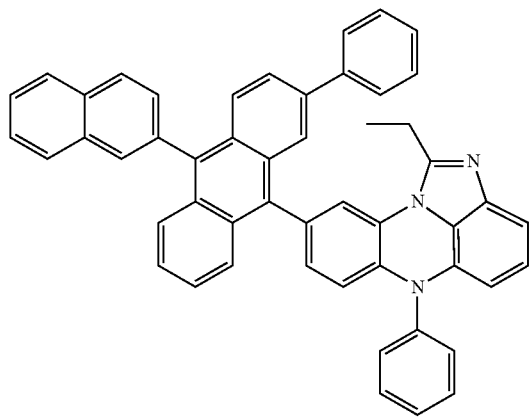
[Chemical Formula 7-19]
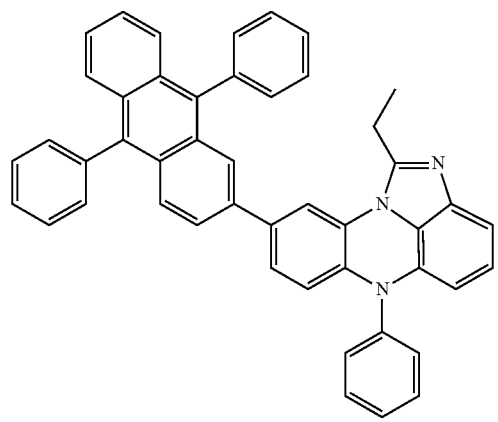
[Chemical Formula 7-17]
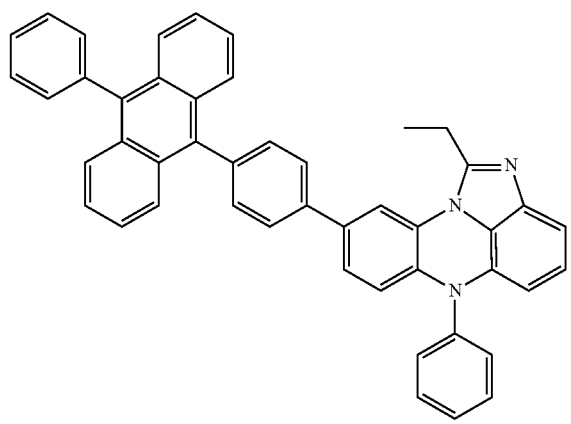
[Chemical Formula 7-20]
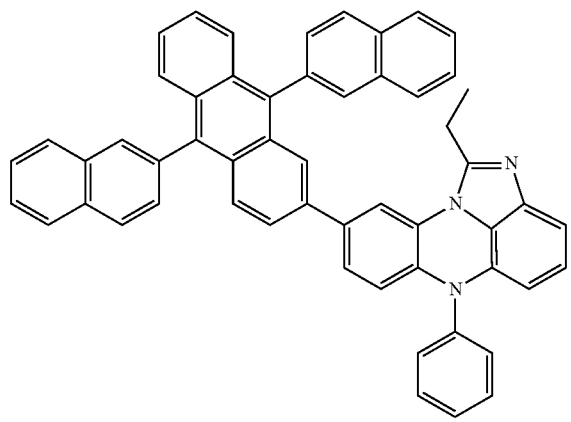
[Chemical Formula 7-18]
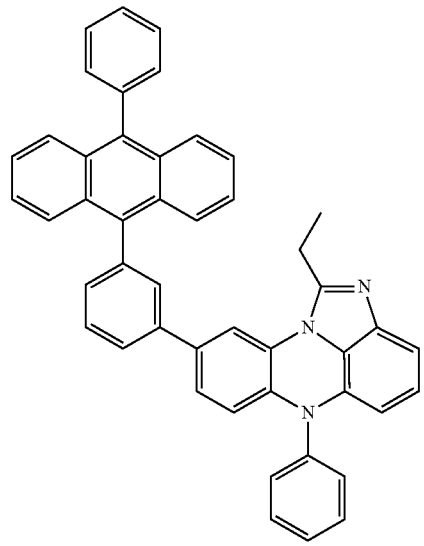
[Chemical Formula 7-21]
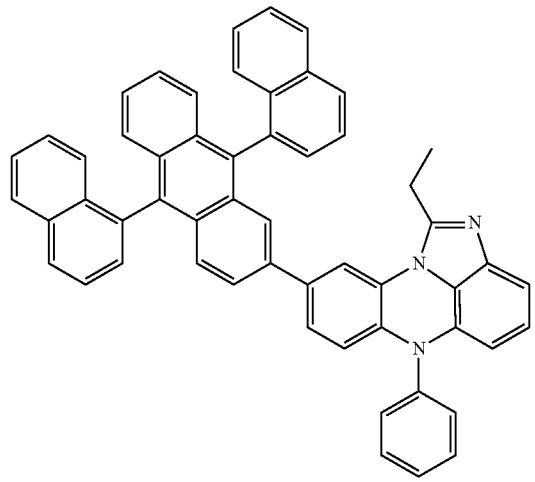

[Chemical Formula 7-22]
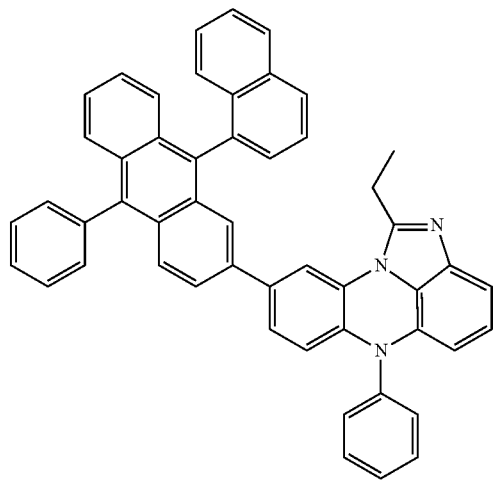
[Chemical Formula 7-23]
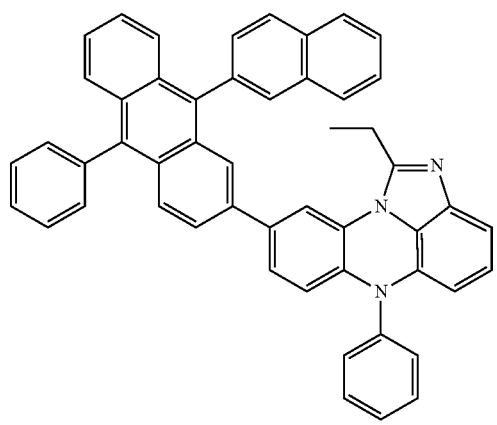
[Chemical Formula 7-24]
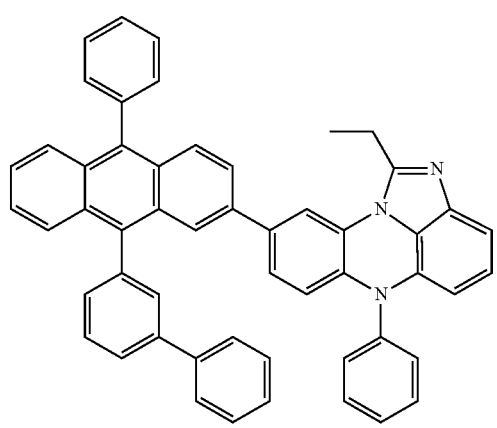
[Chemical Formula 7-25]
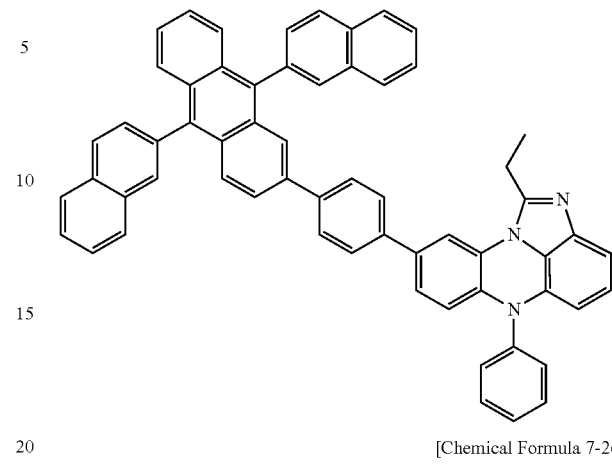
[Chemical Formula 7-26]
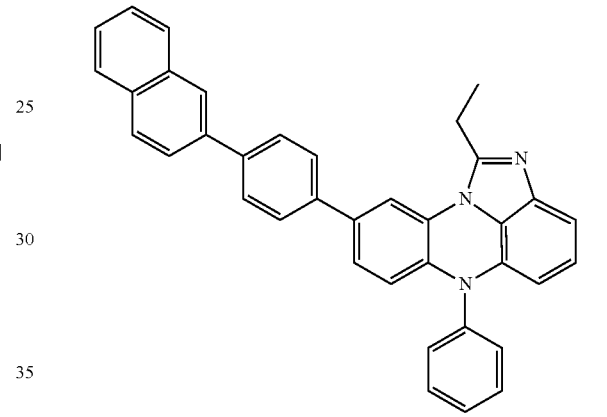
[Chemical Formula 7-27]
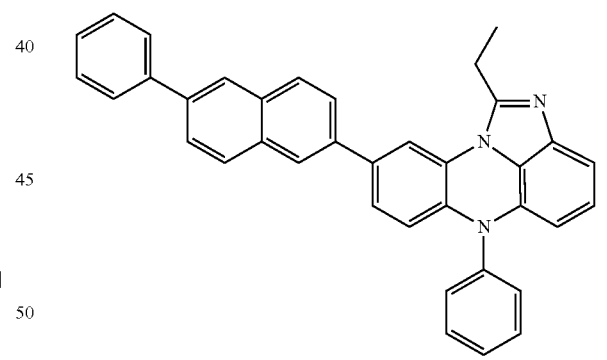
[Chemical Formula 7-28]
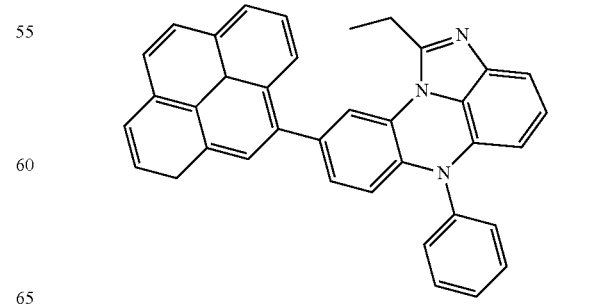

-continued
[Chemical Formula 7-29]
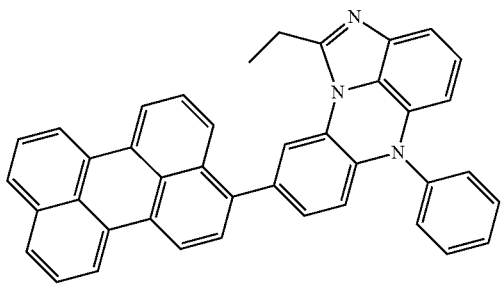
[Chemical Formula 7-30]
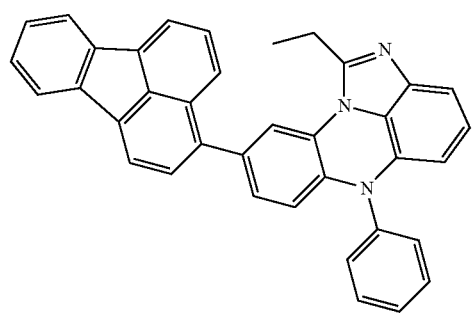
[Chemical Formula 7-31]
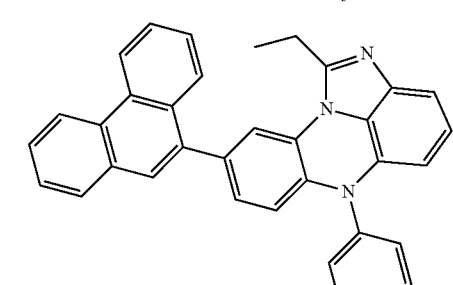
[Chemical Formula 7-32]
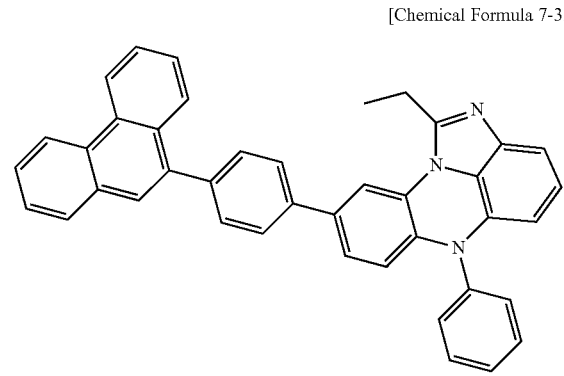
[Chemical Formula 7-33]
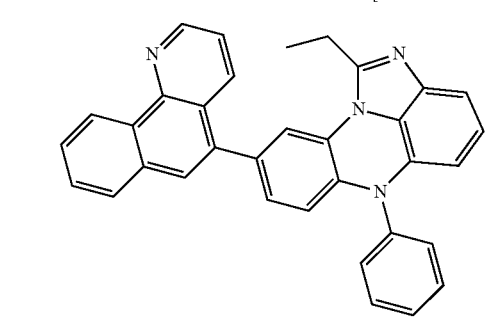
-continued
[Chemical Formula 7-34]
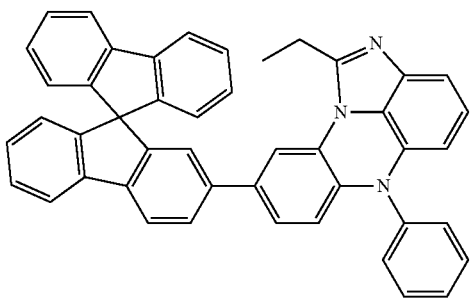
[Chemical Formula 7-35]
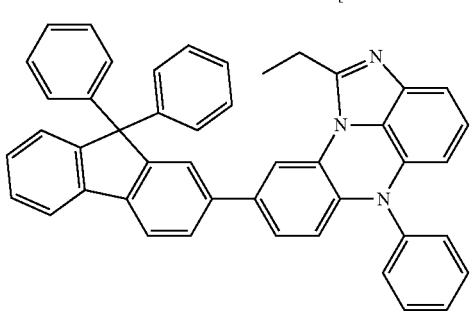
[Chemical Formula 7-36]
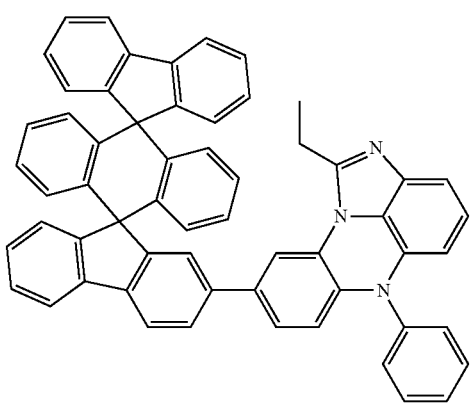
[Chemical Formula 7-37]
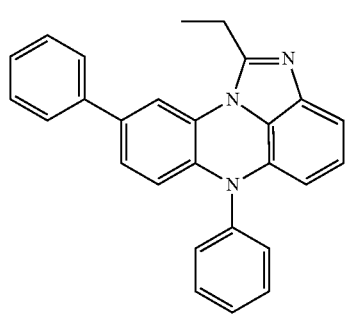

[Chemical Formula 7-38]
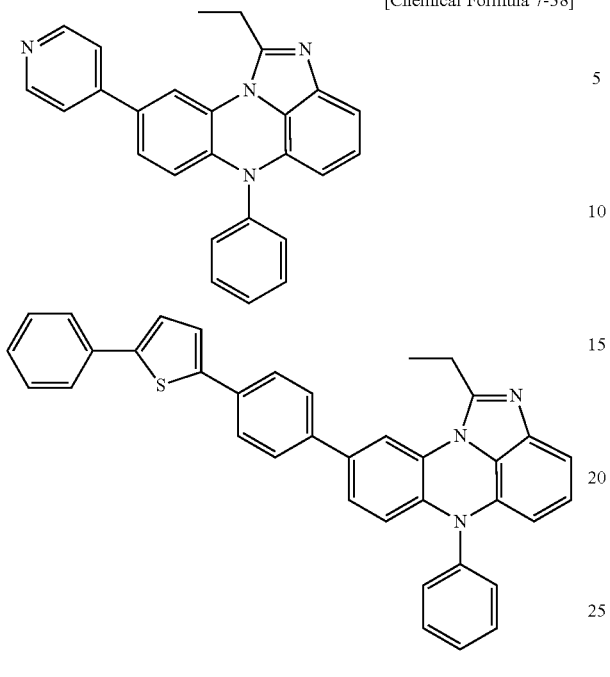
[Chemical Formula 7-40]
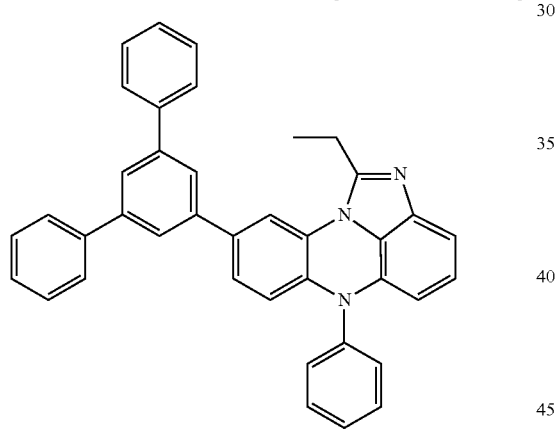
[Chemical Formula 7-41]
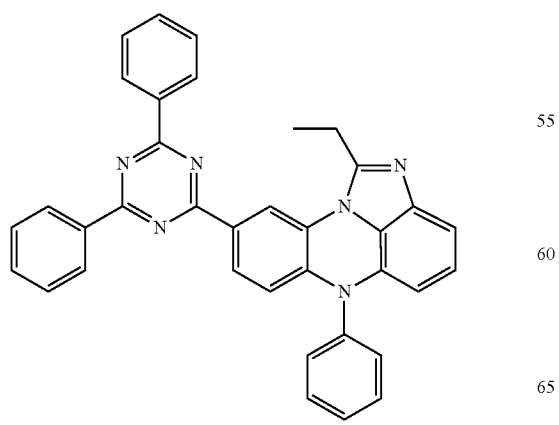
[Chemical Formula 7-42]
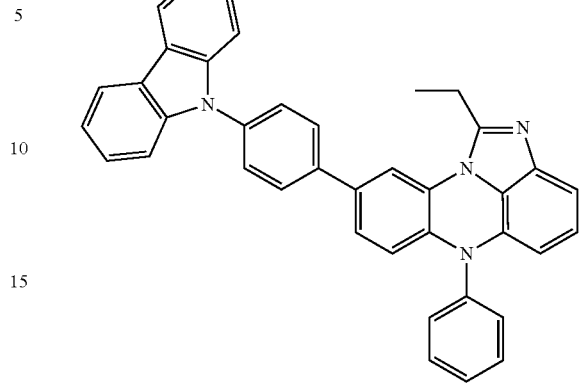
[Chemical Formula 7-43]
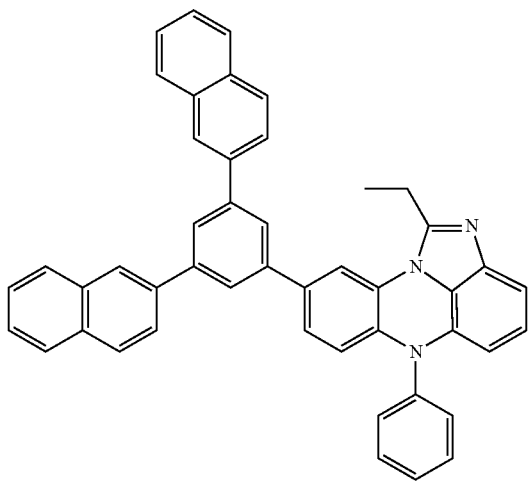
[Chemical Formula 7-44]
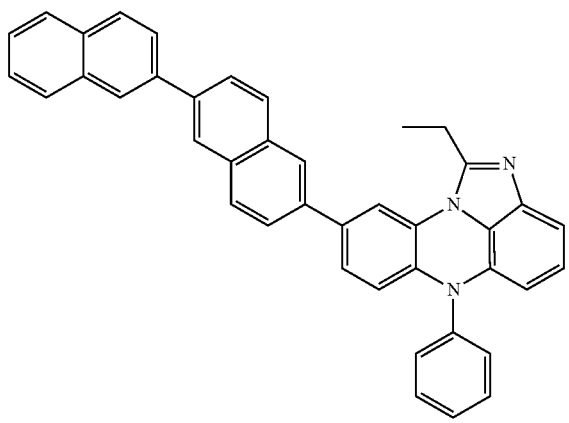

[Chemical Formula 7-45]
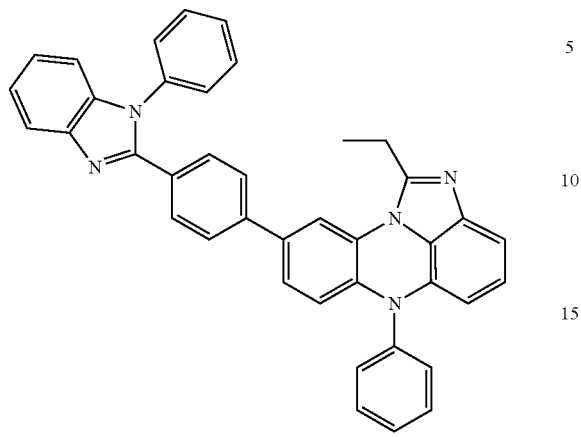
[Chemical Formula 7-46]
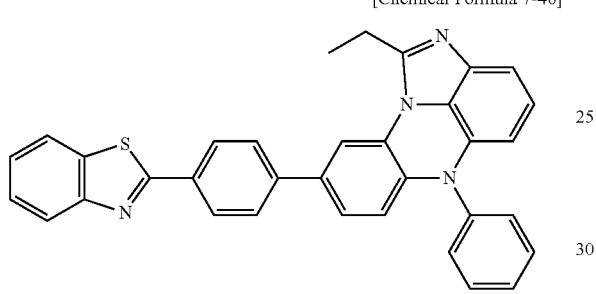
[Chemical Formula 7-47]
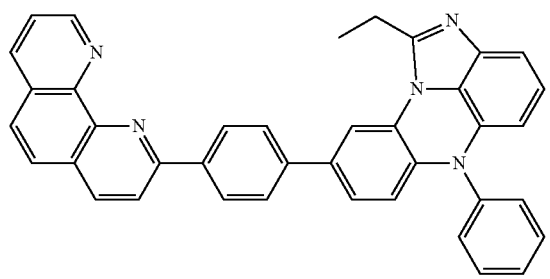
[Chemical Formula 7-49]
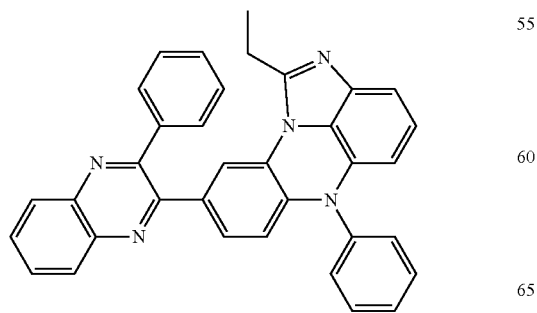
[Chemical Formula 7-50]
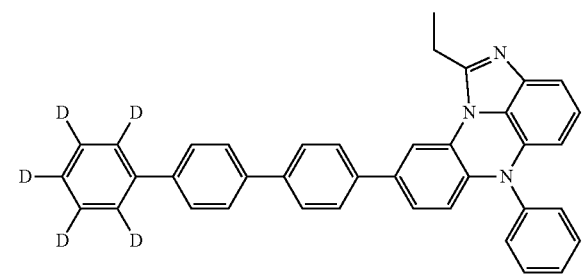
[Chemical Formula 7-51]
[Chemical Formula 7-52]
[Chemical Formula 7-53]
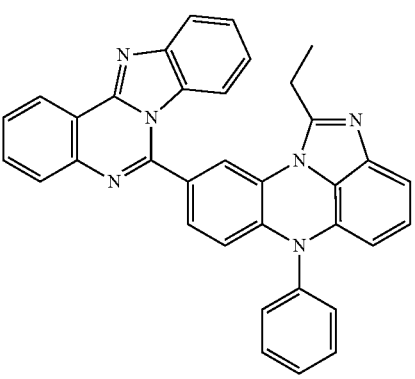

[Chemical Formula 8-1]
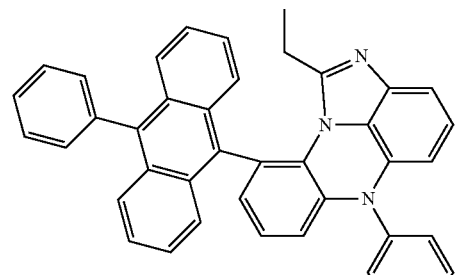
[Chemical Formula 8-2]
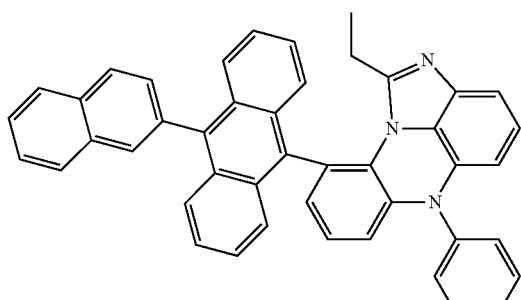
[Chemical Formula 8-3]
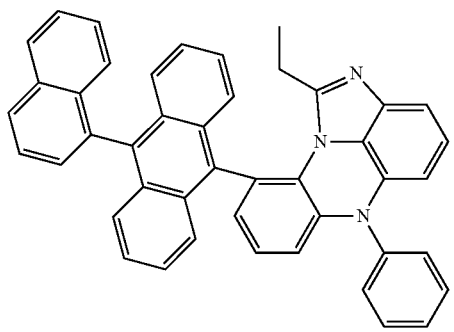
[Chemical Formula 8-4]
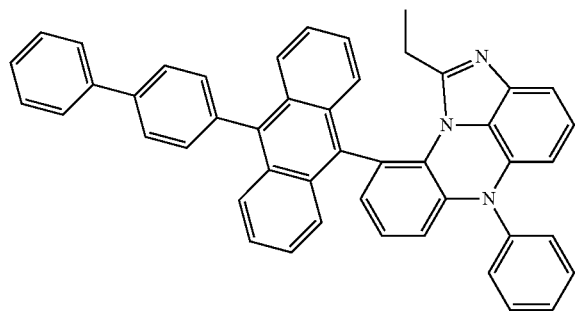
[Chemical Formula 8-5]
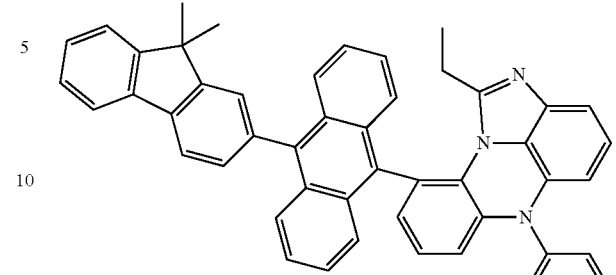
[Chemical Formula 8-6]
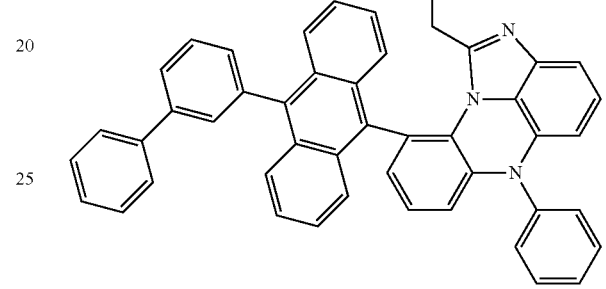
[Chemical Formula 8-7]
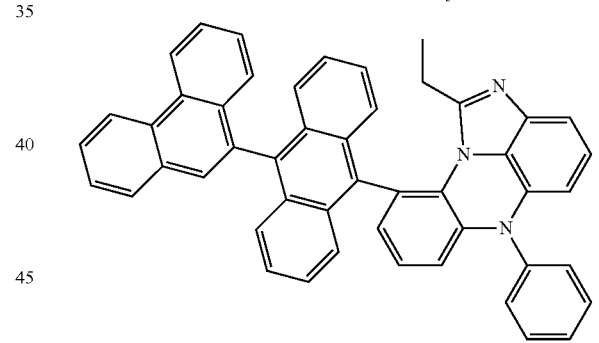
[Chemical Formula 8-8]
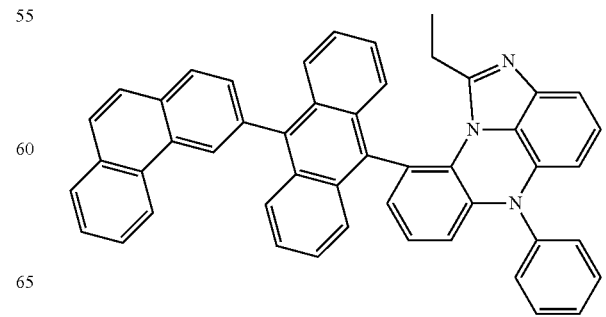

[Chemical Formula 8-9]
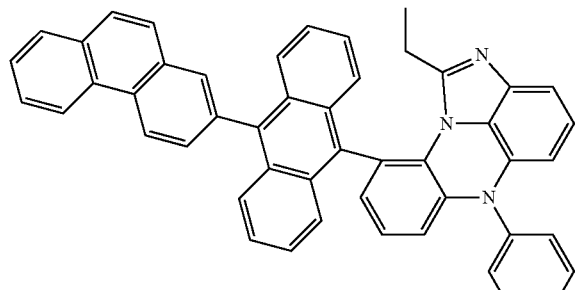
[Chemical Formula 8-10]
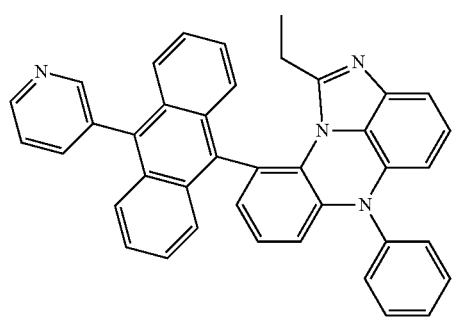
[Chemical Formula 8-11]
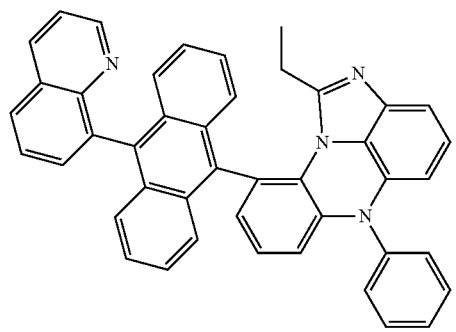
[Chemical Formula 8-12]
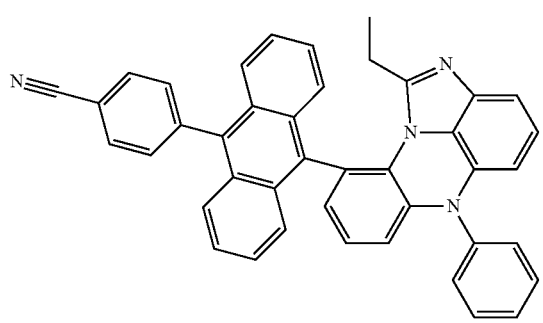
[Chemical Formula 8-13]
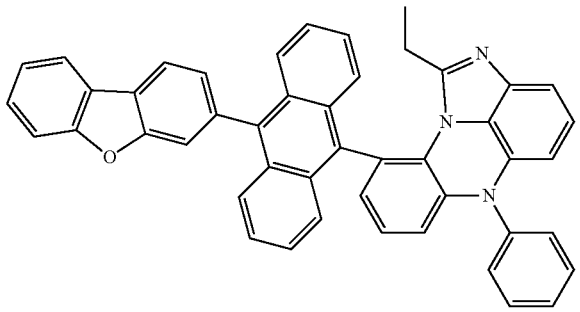
[Chemical Formula 8-14]
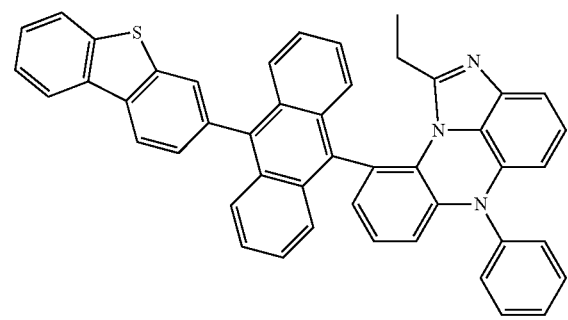
[Chemical Formula 8-15]
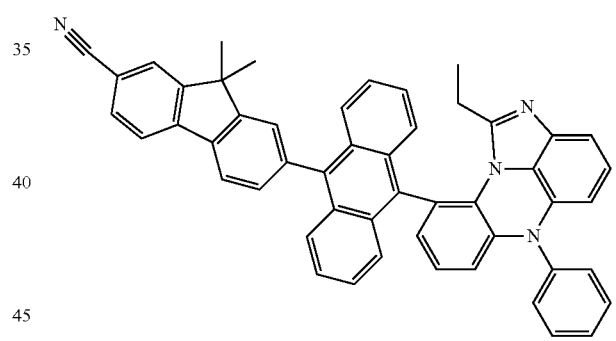
[Chemical Formula 8-16]
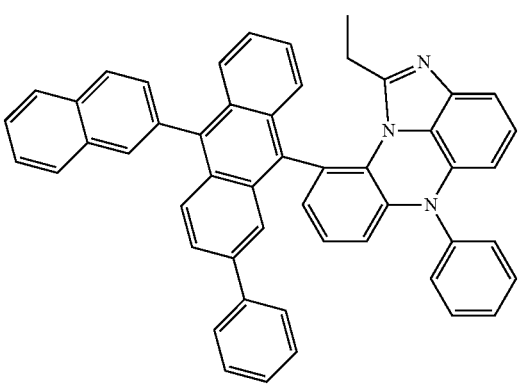

[Chemical Formula 8-17]
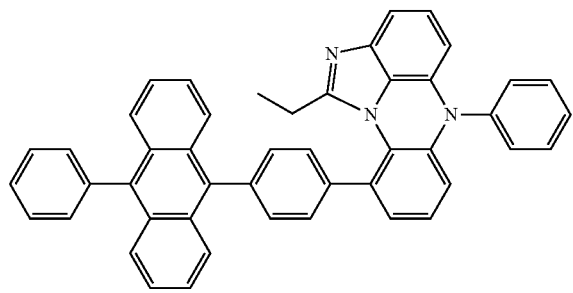
[Chemical Formula 8-18]
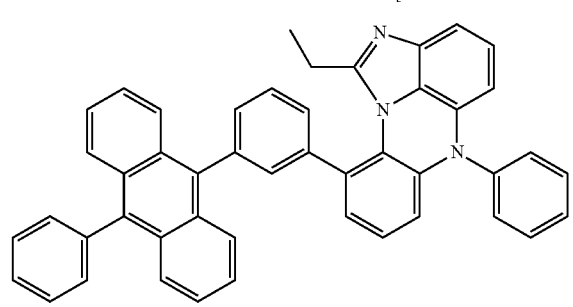
[Chemical Formula 8-19]
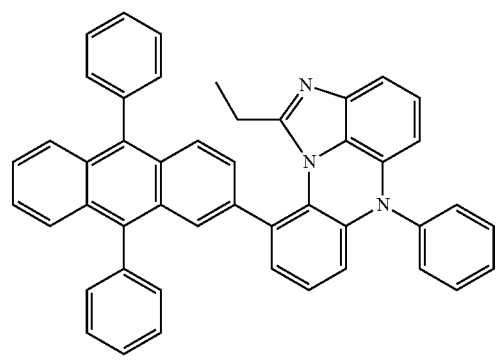
[Chemical Formula 8-20]
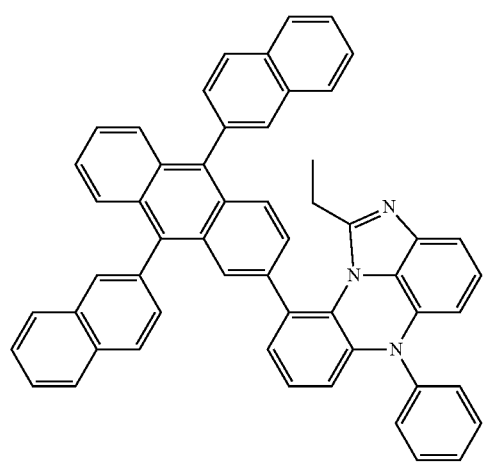
[Chemical Formula 8-21]
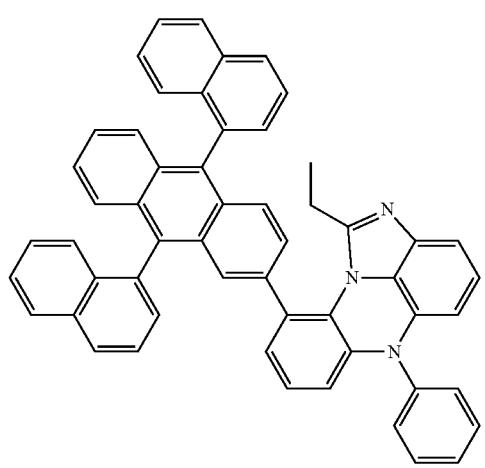
[Chemical Formula 8-22]
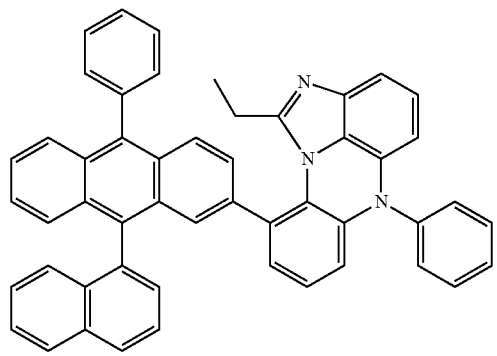
[Chemical Formula 8-23]
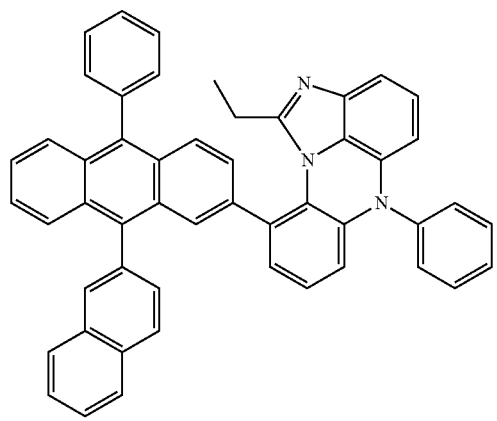

[Chemical Formula 8-24]
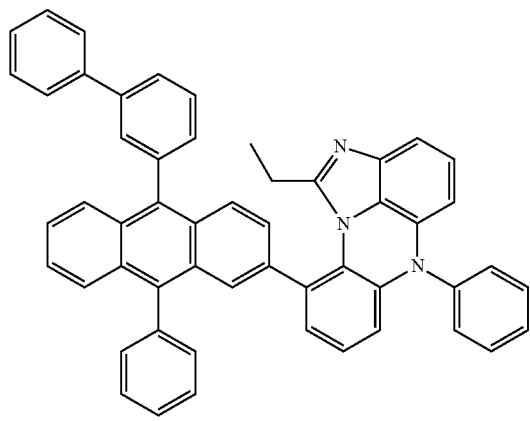
[Chemical Formula 8-25]
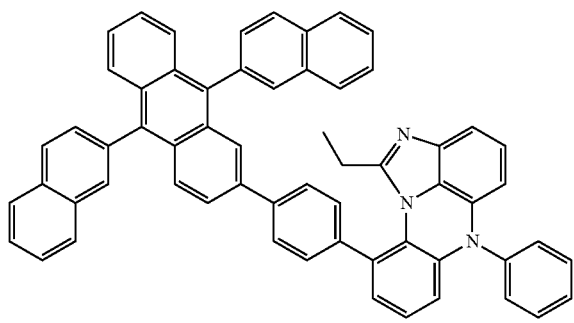
[Chemical Formua 8-26]
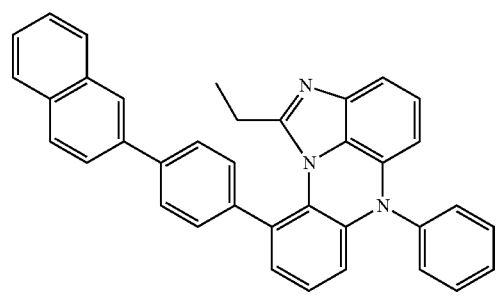
[Chemical Formula 8-27]
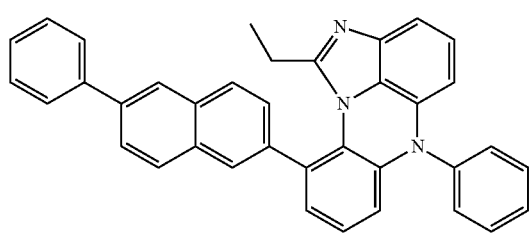
[Chemical Formula 8-28]
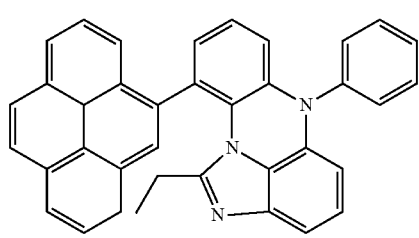
[Chemical Formula 8-29]
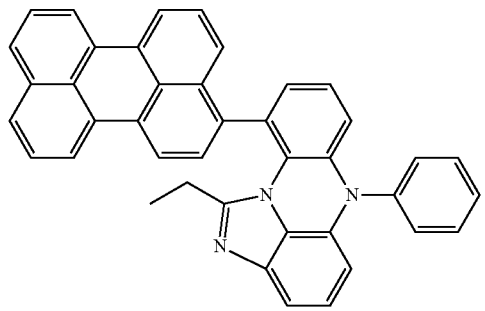
[Chemical Formula 8-30]
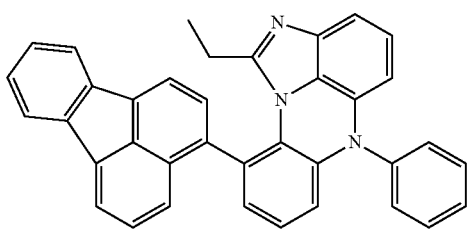
[Chemical Formula 8-31]
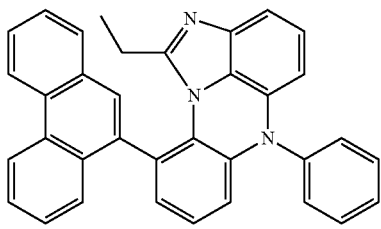
[Chemical Formula 8-32]
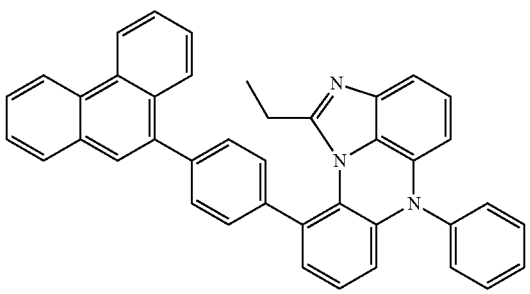
[Chemical Formula 8-33]
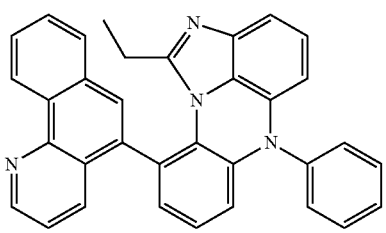

259
-continued
[Chemical Formula 8-34]
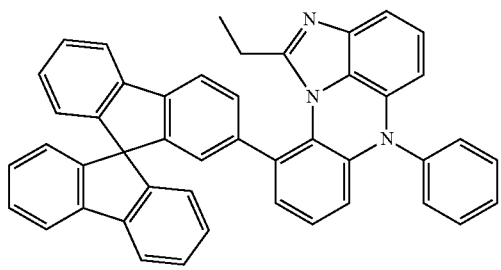
[Chemical Formula 8-35]
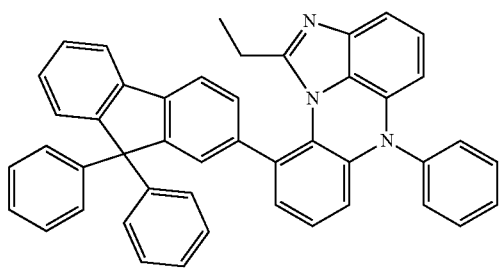
[Chemical Formula 8-36]
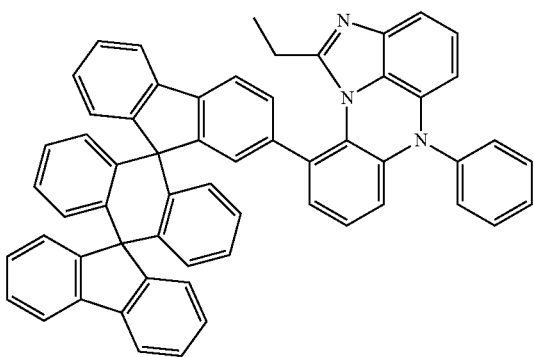
[Chemical Formula 9-1]
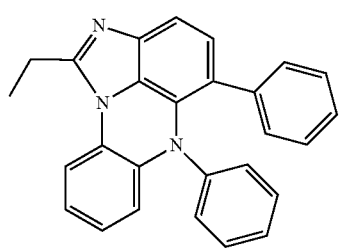
[Chemical Formula 9-2]
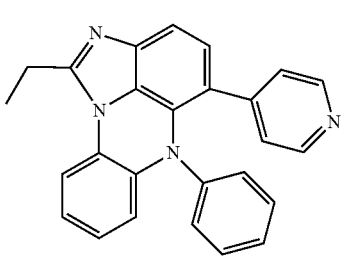
260
-continued
[Chemical Formula 9-3]
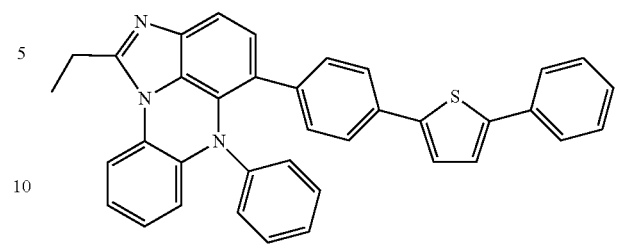
[Chemical Formula 9-6]
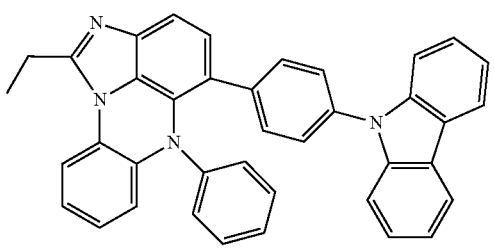
[Chemical Formula 9-7]
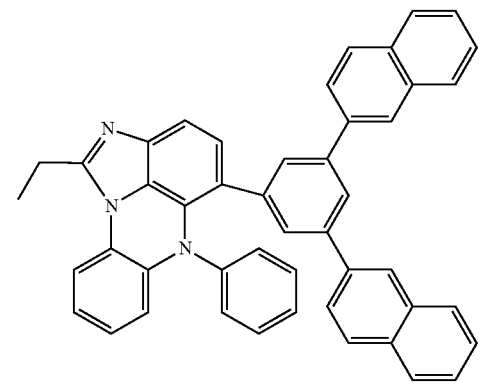
[Chemical Formula 9-8]
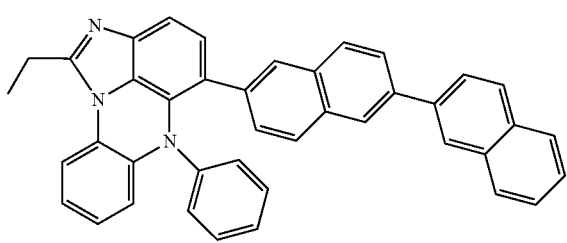
[Chemical Formula 9-9]
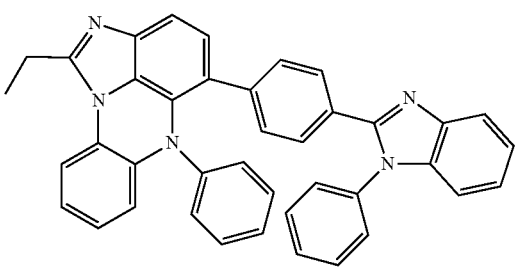

[Chemical Formula 9-10]
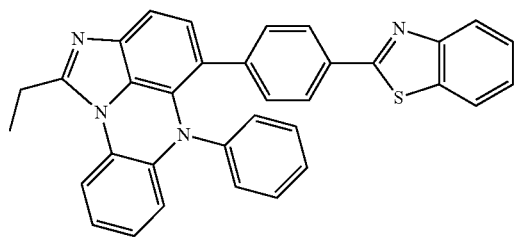
[Chemical Formula 9-11]
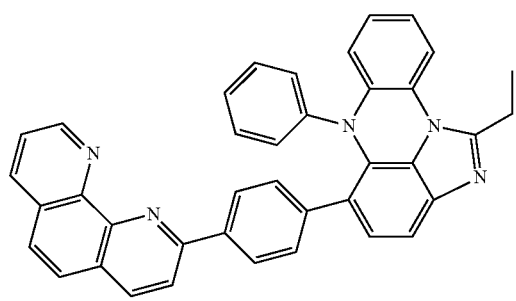
[Chemical Formula 9-13]
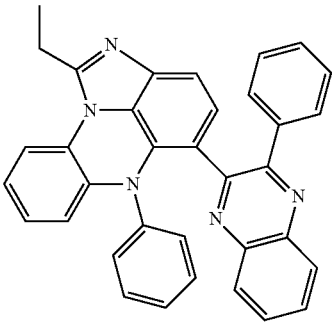
[Chemical Formula 9-14]
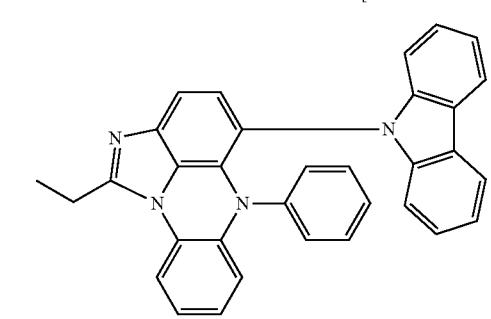
[Chemical Formula 9-15]
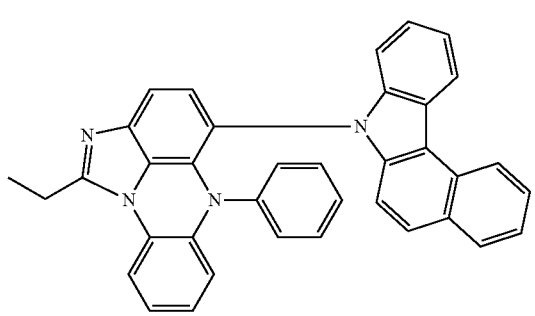
[Chemical Formula 9-16]
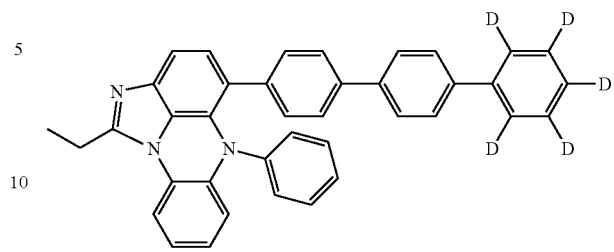
[Chemical Formula 9-17]
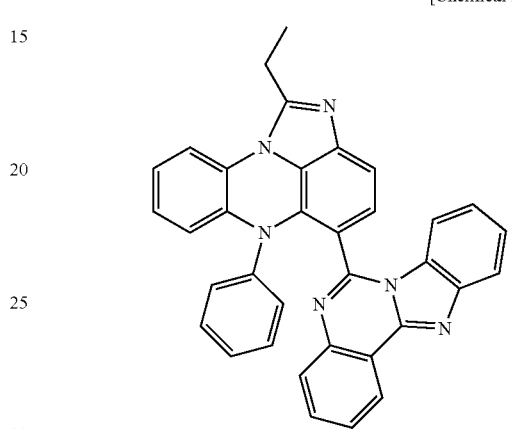
[Chemical Formula 10-1]
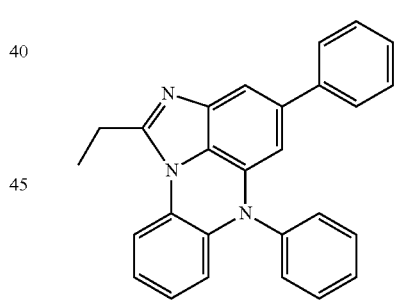
[Chemical Formula 10-2]
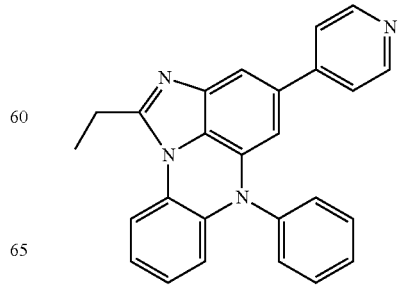

[Chemical Formula 10-3]
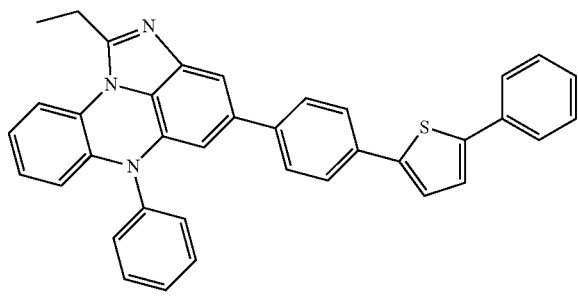
[Chemical Formula 10-6]
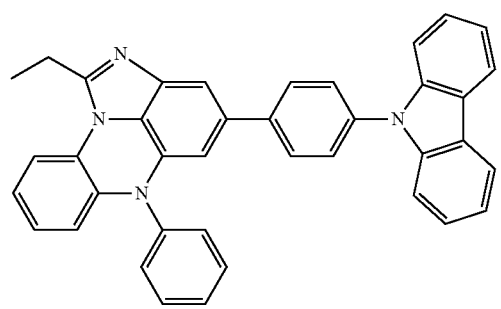
[Chemical Formula 10-7]
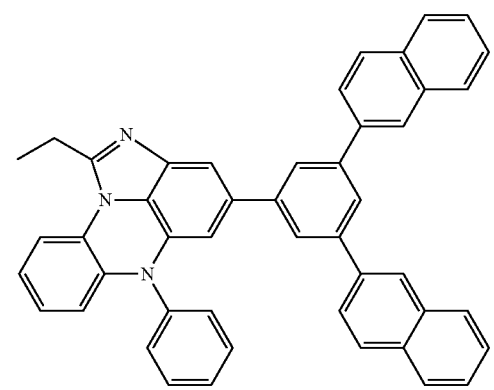
[Chemical Formula 10-8]
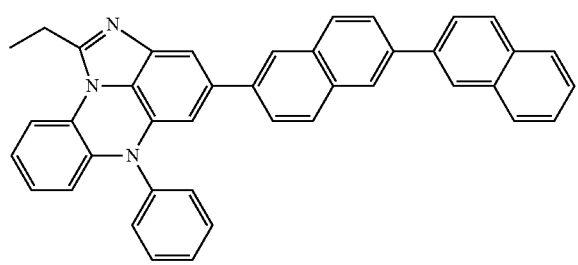
[Chemical Formula 10-9]
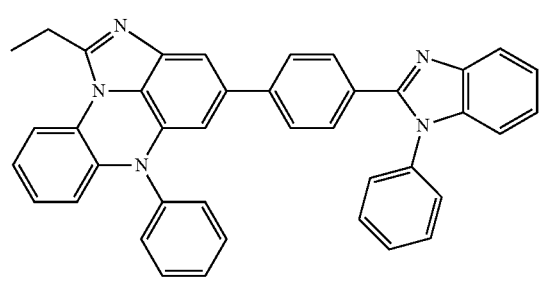
[Chemical Formula 10-10]
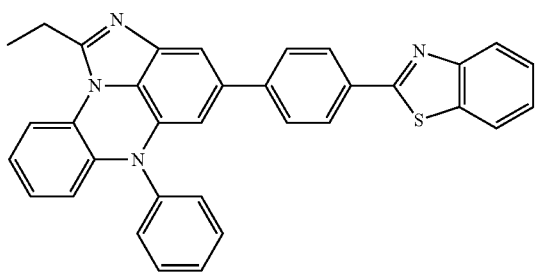
[Chemical Formula 10-11]
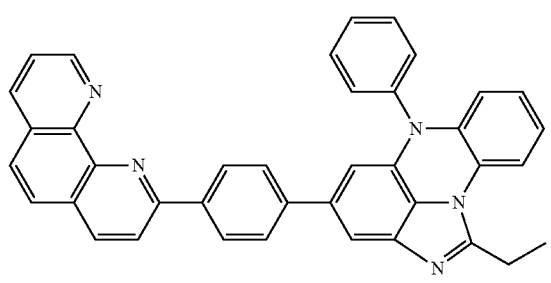
[Chemical Formula 10-13]
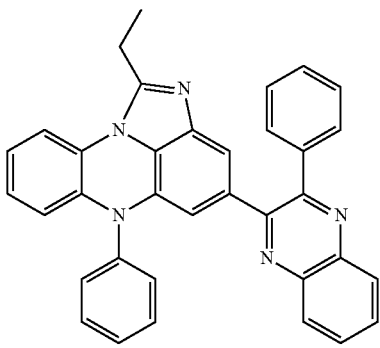
[Chemical Formula 10-14]
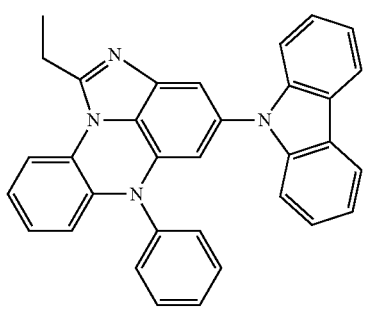
[Chemical Formula 10-15]
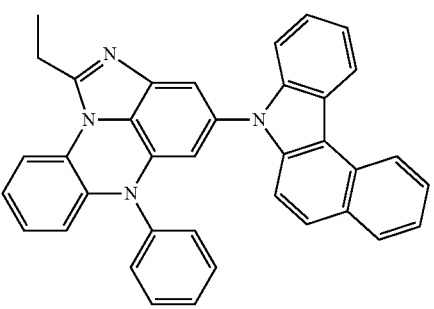

[Chemical Formula 10-16]
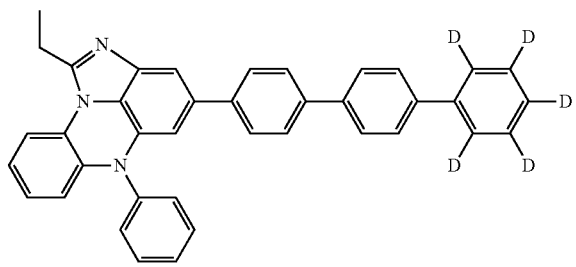
[Chemical Formula 10-17]
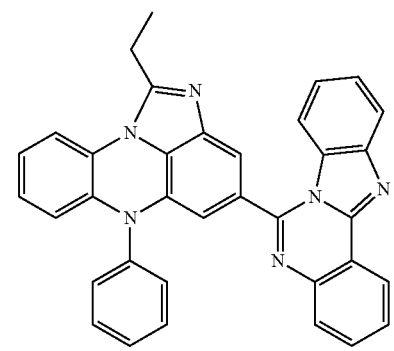
[Chemical Formula 11-1]
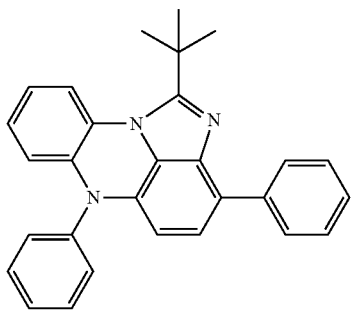
[Chemical Formula 11-2]
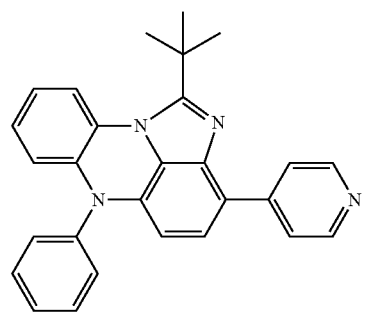
[Chemical Formula 11-3]
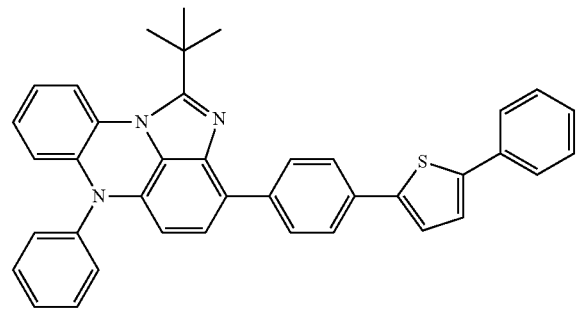
[Chemical Formula 11-6]
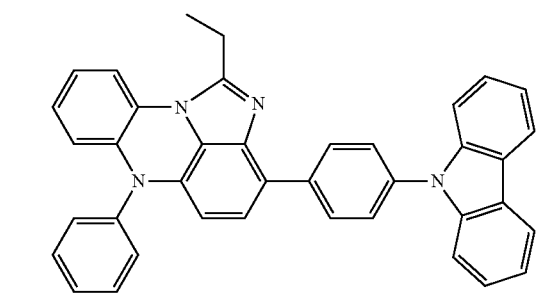
[Chemical Formula 11-7]
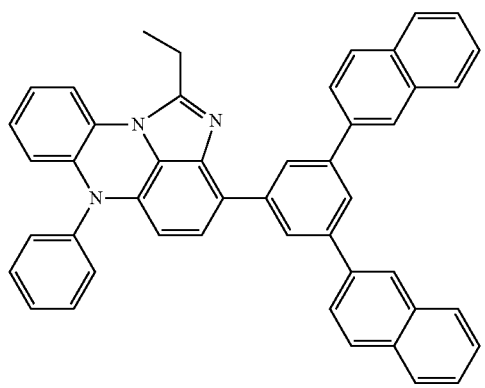
[Chemical Formula 11-8]
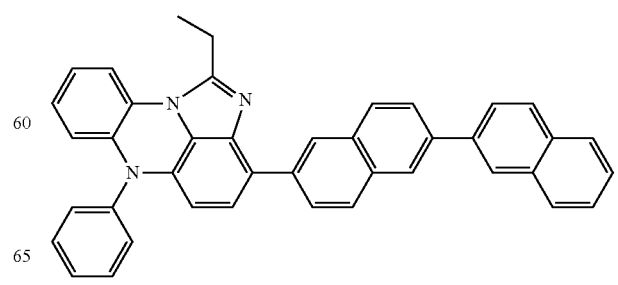

[Chemical Formula 11-9]
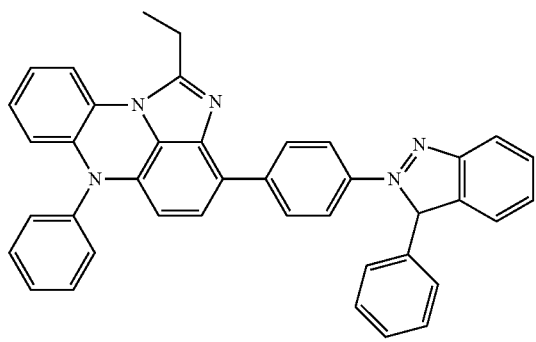
[Chemical Formula 11-10]
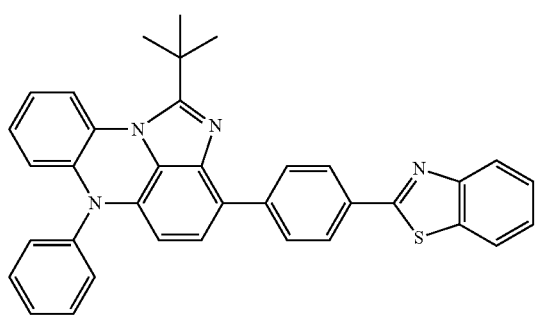
[Chemical Formula 11-11]
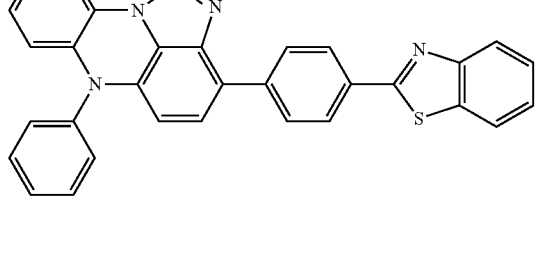
[Chemical Formula 11-13]
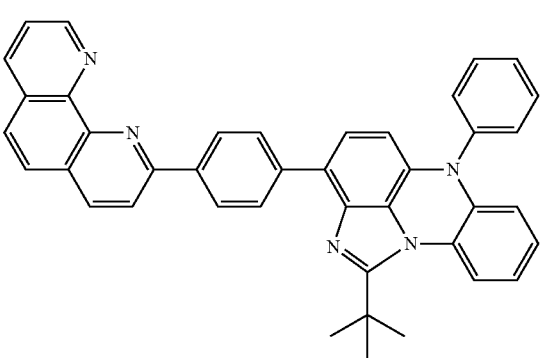
[Chemical Formula 11-14]
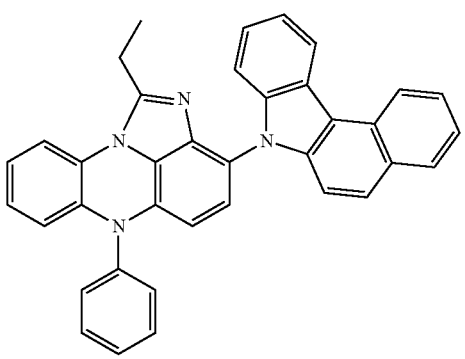
[Chemical Formula 11-15]
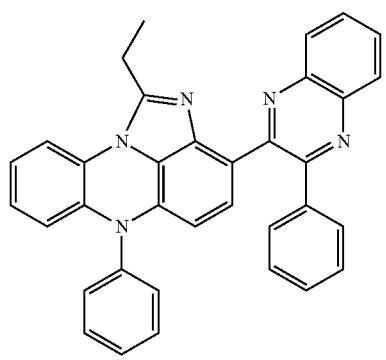
[Chemical Formula 11-16]
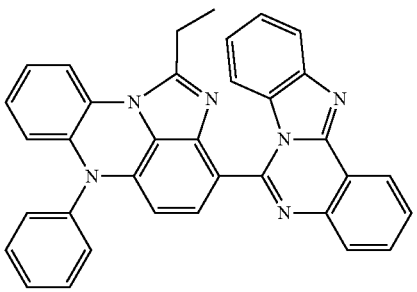
[Chemical Formula 11-17]

[Chemical Formula 13-1]

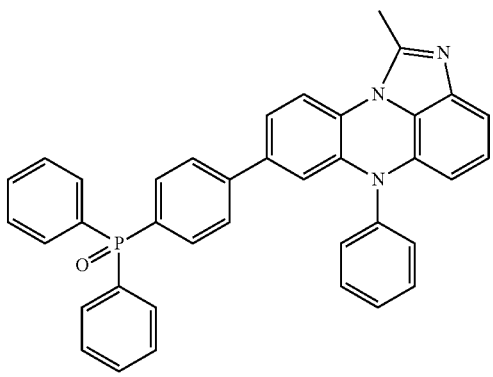

[Chemical Formula 13-2]

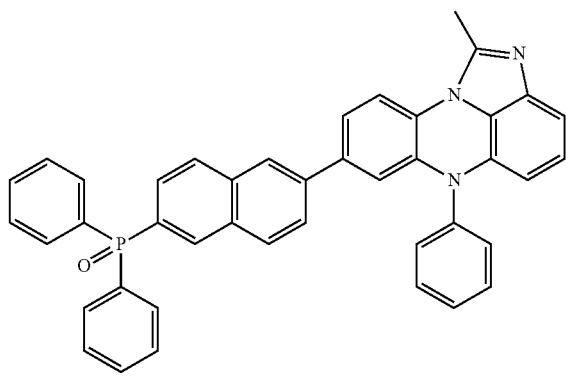

[Chemical Formula 13-6]

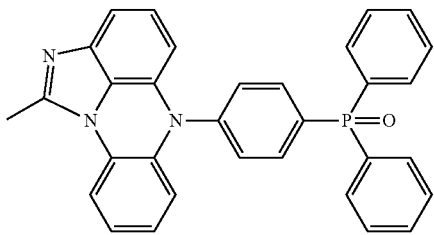

4. An organic light emitting device comprising:
a first electrode;
a second electrode provided opposite to the first electrode; and
one or more organic material layers including a light emitting layer provided between the first electrode and the second electrode,
wherein one or more layers of the organic material layers include the heterocyclic compound of claim 1.

5. The organic light emitting device of claim 4, wherein the organic material layer includes an electron transfer layer, an electron injection layer or a layer carrying out electron transfer and electron injection at the same time, and the electron transfer layer, the electron injection layer or the layer carrying out electron transfer and electron injection at the same time includes the heterocyclic compound.

6. The organic light emitting device of claim 5, wherein the electron transfer layer, the electron injection layer or the layer carrying out electron transfer and electron injection at the same time is formed only with the heterocyclic compound.

7. The organic light emitting device of claim 5, wherein the electron transfer layer, the electron injection layer or the layer carrying out electron transfer and electron injection at the same time includes the heterocyclic compound as a p-type host, and an n-type dopant as a dopant.

8. The organic light emitting device of claim 7, wherein the n-type dopant includes alkali metals, alkali metal compounds, alkaline earth metals, alkaline earth metal compounds, or combinations thereof.

9. The organic light emitting device of claim 4, wherein the light emitting layer includes the heterocyclic compound.

10. The organic light emitting device of claim 9, wherein the light emitting layer includes the heterocyclic compound as a host, and a phosphorous dopant compound as a dopant.

11. The organic light emitting device of claim 4, wherein the organic material layer further includes one, two or more layers selected from the group consisting of a hole injection layer, a hole transfer layer, an electron transfer layer, an electron injection layer, an electron blocking layer and a hole blocking layer.

* * * * *